(12) United States Patent
Barany et al.

(10) Patent No.: US 6,312,892 B1
(45) Date of Patent: Nov. 6, 2001

(54) HIGH FIDELITY DETECTION OF NUCLEIC ACID DIFFERENCES BY LIGASE DETECTION REACTION

(75) Inventors: Francis Barany, New York, NY (US); Jianying Luo, Boston, MA (US); Marilyn Khanna, Milwaukee, WI (US); Donald E. Bergstrom, West Lafayette, IN (US)

(73) Assignees: Cornell Research Foundation, Inc., Ithaca, NY (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 08/891,292

(22) Filed: Jul. 10, 1997

Related U.S. Application Data

(60) Provisional application No. 60/022,535, filed on Jul. 19, 1996.

(51) Int. Cl.[7] ................ C12Q 1/68; C12P 19/34

(52) U.S. Cl. ............ 435/6; 435/91.1; 435/91.2; 435/91.5; 435/91.51

(58) Field of Search .............. 435/6, 91.1, 91.2, 435/91.5, 91.51; 536/24.33; 935/77, 78, 6, 8

(56) References Cited

U.S. PATENT DOCUMENTS

| 4,683,202 | 7/1987 | Mullis et al. ............. 435/91 |
|---|---|---|
| 4,883,750 | 11/1989 | Whiteley et al. ........... 435/6 |
| 5,470,705 | 11/1995 | Grossman et al. .......... 435/6 |
| 5,494,810 | 2/1996 | Barany et al. ............ 435/91.52 |
| 5,496,699 | 3/1996 | Sorenson .................. 435/6 |
| 5,506,137 | 4/1996 | Mathur et al. ............ 435/252.3 |
| 5,516,663 * | 5/1996 | Backman et al. ........... 435/91.2 |
| 5,728,526 * | 3/1998 | George, Jr. et al. ....... 435/6 |
| 5,912,148 | 6/1999 | Eggerding ................. 435/91.2 |

OTHER PUBLICATIONS

Eggerding. PCR Methods and Applications. 4:337–345, Jun. 1995.*
Friedhoff et al. Anal. Biochem. 215:9–16, 1993.*
Kreiner, T., "Rapid Genetic sequence Analysis Using a DNA Probe Array System," *American Laboratory* 40: pp. 39–43 (Mar. 1996).
Kovach, et al., "Mutation Detection by Highly Sensitive Methods Indicates That p53 Gene Mutations in Breast Cancer Can Have Important Prognostic Value," *Proc. Natl. Acad. Sci. USA,* 93:1093–96 (1996).
Lin et al., "Multiplex Genotype Determination at a Large Number of Gene Loci," *Proc. Natl. Acad. Sci. USA,* 93:2582–87 (1996).
Tavormina, et al., "Thanatophoric dysplasia (Types I and II) Caused by Distinct Mutations in Fibroblast Growth Factor Receptor 3," *Nature Genetics,* 9:32128 (1995).
Barany et al., "Cloning, Overexpression and Nucleotide Sequence of a Thermostable DNA Ligase–Encoding Gene," *Gene,* 109:1–11 (1991).
Sidransky et al., "Identification of ras Oncogene Mutations in the Stool of Patients With Curable Colorector Tumors," *Science,* 256:102–105 (1992).

(List continued on next page.)

Primary Examiner—Carla J. Myers
(74) Attorney, Agent, or Firm—Nixon Peabody LLP

(57) ABSTRACT

Ligase detection reaction is utilized to distinguish minority template in the presence of an excess of normal template with a thermostable ligase. This process can be carried out with a mutant ligase, thermostable ligase, or a modified oligonucleotide probe. This procedure is particularly useful for the detection of cancer-associated mutations. It has the advantage of providing a quantitative measure of the amount or ratio of minority template.

88 Claims, 47 Drawing Sheets

(5 of 47 Drawing Sheet(s) Filed in Color)

OTHER PUBLICATIONS

Brennan, et al., "Molecular Assessment of Histopathological Staging in Squamous–Cell Carcinoma of the Head and Neck," *The New England Journal of Medicine*, 332(7):429–35 (1995).

Berthélemy, et al., "Identification of K–ras Mutations in Pancreatic Juice in the Early Diagnosis of Pancreatic Cancer," *Annals of Internal Medicine*, 123(3):188–91 (1995).

Hayashi, et al., "Genetic Diagnosis Identifies Occult Lymph Node Metastases Undetectable by the Histopathological Method," *Cancer Research*, 54:3853–56 (1994).

Tada, et al., "Detection of ras Gene Mutations in Pancreatic Juice and Peripheral Blood of Patients with Pancreatic Adenocarcinoma," *Cancer Research*, 53:2472–74 (1993).

Tada, et al., "Clinical Applications of ras Gene Mutation for Diagnosis of Pancreatic Adenocarcinoma," *Gastroenterology*, 100:233–38 (1991).

Mitsudomi, et al., "Mutations of ras Genes Distinguish a Subset of Non–Small–Cell Lung Cancer Cell Lines From Small–Cell Lung Cancer Cell Lines," *Oncogene*, 6:1353–62 (1991).

Day, et al., "Detection of Steroid 21–Hydroxylase Alleles Using Gene–Specific PCR and a Multiplexed Ligation Detection Reaction," *Genomics*, 29:152–62 (1995).

Frenkel, et al., "Specific, Sensitive, and Rapid Assay for Human Immunodeficiency Virus Type 1 pol Mutations Associated With Resistance to Zidovudine and Didanosine," *J. Clin. Microbiol.*,33(2):342–47 (1995).

Abravaya, et al., "Detection of Point Mutations With a Modified Ligase Chain Reaction (Gap–LCR)," *Nucleic Acids Research*, 23(4):675–82 (1995).

Powell, et al., "Molecular Diagnosis of Familial Adenomatous Polyposis," *The New England Journal of Medicine*, 329(27):1982–87 (1993).

Jen, et al., "Molecular Determinants of Dysplasia in Colorector Lesions," *Cancer Research*, 54:5523–26 (1994).

Redston, et al., "Common Occurrence of APC and K–ras Gene Mutations in the Spectrum of Colitis–Associated Neoplasias," *Gastroenterology*, 108:383–92 (1995).

Lu, et al., "Quantitative Aspects of the Mutant Analysis by PCR and Restriction Enzyme Cleavage (MAPREC)," *PCR Methods and Applications*, 3:176–80 (1993).

Kuppuswamy, et al., "Single Nucleotide Primer Extension to Detect Genetic Diseases: Experimental Application to Hemophilia B (factor IX) and Cystic Fibrosis Genes," *Proc. Natl. Acad. Sci. USA*, 88:1143–47 (1991).

Rust, et al., "Mutagenically Separated PCR (MS–PCR): A Highly Specific One Step Procedure for Easy Mutation Detection," *Nucleic Acid Research*, 21(16):3623–29 (1993).

Suzuki, et al., "Detection of ras Gene Mutations in Human Lung Cancers by Single–Strand Conformation Polymorphism Analysis of Polymerase Chain Reaction Products," *Oncogene*, 5:1037–43 (1990).

Balles, et al., "Facilitated Isolation of Rare Recombinants by Ligase Chain Reaction: Selection for Intragenic Crossover Events in the Drosophila optomotor–blind Gene," *Mol. Gen. Genet.*, 245:734–40 (1994).

Reynolds et al., "Analysis of Genetic Markers in Forensic DNA Samples Using the Polymerase Chain Reaction,"*Anal. Chem.*, 63:2–15 (1991)).

Buyse et al., "Rapid DNA Typing of Class II HLA Antigens Using the Polymerase Chain Reaction and Reverse Dot Blot Hybridization," *Tissue Antigens*, 41:1–14 (1993).

Gyllensten et al., "PCR–Based HLA Class II Typing," *PCR Meth. Appl*, 1:91–98 (1991).

Chamberlain et al., "Deletion Screening of the Duchenne Muscular Dystrophy Locus Via Multiplex DNA Amplification," *Nucleic Acids Res.*, 16:11141–56 (1988).

L. C. Tsui, Mutations and Sequence Variations Detected in the Cystic Fibrosis Transmembrane Conductance Regulator (CFTR) Gene: A Report From the Cystic Fibrosis Genetic Analysis Consortium, *Human Mutat.*, 1:197–203 (1992).

Hollstein et al., "p53 Mutations in Human Cancers," *Science*, 253:49–53 (1991).

R.K. Saiki, et al., "Enzymatic Amplification of β–Globin Genomic Sequences and Restriction Site Analysis for Diagnosis of Sickle Cell Anemia," *Science* 230:1350 (1985).

Wu, et al., "The Ligation Amplification Reaction (LAR)— Amplification of Specific DNA Sequences Using Sequential Rounds of Template–Dependent Ligation," *Genomics* 4:560–69 (1989).

Landegren, et al., "A Ligase–Mediated Gene Detection Technique," *Science* 241:1077–80 (1988).

Winn–Deen, et al., "Sensitive Fluorescence Method for Detecting DNA Ligation Amplification Products," *Clinical Chemistry*, 37(9):1522–23 (1991).

F. Barany, "Genetic Disease Detection and DNA Amplification Using Cloned Thermostable Ligase," *Proc. Nat'l Acad. Sci. USA*, 88:189–93 (1991).

Grossman et al., "High–Density Multiplex Detection of Nucleic Acid Sequences: Oligonucleotide Ligation Assay and Sequence–Coded Separation," *Nucl. Acids Res.*, 22(21):4527–34 (1994).

Jou et al., Deletion Detection in the Dystrophin Gene by Multiplex Gap Ligase Reaction and Immunochromatographic Strip Technology, *Human Mutation*, 5:86–93 (1995).

Gibbs et al., "Detection of Single DNA Base Differences by Competitive Oligonucleotide Priming," *Nucleic Acids Res.*, 17:2437–48 (1989).

F.F. Chehab, et al., "Detection of Specific DNA Sequences by Fluorescence Amplification: A Color Complementation Assay," *Proc. Natl. Acad. Sci. USA*, 86:9178–82 (1989).

Livak et al., "Detection of Single Base Differences Using Biotinylated Nucleotides With Very Long Linker Arms," *Nucleic Acids Res.*, 20(18):4831–37 (1989).

Nickerson et al., "Automated DNA Diagnostics Usi ng an ELISA–Based Oligonucleotide Ligation Assay," *Proc. Natl. Acad. Sci. USA*, 87:8923–27 (1990).

Wallace et al., "Ligase Chain Reaction for the Detection of Specific DNA Sequences and Point Mutations," in Pfeifer, ed., *Technologies for Detection of DNA Damage and Mutations*, New York, NY: Plenum Press, 307–322 (1996).

Reyes et al., "Ligase Chain Reaction Assay for Human Mutations: The Sickle Cell by LCR Assay," *Clinical Chemistry*, 43(1):40–44 (1997).

\* cited by examiner

**PCR/ LDR : Cancer-associated mutations at adjacent alleles.
Quantification using marker allele.**

1. PCR amplify region(s) containing mutations using primers, dNTPs and *Taq* polymerase. ◆

2. Quantify PCR products and spike with marker template. Perform LDR using allele-specific and marker LDR primers and thermostable ligase. ● Allele specific oligonucleotides ligate to common oligonucleotides only when there is perfect complementarity at the junction. Wild-type allele-specific LDR primers excluded to avoid overwelming signal from minority mutant target.

| AA | LDR |
|---|---|
| Cys | 49 |
| Arg | 48 |
| Ser | 47 |
| Val | 46 |
| Ala | 45 |
| Asp | 44 |
| Mk | 43 |

3. Separate fluorescent products on a DNA sequencer and quantify marker and mutant allele signal.

F1-N$_1$ — Gly to Asp mutation
F2 — Marker

FIG. 5

PCR/LDR : Cancer-associated mutations at adjacent alleles

1. PCR amplify region(s) containing mutations using primers, dNTPs and Taq polymerase. ◆

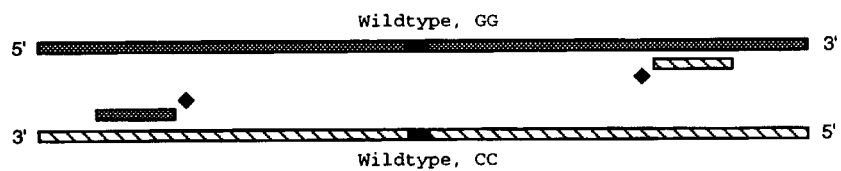

2. Perform LDR using allele-specific LDR primers and thermostable ligase. ● Allele specific oligonucleotides ligate to common oligonucleotides only when there is perfect complementarity at the junction. Wild-type allele-specific LDR primers excluded to avoid overwelming signal from minority mutant target.

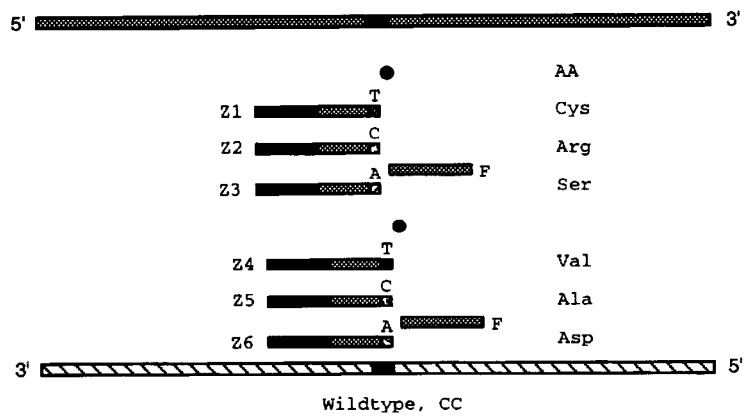

3. Capture fluorescent products on addressable array and quantify each allele.

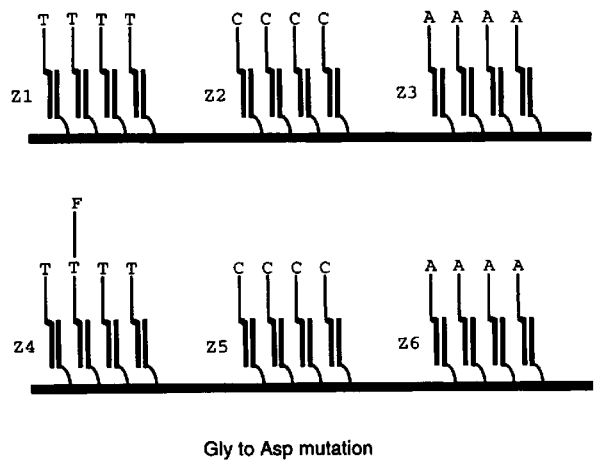

Gly to Asp mutation

*FIG. 7*

**PCR/LDR : Cancer-associated mutations at adjacent alleles.
Quantification using wild-type allele.**

1. PCR amplify region(s) containing mutations using primers, dNTPs and *Taq* polymerase. ◆

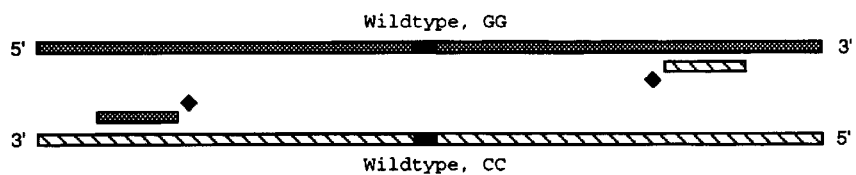

2. Perform LDR using allele-specific LDR primers, including low level and/or modified wild-type LDR primers and thermostable ligase. ● Allele specific oligonucleotides ligate to common oligonucleotides only when there is perfect complementarity at the junction. Low level and/or modified wild-type LDR primers yield less LDR products, and avoid overwelming signal from minority mutant target.

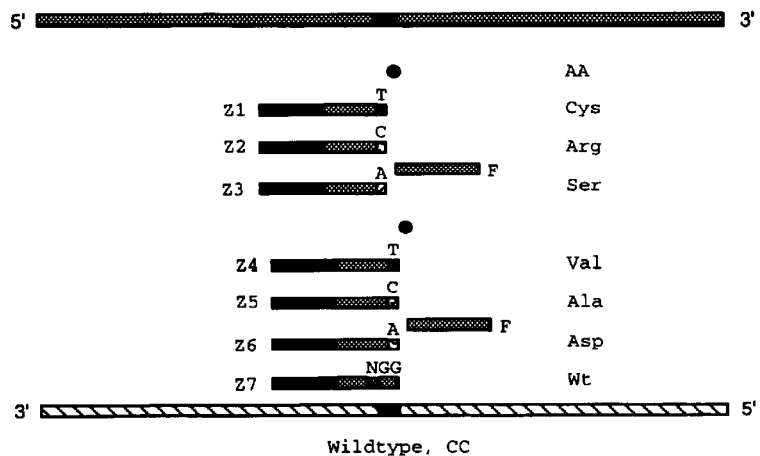

3. Separate fluorescent products on a DNA sequencer and quantify low level wild-type and mutant allele signal.

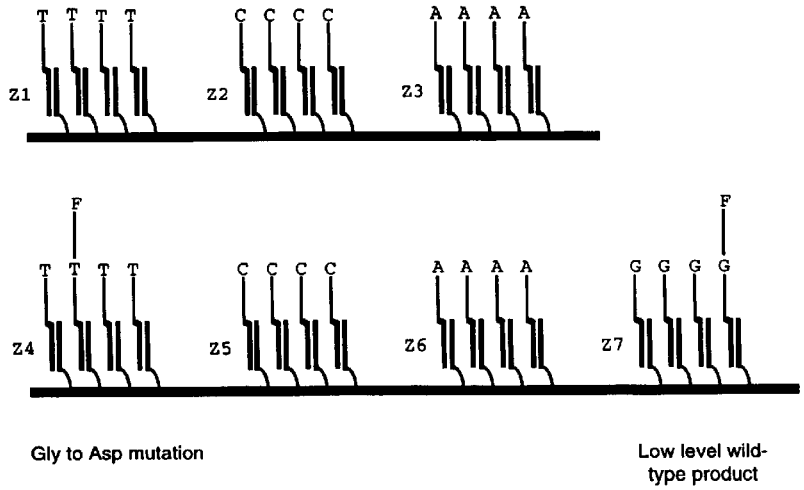

Gly to Asp mutation    Low level wild-type product

FIG. 9

Primers for making mutations at Lys 118 (K118R, K118H, K118L, K118P1, and K118P2).

Primer a (JL501): 5' gAC/CCT/ggA/AgA/ggC/gAg 3'
Primer b (JL503R): 5' CgT/CCA/C(g,C)(T,g,C,A)/ggT/gCT/CCA/Cgg/TgT/Agg 3'
Primer c (JL502): 5' Tgg/AgC/ACC/(A,C,g,T)(C,g)g/Tgg/ACg/ggC/TTT/CCg/T 3'
Primer d (JL504R): 5' gCA/AAC/Tgg/gTC/gCC/AC 3'

Primers for making mutations at 120 (D120N and D120Y).

Primer a (JL501): 5' gAC/CCT/ggA/AgA/ggC/gAg 3'
Primer b1 (JL510R): 5' gAA/AgC/CCg/T(A,T,g)C/ACC/TTg/TgC/TCC/ACg/gT 3'
Primer c1 (JL509): 5' ACA/Agg/Tg(T,A,C)/ACg/ggC/TTT/CCg/TgA/AC 3'
Primer d (JL504R): 5' gCA/AAC/Tgg/gTC/gCC/AC 3'

Primers for making mutations at 120 (D120E, D120G, D120A and D120V).

Primer a (JL501): 5' gAC/CCT/ggA/AgA/ggC/gAg 3'
Primer b2 (JL523R): gAA AgC CCT (A,g,C,T) CC ACC TTg TgC TCC ACg gT 3'
Primer c2 (JL522): 5' ACA Agg Tgg (A,g,C,T) Ag ggC TTT CCg TgA ACC T 3'
Primer d (JL504R): 5' gCA/AAC/Tgg/gTC/gCC/AC 3'

Primers for making mutations at Lys 294 (K294R, K294Q, K294L1, K294L2, and K294P).

Primer a (JL505): 5' CAg/AAC/CTC/CTC/ACC/ATC 3'
Primer b (JL507R): 5' CTC/gTC/CAg/(g,C)(T,g,C,A)g/CAC/CAC/CAC/CCC/gTC 3'
Primer c (JL506): Tgg/Tgg/TgC/(A,C,g,T)(C,g)C/Tgg/ACg/AgC/TTg/CCC/T 3'
Primer d (JL508R): 5' CTC/TAT/gTA/gCT/CTC/gTT/gTg 3'

Primers for making mutations at Arg337 (R337K, R337Q, and R337E).

Primer a (JL505): 5' CAg/AAC/CTC/CTC/ACC/ATC 3'
Primer b (JL537R): 5' CgC/CCg/gTT/T(T,C,g)C/CCC/ACC/Tgg/AAg/ACC/A 3'
Primer c (JL536): 5' ggT/ggg/g(A,g,C)A/AAC/Cgg/gCg/TgT/gAC/C 3'
Primer d (JL508R): 5' CTC/TAT/gTA/gCT/CTC/gTT/gTg 3'

Primers for making mutations at Gly 339 (G339A and G339D).

Primer a (JL505): 5' CAg/AAC/CTC/CTC/ACC/ATC 3'
Primer b (JL535R): 5' gTC/ACC/Cgg/(g,T)Cg/gTg/CgC/CCC/ACC/Tg 3'
Primer c (JL534): 5' CgC/ACC/g(A,C)C/Cgg/gTg/ACC/CCT/gTg 3'
Primer d (JL508R): 5' CTC/TAT/gTA/gCT/CTC/gTT/gTg 3'

Primers for making mutant G339E from the double mutant K294P-G339E.

Primer a (JL505): 5' CAg/AAC/CTC/CTC/ACC/ATC 3'
Primer b (JL525R): 5' CTC/gTC/CAg/CTT/CAC/CAC/CAC/CCC/gTC 3'
Primer c (JL524): 5' Tgg/Tgg/TgA/AgC/Tgg/ACg/AgC/TTg/CCC/T 3'
Primer d (JL508R): 5' CTC/TAT/gTA/gCT/CTC/gTT/gTg 3'

*FIG. 12A*

Primers for making mutations at Cys412 (C412A, C412V, C412T, and C412M).

Primer a (JL505): 5' CAg/AAC/CTC/CTC/ACC/ATC 3'
Primer b (JL527R): 5' TCg/ggC/(A,g)(T,C)g/gTC/TCg/ggC/CAg/CgA 3'
Primer c (JL526): 5' CCC/gAg/ACC/(A,g)(T,C)g/CCC/gAg/TgC/ggC/CA 3'
Primer d (JL518R): 5' Agg CCC ACC Agg TCT TC 3'

Primers for making mutations at Cys415 (C415A, C415V, C415T, and C415M).

Primer a (JL505): 5' CAg/AAC/CTC/CTC/ACC/ATC 3'
Primer b (JL529R): 5' gTg/gCC/C(A,g)(C,T)/CTC/ggg/gCA/ggT/CTC 3'
Primer c (JL528): 5' TgC/CCC/gAg/(A,g)(T,C)g/ggC/CAC/CgC/CTC/CTC/A 3'
Primer d (JL518R): 5' Agg CCC ACC Agg TCT TC 3'

Primers for making mutations at Cys428 (C428A, and C428T).

Primer a (JL505): 5' CAg/AAC/CTC/CTC/ACC/ATC 3'
Primer b (JL531R): 5' gTT/ggg/C(A,g)(T,C)/gCg/gTg/gAC/CTT/CCC/CT 3'
Primer c (JL530): 5' gTC/CAC/CgC/(A,g)(T,C)g/CCC/AAC/CCC/TTg/TgC/C 3'
Primer d (JL518R): 5' Agg CCC ACC Agg TCT TC 3'

Primers for making mutations at Cys433 (C433A, C433V, C433T, and C433M).

Primer a (JL505): 5' CAg/AAC/CTC/CTC/ACC/ATC 3'
Primer b (JL533R): 5' ggC/ggg/C(g,A)(T,C)/CAA/ggg/gTT/ggg/gCA/g 3'
Primer c (JL532): 5' AAC/CCC/TTg/(A,g)(T,C)g/CCC/gCC/AAg/CgC/TTT/g 3'
Primer d (JL518R): 5' Agg CCC ACC Agg TCT TC 3'

*FIG. 12B*

```
RP5'A  5'-                                                      AA GTT GTC ATA GTT TGA TCC TCT AGT CTG GG AAA AAA-3'
RP5'C  5'-                                                      CA GTT GTC ATA GTT TGA TCC TCT AGT CTG GG AAA A   -3'
RP5'G  5'-                                                      GA GTT GTC ATA GTT TGA TCC TCT AGT CTG GG AA      -3'
RP5'T  5'-                                                      TA GTT GTC ATA GTT TGA TCC TCT AGT CTG GG          -3'
Com5F  5'- Fam-CCC TGT TCC AGC GTC TGC GGT GTT GCG T                                                              -3'
ALg    3'-     GGG ACA AGG TCG CAG ACG CCA CAA CGC AAT CAA CAG TAT CAA ACT AGG AGA TCA GAC CC                     -5'

LP3'A  5'- AAA AAA CCC TGT TCC AGC GTC TGC GGT GTT GCG TA                                                         -3'
LP3'C  5'-   A AAA CCC TGT TCC AGC GTC TGC GGT GTT GCG TC                                                         -3'
LP3'G  5'-      AA CCC TGT TCC AGC GTC TGC GGT GTT GCG TG                                                         -3'
LP3'T  5'-         CCC TGT TCC AGC GTC TGC GGT GTT GCG TT                                                         -3'
Com3F  5'-                                                       A GTT GTC ATA GTT TGA TCC TCT AGT CTG GG-Fam     -3'
ALg    3'-     GGG ACA AGG TCG CAG ACG CCA CAA CGC AAT CAA CAG TAT CAA ACT AGG AGA TCA GAC CC                     -5'

GLg    3'-     GGG ACA AGG TCG CAG ACG CCA CAA CGC AGT CAA CAG TAT CAA ACT AGG AGA TCA GAC CC                     -5'
ALg    3'-     GGG ACA AGG TCG CAG ACG CCA CAA CGC AAT CAA CAG TAT CAA ACT AGG AGA TCA GAC CC                     -5'
TLg    3'-     GGG ACA AGG TCG CAG ACG CCA CAA CGC ATT CAA CAG TAT CAA ACT AGG AGA TCA GAC CC                     -5'
CLg    3'-     GGG ACA AGG TCG CAG ACG CCA CAA CGC ACT CAA CAG TAT CAA ACT AGG AGA TCA GAC CC                     -5'
```

*FIG. 13*

| Primer name | Sequence |
|---|---|
| RP5'A | 5' AA GTT GTC ATA GTT TGA TCC TCT AGT CTG GG AAA AAA 3' |
| RP5'C | 5' CA GTT GTC ATA GTT TGA TCC TCT AGT CTG GG AAA A 3' |
| RP5'G | 5' GA GTT GTC ATA GTT TGA TCC TCT AGT CTG GG AA 3' |
| RP5'T | 5' TA GTT GTC ATA GTT TGA TCC TCT AGT CTG GG 3' |
| Com 5F | 5' F-CCC TGT TCC AGC GTC TGC GGT GTT GCG T 3' |
| LP3'A | 5' AAA AAA CCC TGT TCC AGC GTC TGC GGT GTT GCG TA 3' |
| LP3'C | 5' A AAA CCC TGT TCC AGC GTC TGC GGT GTT GCG TC 3' |
| LP3'G | 5' AA CCC TGT TCC AGC GTC TGC GGT GTT GCG TG 3' |
| LP3'T | 5' CCC TGT TCC AGC GTC TGC GGT GTT GCG TT 3' |
| Com 3F | 5' A GTT GTC ATA GTT TGA TCC TCT AGT CTG GG-F 3' |
| ALg | 5' CCC AGA CTA GAG GAT CAA ACT ATG ACA ACT AAC GCA ACA CCG CAG ACG CTG GAA CAG GG 3' |
| CLg | 5' CCC AGA CTA GAG GAT CAA ACT ATG ACA ACT CAC GCA ACA CCG CAG ACG CTG GAA CAG GG 3' |
| GLg | 5' CCC AGA CTA GAG GAT CAA ACT ATG ACA ACT GAC GCA ACA CCG CAG ACG CTG GAA CAG GG 3' |
| TLg | 5' CCC AGA CTA GAG GAT CAA ACT ATG ACA ACT TAC GCA ACA CCG CAG ACG CTG GAA CAG GG 3' |

FIG. 14

Table I: Improving the fidelity of *Tth* DNA ligase.

| Discriminating Probes[a] | Ligase (conc.) | Ligation Substrate[b] | Initial Rates[c] C-G match (fmol/min) | Initial Rates[c] T-G mismatch (fmol/min) | Ligation[d] fidelity $\frac{\text{Rate . match}}{\text{Rate . mismatch}}$ |
|---|---|---|---|---|---|
| Long Probes (LP3'C and LP3'T) | Wild Type (0.25 nM) | —GTN p—F<br>—CAG— | 25 | $5.5 \times 10^{-2}$ | $4.5 \times 10^{2}$ |
| Short Probes (SLP3'C and SLP3'T) | Wild Type (0.25 nM) | —GTN p—F<br>—CAG— | 29 | $2.0 \times 10^{-2}$ | $1.5 \times 10^{3}$ |
| Probes with deliberate mismatches (SLP3'ATC and SLP3'ATT) | Wild Type (2.5 nM) | —ATN p—F<br>—CAG— | 26 | $4.4 \times 10^{-3}$ | $5.9 \times 10^{3}$ |
| Probes with Q base analogue (SLP3'QTC and SLP3'QTT) | Wild Type (2.5 nM) | —QTN p—F<br>—AAG— | 44 | $3.3 \times 10^{-3}$ | $1.3 \times 10^{4}$ |
| Short Probes (SLP3'C and SLP3'T) | K294R (2 nM) | —GTN p—F<br>—CAG— | 65 | $1.2 \times 10^{-2}$ | $5.4 \times 10^{3}$ |
| Short Probes (SLP3'C and SLP3'T) | K294P (4 nM) | —GTN p—F<br>—CAG— | 50 | $3.1 \times 10^{-3}$ | $1.6 \times 10^{4}$ |
| Probes with Q base analogue (SLP3'QTC and SLP3'QTT) | K294R (30 nM) | —QTN p—F<br>—AAG— | 51 | $1.8 \times 10^{-3}$ | $2.8 \times 10^{4}$ |
| Probes with Q base analogue (SLP3'QTC and SLP3'QTT) | K294P (120 nM) | —QTN p—F<br>—AAG— | 38 | $9.0 \times 10^{-4}$ | $4.2 \times 10^{4}$ |

| Primer Name | Size (bp) | Sequence (5'--->3') |
|---|---|---|
| Com610-3'F | 30 | Fam-GGGTCTGATCTCCTAGTTTGATACTGTTGA |
| SLP3'TTT | 21 | ATGCGTCTGCGGTGTTGCTTT |
| SLP3'TTC | 23 | AAATGGCTCTGCGGGTGTTGCTTC |
| SLP3'Q$_2$TT | 21 | ATGCGTCTGCGGTGTTGCQ$_2$TT |
| SLP3'Q$_{18}$TT | 21 | ATGCGTCTGCGGTGTTGCQ$_{18}$TT |

FIG. 20B

| Template Name | Size (bp) | Sequence (5'--->3') |
|---|---|---|
| Glg.m3A | 59 | CCCAGACTAGAGGATCAAACTATGACAACTGAAG CAACACCGCAGAGCGCTGAACAGGG |
| Glg.m3A.Rev | 59 | CCCTGTTCCAGCGTCTGCGGTGTTGCTTCAGTTGT CATAGTTTGATCCTCTAGTCTGGG |
| Alg.m3A | 59 | CCCAGACTAGAGGATCAAACTATGACAACTAAAG CAACACCGCAGAGCGCTGAACAGGG |
| Alg.m3A.Rev | 59 | CCCTGTTCCAGCGTCTGCGGTGTTGCTTTAGTTGT CATAGTTTGATCCTCTAGTCTGGG |

| Amount of Normal Template (fmol) | Amount of Cancer Template (fmol) | LDR Product (fmol) Wild Type | Mutant |
|---|---|---|---|
| 250 | 0 | 1.5 | 1.1 |
| 250 | 0.5 | 3.3 | 3.6 |
| 250 | 1.0 | 6.0 | 5.8 |
| 250 | 2.5 | 11.8 | 9.1 |
| 250 | 5.0 | 18.7 | 22.0 |
| 250 | 10.0 | 27.7 | 28.9 |
| 250 | 25.0 | 61.5 | 57.9 |
| 250 | 50.0 | 63.0 | 73.3 |

| Amount of Normal Template (fmol) | Amount of Cancer Template (fmol) | Signal to Noise Ratio | |
|---|---|---|---|
| | | Wild Type | Mutant |
| 250 | 0 | 1.0 | 1.0 |
| 250 | 0.5 | 2.1 | 3.3 |
| 250 | 1.0 | 3.9 | 5.4 |
| 250 | 2.5 | 7.7 | 8.5 |
| 250 | 5.0 | 12.2 | 20.4 |
| 250 | 10.0 | 18.1 | 26.8 |
| 250 | 25.0 | 40.2 | 53.6 |
| 250 | 50.0 | 41.2 | 67.9 |

Synthetic Templates: G:C Match, 1 Primer Set

| Concentration of Normal Template | LDR Product (fmol) Wild Type | Mutant |
|---|---|---|
| 0 | 0.5 | 0.3 |
| 0.1 | 1.4 | 1.4 |
| 0.25 | 1.9 | 2.4 |
| 0.5 | 4.9 | 4.5 |
| 1.0 | 9.0 | 8.6 |
| 2.5 | 18.1 | 16.3 |
| 5.0 | 33.6 | 26.2 |
| 10.0 | 55.8 | 45.9 |

```
5' A————————QTT                              SLP3'QTT
5' A————————TTT                              SLP3'TTT
               A————————F   3'               Com 610-3'F
3' ————————NANT————————5'                    Template 3' ————————AAGT————————5'    GLg.m3A         "Normal"
5' ————————TTCA————————3'    GLg.m3A.rev     Template 3' ————————AAAT————————5'    ALg.m3A         "Cancer"
5' ————————TTTA————————3'    ALg.m3A.rev     Template
```

*FIG. 24*

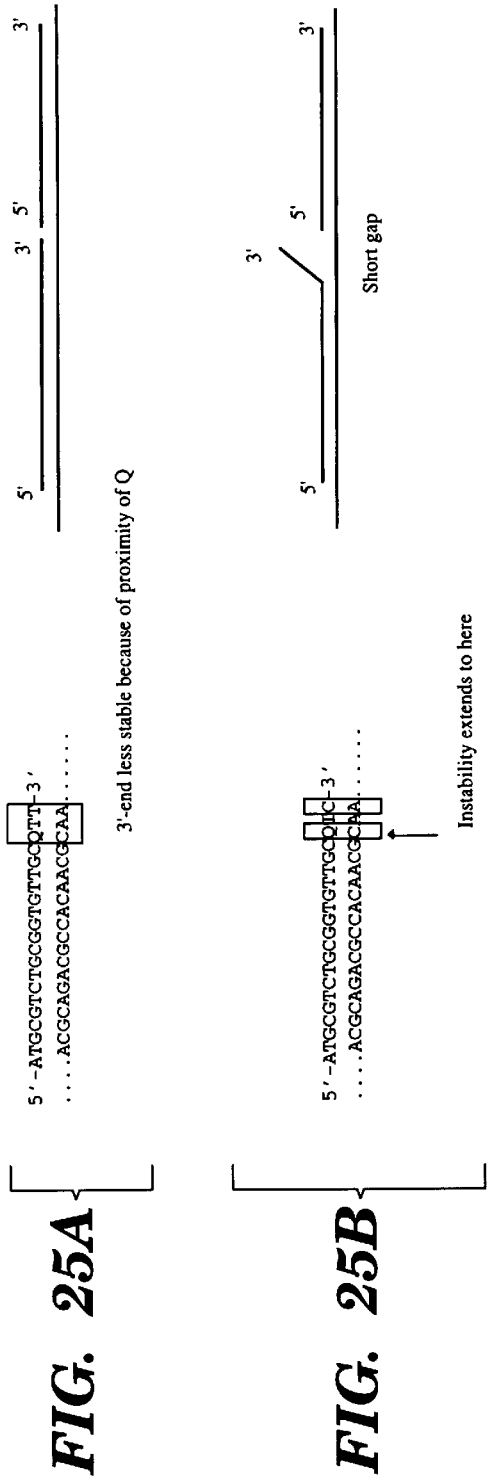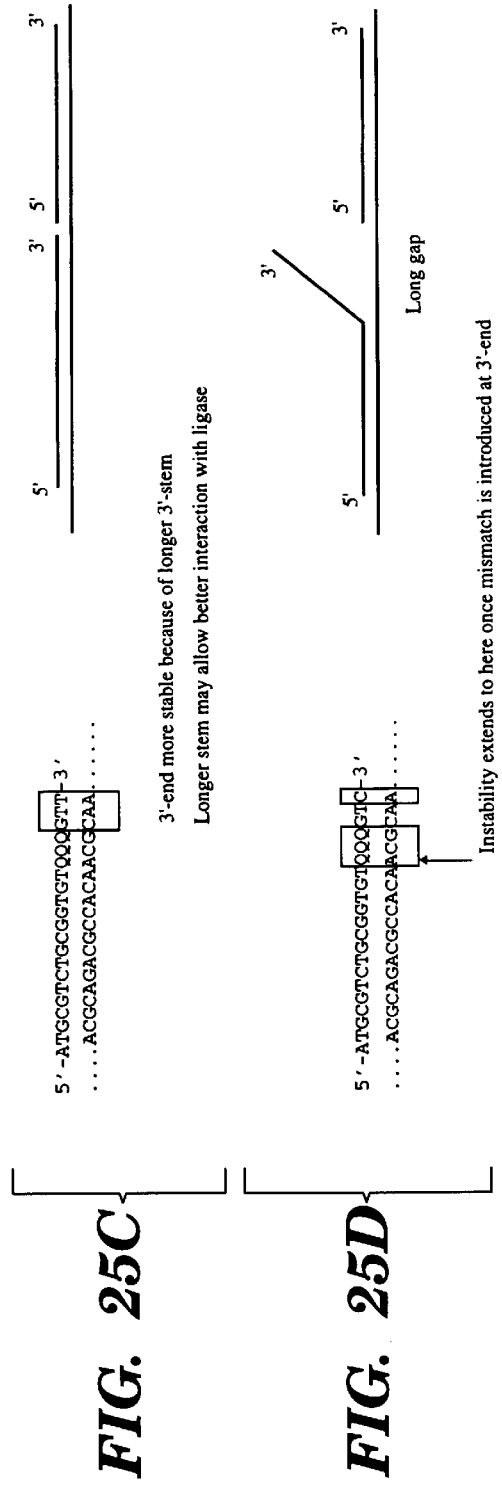
FIG. 25A
FIG. 25B
FIG. 25C
FIG. 25D

Synthetic Templates: C:A Mismatch, 1 Primer Set

Amount of Cancer Template in 250 fmols of Normal Template

| Amount of Normal Template (fmol) | Amount of Cancer Template (fmol) | LDR Product (fmol) | |
|---|---|---|---|
| | | Wild Type | Mutant |
| 250 | 0 | 0.8 | 0.6 |
| 250 | 0.25 | 1.0 | 0.8 |
| 250 | 0.50 | 1.7 | 1.3 |
| 250 | 1.0 | 2.2 | 1.8 |
| 250 | 2.5 | 4.4 | 3.9 |
| 250 | 5.0 | 8.1 | 7.7 |
| 250 | 10.0 | 15.0 | 13.6 |
| 250 | 25.0 | 21.4 | 20.8 |
| 250 | 50.0 | 49.4 | 27.8 |

Synthetic Templates: C:A Mismatch, 1 Primer Set

FIG. 28A Amount Of Cancer Template in 250 fm of Normal Template

| Amount of Normal Template (fmol) | Amount of Cancer Template (fmol) | Signal to Noise Ratio | |
|---|---|---|---|
| | | Wild Type | Mutant |
| 250 | 0 | 1.0 | 1.0 |
| 250 | 0.25 | 1.3 | 1.3 |
| 250 | 0.5 | 2.1 | 2.2 |
| 250 | 1.0 | 2.7 | 3.1 |
| 250 | 2.5 | 5.4 | 6.6 |
| 250 | 5.0 | 9.9 | 13.0 |
| 250 | 10.0 | 18.3 | 23.1 |
| 250 | 25.0 | 26.1 | 35.3 |
| 250 | 50.0 | 60.2 | 47.2 |

Synthetic Templates: T:A Match, 1 Primer Set

FIG. 29A Amount Of Normal Template (fm)

| Concentration of Normal Template | LDR Product (fmol) | |
|---|---|---|
| | Wild Type | Mutant |
| 0 | 0 | 0 |
| 0.1 | 0.7 | 0.7 |
| 0.25 | 1.6 | 3.2 |
| 0.5 | 2.5 | 4.1 |
| 1.0 | 7.2 | 6.5 |
| 2.5 | 13.1 | 13.5 |
| 5.0 | 19.3 | 23.6 |
| 10.0 | 27.3 | 22.2 |

Name and Sequence Of Primers Used For K-*ras* Detection

| K-*ras* LDR primers for Codon 12 | Tm | LDR (bp) | Sequence |
|---|---|---|---|
| Fam-K-*ras* c12.2D<br>(23 + 1 = 24-mer, 5' position 103) | 67.6 °C | 44 | 5' Fam-AAA ACT TGT GGT AGT TGG AGC TGA 3' |
| Tet-K-*ras* c12.2A<br>(23 + 2 = 25-mer, 5' position 103) | 67.6 °C | 45 | 5' Tet-CAA AAC TTG TGG TAG TTG GAG CTG C 3' |
| Fam-K-*ras* c12.2V<br>(23 + 3 = 26-mer, 5' position 103) | 67.6 °C | 46 | 5' Fam-ACA AAA ACT TGT GGT AGT TGG AGC TGT 3' |
| K-*ras* c12 Com-2<br>(20-mer, 5' position 126) | 69.8 °C |  | 5' p TGG CGT AGG CAA GAG TGC CT-Bk 3' |
| Tet-K-*ras* c12.1S<br>(26-mer, 5' position 99) | 66.6 °C | 47 | 5' Tet-ATA TAA ACT TGT GGT AGT TGG AGC TA 3' |
| Fam-K-*ras* c12.1R<br>(26 + 1 = 27-mer, 5' position 99) | 66.6 °C | 48 | 5' Fam-AAT ATA AAC TTG TGG TAG TTG GAG CTC 3' |
| Tet-K-*ras* c12.1C<br>(26 + 2 = 28-mer, 5' position 99) | 66.6 °C | 49 | 5' Tet-CAA TAT AAA CTT GTG GTA GTT GGA GCT T 3' |
| K-*ras* c12 Com-1<br>(20 + 1 = 21-mer, 5' position 125) | 69.6 °C |  | 5' p GTG GCG TAG GCA AGA GTG CCA A-Bk 3' |

| K-*ras* LDR primers for Codon 13 | Tm | LDR (bp) | Sequence |
|---|---|---|---|
| Fam-K-*ras* c13.4D<br>(21-mer, 5' position 108) | 67.2 °C | 51 | 5' Fam-TGT GGT AGT TGG AGC TGG TGA 3' |
| Tet-K-*ras* c13.4A<br>(21 + 1 = 22-mer, 5' position 108) | 67.2 °C | 52 | 5' Tet-ATG TGG TAG TTG GAG CTG GTG C 3' |
| Fam-K-*ras* c13.4V<br>(21 + 2 = 23-mer, 5' position 108) | 67.2 °C | 53 | 5' Fam-AAT GTG GTA GTT GGA GCT GGT GT 3' |
| K-*ras* c13 Com-4<br>(21 + 9 = 30-mer, 5' position 129) | 66.8 °C |  | 5' p CGT AGG CAA GAG TGC CTT GAC AAA AAA AAA-Bk 3' |
| Tet-K-*ras* c13.3S<br>(22-mer, 5' position 106) | 66.6 °C | 54 | 5' Tet-CTT GTG GTA GTT GGA GCT GGT A 3' |
| Fam-K-*ras* c13.3R<br>(22 + 1 = 23-mer, 5' position 106) | 66.6 °C | 55 | 5' Fam-ACT TGT GGT AGT TGG AGC TGG TC 3' |
| Tet-K-*ras* c13.3C<br>(22 + 2 = 24-mer, 5' position 106) | 66.6 °C | 56 | 5' Tet-AAC TTG TGG TAG TTG GAG CTG GTT 3' |
| K-*ras* c13 Com-3<br>(21 + 11 = 32-mer, 5' position 128) | 69.7 °C |  | 5' p GCG TAG GCA AGA GTG CCT TGA AAA AAA AAA AA-Bk 3' |

*FIG. 31A*

| K-ras LDR primers for Codon 61 | Tm | LDR (bp) | Sequence |
|---|---|---|---|
| Tet-K-ras c61.7HT (24 + 1 = 25-mer, 5' position 202) | 68.2 °C | 59 | 5' Tet-AGA TAT TCT CGA CAC AGC AGG TCA T 3' |
| Fam-K-ras c61.7HC (24 + 2 = 26-mer, 5' position 202) | 68.2 °C | 60 | 5' Fam-AAG ATA TTC TCG ACA CAG CAG GTC AC 3' |
| K-ras c61 Com-7 (24 + 10 = 36-mer, 5' position 226) | 68.9 °C | | 5' p GAG GAG TAC AGT GCA ATG AGG GAC AAA AAA AAA A-Bk 3' |
| Tet-K-ras c61.6R (23-mer, 5' position 202) | 66.2 °C | 61 | 5' Tet-GAT ATT CTC GAC ACA GCA GGT CG 3' |
| Fam-K-ras c61.6L (23 + 1 = 24-mer, 5' position 202) | 66.2 °C | 62 | 5' Fam-AGA TAT TCT CGA CAC AGC AGG TCT 3' |
| Tet-K-ras c61.6P (23 + 2 = 25-mer, 5' position 202) | 66.2 °C | 63 | 5' Tet-AAG ATA TTC TCG ACA CAG CAG GTC C 3' |
| K-ras c61 Com-6 (24 + 14 = 38-mer, 5' position 225) | 69.1 °C | | 5' p AGA GGA GTA CAG TGC AAT GAG GGA AAA AAA AAA AAA AA-Bk 3' |
| Fam-K-ras c61.5K (23-mer, 5' position 201) | 67.4 °C | 64 | 5' Fam-GGA TAT TCT CGA CAC AGC AGG TA 3' |
| Tet-K-ras c61.5E (23 + 1 = 24-mer, 5' position 201) | 67.4 °C | 65 | 5' Tet-AGG ATA TTC TCG ACA CAG CAG GTG 3' |
| K-ras c61 Com-5 (24 + 17 = 41-mer, 5' position 224) | 69.0 °C | | 5' p AAG AGG AGT ACA GTG CAA TGA GGG CAA AAA AAA AAA AAA AA-Bk 3' |

*FIG. 31B*

K-*ras* Detection: 1 Primer Set, Gly to Asp Mutation for Codon 12

| Amount of Normal Template (fmol) | Amount of Cancer Template (fmol) | LDR Product (fmol) | |
|---|---|---|---|
| | | Wild Type | Mutant |
| 2000 | 0 | 0.4 | 0.4 |
| 2000 | 0.5 | 0.3 | 0.5 |
| 2000 | 1 | 0.6 | 0.7 |
| 2000 | 2 | 1.4 | 1.2 |
| 2000 | 4 | 3.2 | 2.3 |
| 2000 | 8 | 4.2 | 4.3 |
| 2000 | 20 | 14.5 | 11.8 |
| 2000 | 40 | 29.1 | 25.5 |
| 2000 | 100 | 62.0 | 62.4 |

K-*ras* Detection: 1 Primer Set, Gly to Asp Mutation for Codon 12

| Amount of Normal Template (fmol) | Amount of Cancer Template (fmol) | Signal to Noise Ratio | |
|---|---|---|---|
| | | Wild Type | Mutant |
| 2000 | 0 | 1.0 | 1.0 |
| 2000 | 0.5 | 0.8 | 0.8 |
| 2000 | 1 | 1.6 | 1.7 |
| 2000 | 2 | 3.7 | 3.2 |
| 2000 | 4 | 8.4 | 6.1 |
| 2000 | 8 | 11.1 | 11.3 |
| 2000 | 20 | 38.2 | 31.1 |
| 2000 | 40 | 76.6 | 67.1 |
| 2000 | 100 | 163 | 164 |

| Amount of Normal Template (fmol) | Amount of Cancer Template (fmol) | LDR Product (fmol) Wild Type | Mutant |
|---|---|---|---|
| 2000 | 0 | 1.1 | 0.9 |
| 2000 | 2 | 3.7 | 2.9 |
| 2000 | 4 | 4.5 | 4.9 |
| 2000 | 8 | 9.2 | 9.5 |
| 2000 | 20 | 15.3 | 19.2 |
| 2000 | 40 | 30.5 | 35.4 |
| 2000 | 80 | 64.6 | 93.6 |
| 2000 | 100 | 81.2 | 96.9 |
| 2000 | 200 | 117 | 126 |

**K-*ras* Detection: C:A Mismatch, 6 Primer Set for Codon 12**

| Amount of Normal Template (fmol) | Amount of Cancer Template (fmol) | Signal to Noise Ratio | |
|---|---|---|---|
| | | Wild Type | Mutant |
| 2000 | 0 | 1.0 | 1.0 |
| 2000 | 2 | 3.4 | 3.2 |
| 2000 | 4 | 4.1 | 5.5 |
| 2000 | 8 | 8.4 | 10.6 |
| 2000 | 20 | 13.9 | 21.6 |
| 2000 | 40 | 27.7 | 39.8 |
| 2000 | 80 | 58.7 | 105 |
| 2000 | 100 | 73.8 | 109 |
| 2000 | 200 | 106 | 141 |

K-*ras* Detection: C:A Mismatch, 19 Primer Set for Codon 12, 13, and 61

| Amount of Normal Template (fmol) | Amount of Cancer Template (fmol) | LDR Product (fmol) | |
|---|---|---|---|
| | | Wild Type | Mutant |
| 2000 | 0 | 0.5 | 0.5 |
| 2000 | 2 | 0.6 | 1.2 |
| 2000 | 4 | 1.5 | 2.3 |
| 2000 | 8 | 3.3 | 4.3 |
| 2000 | 10 | 2.2 | 3.8 |
| 2000 | 20 | 4.5 | 6.7 |
| 2000 | 40 | 11.8 | 16.6 |
| 2000 | 100 | 34.9 | 37.1 |
| 2000 | 200 | 49.9 | 52.5 |

K-*ras* Detection: C:A Mismatch, 19 Primer Set for Codon 12, 13, and 61

| Amount of Normal Template (fmol) | Amount of Cancer Template (fmol) | Signal to Noise Ratio | |
|---|---|---|---|
| | | Wild Type | Mutant |
| 2000 | 0 | 1.0 | 1.0 |
| 2000 | 2 | 1.1 | 1.2 |
| 2000 | 4 | 2.9 | 3.2 |
| 2000 | 8 | 6.3 | 7.2 |
| 2000 | 10 | 4.2 | 6.2 |
| 2000 | 20 | 8.6 | 12.6 |
| 2000 | 40 | 22.7 | 31.3 |
| 2000 | 100 | 67.1 | 70.0 |
| 2000 | 200 | 96.0 | 99.0 |

| Lane Number | Sample | Expected Mutation | LDR Product | Called Mutation |
|---|---|---|---|---|
| 1 | Neg. Control | WT | - | WT |
| 2 | Pos. Control | Val-12 | 46-Fam | Val-12 |
| 3 | 126 | Cys-12 | 49-Tet | Cys-12 |
| 4 | 140 | Val-12 | 46-Fam | Val-12 |
| 5 | 142 | Cys-12 | 49-Tet | Cys-12 |
| 6 | 146 | Asp-12 | 44-Fam | Asp-12 |
| 7 | 150 | Asp-12 | 44-Fam | Asp-12 |
| 8 | 152 | Cys-12 | 49-Tet | Cys-12 |
| 9 | 166 | Cys-12 | 49-Tet | Cys-12 |
| 10 | 172 | Val-12 | 46-Fam | Val-12 |
| 11 | 214 | Ala-12 | 45-Tet | Ala-12 |
| 12 | 224 | Cys-12 | 49-Tet | Cys-12 |
| 13 | 228 | Asp-13 | 51-Fam | Asp-13 |
| 14 | 232 | Ser-12 | 47-Tet | Ser-12 |
| 15 | 234 | Asp-12 | 44-Fam | Asp-12 |
| 16 | 258 | Asp-13 | 51-Fam | Asp-13 |
| 17 | 262 | Val-12 | 46-Fam | Val-12 |
| 18 | 268 | Ser-12 | 47-Tet | Ser-12 |
| 19 | 270 | Ala-12 | 45-Tet | Ala-12 |
| 20 | 276 | Asp-13 | 51-Fam | Asp-13 |
| 21 | 290 | Val-12 | 46-Fam | Val-12 |
| 22 | 292 | Val-12 | 46-Fam | Val-12 |

*FIG. 42*

Results of PCR/LDR of K-*ras* mutations in clinical specimens

| Sample # | Mutation called by PCR/LDR (GENESCAN) | | Mutation called by SEQUENCING |
|---|---|---|---|
| | 19 Primer Set | 1 Primer Set | |
| 30 | Val-12 | Val-12 | wild-type |
| 32 | Val-12 | Val-12 | wild-type |
| 46 | Cys-12 | Cys-12 | wild-type |
| 54 | Asp-12; Cys12 [a] | Asp-12; Cys12 [a] | wild-type |
| 84 | Asp-12 (weak) | Asp-12 (weak) | wild-type |
| 92 | Asp-12 (weak) | Asp-12 (weak) | wild-type |
| 80 | wild-type | wild-type | Asp-13 |
| 104 | Asp-12 (weak) | Asp-12 (weak) | wild-type |
| 178 | wild-type | wild-type | Leu-12 |
| 240 | Asp-12 | Asp-12 | ? |

[a] : Double mutation

*FIG. 43*

| Amount of Normal Template (fm) | 10W | 10M | 50W | 50M | 100W | 100M |
|---|---|---|---|---|---|---|
| 500 | 5 | 10.6 | 10.9 | 10.7 | 18.2 | 23.4 |
| 1000 | 6.1 | 12.9 | 16.9 | 22.9 | 25.6 | 33.9 |
| 2000 | 8.9 | 13.8 | 25.8 | 28.4 | 39.1 | 50.3 |

HIGH FIDELITY DETECTION OF NUCLEIC ACID DIFFERENCES BY LIGASE DETECTION REACTION

This application claims the benefit of U.S. Provisional Patent Application Ser. No. 60/022,535, filed Jul. 19, 1996.

This invention was developed with government funding under National Institutes of Health Grant No. GM41337-06. The U.S. Government may retain certain rights.

FIELD OF THE INVENTION

The present invention relates to the high fidelity detection of nucleic acid sequence differences using ligase detection reaction ("LDR"). One aspect of the present invention involves use of a ligase detection reaction to distinguish minority template in the presence of an excess of normal template with a thermostable ligase. Another aspect of the present invention relates to the use of a mutant ligase to carry out a ligase detection reaction. A third aspect of the present invention involves use of a modified oligonucleotide probe to carry out a ligase detection reaction.

BACKGROUND OF THE INVENTION

Multiplex Detection

Large-scale multiplex analysis of highly polymorphic loci is needed for practical identification of individuals, e.g., for paternity testing and in forensic science (Reynolds et al., *Anal. Chem.*, 63:2–15 (1991)), for organ-transplant donor-recipient matching (Buyse et al., *Tissue Antigens*, 41:1–14 (1993) and Gyllensten et al., *PCR Meth. Appl*, 1:91–98 (1991)), for genetic disease diagnosis, prognosis, and pre-natal counseling (Chamberlain et al., *Nucleic Acids Res.*, 16:11141–11156 (1988) and L. C. Tsui, *Human Mutat.*, 1:197–203 (1992)), and the study of oncogenic mutations (Hollstein et al., *Science*, 253:49–53 (1991)). In addition, the cost-effectiveness of infectious disease diagnosis by nucleic acid analysis varies directly with the multiplex scale in panel testing. Many of these applications depend on the discrimination of single-base differences at a multiplicity of sometimes closely spaced loci.

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter moiety.

Another widely used method is Southern blotting. In this method, a mixture of DNA fragments in a sample is fractionated by gel electrophoresis, then fixed on a nitrocellulose filter. By reacting the filter with one or more labeled probes under hybridization conditions, the presence of bands containing the probe sequences can be identified. The method is especially useful for identifying fragments in a restriction-enzyme DNA digest which contains a given probe sequence and for analyzing restriction-fragment length polymorphisms ("RFLPs").

Another approach to detecting the presence of a given sequence or sequences in a polynucleotide sample involves selective amplification of the sequence(s) by polymerase chain reaction. U.S. Pat. No. 4,683,202 to Mullis, et al. and R. K. Saiki, et al., *Science* 230:1350 (1985). In this method, primers complementary to opposite end portions of the selected sequence(s) are used to promote, in conjunction with thermal cycling, successive rounds of primer-initiated replication. The amplified sequence(s) may be readily identified by a variety of techniques. This approach is particularly useful for detecting the presence of low-copy sequences in a polynucleotide-containing sample, e.g., for detecting pathogen sequences in a body-fluid sample.

More recently, methods of identifying known target sequences by probe ligation methods have been reported. U.S. Pat. No. 4,883,750 to N. M. Whiteley, et al., D. Y. Wu, et al., *Genomics* 4:560 (1989), U. Landegren, et al., *Science* 241:1077 (1988), and E. Winn-Deen, et al., *Clin. Chem.* 37:1522 (1991). In one approach, known as oligonucleotide ligation assay ("OLA"), two probes or probe elements which span a target region of interest are hybridized to the target region. Where the probe elements basepair with adjacent target bases, the confronting ends of the probe elements can be joined by ligation, e.g., by treatment with ligase. The ligated probe element is then assayed, indicating the presence of the target sequence.

In a modification of this approach, the ligated probe elements act as a template for a pair of complementary probe elements. With continued cycles of denaturation, hybridization, and ligation in the presence of pairs of probe elements, the target sequence is amplified linearly, allowing very small amounts of target sequence to be detected and/or amplified. This approach is referred to as ligase detection reaction. When two complementary pairs of probe elements are utilized, the process is referred to as the ligase chain reaction which achieves exponential amplification of target sequences. F. Barany, "Genetic Disease Detection and DNA Amplification Using Cloned Thermostable Ligase," *Proc. Nat'l Acad. Sci. USA*, 88:189–93 (1991) and F. Barany, "The Ligase Chain Reaction (LCR) in a PCR World," *PCR Methods and Applications*, 1:5–16 (1991).

Another scheme for multiplex detection of nucleic acid sequence differences is disclosed in U.S. Pat. No. 5,470,705 to Grossman et. al. where sequence-specific probes, having a detectable label and a distinctive ratio of charge/translational frictional drag, can be hybridized to a target and ligated together. This technique was used in Grossman, et. al., "High-density Multiplex Detection of Nucleic Acid Sequences: Oligonucleotide Ligation Assay and Sequence-coded Separation," *Nucl. Acids Res.* 22(21): 4527–34 (1994) for the large scale multiplex analysis of the cystic fibrosis transmembrane regulator gene.

Jou, et. al., "Deletion Detection in Dystrophia Gene by Multiplex Gap Ligase Chain Reaction and Immunochromatographic Strip Technology," *Human Mutation* 5:86–93 (1995) relates to the use of a so called "gap ligase chain reaction" process to amplify simultaneously selected regions of multiple exons with the amplified products being read on an immunochromatographic strip having antibodies specific to the different haptens on the probes for each exon.

There is a growing need (e.g., in the field of genetic screening) for methods useful in detecting the presence or absence of each of a large number of sequences in a target polynucleotide. For example, as many as 400 different mutations have been associated with cystic fibrosis. In screening for genetic predisposition to this disease, it is optimal to test all of the possible different gene sequence mutations in the subject's genomic DNA, in order to make a positive identification of "cystic fibrosis". It would be ideal to test for the presence or absence of all of the possible mutation sites in a single assay. However, the prior-art methods described above are not readily adaptable for use in detecting multiple selected sequences in a convenient, automated single-assay format.

Solid-phase hybridization assays require multiple liquid-handling steps, and some incubation and wash temperatures must be carefully controlled to keep the stringency needed for single-nucleotide mismatch discrimination. Multiplexing of this approach has proven difficult as optimal hybridization conditions vary greatly among probe sequences.

Developing a multiplex PCR process that yields equivalent amounts of each PCR product can be difficult and laborious. This is due to variations in the annealing rates of the primers in the reaction as well as varying polymerase extension rates for each sequence at a given $Mg^{2+}$ concentration. Typically, primer, $Mg^{2+}$, and salt concentrations, along with annealing temperatures are adjusted in an effort to balance primer annealing rates and polymerase extension rates in the reaction. Unfortunately, as each new primer set is added to the reaction, the number of potential amplicons and primer dimers which could form increases exponentially. Thus, with each added primer set, it becomes increasingly more difficult and time consuming to work out conditions that yield relatively equal amounts of each of the correct products.

Allele-specific PCR products generally have the same size, and an assay result is scored by the presence or absence of the product band(s) in the gel lane associated with each reaction tube. Gibbs et al., *Nucleic Acids Res.*, 17:2437–48 (1989). This approach requires splitting the test sample among multiple reaction tubes with different primer combinations, multiplying assay cost. In PCR, discrimination of alleles can be achieved by attaching different fluorescent dyes to competing allelic primers in a single reaction tube (F. F. Chehab, et al., *Proc. Natl. Acad. Sci. USA*, 86:9178–9182 (1989)), but this route to multiplex analysis is limited in scale by the relatively few dyes which can be spectrally resolved in an economical manner with existing instrumentation and dye chemistry. The incorporation of bases modified with bulky side chains can be used to differentiate allelic PCR products by their electrophoretic mobility, but this method is limited by the successful incorporation of these modified bases by polymerase, and by the ability of electrophoresis to resolve relatively large PCR products which differ in size by only one of these groups. Livak et al., *Nucleic Acids Res.*, 20:4831–4837 (1989). Each PCR product is used to look for only a single mutation, making multiplexing difficult.

Ligation of allele-specific probes generally has used solid-phase capture (U. Landegren et al., *Science*, 241:1077–1080 (1988); Nickerson et al., *Proc. Natl. Acad. Sci. USA*, 87:8923–8927 (1990)) or size-dependent separation (D. Y. Wu, et al., *Genomics*, 4:560–569 (1989) and F. Barany, *Proc. Natl. Acad. Sci.*, 88:189–193 (1991)) to resolve the allelic signals, the latter method being limited in multiplex scale by the narrow size range of ligation probes. Further, in a multiplex format, the ligase detection reaction alone cannot make enough product to detect and quantify small amounts of target sequences. The gap ligase chain reaction process requires an additional step—polymerase extension. The use of probes with distinctive ratios of charge/translational frictional drag for a more complex multiplex process will either require longer electrophoresis times or the use of an alternate form of detection.

The need thus remains for a rapid single assay format to detect the presence or absence of multiple selected sequences in a polynucleotide sample when those sequences are in low abundance. Such detection is required when cancer-associated mutations are present in an excess of normal cells.

DNA Ligase

DNA ligases catalyze the formation of phosphodiester bonds at single-stranded breaks (nicks) in double-stranded DNA, and are required in DNA replication, repair, and recombination. The general mechanism of ligation reactions involves three reversible steps, as shown below for $NAD^+$-dependent ligases. In this example, the nicked DNA substrate is formed by annealing two short oligonucleotides (oligo A and B) to a longer complementary oligonucleotide. First, a covalently adenylated enzyme intermediate is formed by transfer of the adenylate group of $NAD^+$ to the e-NH2 group of lysine in the enzyme. Second, the adenylate moiety is transferred from the enzyme to the 5'-terminal phosphate on oligo B. Finally, a phosphodiester bond is formed by a nucleophilic attack of the 3'-hydroxyl terminus of oligo A on the activated 5'-phosphoryl group of oligo B (Gumport, R. I., et al., *Proc. Natl. Acad. Sci. USA*, 68:2559–63 (1971); Modrich, P., et al., *J. Biol. Chem.*, 248:7495–7501 (1973); Modrich, P., et al., *J. Biol. Chem.*, 248:7502–11 (1973); Weiss, B., et al., *J. Biol. Chem.*, 242:4270–72 (1967); Weiss, B., et al., *J. Biol. Chem.*, 243:4556–63 (1968); Becker, A., et al., *Proc. Natl. Acad. Sci. USA*, 58:1996–2003 (1967); Yudelevich, A., et al., *Proc. Natl. Acad. Sci. USA*, 61:1129–36 (1968); Zimmerman, S. B., et al., *Proc. Natl. Acad. Sci. USA*, 57:1841–48 (1967); Zimmerman, S. B., et al., *J. Biol. Chem.*, 244:4689–95 (1969); and Lehman, I. R., *Science*, 186:790–97 (1974)).

(i) E-(lys)-$NH_2$+AMP~$PRN^+$↔E-(lys)-$NH_2^+$~AMP+NMN (ii) E-(lys)-$NH_2^+$~AMP+5'P-Oligo B↔AMP~P-Oligo B+E-(lys)-$NH_2$ (iii) Oligo A-3'OH+AMP~P-Oligo B↔Oligo A-P-Oligo B+AMP Within the last decade, genes encoding ATP-dependent DNA ligases have been cloned and sequenced from bacteriophages T3, T4, and T7 (Dunn, J. J., et al., *J. Mol. Biol.*, 148:303–30 (1981); Armstrong, J., et al., *Nucleic Acids Res.*, 11:7145–56 (1983); and Schmitt, M. P., et al., *J. Mol. Biol.*, 193:479–95 (1987)), African swine fever virus (Hammond, J. M., et al., *Nucleic Acids Res.*, 20:2667–71 (1992)), Vaccinia virus (Smith, G. L., et al., *Nucleic Acids Res.*, 17:9051–62 (1989)), Shope fibroma virus (Parks, R. J., et al., *Virology*, 202:642–50 (1994)), an extremely thermophilic archaeon *Desulfurolobus ambivalens* (Kletzin, A., *Nucleic Acids Res.*, 20:5389–96 (1992)), *S. cerevisiae* (CDC9 gene) (Barker, D. G., et al., *Mol. Gen. Genet.*, 200:458–62 (1985)); *S. pombe* (cdcl7+) (Barker, D. G., et al., *Eur. J. Biochem.*, 162:659–67 (1988)), Xiphophorus (Walter, R. B., et al., *Mol. Biol. Evol.*, 10:1227–38 (1993)); mouse fibroblast (Savini, E., et al., *Gene*, 144:253–57 (1994)); and *Homo sapiens* (human DNA ligase I, III, and IV) (Barnes, D. E., et al., *Proc. Natl. Acad. Sci. USA*, 87:6679–83 (1990); Chen, J., et al., *Molec. and Cell. Biology*, 15:5412–22 (1995); and Wei, Y. F., et al., *Molec. & Cell. Biology*, 15:3206–16 (1995)). In addition, five $NAD^+$-dependent bacterial DNA ligases have also been cloned: *E. coli* (Ishino, Y., et al., *Mol. Gen. Genet.*, 204:1–7 (1986)), *Zymomonas mobilis* (Shark, K. B., et al., *FEMS Microbiol. Lett.*, 96:19–26 (1992)), *Thermus thermophilus* (Barany, F., et al., *Gene*, 109:1–11 (1991) and Lauer, G., et al., *J. Bacteriol.*, 173:5047–53 (1991)), *Rhodothermus marinus* (Thorbjarnardottir, S. H., et al., *Gene*, 161:1–6 (1995)), and *Thermus scotoductus* (Jonsson, Z. O., et al., *Gene*, 151:177–80 (1994)). ATP-dependent DNA ligases, as well as mammalian DNA ligases I and II contain a conserved active site motif, K(Y/A) DGXR, which includes the lysine residue that becomes adenylated (Tomkinson, A. E., et al, *Proc. Natl. Acad. Sci. USA*, 88:400–04 (1991) and Wang, Y.

C., et al., *J. Biol. Chem.*, 269:31923–28 (1994)). NAD⁺-dependent bacterial DNA ligases contain a similar active site motif, KXDG, whose importance is confirmed in this work.

In vitro experiments using plasmid or synthetic oligonucleotide substrates reveal that T4 DNA ligase exhibits a relaxed specificity; sealing nicks with 3'- or 5'-AP sites (apurinic or apyrimidinic) (Goffin, C., et al., *Nucleic Acids Res.*, 15(21): 8755–71 (1987)), one-nucleotide gaps (Goffin, C., et al., *Nucleic Acids Res.*, 15(21): 8755–71 (1987)), 3'- and 5'-A-A or T-T mismatches (Wu, D. Y., et al., *Gene*, 76:245–54 (1989)), 5'-G-T mismatches (Harada, K., et al., *Nucleic Acids Res.*, 21(10): 2287–91 (1993)), 3'-C-A, C-T, T-G, T-T, T-C, A-C, G-G, or G-T mismatches (Landegren, U., et al., *Science*, 241:1077–80 (1988)). The apparent fidelity of T4 DNA ligase may be improved in the presence of spermidine, high salt, and very low ligase concentration, where only T-G or G-T mismatch ligations were detected (Wu, D. Y., et al., *Gene*, 76:245–54 (1989) and Landegren, U., et al., *Science*, 241:1077–80 (1988)). DNA ligase from *Saccharomyces cerevisiae* discriminates 3'-hydroxyl and 5'-phosphate termini separated by a one-nucleotide gap and 3'-A-G or T-G mismatches, however 5'-A-C, T-C, C-A, or G-A mismatches had very little effect on ligation efficiency (Tomkinson, A. E., et al., *Biochemistry*, 31:11762–71 (1992)). Mammalian DNA ligases I and III show different efficiencies in ligating 3° C.-T, G-T, and T-G mismatches (Husain, I., et al., *J. Biol. Chem.*, 270:9638–90 (1995)). The Vaccinia DNA virus efficiently discriminates against one-nucleotide, two-nucleotide gaps and 3'-G-A, A-A, G-G, or A-G (purine-purine) mismatches, but easily seals 5'-C-T, G-T, T-T, A-C, T-C, C-C, G-G, T-G, or A-G mismatches as well as 3'-C-A, C-T, G-T, T-T, or T-G mismatches (Shuman, S., *Biochem.*, 34:16138–47 (1995)).

The thermostable *Thermus thermophilus* DNA ligase (Tth DNA ligase) has been cloned and used in the ligase chain reaction (LCR) and ligase detection reaction (LDR) for detecting infectious agents and genetic diseases (Barany, F., *Proc. Natl. Acad. Sci. USA*, 88:189–93 (1991); Day, D., et al., *Genomics*, 29:152–62 (1995); Eggerding, F. A., *PCR Methods and Applications*, 4:337–45 (1995); Eggerding, F. A., et al., *Human Mutation*, 5:153–65 (1995); Feero, W., et al., *Neurology*, 43:668–73 (1993); Frenkel, L. M., et al., *J. Clin. Micro.*, 33(2): 342–47 (1995); Grossman, P. D., et al., *Nucleic Acids Res.*, 22:4527–34 (1994); Iovannisci, D. M., et al., *Mol. Cell. Probes*, 7:35–43 (1993); Prchal, J. T., et al., *Blood*, 81:269–71 (1993); Ruiz-Opaz, N., et al., *Hypertension*, 24:260–70 (1994); Wiedmann, M., et al., *Appl. Environ. Microbiol.*, 58:3443–47 (1992); Wiedmann, M., et al., *Appl Environ Microbiol*, 59(8): 2743–5 (1993); Winn-Deen, E., et al., *Amer. J. Human Genetics*, 53:1512 (1993); Winn-Deen, E. S., et al., *Clin. Chem.*, 40:1092 (1994); and Zebala, J., et al., "Detection of Leber's Hereditary Optic Neuropathy by nonradioactive-LCR. PCR Strategies," (Innis, M. A., Gelfand, D. H., and Sninsky, J. J., Eds.), Academic Press, San Diego (1996)). The success of these and future disease detection assays, such as identifying tumor associated mutations in an excess of normal DNA, depend on the exquisite fidelity of Tth DNA ligase.

Cancer Detection

As the second leading cause of death in this country, almost 600,000 people will die from cancer per year making cancer one of the most alarming of all medical diagnosis. Lifetime risks for developing invasive cancers in men and women are 50 percent and 33 percent, respectively. Expectations are that more than 1.2 million new cases of cancer will be diagnosed in the United States in 1995. Healthcare expenses for cancer in 1994 were approximately $104 billion. However, the full impact of cancer on families and society is not measured only by the amount of money spent on its diagnosis and treatment. A significant number of people are stricken with cancer in their most productive years. Cancers accounted for 18 percent of premature deaths in 1985 and in 1991 more than 9,200 women in the U.S. died from breast cancer before the age of 55. For colorectal and breast cancers, estimates are that nearly 140,000 and 183,000 new diagnoses, respectively, are predicted for 1995.

Currently, diagnosis of cancer is based on histological evaluation of tumor tissue by a pathologist. After a cancer is diagnosed, treatment is determined primarily by the extent or stage of the tumor. Tumor stage is defined by clinical, radiological, and laboratory methods. Standardized classification systems for the staging of tumors have been developed to clearly convey clinical information about cancer patients. Staging provides important prognostic information and forms the basis of clinical studies which allow the testing of new treatment strategies. A staging system was developed (TNM staging system), which classifies tumors according to the size of the primary tumor, the number of regional lymph nodes in which cancer is found, and the presence or absence of metastases to other parts of the body. Smaller cancers with no affected lymph nodes and no distant metastases are considered early stage cancers, which are often amenable to cure through surgical resection. A common measure of prognosis is the 5-year survival rate, the proportion of patients alive five years after the diagnosis of a cancer at a given stage. While 5-year survival rates for many cancers have improved over the last few decades, the fact that some early stage cancers recur within five years or later has led researchers to explore other additional prognostic markers including histological grade, cytometry results, hormone receptor status, and many other tumor markers. Most recently, investigators have explored the use of molecular alterations in cancers as markers of prognosis.

Genetic alterations found in cancers, such as point mutations and small deletions mentioned above, can act as markers of malignant cells.

Detection of Minority Nucleic Acid Sequences

A number of procedures have been disclosed to detect cancer using PCR. Sidransky, et. al., "Identification of ras Oncogene Mutations in the Stool of Patients with Curable Colorectal Tumors," *Science* 256: 102–05 (1992) detects colon cancer by identification of K-ras mutations. This involves a PCR amplification of total DNA, cloning into a phage vector, plating out the phage, repeated probing with individual oligonucleotides specific to several different K-ras mutations, and counting the percentage of positive plaques on a given plate. This is a technically difficult procedure which takes three days to complete, whereby the ratio of mutant to wild-type DNA in the stool sample is determined. Brennan, et. al., "Molecular Assessment of Histopathological Staging in Squamous-Cell Carcinoma of the Head and Neck," *N. Engl. J. Med.* 332(7): 429–35 (1995) finds p53 mutations by sequencing. This specific mutation is then probed for in margin tissue using PCR amplification of total DNA, cloning into a phage vector, plating out the phage, probing with an individual oligonucleotide specific to the mutation found by sequencing, and counting the percentage of positive plaques on a given plate. Berthelemy, et. al., "Brief Communications—Identification of K-ras Mutations in Pancreatic Juice in the Early Diagnosis of Pancreatic Cancer," *Ann. Int. Med.* 123(3): 188–91 (1995) uses a PCR/restriction enzyme process to detect K-ras mutations in pancreatic secretions. This technique is deficient, however, in that mutations are not quantified. Similarly, Tada, et. al., "Detection of ras Gene Mutations in Pancreatic Juice and Peripheral Blood of Patients with Pancreatic Adenocarcinoma," *Cancer Res.* 53: 2472–74 (1993) and Tada, et. al., "Clinical Application of ras Gene Mutation for Diagnosis of Pancreatic Adenocarcinoma," *Gastroent.* 100: 233–38 (1991) subject such samples to allele-specific PCR to detect pancreatic cancer. This has the disadvantages of providing false positives due to polymerase extension off normal template, requiring electrophoretical separation of products to distinguish from primer dimers, being unable to multiplex closely-clustered sites due to interference of overlapping primers, being unable to detect single base or small insertions and deletions in small repeat sequences, and not being ideally suitable for quantification of mutant DNA in a high background of normal DNA. Hayashi, et. al., "Genetic Detection Identifies Occult Lymph Node Metastases Undetectable by the Histopathological Method," *Cancer Res.* 54: 3853–56 (1994) uses an allele-specific PCR technique to find K-ras or p53 mutations to identify occult lymph node metastases in colon cancers. A sensitivity of one tumor cell in one thousand of normal cells is claimed; however, obtaining quantitative values requires laborious cloning, plating, and probing procedures. In Mitsudomi, et. al., "Mutations of ras Genes Distinguish a Subset of Non-small-cell Lung Cancer Cell Lines from Small-cell Lung Cancer Cell Lines," *Oncogene* 6: 1353–62 (1991), human lung cancer cell lines are screened for point mutations of the K-, H-, and N-ras genes using restriction fragment length polymorphisms created through mismatched primers during PCR amplification of genomic DNA. The disadvantages of such primer-mediated RFLP include the requirement of electrophoretical separation to distinguish mutant from normal DNA, limited applicability to sites that may be converted into a restriction site, the requirement for additional analysis to determine the nature of the mutation, and the difficulty in quantifying mutant DNA in a high background of normal DNA. Further, these procedures tend to be laborious and inaccurate.

Coupled PCR/ligation processes have been used for detection of minority nucleotide sequences in the presence of majority nucleotide sequences. A PCR/LDR process is used in Frenkel, "Specific, Sensitive, and Rapid Assay for Human Immunodeficiency Virus Type 1 pol Mutations Associated with Resistance to Zidovudine and Didanosine," *J. Clin. Microbiol.* 33(2): 342–47 (1995) to detect HIV mutants. This assay, however, cannot be used for multiplex detection. See also Abravaya, et. al., "Detection of Point Mutations With a Modified Ligase Chain (Gap-LCR)," *Nucl. Acids Res.* 23(4): 675–82 (1995) and Balles, et. al., "Facilitated Isolation of Rare Recombinants by Ligase Chain Reaction: Selection for Intragenic Crossover Events in the Drosophila optomotor-blind Gene," *Molec. Gen. Genet.* 245: 734–40 (1994).

Colorectal lesions have been detected by a process involving PCR amplification followed by an oligonucleotide ligation assay. See Jen, et. al., "Molecular Determinants of Dysplasia in Colorectal Lesions," *Cancer Res.* 54: 5523–26 (1994) and Redston, et. al., "Common Occurrence of APC and K-ras Gene Mutations in the Spectrum of Colitis-Associated Neoplasias," *Gastroenter.* 108: 383–92 (1995). This process was developed as an advance over Powell, et. al., "Molecular Diagnosis of Familial Adenomatous Polyposis," *N. Engl. J. Med.* 329(27): 1982–87 (1993). These techniques tend to be limited and difficult to carry out.

Other procedures have been developed to detect minority nucleotide sequences. Lu, et. al., "Quanititative Aspects of the Mutant Analysis by PCR and Restriction Enzyme Cleavage (MAPREC)" *PCR Methods and Appl.* 3: 176–80 (1993) detects virus revertants by PCR and restriction enzyme cleavage. The disadvantages of MAPREC include the requirement for electrophoretical separation to distinguish mutant from normal DNA, limited applicability to sites that may be converted into a restriction site, the requirement for additional analysis to determine the nature of the mutation, and difficulty in quantifying mutant DNA in a high background of normal DNA. In Kuppuswamy, et. al., "Single Nucleotide Primer Extension to Detect Genetic Diseases: Experimental Application to Hemophilia G (Factor IX) and Cystic Fibrosis Genes," *Proc. Natl. Acad. Sci. USA* 88: 1143–47 (1991), a PCR process is carried out using 2 reaction mixtures for each fragment to be amplified with one mixture containing a primer and a labeled nucleotide corresponding to the normal coding sequence, while the other mixture contains a primer and a labeled nucleotide corresponding to the mutant sequence. The disadvantages of such mini sequencing (i.e. SNuPe) are that the mutations must be known, it is not possible to multiplex closely clustered sites due to interference of overlapping primers, it is not possible to detect single base or small insertions and deletions in small repeat sequences, and four separate reactions are required. A mutagenically separated PCR process is disclosed in Rust, et. al., "Mutagenically Separated PCR (MS-PCR): a Highly Specific One Step Procedure for easy Mutation Detection" *Nucl. Acids Res.* 21(16): 3623–29 (1993) to distinguish normal and mutant alleles, using different length allele-specific primers. The disadvantages of MS-PCR include possibly providing false positives due to polymerase extension off normal template, requiring electrophoretical separation of products to distinguish from primer dimers, the inability to multiplex closely-clustered sites due to interference of overlapping primers, the inability to detect single base or small insertions and deletions in small repeat sequences, and not being ideally suited for quantification of mutant DNA in high background of normal DNA. In Suzuki, et. al., "Detection of ras Gene Mutations in Human Lung Cancers by Single-Strand Conformation Polymorphism Analysis of Polymerase Chain Reaction Products," *Oncogene* 5: 1037–43 (1990), mutations are detected in a process having a PCR phase followed by phase involving single strand conformation polymorphism ("SSCP") of the amplified DNA fragments. The disadvantages of SSCP include the requirement for electrophoretical separation to distinghish mutant conformer from normal conformer, the failure to detect 30% of possible mutations, the requirement for additional analysis to determine the nature of the mutation, and the inability to distinguish mutant from silent polymorphisms.

Despite the existence of techniques for detecting minority nucleotide sequences in the presence of majority sequences, the need remains for improved procedures of doing so. It is particularly desirable to develop such techniques where minority nucleotide sequences can be quantified.

SUMMARY OF THE INVENTION

One aspect of the present invention relates to a method for detecting in a sample one or more minority target nucleotide sequences which differ from one or more majority target nucleotide sequences by one or more single-base changes, insertions, deletions, or translocations, wherein the minority target nucleotide sequences are present in the sample in lesser amounts than the majority nucleotide sequences.

One or more oligonucleotide probe sets are provided for use in conjunction with this method. Each set includes (a) a first oligonucleotide probe having a target-specific portion and (b) a second oligonucleotide probe having a target-specific portion. The oligonucleotide probes in a particular set are suitable for ligation together when hybridized adjacent to one another on a corresponding target nucleotide sequence, but have a mismatch which interferes with such ligation when hybridized to any other nucleotide sequence present in the sample.

The sample, the one or more oligonucleotide probe sets, and a ligase are blended to form a ligase detection reaction mixture. The ligase detection reaction mixture is subjected to one or more ligase detection reaction cycles comprising a denaturation treatment and a hybridization treatment. In the denaturation treatment, any hybridized oligonucleotides are separated from the target nucleotide sequences. The hybridization treatment involves hybridizing the oligonucleotide probe sets at adjacent positions in a base-specific manner to the respective target nucleotide sequences, if present in the sample. The hybridized oligonucleotide probes from each set ligate to one another to form a ligation product sequence containing the target-specific portions connected together. The ligation product sequence for each set is distinguishable from other nucleic acids in the ligase detection reaction mixture. The oligonucleotide probe sets may hybridize to adjacent sequences in the sample other than the respective target nucleotide sequences but do not ligate together due to the presence of one or more mismatches. When hybridized oligonucleotide probes do not ligate, they individually separate during the denaturation treatment.

After the ligase detection reaction mixture is subjected to one or more ligase detection reaction cycles, ligation product sequences are detected. As a result, the presence of the minority target nucleotide sequence in the sample can be identified.

The second aspect of the present invention also relates to a method for identifying one or more of a plurality of sequences differing by one or more single-base changes, insertions, deletions, or translocations in a plurality of target nucleotide sequences. As noted above, a sample and one or more oligonucleotide probe sets are blended with a ligase to form a ligase detection reaction mixture. The ligase detection reaction mixture is subjected to one or more ligase detection reaction cycles, and the presence of ligation product sequences is detected. Here, however, a thermostable mutant ligase is utilized. This ligase is characterized by a fidelity ratio which is defined as the initial rate constant for ligating the first and second oligonucleotide probes hybridized to a target nucleotide sequence with a perfect match at the ligation junction between the target nucleotide sequence and the oligonucleotide probe having its 3' end at the ligation junction to the initial rate constant for ligating the first and second oligonucleotide probes hybridized to a target with a mismatch at the ligation junction between the target nucleotide sequence and the oligonucleotide probe having its 3' end at the ligation junction. The fidelity ratio for the thermostable mutant ligase is greater than the fidelity ratio for wild-type ligase.

The third aspect of the present invention also relates to a method for identifying one or more of a plurality of sequences differing by one or more single-base changes, insertions, deletions, or translocations in a plurality of target nucleotide sequences. As noted above, a sample and one or more oligonucleotide probe sets are blended with a ligase to form a ligase detection reaction mixture. The ligase detection reaction mixture is subjected to one or more ligase detection reaction cycles, and the presence of ligation product sequences is then detected. Here, however, with regard to the oligonucleotide probe sets, the oligonucleotide probe which has its 3' end at the junction where ligation occurs has a modification. This modification differentially alters the ligation rate when the first and second oligonucleotide probes hybridize to a minority target nucleotide sequence in the sample with a perfect match at the ligation junction between the minority target nucleotide sequence and the oligonucleotide probe having its 3' end at the ligation junction compared to the ligation rate when the first and second oligonucleotide probes hybridize to the sample's majority target nucleotide sequence with a mismatch at the ligation junction between the majority target nucleotide sequence and the nucleotide probe having its 3' end at the ligation junction. Ligation with the modified oligonucleotide probe has a signal-to-noise ratio, of the ligation product sequence amounts for the minority and majority target nucleotide sequences to the amount of ligation product sequences produced from the same amount of majority target sequence alone, which is greater than the signal-to-noise ratio for ligation using an oligonucleotide probe lacking the modification.

In developing a procedure for detection of cancer-associated mutations or the presence of a minority target nucleotide sequence, it is necessary for the procedure to be capable of diagnosing cancer at an early stage. This requires that at least one clonal mutation be identified and accurately quantified from clinical samples. An ideal test of this type would rapidly screen up to hundreds of common mutations in multiple genes. It must accurately quantify less than 1% mutant DNA in the presence of normal DNA and correctly distinguish many closely clustered mutations in a multiplex format. For point mutations generally and, in small repeat sequences particularly, small insertions and deletions must be accurately identified. There must be internal controls against false-positive results and amenability to high throughput automation. The LDR process of the present invention is able to meet all of these objectives.

BRIEF DESCRIPTION OF THE DRAWINGS

The file of this patent contains at least one drawing executed in color. Copies of this patent with color drawings will be provided by the Office upon request and payment of the necessary fee.

FIG. 5 is a schematic diagram depicting the PCRILDR process of FIG. 2 using electrophoresis to separate ligation products.

FIG. 7 is a schematic diagram depicting the PCR/LDR process of FIG. 1 using an addressable array.

FIG. 9 is a schematic diagram depicting the PCR/LDR process of FIG. 3 using an addressable array.

FIGS. 12A–B show the primers for making the mutant ligases of FIG. 11. These primers bear the following sequence numbers: Primer a is identified as SEQ. ID. No. 1 (JL501) and SEQ. ID. No. 78 (JL505); Primer b is identified as SEQ. ID. No. 2 (JL503R), SEQ. ID. No. 79 (JL507R), SEQ. ID. No. 80 (JL537R), SEQ. ID. No. 81 (JL535R), SEQ. ID. No. 82 (JL525R), SEQ. ID. No. 83 (JL527R), SEQ. ID. No. 84 (JL529R), SEQ. ID. No. 85 (JL531R), and SEQ. ID. No. 86 (JL533R); Primer c is identified as SEQ. ID. No. 3 (JL502), SEQ. ID. No. 87 (JL509), SEQ. ID. No. 88 (JL506), SEQ. ID. No. 89 (JL136), SEQ. ID. No. 90 (JL534), SEQ. ID. No. 91 (JL524), SEQ. ID. No. 92 (JL526), SEQ. ID. No. 93 (JL528), SEQ. ID. No. 94 (JL530), and SEQ. ID. No. 95 (JL532); Primer d is identified as SEQ. ID. No. 4 (JL504R), SEQ. ID. No. 96 (JL508R), and SEQ. ID. No. 97 (JL5181); Primer b1 is identified as SEQ. ID. No. 5; Primer c1 is identified as SEQ. ID. No. 6; Ptimer b2 is identified as SEQ. ID. No. 8; and Primer c2 is identified as SEQ. ID. No. 7.

FIG. 13 show a schematic representation of oligonucleotides used for ligation assays. Probe sequences were derived from human eukaryotic protein synthesis initiation factor eIF-4E (Rychlik, W., et al., *Proc. Natl. Acad. Sci. USA*, 84:945–49 (1987), which is hereby incorporated by reference). This random eukaryotic DNA sequence was chosen to avoid any false signal arising from bacterial DNA contamination in partially purified mutant Tth DNA ligase preparations. The melting temperature of probes were predicted using the nearest neighbor thermodynamic method (Breslauer, K. J., et al., *Proc. Natl. Acad. Sci. USA*, 83:3746–3750 (1986), which is hereby incorporated by reference) (OLIGO 4.0 program, National Biosciences Inc., Plymouth, Minn.). FIG. 13A and FIG. 13B represent the formation of nicked DNA duplex using one of the template strands, ALg, as an example. Shown in FIG. 13A, 4 different nicked DNA substrates are formed by annealing the the common fluorescently labeled oligonucleotide, com5F (SEQ ID NO: 9), and one of the discriminating oligos (RP5'A (SEQ. ID. No.10), RP5° C. (SEQ. ID. No. 1), ItP5'G (SEQ. ID. No. 12), RP5'T (SEQ. ID. No. 13) to the template strand, ALg (SEQ. ID. No. 14) In the FIG. 13B, 4 different nicked DNA substrates are formed by annealing the fluorescently labeled oligonucleotide, com3F (SEQ. ID. No. 15), and one of the discriminating oligos (LP3'A (SEQ. ID. No. 16), LP3° C. (SEQ, ID. No. 17), LP3'G (SEQ. ID. No. 18), LP3'T (SEQ. ID. No. 19)) to the temr late strand ALg (SEQ. ID. No. 14). The full set of all 16 combinations of match and mismatch base pairing are thus formed by using ALg (SEQ. ID. No. 14), GLg (SEQ. ID. No. 20), TLg (SEQ. ID. No. 21), and CLg (S EQ. ID. No. 22) (shown in FIG. 13C) as the template strand, which vary at the underlined base. Products formed by ligation to the common fluorescently labeled probe can be discriminated by size on denaturing polyacrylamide gel due to the incorporation of different length of "A" tails.

FIG. 14 shows the sequences for the probes used to make the oligonucleotides of FIG. 13.

FIGS. 15B–E represent results obtained with the same discriminating oligo, but with a different template strand. In panel 3'-A (FIG. 15B), the discriminating oligonucleotide was LP3'A. A-T (♦), A-C (Δ), A-A (▽), and A-G (○) represent DNA substrates containing TLg, CLg, ALg, and GLg as the template strand, respectively. In panel 3 '-G (FIG. 1 SD), the discriminating oligonucleotide was LP3'G. G-C (♦), G-T (Δ), G-A (▽), and G-G (○) represent DNA substrates with CLg, TLg, ALg, and GLg as the template strand, respectively. In panel 3'-C (FIG. 15C), LP3° C. was the discriminating oligonucleotide. C-G (♦), C-A (Δ), C-T (▽), and C-C (○) indicate DNA substrates containing GLg, ALg, TLg, and CLg as the template strand, respectively. In panel 3'-T (FIG. 15E), LP3'T was the discriminating oligonucleotide. T-A (♦), T-G (Δ), T-T (▽), and T-C (○) represent DNA substrates containing ALg, GLg, TLg, or CLg as the template strand, respectively.

FIG. 18 shows a table for improving the fidelity of *Thermus thermophilus* ligase. Sequences of probes LP3° C., LP3'T, and Com 3F are shown in FIG. 14. Sequences for other discriminating probes are as the follows:

SLP3'C (SEQ ID NO: 23): 5'TACGTCTGCGGTGT-TGCGTC 3'

SLP3'T (SEQ ID NO: 24): 5' CGTCTGCGGTGT-TGCGTT 3'

SLP3'ATC (SEQ ID NO: 25): 5' ATGCGTCTGCGGT-GTTGCATC 3'

SLP3'ATT (SEQ ID NO: 26): 5' GCGTCTGCGGTGT-TGCATT 3'

SLP3'QTC (SEQ ID NO: 27): 5' AAATGCGTCTGCG-GTGTTGCQTC 3'

SLP3'QTT (SEQ ID NO: 28): 5' ATGCGTCTGCGGT-GTTGCQTT 3'

Figure 17A:
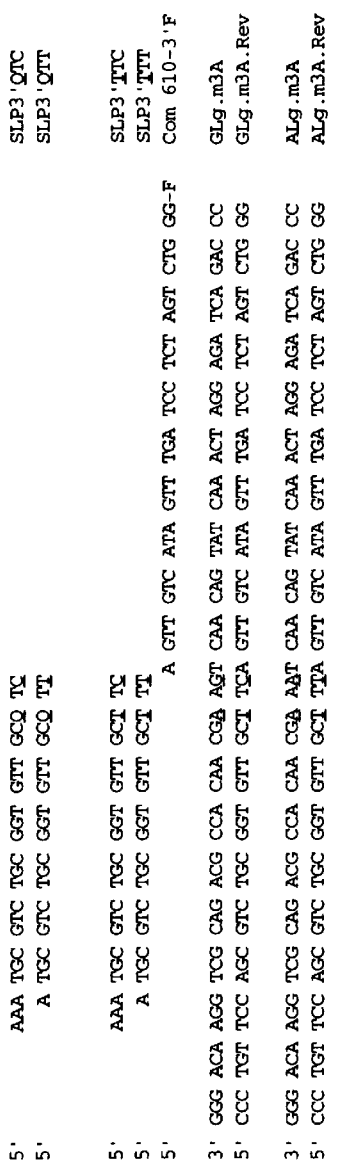
FIGS. 17A–C are diagrams of oligonucleotide probes containing a base analogue and mismatch in the third position on the 3' side of the nick.
Figure 17B:
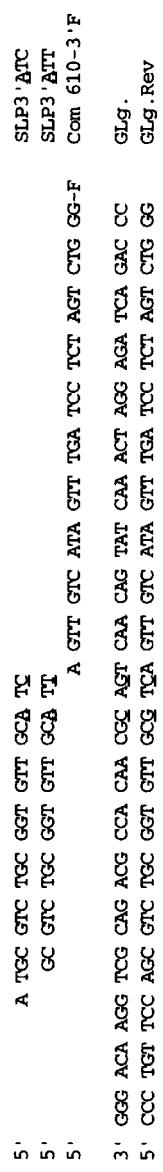

Base "N" in the discriminating oligonucleotide represents either C or T. "Q" indicates the Q base analogue. The template strand for all substrates tested except those containing Q base analogues is GLg, and its sequence is shown in FIG. 14. The template strand in substrates containing Q base analogues is GLg.m3A which differs from GLg at a single site shown as bold. Initial rates of ligation (fmol/min) were calculated as the slope of the linear graph with the X-axis as the time in min., and the y-axis as the amount of products in fmol. Ligation fidelity of Tth DNA ligase is defined as a ratio of the initial rate of perfect match ligation over the initial rate of mismatch ligation. FIG. 17 also shows the sequences for primers SLP3'TTC (SEQ. ID. No. 29), SLP3'TTT (SEQ. 1). No. 30), Corn 610-3'F (SEQ. ID. No. 31), GLg.m3A (SEQ. ID. No. 32), GLg.m3A.Rev (SEQ. ID. No. 33), ALg.m3A (SEQ. ID. No. 34), ALg.m3A.Rev (SEQ. ID. No. 35), GLg. (SEQ. ID. No. 36), GLg.Rev (SEQ. ID. No. 37), SLP3'GTC (SEQ. ID. No. 38), SLP3'GTT (EQ. ID. No. 39), GLg.m3T (SEQ. ID. No. 40), and GLg.m3T.Rev (SEQ. ID. No. 41).

Figure 19:
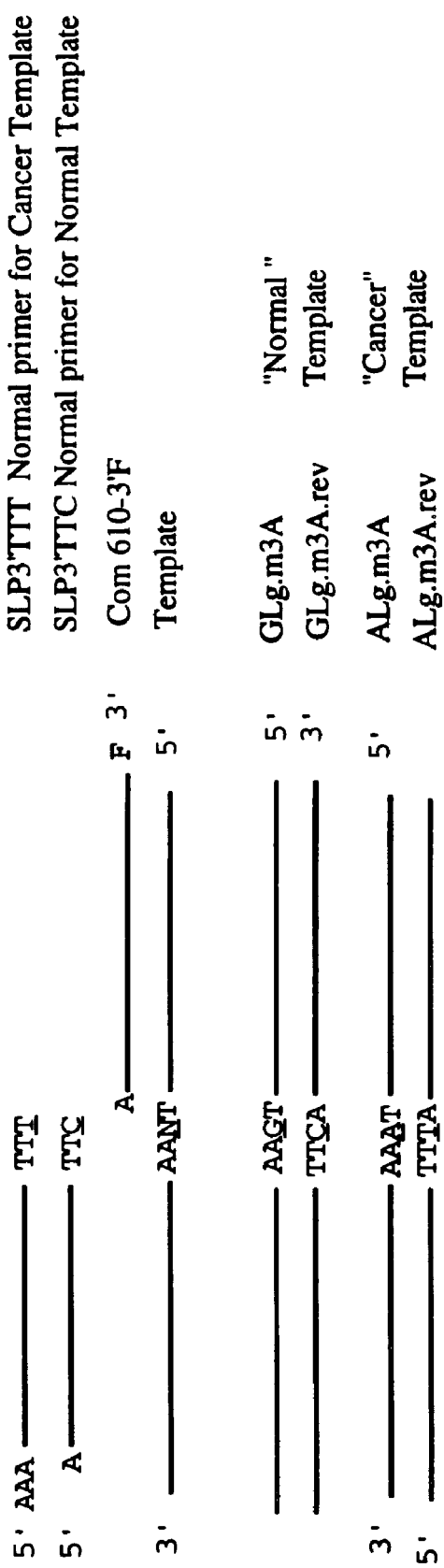

FIG. 19 shows the primers used for quantitative detection of single-base mutations in an excess of normal DNA by either wild-type or K294R Tth DNA ligase. LDR reactions contained 12.5 nM (250 fmole) of the mismatched template (GLg.m3A and GLg.m3A.rev=Normal template), containing from 0 to 2.5 nM (50 fmole) of perfect matched template (ALg.m3A and ALg.m3A.rev=Cancer template) in the presence of 25 fmol of either purified wild-type or mutant enzyme K294R. Each reaction was carried out in a 20 μl mixture containing 20 mM Tris-HCl, pH 7.6; 10 mM $MgCl_2$; 100 mM KCl; 10 mM DTT; 1 mM $NAD^+$; 25 nM (500 fmol) of the two short detecting primers and mixtures of templates. The reaction mixture was heated in GeneAmp 9600 (Perkin Elmer) for 15 sec. at 94° C. before adding 25 fmol of the wild-type or mutant Tth DNA ligase. After incubation with the enzymes for another 30 sec at 94° C., LDR reactions were run for 15 sec at 94° C., and 4 min. at 65° C. per cycle for 20 cycles. Reactions were completely stopped by chilling the tubes in an ethanol-dry ice bath, and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan Rox-1000 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were analyzed and quantified using the ABI GeneScan 672 software.

FIGS. 20A–B show the LDR oligonucleotide probes (FIG. 20A) and template sequences (FIG. 20B) for a T:G mismatch in an excess of normal DNA by either wild-type or mutant K294R Tth DNA ligase. GLg.m3A and GLg.m3A.rev represent the mismatched template (Normal template), whereas ALg.m3A and ALg.m3A.rev represent the perfect matched template (Cancer template ); Primers SLP3'TTT represents the Normal primer for the perfect matched (Cancer) template; whereas SLP3'TTC represents the Normal primer for the mismatched (Normal) template. Similarly, experiments with the Q-analogue for a T:G mismatch use primers SLP3'$Q_2$TT and SLP3'$Ql_8$TT' jt-SLP3'$Q_2$TT (SEQ. ID. No. 42) and SLP3'$Ql_8$TT (SEQ. ID. No. 43) as Normal primers for the matched (Cancer) template. The remaining sequences in FIG. 20 bear the SEQ. ID. Nos. set forth with respect to FIG. 17.

Figures 21A, 21B:
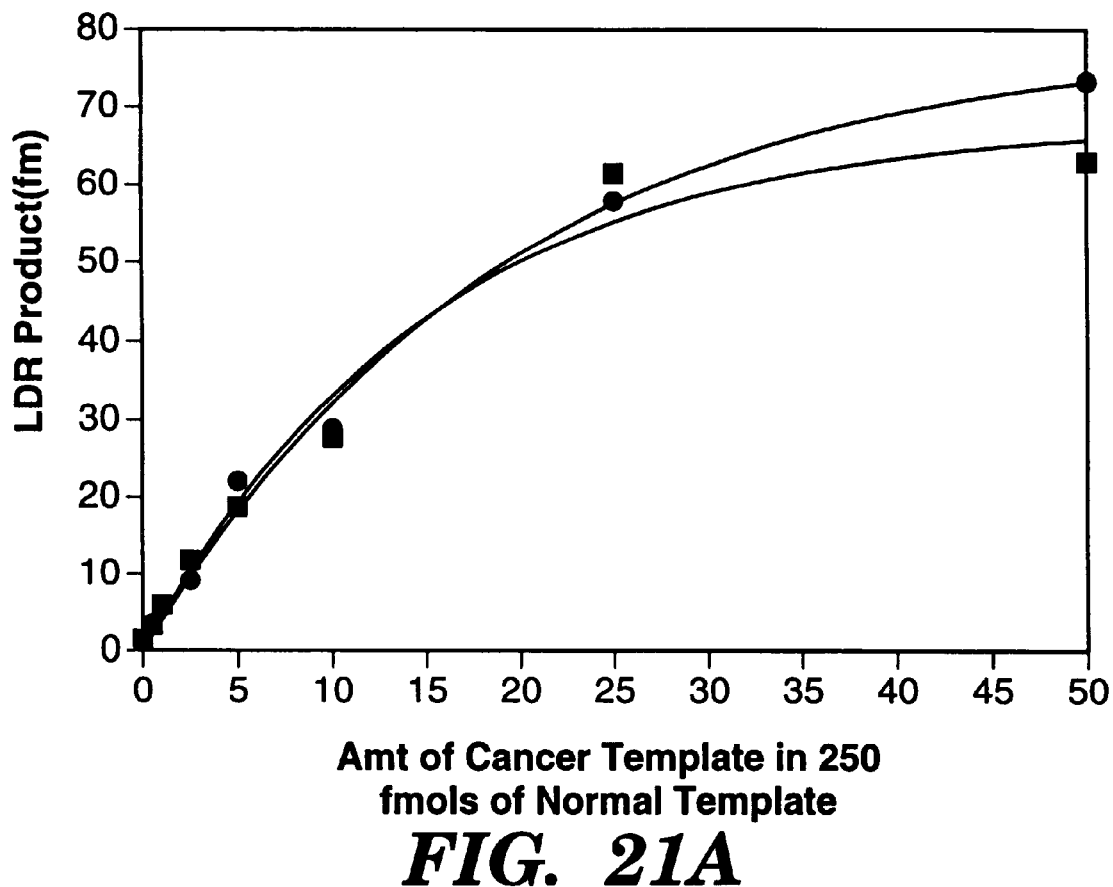

FIGS. 21A–B show the quantitative detection of single-base mutations (a T:G mismatch) in an excess of normal DNA by either wild-type or K294R Tth DNA ligase. The amount of LDR product formed when 0, 0.025 nM (0.5 fmol), 0.05 nM (1 fmol), 0.125 nM (2.5 fmol), 0.25 nM (5 fmol), 1.25 nM (25 fmol), and 2.5 nM (50 fmol) of "Cancer" template was used in combination with 12.5 nM (250 fmol) of the "Normal" template. The reaction was carried out in the presence of 25 nM (500 fmol) of regular primers (SLP3'TTT and Com 610 3'F), and 1.25 nM (25 fmol) of the wild-type or K294R mutant enzymes. The oligonucleotide probes used in this reaction create a T:G mismatch on the "Normal" template and a T:A match on the "Cancer" template at the ligation junction. LDR reactions were run for 15 sec at 94° C., and 4 min. at 65° C. per cycle for 20 cycles. Reactions were completely stopped by chilling the tubes in an ethanol-dry ice bath and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan Rox-1000 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were analyzed and quantified using the ABI GeneScan 672 software. The table (FIG. 21B) describes the raw data for graph (FIG. 21A). The data were analyzed and parameters of an exponential equation were fit to the data using the Deltagraph Pro 3.5. software. The X-axis indicated the different amounts of Cancer Template in 12.5 nM (250 fmol) of the Normal Template, while the Y-axis indicated the amount of LDR product generated. (■) represents 1.25 nM (25 fmol) of the wild-type enzyme whereas (●) represents 1.25 nM (25 fmol) of mutant K294 R enzyme.

Figures 22A, 22B:
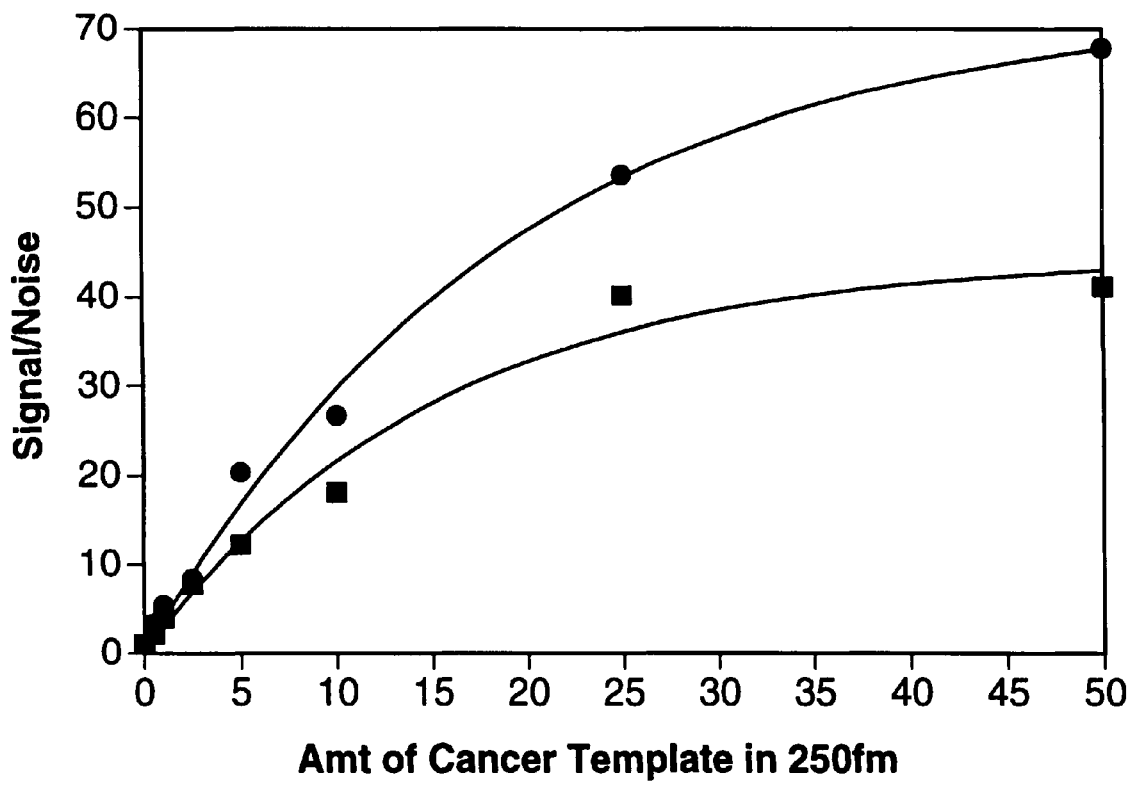

FIGS. 22A–B show the signal-to-noise ratio of the LDR product with different concentrations of mutant template in normal DNA. The single-base mutation template ("Cancer") was diluted into 12.5 nM (250 fmol) of the "Normal" template, and assayed using 0.125 nM (25 fmol) of either wild-type or mutant K294R Tth DNA ligase. The oligonucleotide probes used in this reaction create a T:G mismatch on the "Normal" template and a T:A match on the "Cancer" template at the ligation junction. The signal-to-noise ratio is defined as the ratio of the amount of product formed with "Cancer" Template in the presence of "Normal" template (12.5 nM=250 fmol template) to the amount of product formed by the same amount of Normal template alone. The table (FIG. 22B) describes the raw data for the graph (FIG. 22A). The data were analyzed and parameters of an exponential equation fit to the data using the Deltagraph Pro 3.5. software. The X-axis displayed different amounts of "Cancer" template in 12.5 nM (250 fmol) of the "Normal" template, while the Y-axis indicated the amount of LDR product generated. (■) represents 1.25 nM (25 fmol) of the wild-type enzyme whereas (●) represents 1.25 nM (25 fmol) of mutant K294 R enzyme.

Figures 23A, 23B:
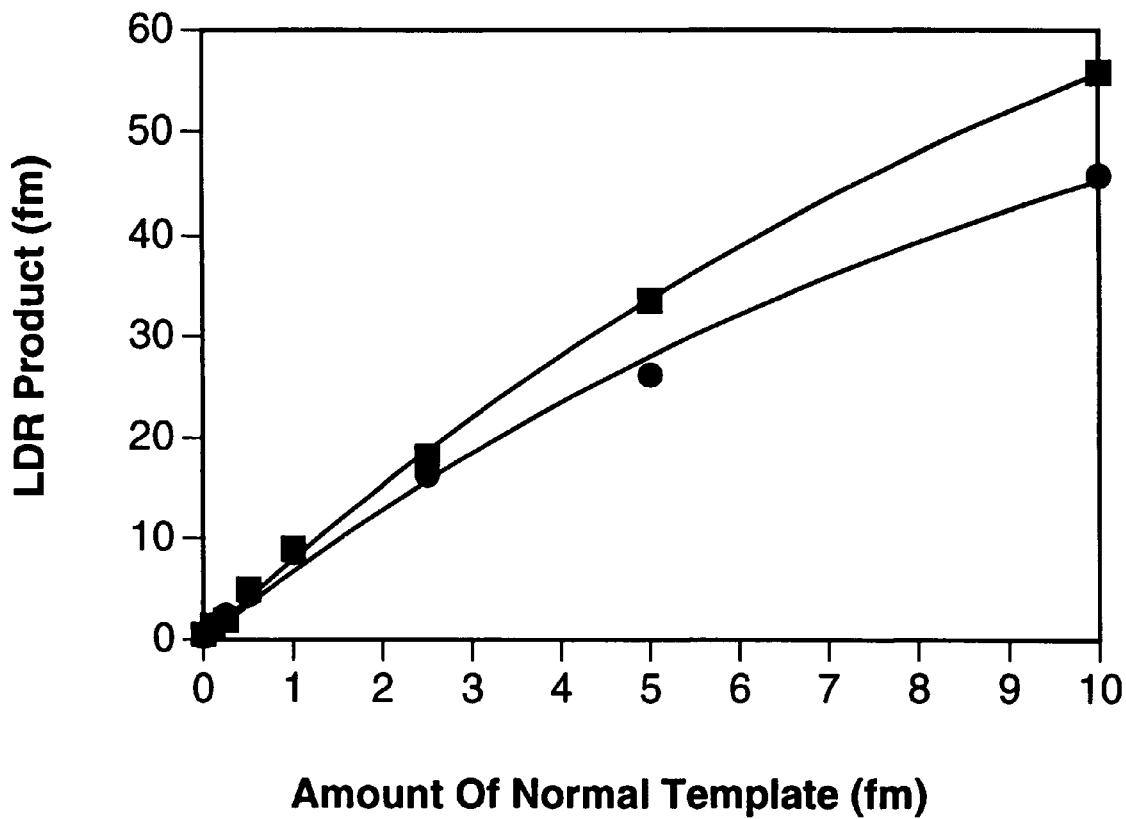

FIGS. 23A–B show the amount of LDR product formed when 0, 0.005 nM (0.1 fmol), 0.0125 nM (0.25 fmol), 0.025 nM (0.5 fmol), 0.05 nM (1.0 fmol), 0.125 nM (2.5 fmol), 0.25 nM (5 fmol), and 0.5 nM (10 fmol) of Normal template (Glg.m3A and GLg.m3.Arev), are mixed with 25 nM (500 fmol) of regular primers (SLP3'TTC and Com 610 3'F), and 1.25 nM (25 fmol) of the wild-type or mutant enzymes. The primers used in this reaction create a C:G match on the "Normal" template at the ligation junction. LDR reactions were run for 15 sec at 94° C., and 4 min. at 65° C. per cycle for 20 cycles. Reactions were completely stopped by chilling the tubes in an ethanol-dry ice bath, and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan Rox-1000 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were analyzed and quantified using the ABI GeneScan 672 software. The table (FIG. 23B) describes the raw data for the graph (FIG. 23A). The data were analyzed and parameters of an exponential equation fit to the data using the Deltagraph Pro 3.5. software. The X-axis indicated the different amounts of Cancer Template in 12.5 μnM (250 fmol) of the Normal Template, while the Y-axis indicated the amount of LDR product generated. (■) represents 1.25 nM (25 fmol) of the wild-type enzyme whereas (●) represents 1.25 nM (25 fmol) of mutant K294 R enzyme.

FIG. 24 shows nucleotide analogue containing primers used for assaying ligase fidelity. Four different conditions were used to assess the fidelity of the wild-type and mutant Tth DNA ligase in a typical LDR assay. Each reaction was carried out in a 20 μl mixture containing 20 mM Tris-HCl, pH 7.6; 10 mM MgCl$_2$; 100 mM KCl; 10 mM DTT; 1 mM NAD$^+$; 25 nM (500 fmol) of the two short detecting primers and 12.5 nM (250 fmol) of the normal template when used alone, or 125 nM (2.5 fmol), and 0.5 nM (10 fmol), of the cancer template when used together with the normal template in a ratio of 1:100 and 1:25, respectively. The oligonucleotide probes used in this reaction create a T:G mismatch on the "Normal" template and an T:A match on the "Cancer" template at the ligation junction. In addition, oligonucleotide probes SLP3'QTT create a Q$_2$:A or Q$_{18}$:T pairing at the 3rd position from the 3' end. The reaction mixture was heated in a GeneAmp 9600 thermocycler (Perkin Elmer) for 1.5 sec. at 94° C. before adding 25 fmol of the wild-type and mutant Tth DNA ligase. After incubation with the enzymes for another 30 sec, LDR reactions were run for 15 sec at 94° C., and 4 min. at 65° C. per cycle for 20 cycles. Reactions were completely stopped by chilling the tubes in an ethanol-dry ice bath, and adding 0.5 μl of 0.5 mM EDTA. 2.5 μl of reaction product was mixed with 2.5 μl of loading buffer (83% Formamide, 8.3 mM EDTA, and 0.17% Blue Dextran) and 0.5 μl Gene Scan Rox-1000 molecular weight marker, denatured at 94° C. for 2 min, chilled rapidly on ice prior to loading on an 8 M urea-10% polyacrylamide gel, and electrophoresed on an ABI 373 DNA sequencer. Fluorescent labeled ligation products were analyzed and quantified using the ABI Gene Scan 672 software.

FIGS. 25A–D show different forms of oligonucleotide probes with nucleotide analogues for the LDR phase of the PCR/LDR process of the present invention. The probes in FIG. 25A, B, C, and D with the nucleotide analog Q are designated SEQ. ID. Nos. 44, 45, 46, and 47, respectively. In each of these figures, the target DNA sequence is the same and is designated SEQ. ID. No.4.

Figure 26:
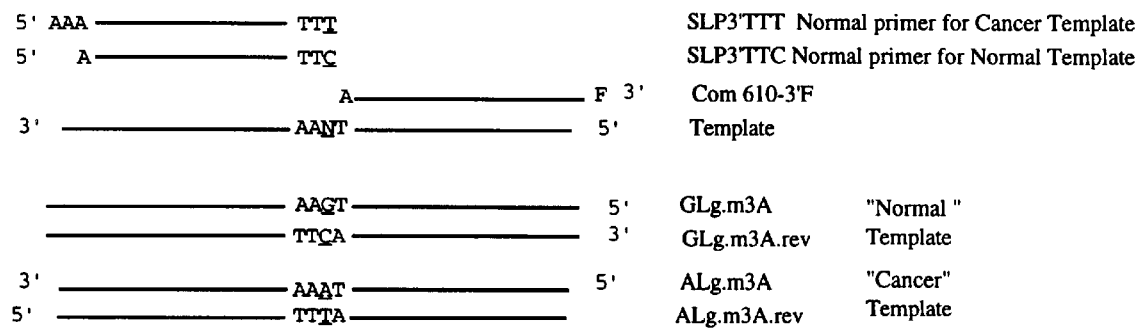

FIG. 26 shows primers used for quantitative detection of single-base mutations in an excess of normal DNA by either wild-type or K294R Tth DNA ligase (C:A mismatch). LDR reactions contained 12.5 nM (250 fmole) of the mismatched template (ALg.m3A and ALg.m3A.rev=Normal template) containing from 0 to 2.5 nM (50 fmole) of perfect matched template (GLg.m3A and GLg.m3A.rev=Cancer template ), in the presence of 25 fmol of either purified wild-type or mutant enzyme K294R. Each reaction was carried out in a 20 μl mixture containing 20 mM Tris-HCl, pH 7.6; 10 mM MgCl$_2$; 100 mM KCl; IO mM DTT; 1 mM NAD$^+$; 25 nM (500 fmol) of the two short detecting oligonucleotides probes and mixtures of templates. The probes used in this reaction create a C:A mismatch on the "Normal" template and an C:G match on the "Cancer" template at the ligation junction. The reaction mixture was heated in GeneAmp 9600 (Perkin Elmer) for 1.5 sec. at 94° C. before adding 25 fmol of the wild-type or mutant Tth DNA ligase. After incubation with the enzymes for another 30 sec, LDR reactions were run for 15 sec at 94° C., and 4 min. at 65° C. per cycle for 20 cycles. Reactions were completely stopped by chilling the tubes in an ethanol-dry ice bath, and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan Rox-1000 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were analyzed and quantified using the ABI GeneScan 672 software.

Figures 27A, 27B:
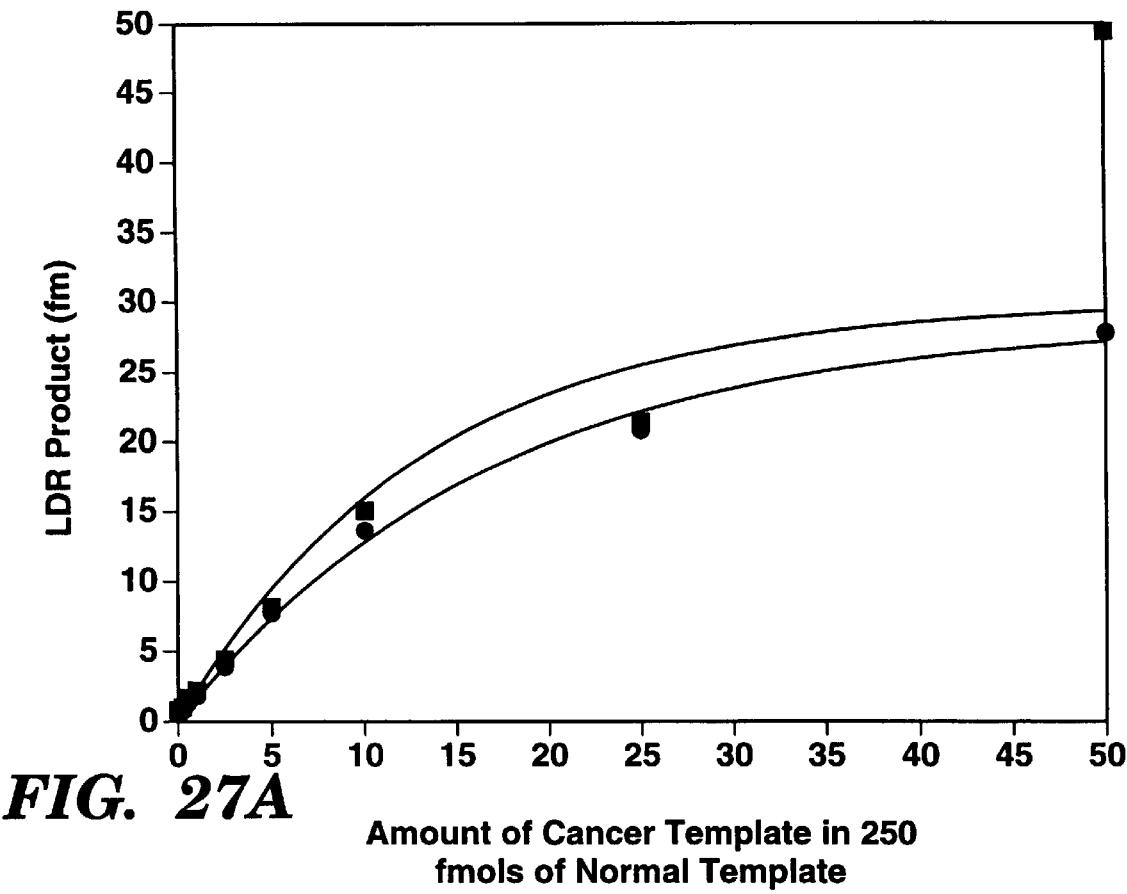

FIGS. 27A–B show the quantitative detection of single-base mutations (a C:A mismatch) in an excess of normal DNA by either wild-type or K294R Tth DNA ligase. The amount of LDR product formed when 0, 0.025 nM (0.5 fmol), 0.05 nM (1 fmol), 0.125 nM (2.5 fmol), 0.25 nM (5 fmol), 1.25 nM (25 fmol), and 2.5 nM (50 fmnol) of "Cancer" (i.e. Glg.m3A/Glg.m3A.rev) template was used in combination with 12.5 nM (250 fmol) of the "Normal" template (i.e. ALg.m3A/ALg.m3A.rev). The reaction was carried out in the presence of 25 nM (500 fmol) of regular oligonucleotide probes (SLP3'TTC and Corn 610 3'F), and 1.25 nM (25 fmol) of the wild-type or mutant enzymes. The oligonucleotide probes used in this reaction create a C:A mismatch on the "Normal" template and a C:G match on the "Cancer" template at the ligation junction. LDR reactions were run for 15 sec at 94° C. and 4 min. at 65° C. per cycle for 20 cycles. Reactions were completely stopped by chilling the tubes in an ethanol-dry ice bath, and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan Rox-1000 molecular weight marker, denatured at 94° C. for 2 min, chilled rapidly on ice prior to loading on an 8 M urea-i 0% polyacrylamide gel, and electrophoresed on an ABI 373 DNA sequencer. Fluorescent ligation products were analyzed and quantified using the ABI GeneScan 672 software. The table (FIG. 26B) describes the raw data for the graph (FIG. 26A). The data were analyzed and parameters of an exponential equation fit to the data using the Deltagraph Pro 3.5. software. The X-axis indicated the different amounts of Cancer Template in 12.5 nM (250 fmol) of the Normal Template, while the Y-axis indicated the amount of LDR product generated. (■) represents 1.25 rnM (25 fmol) of the wild-type enzyme whereas (●) represents 1.25 nM (25 fmol) of mutant K294 R enzyme.

Figure 28B:
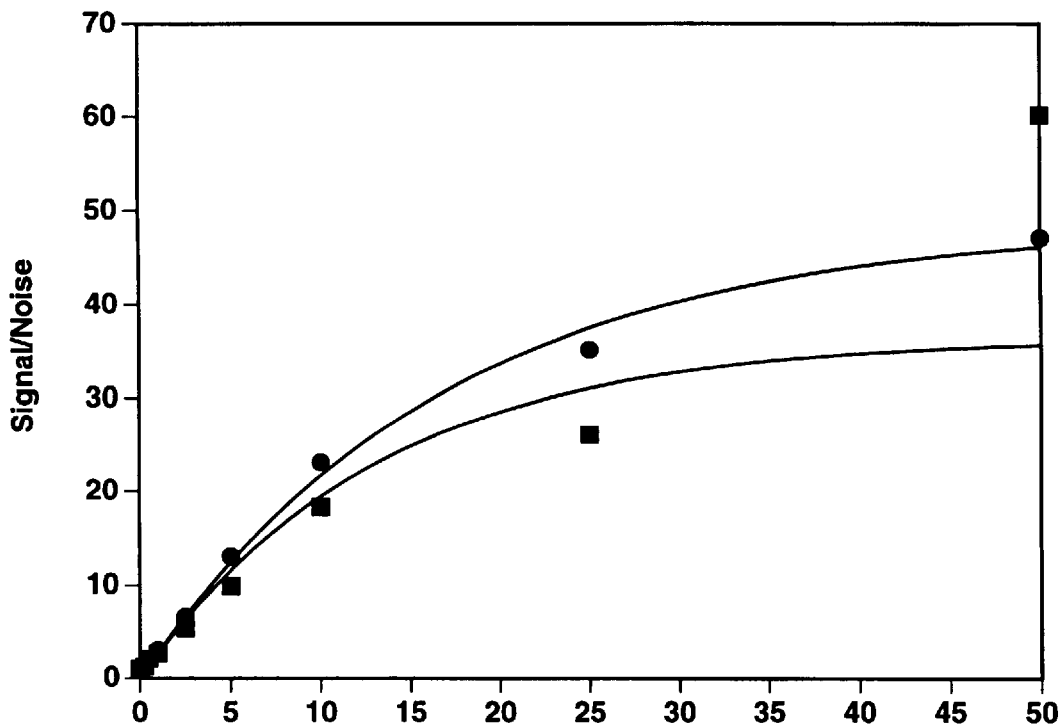

FIGS. 28A–B show the signal-to-noise ratio of the LDR product with different concentrations of the single-base mutation template ("Cancer") in combination with 12.5 nM (250 fmol) of the "Normal" template with 0.125 nM (25 fmol) by either wild-type or mutant K294R Tth DNA ligase. The signal-to-noise ratio is described as the ratio of the amount of product formed with varying concentrations of Cancer Template in the presence of 12.5 nM (250 fmol) of Normal template to the amount of product formed by 12.5 nM (250 fmol) of Normal template alone. The oligonucleotide probes (SLp3' TTC and Corn 6103'F) used in this reaction create a C:A mismatch on the "Normal" template (ALg.m3A/ALg.m3A.rev) and an C:G match on the "Cancer" template (GLg.m3A/GLg.m3A.rev) at the ligation junction. The table (FIG. 28B) describes the raw data for the graph (FIG. 28A). The data were analyzed and parameters of an exponential equation fit to the data using the Deltagraph Pro 3.5. software. The X-axis displayed different amounts of "Cancer" template in 12.5 nM (250 fmol) of the "Normal" template, while the Y-axis indicated the amount of LDR product generated. (■) represents 1.25 nM (25 fmol) of the wild-type enzyme whereas (●) represents 1.25 nM (25 fmol) of mutant K294 R enzyme.

Figure 29B:
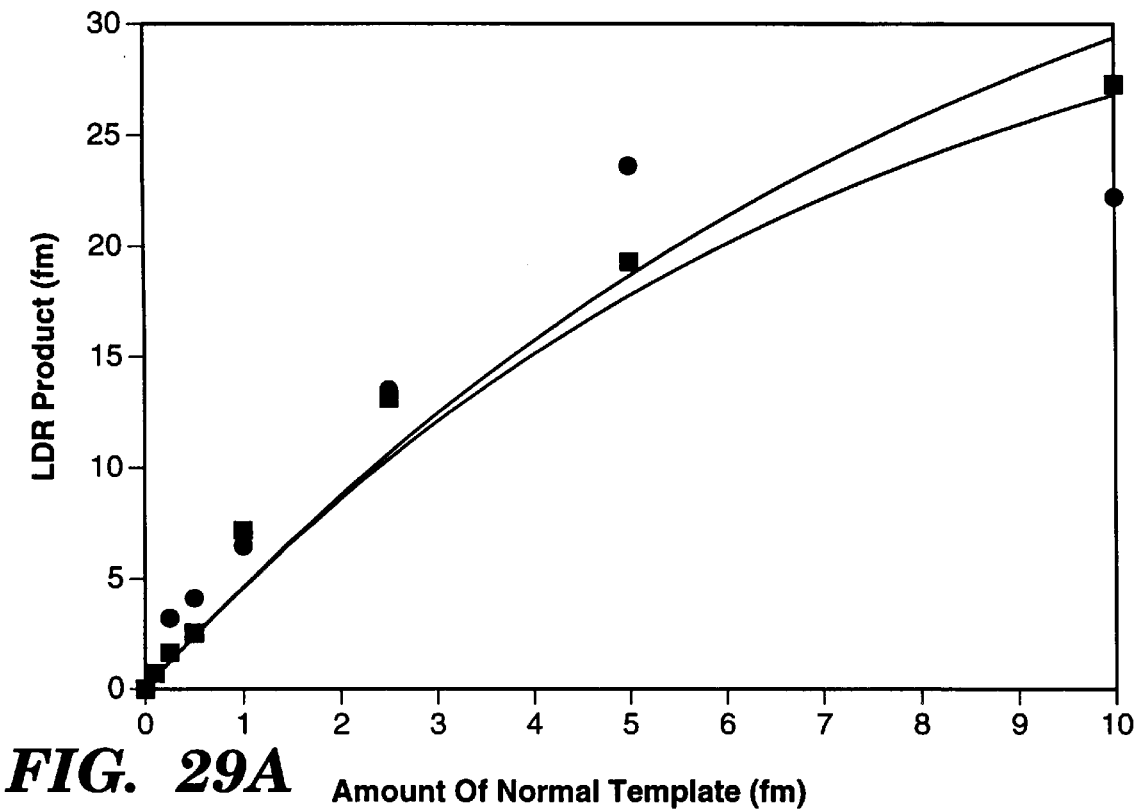

FIGS. 29A–B show the amount of LDR product formed when 0, 0.005 nM (0.1 fmol), 0.0125 nM (0.25 fmol), 0.025 nM (0.5 fmol), 0.05 nM (1.0 fmol), 0.125 nM (2.5 fmol), 0.25 nM (5 fmol), and 0.5 nM (10 fmol) of Normal template (i.e. ALg.m3A/ALg.m3A.rev) alone, are reacted with 25 nM (500 fmol) of regular primers (SLP3'TTT and Corn 610 3'F), and 1.25 nM (25 fmol) of the wild-type or mutant enzymes. LDR reactions were run for 15 sec at 94° C. and 4 min. at 65° C. per cycle for 20 cycles. The oligonucleotide probes used in this reaction create a T:A match on the "Normal" template at the ligation junction. Reactions were completely stopped by chilling the tubes in an ethanol-dry ice bath, and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan Rox-1000 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were analyzed and quantified using the ABI GeneScan 672 software. The table (FIG. 29B) describes the raw data for the graph (FIG. 29A). The data were analyzed and parameters of an exponential equation fit to the data using the Deltagraph Pro 3.5. software. The X-axis indicated the amounts of the Normal Template used, while the Y-axis indicated the amount of LDR product generated. (■) represents 1.25 nM (25 fmol) of the wild-type enzyme whereas (9) represents 1.25 nM (25 fmol) of mutant K294 R enzyme.

Figures 30A, 30B, 30C:
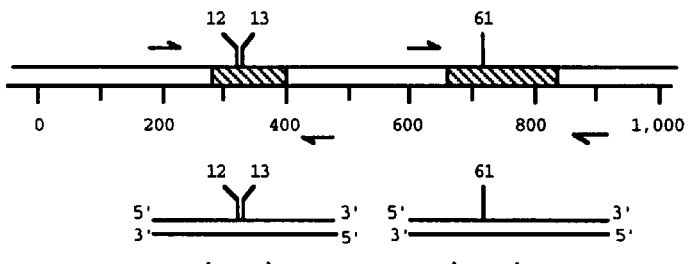

FIGS. 30A–C show a scheme for PCR/LDR detection of mutations in codons 12, 13, and 61 of K-ras. At the top of the drawing (FIG. 30A) is a schematic representation of the chromosomal DNA containing the K-ras gene. Exons are shaded and the position of codons 12, 13, and 61 shown. Exon-specific primers are used to amplify selectively K-ras DNA flanking these three codons. The middle (FIG. 30B) and bottom (FIG. 30C) of the diagram gives a schematic representation of primer design for LDR detection of all possible amino acid changes in codons 12, 13, and 61. For example, codon 12 (GGT) may mutate to GAT, GCT, or G TT. Allele-specific LDR oligonucleotide probes contain the discriminating base on the 3' end and a fluorescent label on the 5' end. Common oligonucleotides are phosphorylated on the 5' end and contain a poly-A tail and blocking group on the 3' end. Different mutations are distinguished by separating the products on a polyacrylamide gel. Note that LDR oligonucleotide probes used for detecting mutations at codon 12 may interfere with hybridization of oligonucleotide probes used to detect mutations at codon 13. It will be necessary to determine experimentally if these probes can correctly identify mutant signal in the presence of the other LDR probes.

FIGS. 31A–B provide the name and sequence of K-ras LDR oligonucleotide probes used to detect different mutations at codons 12, 13, and 61 in a typical LDR reaction in an excess of normal DNA by either wild-type or mutant K294R Tth DNA ligase. FIGS. 31A–B show the sequences for the following primers: Fam-K-ras c12.2D (SEQ. ID. No.49), Tet-K-ras c12.2A (SEQ. ID. No.50), Fam-K-ras c12.2V (SEQ. ID. No.51), K-ras c12 Com-2 (SEQ. ID. No. 52), Tet-K-ras c12.IS (SEQ. ID. No. 53), Fam-K-ras c12.1R (SEQ. ID. No. 54), 1et-K-ras c12.1C (SEQ. ID. No. 55), K-ras c12 Com-1 (SEQ. ID. No. 56), Fam-K-ras c13. ID (SEQ. ID. No. 57), Tet-K-ras c13.4A (SEQ. ID. No.58), Fam-K-ras c13.4V (SEQ. ID. 0o.59), K-ras c13 Com-4 (SEQ. ID. No. 60), Tet-K-ras c13.3S (SEQ. ID. No. 61), Fam-K-ras c13.3R (SEQ. ID. No. 62), Tet-K-ras c13.3C (SEQ. ID. No. 63), K-ras c13 Com-3 (SE (. ID. No. 64), Tet-K-ras c61.7HT (SEQ. ID. No. 65), Fam-K-ras c61.7HC (SEQ. ID. No. 6(-), K-ras Com-7 (SEQ. ID. No. 67), Tet-K-ras c61.6R (SEQ. ID. No. 68), Fam-K-ras c61.: )P (SEQ. ID. No. 69), Tet-K-ras c61.6P (SEQ. ID. No. 70), K-ras Com-6 (SEQ. ID. No.71, Fam-K-ras c6l.5K (SEQ. ID. No. 72), Tet-K-ras c61.5E (SEQ. ID. No. 73), and K-ras Com-5 (SEQ. ID. No. 74).

Figure 32:
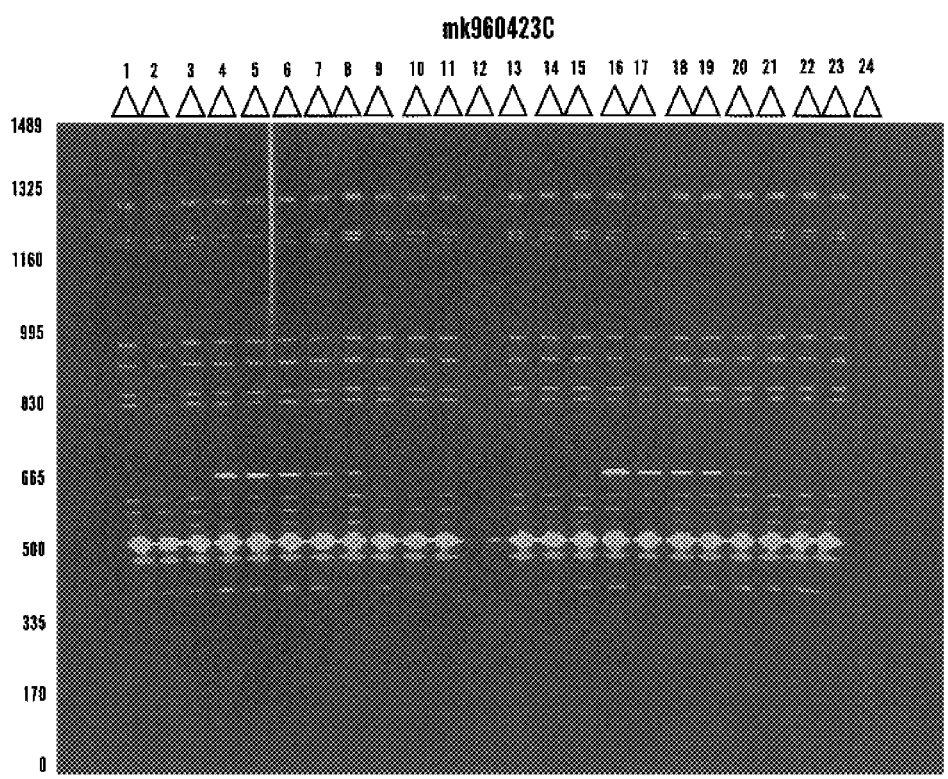
Figures 33A, 33B:
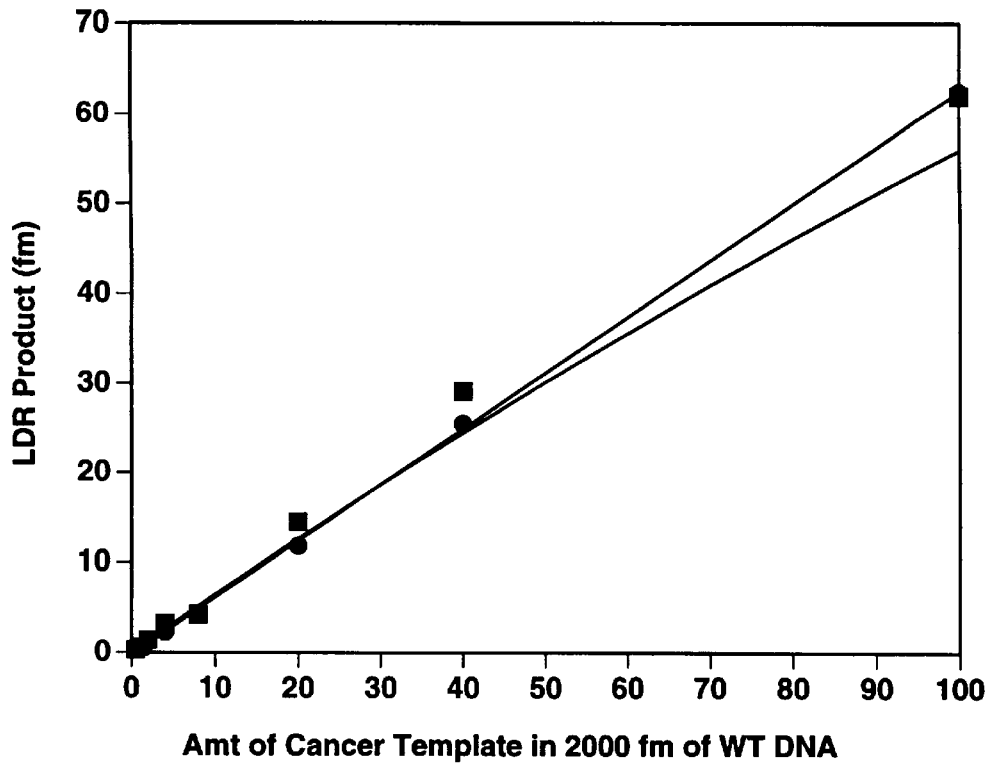

FIGS. 32 and 33A–B show the quantitative detection of a Gly –> Asp mutation (C:A mismatch) in Codon 12 of the K-ras gene (G12D) in an excess of normal K-ras sequence by either wild-type or K294R Tth DNA ligase. The eleven lanes on the left of gel # mk960423 (#1-11) of FIG. 32 represent data obtained when using wild-type Tth DNA ligase, while the eleven lanes on the right (#13-23) of FIG. 32 represent data obtained when using the mutant Tth DNA ligase, K294R. The first three lanes in each case are negative controls without any added mutant K-ras sequence. The next eight lanes depict the amount of LDR product formed when 5 nM (100 fmol), 2 nM (40 fmol), 0.8 nM (20 fmol), 0.4 nM (8 fmol), 0.2 nM (4 fmol), 0.1 nM (2.0 fmol), 0.05 nM (1 fmol), and 0.025 nM (0.5 fmol) of mutant K-ras template, respectively, was used in combination with 100 nM (2000 fmol) of the wild-type K-ras DNA. The reaction was carried out in the presence of 25 nM (500 fmol) of one discriminating oligonucleotide probes (Fam-K-ras c12.2D, and a common primer K-ras c12 Com-2) and 5 nM (100 fmol) of the wild-type or K294R mutant enzymes. The LDR probe for detecting the Gly–> Asp mutation used in this reaction creates a C:A mismatch on the wild-type template and a T:A match on the Gly–> Asp mutant K-ras template at the ligation junction. PCR reactions were run for 15 sec at 94° C., 1 min at 55° C., and 1 min. (+3 sec/cycle) at 72° C. per cycle for 30 cycles. LDR reactions were run for 15 sec at 94° C., and 4 min. at 65° C. per cycle for 20 cycles. Reactions were completely stopped by chilling the tubes in an ethanol-dry ice bath, and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan TAMRA 350 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were quantified using the ABI GeneScan 672 software. The table (FIG. 33B) describes the raw data for the graph (FIG. 33A). The data were analyzed and parameters of an exponential equation fit to the data using the Deltagraph Pro 3.5. software. The X-axis indicated the different amounts of G12D template in 100 nM (2000 fmol) of the wild-type template, while the Y-axis indicated the amount of LDR product generated. (■) represents 5 nM (100 fmol) of the wild-type enzyme whereas (●) represents 5 nM (100 fmol) of mutant K294 R enzyme.

Figures 34A, 34B:
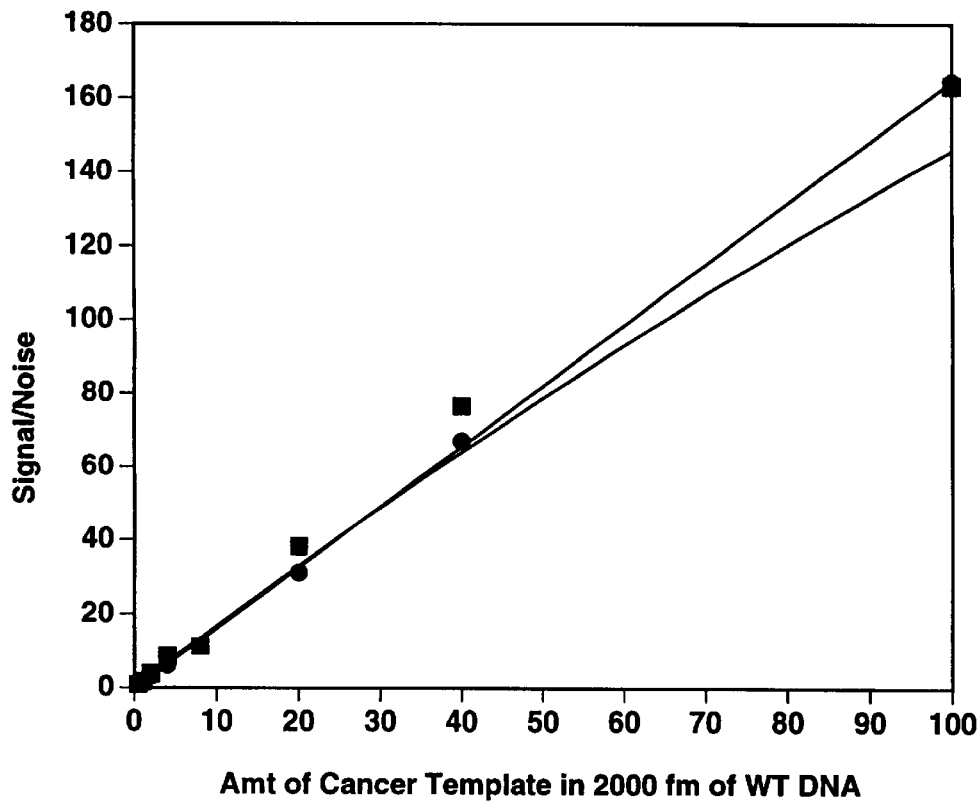

FIGS. 34A–B show the signal-to-noise ratio of the LDR product with different concentrations of the K-ras gene (from 0.025 nM [0.5 fmol] to 5 nM [100 fmol]) containing a single-base mutation (G12D) in combination with 100 nM (2000 fmol) of the wild-type K-ras template using 5 nM (100 fmol) of either wild-type or mutant K294R Tth DNA ligase. The probes used in this reaction create a C:A mismatch on the wild-type template and a T:A match on the G12D template at the ligation junction. The signal-to-noise ratio is defined as the ratio of the amount of product formed with G12D template in the presence of wild-type template (100 nM 2000 fmol template) to the amount of product formed by the same amount of wild-type template alone. The table (FIG. 34B) describes the raw data for the graph (FIG. 34A). The data were analyzed and parameters of an exponential equation fit to the data using the Deltagraph Pro 3.5. software. The X-axis displayed different amounts of G12D template in 100 nM (2000 fmol) of wild-type template, while the Y-axis indicated the amount of LDR product generated. (■) represents 5 nM (100 fmol) of the wild-type enzyme whereas (●) represents 5 nM (100 fmol) of mutant K294 R enzyme.

Figure 35:
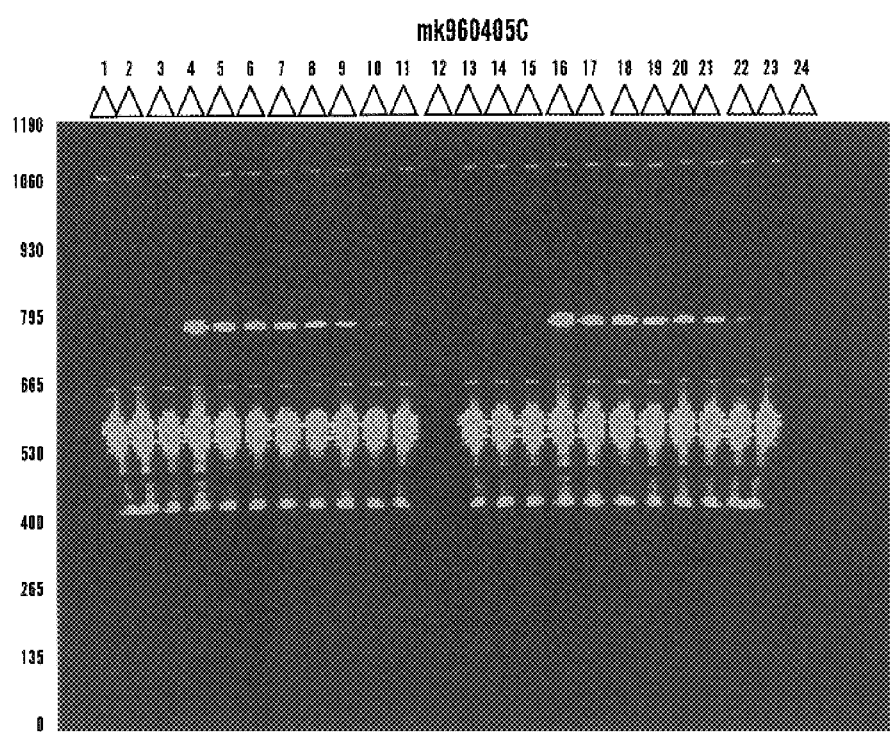
Figures 36A, 36B:
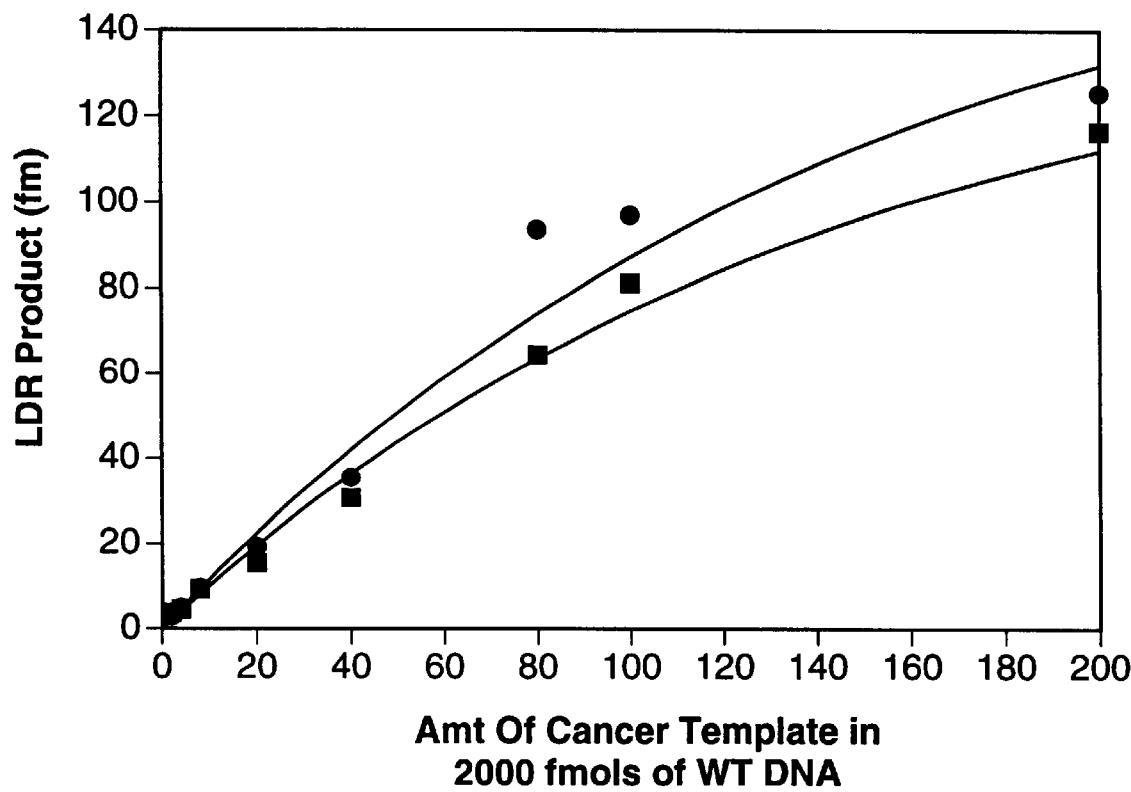

FIGS. 35 and 36A–B show the quantitative detection of a Gly–> Val mutation (a C:T mismatch) in Codon 12 of the K-ras gene (G12V) in an excess of normal K-ras sequence by either wild-type or K294R Tth DNA ligase. The eleven lanes on the left of gel # mk960405 (#1-11) (FIG. 35) represent data obtained when using wild-type Tth DNA ligase, while the eleven lanes on the right (#13-23) (FIG. 35) represent data obtained when using the mutant Tth DNA ligase, K294R. The first three lanes (FIG. 35) in each case are negative controls without any added mutant K-ras sequence. The next eight lanes (FIG. 35) depict the amount of LDR product formed when 0.1 nM (2.0 fmol), 0.2 nM (4 fmol), 0.4 nM (8 fmol), 0.8 nM (20 fmol), 2 nM (40 fmol), 4 nM (80 fmol), 5 nM (100 fmol), and 20 nM (200 fmol) of mutant K-ras template was used in combination with 100 nM (2000 fmol) of the wild-type K-ras template. The reaction was carried out in the presence of 25 nM (500 fmol) of six discriminating probes (Tet-K-ras c12.2A, Tet-K-ras c12.1S, Tet-K-ras c12.1C, Fam-K-ras c12. 1R, Fam-K-ras c12. 2D, Fam-K-ras c12. 2V); 75 nM (1500 fmol) of two common probes (K-ras c12 Com-2 and K-ras c12 Com-1) and 5 nM (100 fmol) of the wild-type or K294R mutant enzymes. Tet is tetrachlorinated-6-carboxyfluorescein; fluorescent dye used in sequencing/mutation detection, while Corn is an oligonucleotide probe using a 3' amino modified C3CPG column. This column is designed to produce a primary amine to the 3' terminus of a target oligonucleotide. The primary use of these 3' amino modifiers are for subsequent labelling as diagnostic probes and to generate an oligonucleotide resistant to the 3' exonuclease activity. This set of probes is capable of detecting the presence of all six single-base mutations in Codon 12 of the K-ras gene in a multiplex reaction. The LDR probe for detecting the Gly–> Val mutation used in this reaction creates a C:T mismatch on the wild-type template and an A:T match on the Gly–> Val mutant K-ras template at the ligation junction. PCR reactions were run for 15 sec at 940C, 1 min at 55° C., and 1 min. (+3 sec/cycle) at 72° C. per cycle for 30 cycles. LDR reactions were run for 15 sec at 94° C., and 4 min. at 65° C. per cycle for 20 cycles. Reactions were completely stopped by chilling the tubes in an ethanol-dry ice bath, and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan TAMRA 350 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were quantified using the ABI GeneScan 672 software. The table (FIG. 36B) describes the raw data for the graph (FIG. 36A). The data were analyzed and parameters of an exponential equation fit to the data using the Deltagraph Pro 3.5. software. The X-axis indicated the different amounts of G12V template in 100 nM (2000 fmol) of the wild-type template, while the Y-axis indicated the amount of LDR product generated. (■) represents 5 nM (100 fmol) of the wild-type enzyme whereas (●) represents 5 nM (100 fmol) of mutant K294 R enzyme.

Figures 37A, 37B:
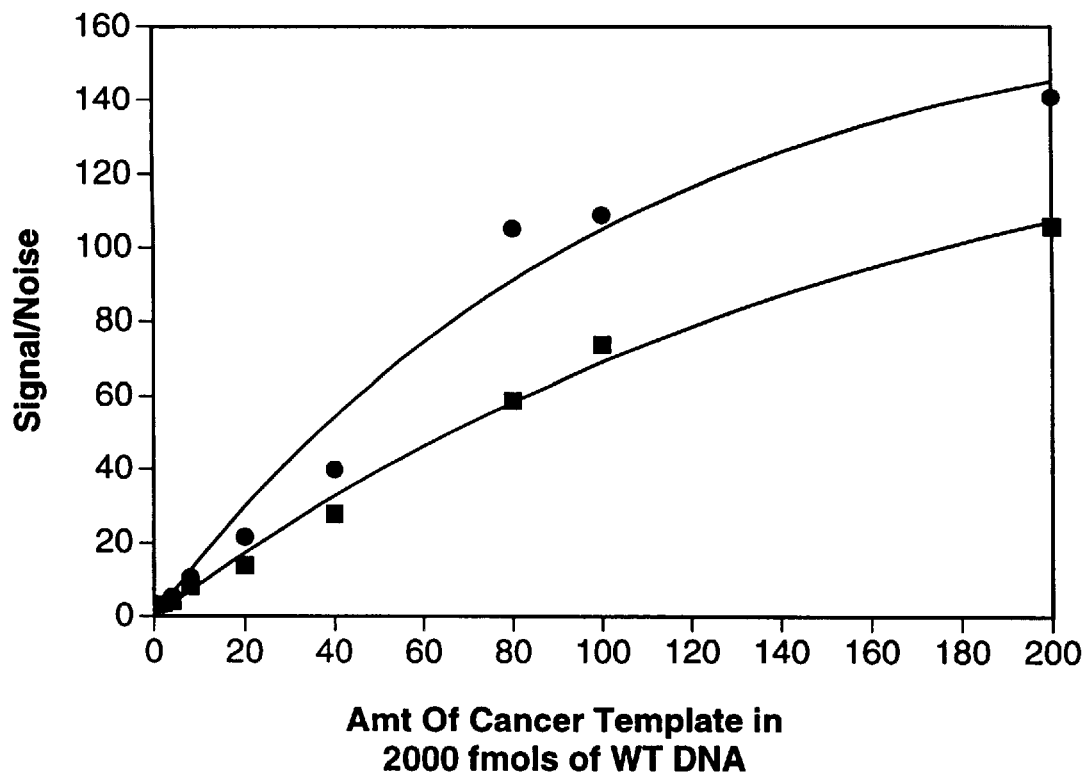

FIGS. 37A–B show the signal-to-noise ratio of the LDR product in 26 primer multiplex reaction with different concentrations of the K-ras gene (from 0.1 nM [2 fmol] to 10 nM [200 fmol]) containing a single-base mutation (G12V) in combination with 100 nM (2000 fmol) of the wild-type K-ras template using 5 nM (100 fmol) of either wild-type or mutant K294R Tth DNA ligase. The G12V specific probes used in this reaction create a C:T mismatch on the wild-type template and an A:T match on the G12V template at the ligation junction. The greatest background noise in this multiplexed reaction was from probes designed to detect $Q_{61}R$, representing a G:T mismatch, which was about 10-fold higher than from probes designed to detect G12D, i.e. representing a C:A mismatch. For consistency with other assays, the signal-to-noise ratio in this multiplexed assay is defined as the ratio of the amount of product formed with G12V templates in the presence of wild-type template (100 nM=2000 fmol template) to the amount of G12D LDR product formed by the same amount of wild-type template alone (representing a C:A mismatch). The table (FIG. 37B) describes the raw data for the graph (FIG. 37A). The data were analyzed and parameters of an exponential equation fit to the data using the Deltagraph Pro 3.5. software. The X-axis displayed different amounts of "Cancer" template in 100 nM (2000 fmol) of the "Normal" template, while the Y-axis indicated the amount of LDR product generated. (■) represents 5 nM (100 fmol) of the wild-type enzyme whereas (●) represents 5 nM (100 fmol) of mutant K294 R enzyme.

Figure 38:
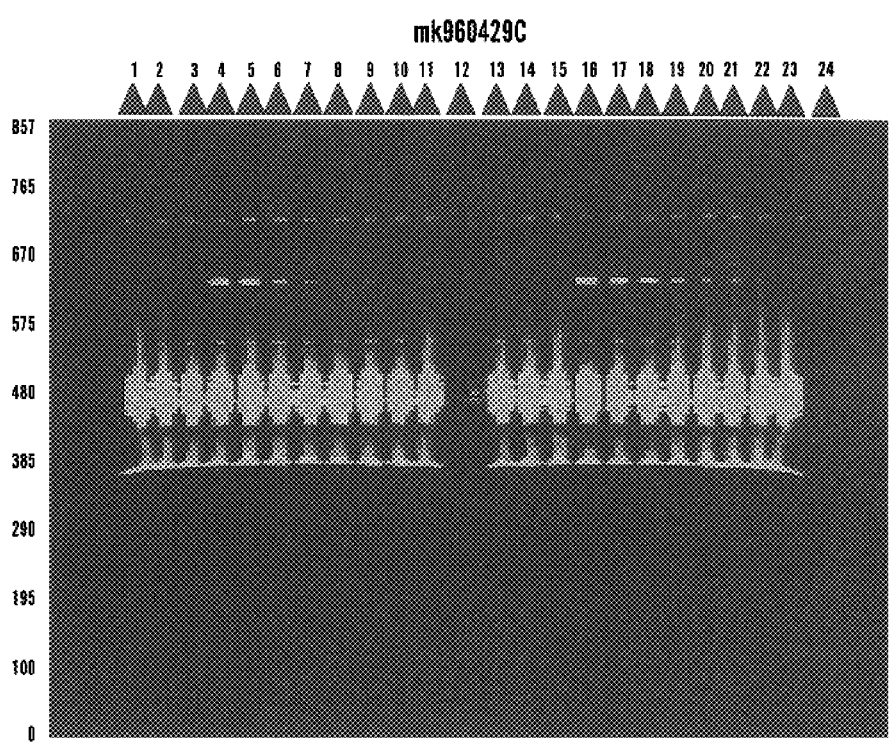
Figures 39A, 39B:
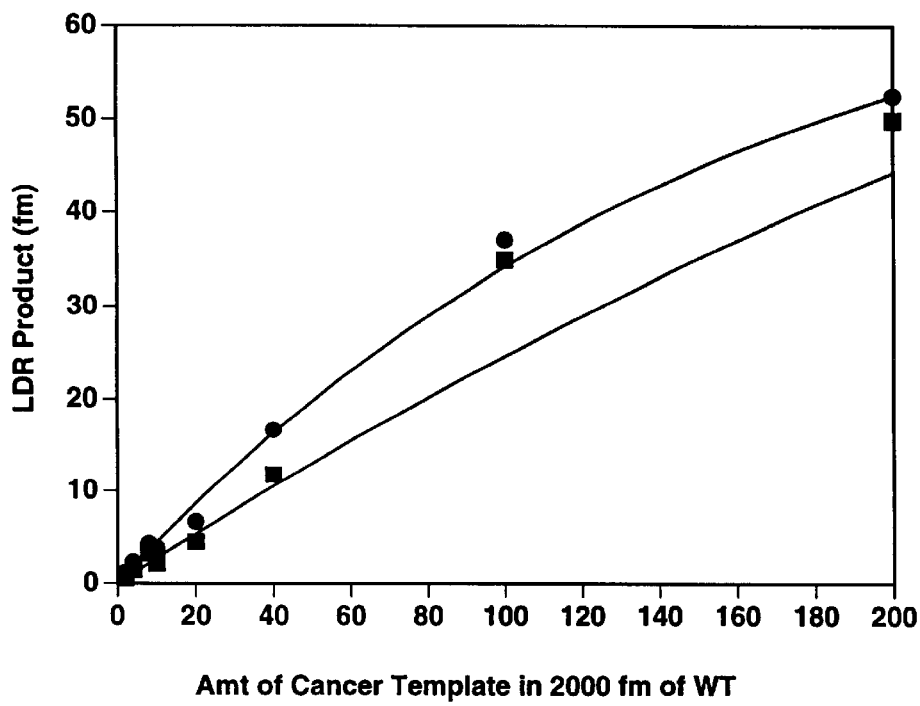

FIGS. 38 and 39A–B show the quantitative detection of a Gly–> Val mutation (a C:T mismatch) in Codon 12 of the K-ras gene in an excess of normal K-ras sequence by either wild-type or K294R Tth DNA ligase. The eleven lanes on the left of gel # mk960429 (#1-11) (FIG. 38) represent data obtained when using wild-type Tth DNA ligase, while the eleven lanes on the right (#13-23) (FIG. 38) represent data obtained when using the mutant Tth DNA ligase, K294R. The first three lanes in each case are negative controls without any added mutant K-ras sequence. The next eight lanes depict the amount of LDR product formed when 0.1 nM (2.0 fmol), 0.2 nM (4 fmol), 0.4 nM (8 fmol), 0.8 nM (10 fmol), 2 nM (20 fmol), 4 nM (40 fmol), 5 nM (100 fmol), and 20 nM (200 fmol) of mutant K-ras template was used in combination with 100 nM (2000 fmol) of the wild-type K-ras template. The reaction was carried out in the presence of 25 nM (500 fmol) of nineteen discriminating primers (Tet-K-ras c12.2A, Tet-K-ras c12.1S, Tet-K-ras c12.1C, Tet-K-ras c13.4A, Tet-K-ras c13.3S, Tet-K-ras c13.3C, Tet-K-ras c61.7HT, Tet-K-ras c61.6R, Tet-K-ras c61.5K, Tet-K-ras c61.6P, Fam-K-ras c12.1R, Fam-K-ras c12.2D, Fam-K-ras c12.2V, Fam-K-ras c13.4D, Fam-K-ras c13.4V, Fam-K-ras c13.3R, Fam-K-ras c61.7HC, Fam-K-ras c61.6L, Fam-K-ras c61.5K); 50 nM (1000 fmol) of two common probes (K-ras c61 Com-7 and K-ras c12 Com-5); and 75 nM (1500 fmol) of five common primers (K-ras c12 Com-2, K-ras c12 Com-1, K-ras c13 Com-4, K-ras c13 Com-3, and K-ras c61 Com-6) and 5 nM (100 fmol) of the wild-type or K294R mutant enzymes. This set of probes is capable of detecting the presence of all nineteen mutations in Codons 12, 13, and 61, of the K-ras gene in a multiplex reaction. The LDR probe for detecting the Gly–> Val mutation used in this reaction creates a C:T mismatch on the wild-type K-ras template and an A:T match on the Gly–> Val mutant K-ras template at the ligation junction. PCR reactions were run for 15 sec at 94° C., 1 min at 55° C., and 1 min. (+3 sec/cycle) at 72° C. per cycle for 30 cycles. LDR reactions were run for 15 sec at 94° C., and 4 min. at 65° C. per cycle for 20 cycles. Reactions were completely stopped by chilling the tubes in an ethanol-dry ice bath, and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan TAMRA 350 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were quantified using the ABI GeneScan 672 software. The table (FIG. 39B) describes the raw data for the graph (FIG. 39A). The data were analyzed and parameters of an exponential equation fit to the data using the Deltagraph Pro 3.5. software. The X-axis indicated the different amounts of G12V template in 100 nM (2000 fmol) of the wild-type template, while the Y-axis indicated the amount of LDR product generated. (■) represents 5 nM (100 fmol) of the wild-type enzyme whereas (●) represents 5 nM (100 fmol) of mutant K294 R enzyme.

Figures 40A, 40B:
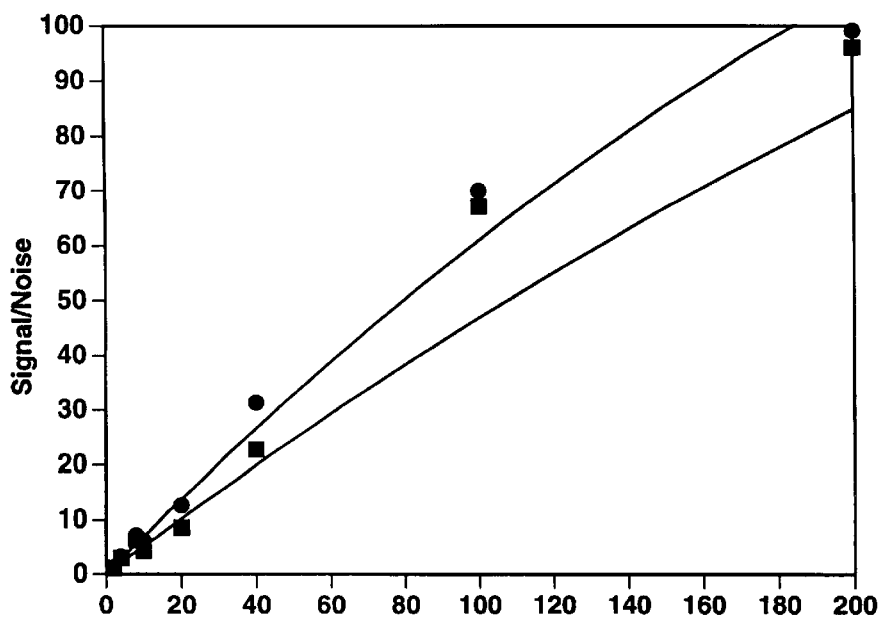

FIGS. 40A–B show the signal-to-noise ratio of the LDR product in a 26 primer multiplex reaction with different concentrations of the K-ras gene (from 0.1 nM [2 fmol] to 10 nM [200 fmol]) containing a single-base mutation (G12V) in combination with 100 nM (2000 fmol) of the wild-type K-ras template using 5 nM (100 fmol) of either wild-type or mutant K294R Tth DNA ligase. The G12V specific probes used in this reaction create a C:T mismatch on the wild-type template and an A:T match on the Gl2V template at the ligation junction. The greatest background noise in this multiplexed reaction was from probes designed to detect $Q_{61}R$, representing a G:T mismatch, which was about 10-fold higher than from probes designed to detect GI 2D, i.e. representing a C:A mismatch. For consistency with our other assays, the signal-to-noise ratio in this multiplexed assay is defined as the ratio of the amount of product formed with G12V templates in the presence of wild-type template (100 nM=2000 fmol template) to the amount of G12D LDR product formed by the same amount of wild-type template alone (representing a C:A mismatch). The table (FIG. 40B) describes the raw data for the graph (FIG. 40A). The data were analyzed and parameters of an exponential equation fit to the data using the Deltagraph Pro 3.5. software. The X-axis displayed different amounts of "Cancer" template in 100 nM (2000 fmol) of the "Normal" template, while the Y-axis indicated the amount of LDR product generated. (■) represents 5 nM (100 fmol) of the wild-type enzyme whereas (●) represents 5 nM (100 fmol) of mutant K294 R enzyme.

Figure 41:
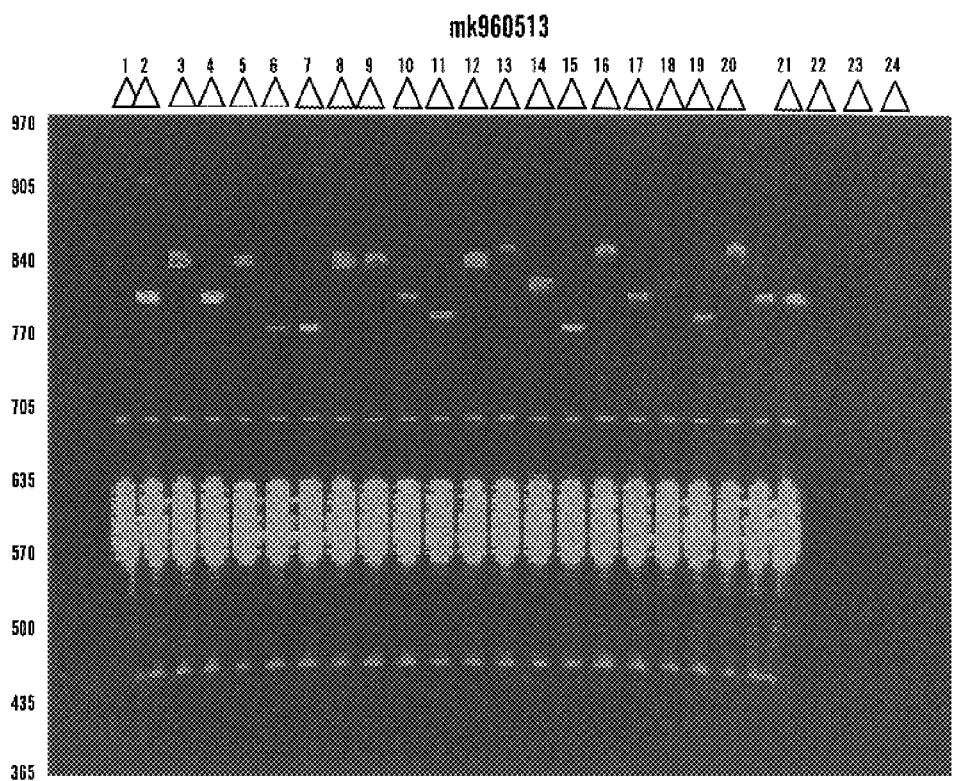

FIGS. 41–42 show the quantitative detection of mutations in the K-ras gene by K294 mutant Tth DNA ligase. The first lane (FIG. 41) in gel # mk950513 is a negative control using wild-type K-ras DNA. The second lane (FIG. 41) is a positive control which contains mutant Gly–> Val K-ras DNA. The next twenty lanes (FIG. 41) represent a blind test of LDR reactions on twenty samples containing different mutant K-ras DNA. The reactions were carried out in the presence of 25 nM (500 fmol) of nineteen discriminating primers (Tet-K-ras ci2.2A, Tet-K-ras c12.1S, Tet-K-ras c12.1C, Tet-K-ras c13.4A, Tet-K-ras c13.3S, Tet-K-ras ci3.3C, Tet-K-ras c61.7HT, Tet-K-ras c61.6R, Tet-K-ras c61.5K, Tet-K-ras c61.6P, Fam-K-ras c12.1R, Fam-K-ras c12.2D, Fam-K-ras c12.2V, Fam-K-ras c13.4D, Fam-K-ras c13.4V, Fam-K-ras c13.3R, Fam-K-ras c61.7HC, Fam-K-ras c61.6L, Fam-K-ras c61.5K); 50 nM (1000 fmol) of two common probes (K-ras c61 Com-7 and K-ras c12 Com-5); and 75 nM (1500 fmol) of five common probes (K-ras c12 Com-2, K-ras c12 Com-1, K-ras c13 Com-4, K-ras c13 Com-3, and K-ras c61 Com-6) and 5 nM (100 fmol) of the wild-type or K294R mutant enzymes. This set of probes is capable of detecting the presence of all nineteen mutations in Codons 12, 13, and 61, of the K-ras gene in a multiplex reaction. Microdissected tissue was transferred to a PCR tube, exposed to xylene for 10 min, washed 3×in 95% ethanol, and desiccated. PCR reactions were run for 30 sec at 94° C., 1.5 min at 54° C., and 1 min. at 72° C. per cycle for 35 cycles. LDR reactions were run for 15 sec at 94° C., and 4 min. at 65° C. per cycle for 20 cycles. Reactions were completely stopped by chilling the tubes in an ethanol-dry ice bath, and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan TAMRA 350 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were quantified using the ABI GeneScan 672 software. The data were analyzed and the results are presented in FIG. 42 (called mutation) where they are compared with the results determined by dideoxy-sequencing (expected mutation).

FIG. 43 is a table comparing 10 discordant samples from the PCR/LDR process described above with reference to FIGS. 41–42.

Figure 44:
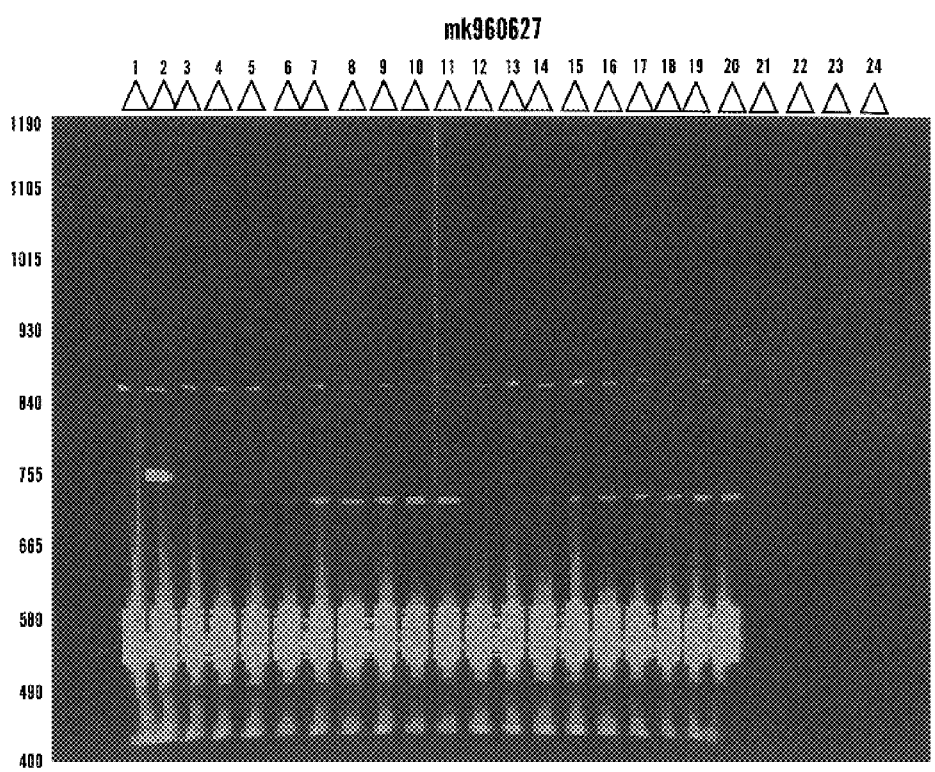
Figures 45A, 45B:
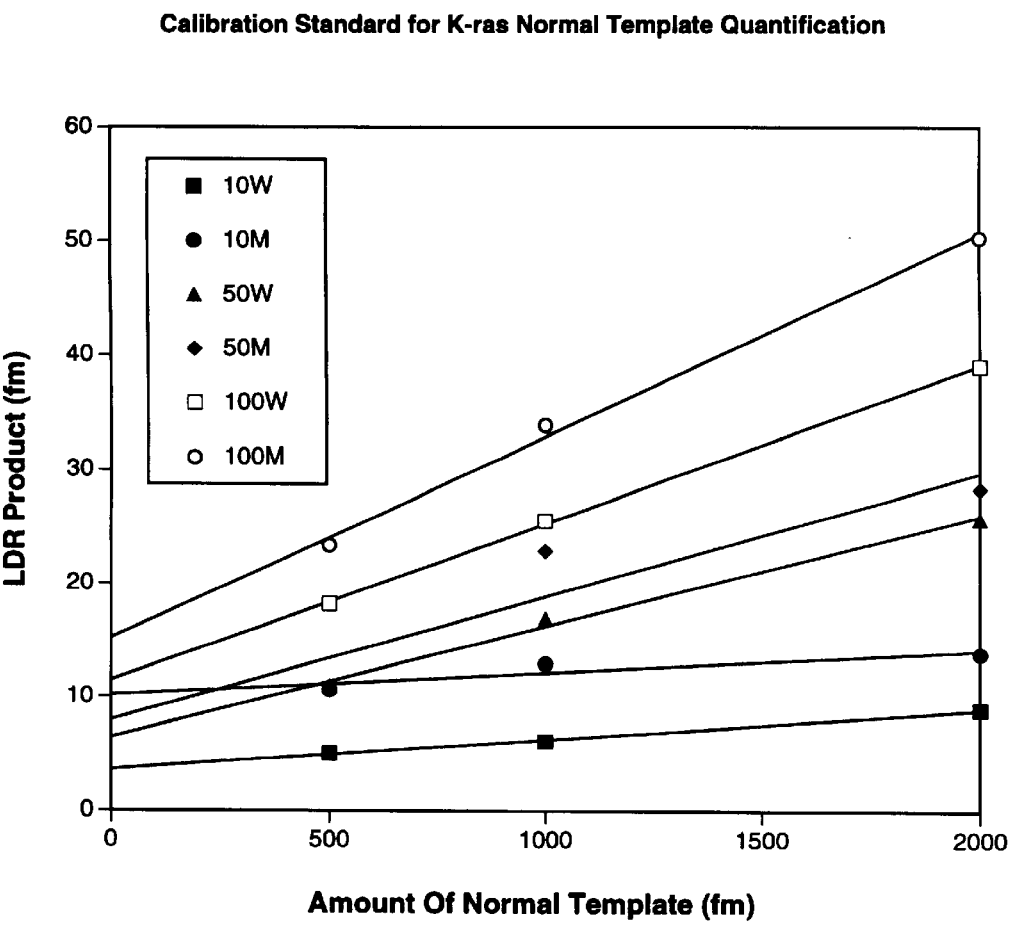

FIGS. 44 and 45A–B show the quantitative detection of different amounts of K-ras Normal template when varying amounts of wild-type probes were used by either wild-type or K294R Tth DNA ligase. Amount of LDR product formed when 25 nM (500 fmol), 50 nM (1000 fmol), and 100 nM (2000 fmol) of the "Normal" template was reacted with 0.5 nM (10 fmol), 2.5 nM (50 fmol), and 5 nM (100 fmol) of the wild type discriminating probe (Tet-K-ras c12.2 WtG) and common probe (K-ras c12 Com-2) in the presence of 25 nM (500 fmol) of nineteen discriminating probes (Tet-K-ras c12.2A, Tet-K-ras c12. 1 S, Tet-K-ras c12. 1 C, Tet-K-ras c13.4A, Tet-K-ras c13.3S, Tet-K-ras c13.3C, Tet-K-ras c61.7HT, Tet-K-ras c61.6R, Tet-K-ras c61.5K, Tet-K-ras c61.6P, Fam-K-ras c12.1R, Fam-K-ras c12.2D, Fam-K-ras c12.2V, Fam-K-ras c13.4D, Fam-K-ras c13.4V, Fam-K-ras c13.3R, Fam-K-ras c61.7HC, Fam-K-ras c61.6L, Fam-K-ras c61.5K); 50 nm (1000 fmol) of two common probes (K-ras c61 Com-7 and K-ras c12 Com-5); and 75 nm (1500 fmol) of five common probes (K-ras c12 Com-2, K-ras c12 Com-1, K-ras c13 Com-4, K-ras c13 Com-3, and K-ras c61 Com-6) and 5 nm (100 fmol) of the wild type or K294R mutant enzymes. LDR reactions were run for 15 sec at 94° C. and 4 min. at 65° C. per cycle for 20 cycles. The reactions were completely stopped by chilling the tubes in an ethanol-dry ice bath, and adding 0.5 µl of 0.5 mM EDTA. Aliquots of 2.5 µl of the reaction products were mixed with 2.5 µl of loading buffer (83% Formamide, 8.3 mM EDTA, and 0.17% Blue Dextran) and 0.5 µl GeneScan TAMRA 350 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were analyzed and parameters of an exponential equation fit to the data using the Deltagraph Pro 3.5. software. The X-axis indicated the different amounts of the Normal Template, while the Y-axis indicated the amount of LDR product generated. (■, ∆, □) represents 0.5 nM (10 fmol), 2.5 nM (50 fmol), and 5 nM (100 fmol), respectively of the wild type probes used with the wild-type enzyme whereas (●, ♦, ○) represents 0.5 (10 fmol), 2.5 nM (50 fmol), and 5 nM (100 fmol), of the wild type probes used with the K294R mutant enzyme.

DETAILED DESCRIPTION OF THE INVENTION

One aspect of the present invention relates to a method for detecting in a sample one or more minority target nucleotide sequences which differ from one or more majority target nucleotide sequences by one or more single-base changes, insertions, deletions, or translocations, wherein the minority target nucleotide sequences are present in the sample in lesser amounts than the majority nucleotide sequences.

One or more oligonucleotide probe sets are provided for use in conjunction with this method. Each set includes (a) a first oligonucleotide probe having a target-specific portion and (b) a second oligonucleotide probe having a target-specific portion. The oligonucleotide probes in a particular set are suitable for ligation together when hybridized adjacent to one another on a corresponding target nucleotide sequence, but have a mismatch which interferes with such ligation when hybridized to any other nucleotide sequence present in the sample.

The sample, the one or more oligonucleotide probe sets, and a ligase are blended to form a ligase detection reaction mixture. The ligase detection reaction mixture is subjected to one or more ligase detection reaction cycles comprising a denaturation treatment and a hybridization treatment. In the denaturation treatment, any hybridized oligonucleotides are separated from the target nucleotide sequences. The hybridization treatment involves hybridizing the oligonucleotide probe sets at adjacent positions in a base-specific manner to the respective target nucleotide sequences, if present in the sample. The hybridized oligonucleotide probes from each set ligate to one another to form a ligation product sequence containing the target-specific portions connected together. The ligation product sequence for each set is distinguishable from other nucleic acids in the ligase detection reaction mixture. The oligonucleotide probe sets may hybridize to adjacent sequences in the sample other than the respective target nucleotide sequences but do not ligate together due to the presence of one or more mismatches. When hydrizided oligonucleotide probes do not ligate, they individually separate during the denaturation treatment.

After the ligase detection reaction mixture is subjected to one or more ligase detection reaction cycles, ligation product sequences are detected. As a result, the presence of the minority target nucleotide sequence in the sample can be identified.

In effecting detection/quantification, there are 3 techniques of practicing the PCR/LDR process in accordance with the present invention with each being practiced using either of two formats. More particularly, the LDR phase can be carried out by (1) excluding wild-type allele-specific oligonucleotide probes from the LDR phase to avoid overwhelming signal from the minority mutant target and adding no marker, (2) excluding wild-type allele-specific oligonucleotide probes from the LDR phase but adding a marker to that phase, and (3) utilizing wild-type allele-specific oligonucleotide probes in the LDR phase at low levels and/or modified forms of those probes to yield less ligation product corresponding to the majority target which prevents signal from the minority mutant target from being overwhelmed. One detection format alternative involves use of capillary electrophoresis or gel electrophoresis and a fluorescent quantification procedure. Alternatively, detection can be carried out by capture on an array of capture oligonucleotide addresses and fluorescent quantification. These alternatives are explained more fully with reference to FIGS. 1–9.

Figure 1:
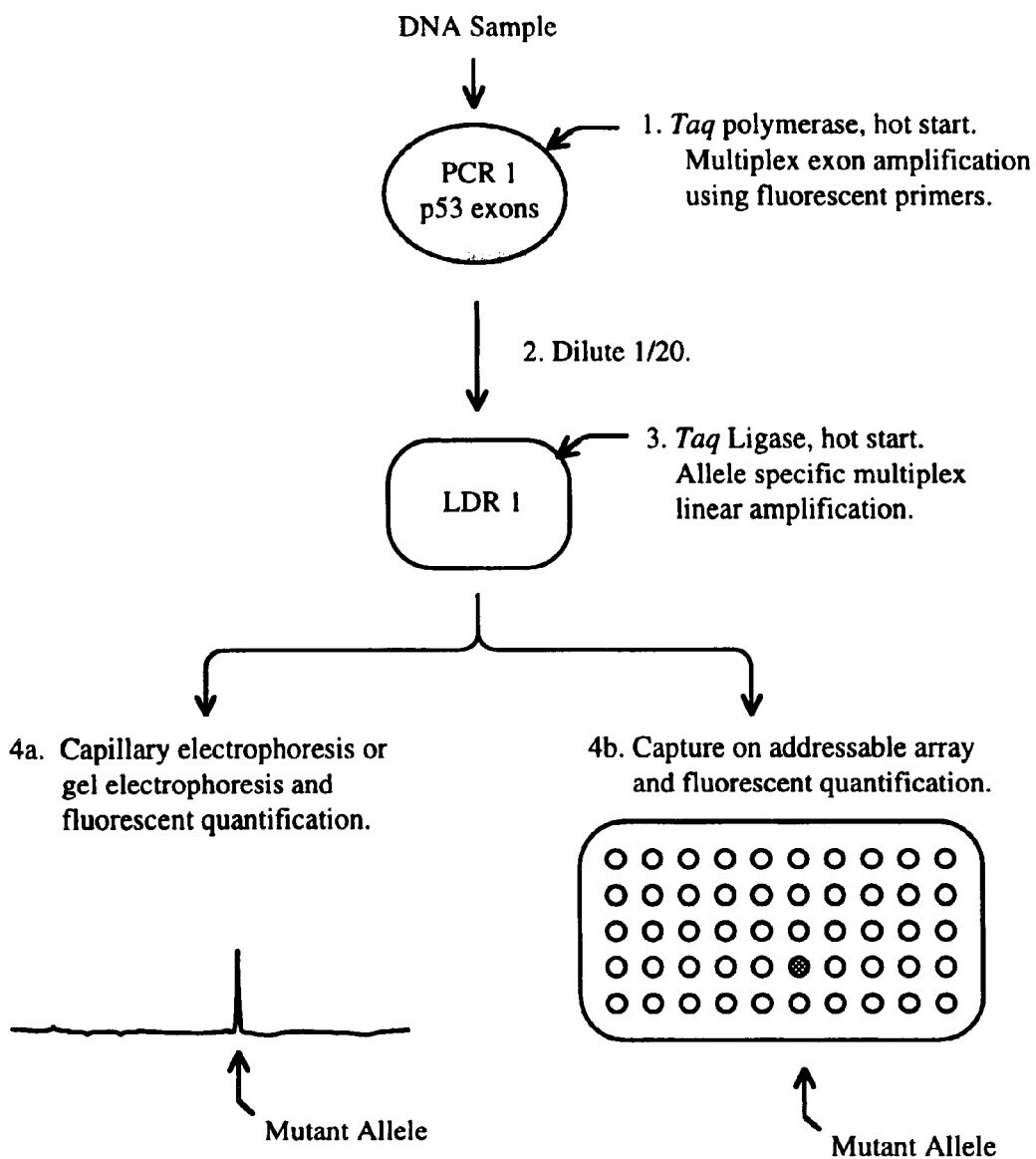
FIG. 1 is a flow diagram depicting a PCR/LDR process for detection of cancer-associated mutations by electrophoresis or capture on an addressable array where wild-type allele-specific oligonucleotide probes are excluded from the LDR phase to avoid overwhelming signal from minority mutant target and no marker is added to the LDR phase.

FIG. 1 depicts the detection of cancer-associated mutations where wild-type allele-specific oligonucleotide probes are excluded from the LDR phase to avoid overwhelming signal from minority mutant target and no marker is added to the LDR phase. In step 1, after DNA sample preparation, multiple exons are subjected to PCR amplification using Taq polymerase under hot start conditions with target-specific oligonucleotide primers. The extension products produced during PCR are then diluted 1/20 during step 2. In step 3, the extension products are mixed with oligonucleotide probes containing allele-specific portions and common portions and the LDR phase of the process is initiated by addition of Taq ligase under hot start conditions. During LDR, oligonucleotide probes ligate to their adjacent oligonucleotide only in the presence of target sequence which gives perfect complementarity at the ligation junction. Absence of wild-type allele-specific oligonucleotide probes, and consequently absence of wild-type specific ligation product prevents the ligation detection reaction signal generated by minority mutant target from being overwhelmed.

The products can be detected by either of two formats. In the format of step 4a, products are separated by capillary gel electrophoresis, and fluorescent signals are quantified. On the other hand, in the format of step 4b, products are detected by specific hybridization to complementary sequences on an addressable array.

Figure 2:
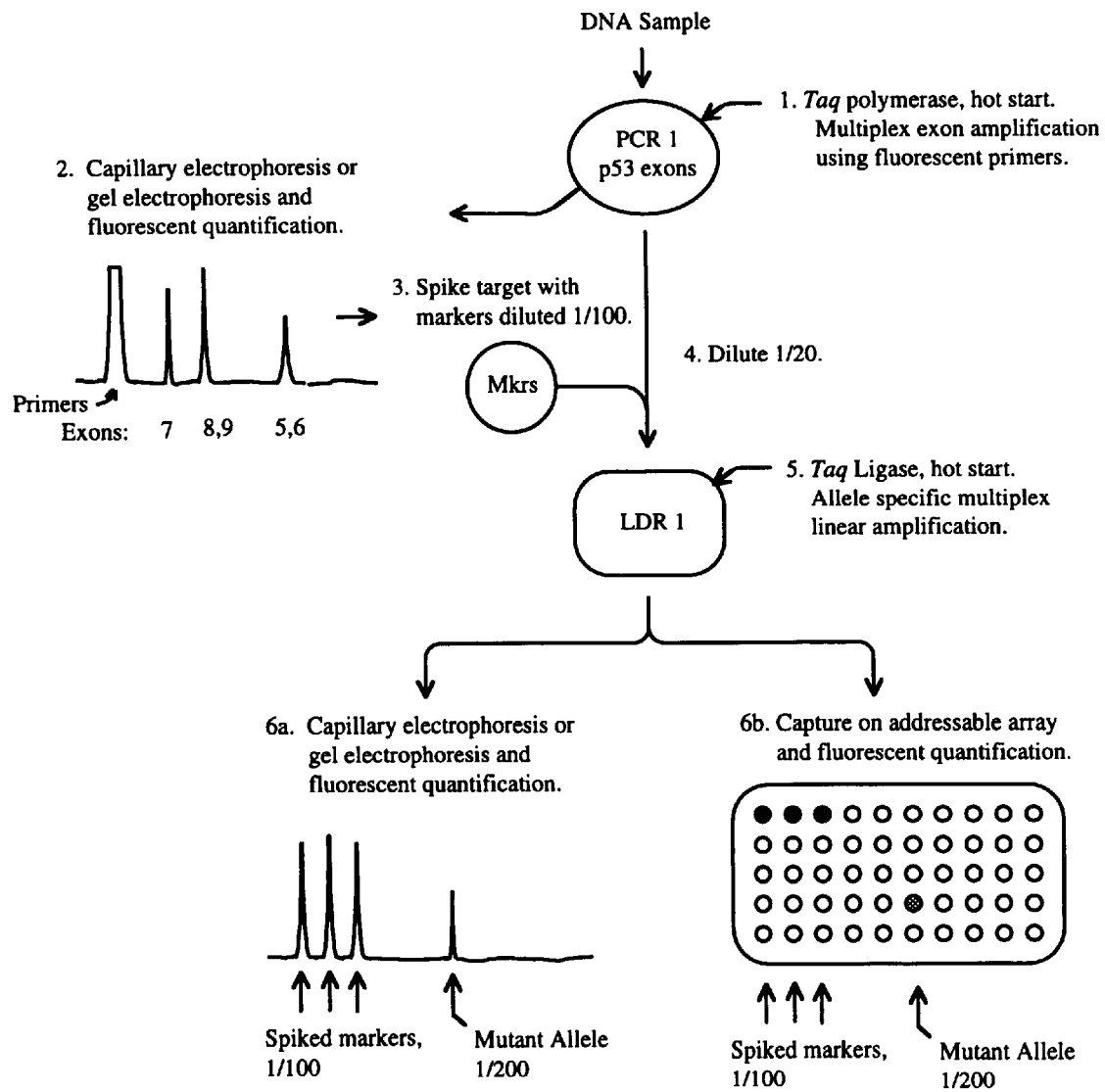
FIG. 2 is a flow diagram depicting a PCRILDR process for detection of cancer-associated mutations by electrophoresis or capture on an addressable array where wild-type allele-specific oligonucleotide probes are excluded from the LDR phase to avoid overwhelming signal from minority mutant target and a marker is added to the LDR phase.

FIG. 2 depicts the detection of cancer-associated mutations where wild-type allele-specific oligonucleotide probes are excluded from the LDR phase to avoid overwhelming signal from minority mutant target and a marker is added to the LDR phase. In step 1, after DNA sample preparation, multiple exons are subjected to PCR amplification using Taq polymerase under hot start conditions with target-specific oligonucleotide primers. Fluorescent quantification of PCR products can be achieved using capillary or gel electrophoresis in step 2. In step 3, the products are spiked with a 1/100 dilution of marker DNA (for each of the fragments). This DNA is homologous to wild type DNA, except it contains a mutation which is not observed in cancer cells, but which may be readily detected with the appropriate LDR probes. In step 4, the mixed DNA products from the PCR phase are then diluted 20-fold into fresh LDR buffer containing LDR oligonucleotide probes containing allele-specific portions and common portions. Step 5 involves the LDR phase of the process which is initiated by addition of Taq ligase under hot start conditions. During LDR, oligonucleotide probes ligate to their adjacent oligonucleotide probes only in the presence of target sequence which gives perfect complementarity at the junction site.

The products may be detected in either of two formats. In the format of step 6a, products are separated by capillary or gel electrophoresis, and fluorescent signals are quantified. Ratios of mutant peaks to marker peaks give the approximate amount of cancer-associated mutations present in the original sample divided by 100. In the format of step 6b, products are detected by specific hybridization to complementary sequences on an addressable array. Ratios of fluorescent signals in mutant dots to marker dots give the approximate amount of cancer mutations present in the original sample divided by 100.

Figure 3:
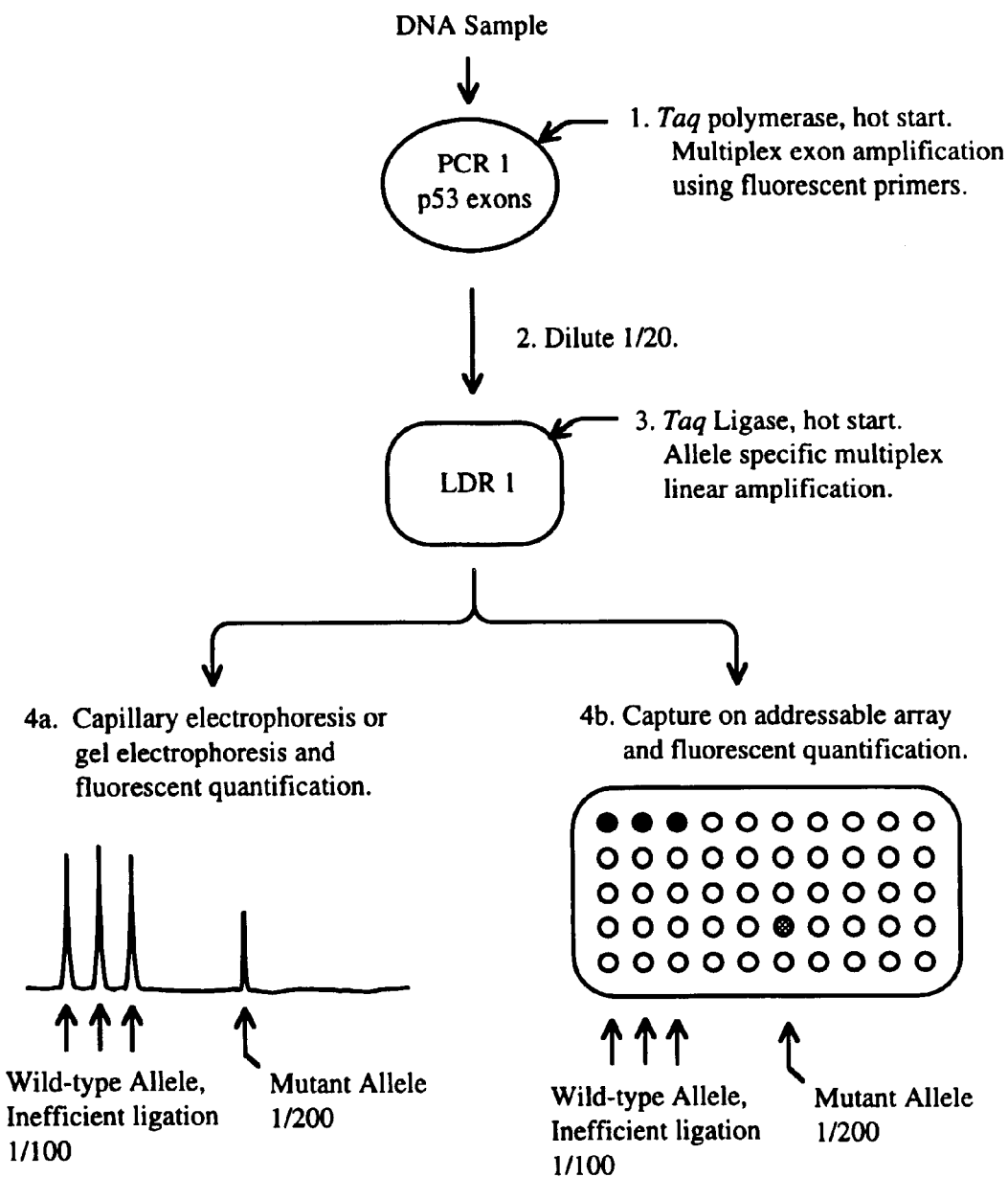
FIG. 3 is a flow diagram depicting a PCR/LDR process for detection of cancer-associated mutations by electrophoresis or capture on an addressable array where wild-type allele-specific oligonucleotide probes are utilized in the LDR phase at low levels and/or are modified to yield less ligation product corresponding to the majority target. This prevents the signal from minority mutant target from being overwhelmed.

FIG. 3 depicts the detection of additional cancer-associated mutations where additional wild-type allele-specific oligonucleotide probes are utilized in the LDR phase at low levels and/or are modified to yield less ligation product corresponding to the majority target. In step 1, after DNA sample preparation, multiple exons are subjected to PCR amplification using Taq polymerase under hot start conditions with target-specific oligonucleotide primers. The extension products produced during PCR are then diluted 1/20 during step 2. In step 3, the extension products are mixed with oligonucleotide probes containing allele-specific portions and common portions and the LDR phase of the process is initiated by addition of Taq ligase under hot start conditions. During LDR, oligonucleotide probes ligate to their adjacent oligonucleotide only in the presence of target sequence which gives perfect complementarity at the ligation junction. Due to the concentration and/or modification of the wild-type allele-specific oligonucleotide probes, the level of ligation product generated with these probes is comparable to the amount of ligation product generated from the minority target nucleotide sequences.

The products can be detected by either of two formats. In the format of step 4a, products are separated by capillary or gel electrophoresis, and fluorescent signal quantified. By way of example, consider the low level and/or modified wild-type allele-specific oligonucleotide probes ligating on a given amount of majority target nucleotide sequence (i.e. 1 picomole) generating the same amount of ligation product as generated from a given minority target sequence (using minority allele-specific oligonucleotide probes) present as a 100-fold dilution (i.e. 10 femtomoles) in the same amount (i.e. 1 picomole) of majority target nucleotide sequence. The ratio of mutant peaks to wild-type peaks gives the approximate amount of minority target (cancer-associated mutations) present in the original sample divided by 100. In the format of step 4b, products are detected by specific hybridization to complementary sequences on an addressable array. Amount of minority product is quantified as described above.

The ligase detection reaction is described generally in WO 90/17239 to Barany et al., F. Barany et al., "Cloning, Overexpression and Nucleotide Sequence of a Thermostable DNA Ligase-Encoding Gene," *Gene,* 109:1–11 (1991), and F. Barany, "Genetic Disease Detection and DNA Amplification Using Cloned Thermostable Ligase," *Proc. Natl. Acad. Sci. USA,* 88:189–193 (1991), the disclosures of which are hereby incorporated by reference. In accordance with the present invention, the ligase detection reaction can use 2 sets of complementary oligonucleotides. This is known as the ligase chain reaction which is described in the 3 immediately preceding references, which are hereby incorporated by reference. Alternatively, the ligase detection reaction can involve a single cycle which is known as the oligonucleotide ligation assay. See Landegren, et al., "A Ligase-Mediated Gene Detection Technique," *Science* 241:1077–80 (1988); Landegren, et al., "DNA Diagnostics—Molecular Techniques and Automation," *Science* 242:229–37 (1988); and U.S. Pat. No. 4,988,617 to Landegren, et al., which are hereby incorporated by reference.

During the ligase detection reaction phase, the denaturation treatment is carried out at a temperature of 80–105 C, while hybridization takes place at 50–85 C. Each cycle comprises a denaturation treatment and a thermal hybridization treatment which in total is from about one to five minutes long. Typically, the ligation detection reaction involves repeatedly denaturing and hybridizing for 2 to 50 cycles. The total time for the ligase detection reaction phase is 1 to 250 minutes.

The oligonucleotide probe sets can be in the form of ribonucleotides, deoxynucleotides, modified ribonucleotides, modified deoxyribonucleotides, modified phosphate-sugar-backbone oligonucleotides (described infra), nucleotide analogs, and mixtures thereof.

In one variation, the oligonucleotides of the oligonucleotide probe sets each have a hybridization or melting temperature (i.e. $T_m$) of 66–70 C. These oligonucleotides are 20–28 nucleotides long.

The oligonucleotide probe sets, as noted above, have a reporter label suitable for detection. Useful labels include chromophores, fluorescent moieties, enzymes, antigens, heavy metals, magnetic probes, dyes, phosphorescent groups, radioactive materials, chemiluminescent moieties, and electrochemical detecting moieties.

The polymerase chain reaction process is fully described in H. Erlich, et. al., "Recent Advances in the Polymerase Chain Reaction," Science 252: 1643–50 (1991); M. Innis, et. al., *PCR Protocols: A Guide to Methods and Applications,* Academic Press: New York (1990); and R. Saiki, et. al., "Primer-directed Enzymatic Amplification of DNA with a Thermostable DNA Polymerase," *Science* 239: 487–91 (1988), which are hereby incorporated by reference.

A particularly important aspect of the present invention is its capability to quantify the amount of target nucleotide sequence in a sample. This can be achieved in a number of ways by establishing standards which can be internal (i.e. where the standard establishing material is amplified and detected with the sample) or external (i.e. where the standard establishing material is not amplified, and is detected with the sample).

In accordance with one quantification method, the signal generated by ligation product sequences produced from the sample being analyzed, are detected. The strength of this signal is compared to a calibration curve produced from signals generated by ligation product sequences in samples with known amounts of target nucleotide sequence. As a result, the amount of target nucleotide sequence in the sample being analyzed can be determined. This technique involves use of an external standard.

Another quantification method, in accordance with the present invention, relates to an internal standard. Here, a known amount of one or more marker target nucleotide sequences is added to the sample. In addition, one or a plurality of marker-specific oligonucleotide probe sets are added along with the ligase, the previously-discussed oligonucleotide probe sets, and the sample to a mixture. The marker-specific oligonucleotide probe sets have (1) a first oligonucleotide probe with a target-specific portion complementary to the marker target nucleotide sequence, and (2) a second oligonucleotide probe with a target-specific portion complementary to the marker target nucleotide sequence and a detectable reporter label. The oligonucleotide probes in a particular marker-specific oligonucleotide set are suitable for ligation together when hybridized adjacent to one another on a corresponding marker target nucleotide sequence. However, there is a mismatch which interferes with such ligation when hybridized to any other nucleotide sequence present in the sample or added marker sequences. The presence of ligation product sequences is identified by detection of reporter labels. The amount of target nucleotide sequences in the sample is then determined by comparing the amount of ligation product sequence generated from known amounts of marker target nucleotide sequences with the amount of other ligation product sequences.

Another quantification method, in accordance with the present invention, involves analysis of a sample containing two or more of a plurality of target nucleotide sequences with a plurality of sequence differences. Here, ligation product sequences corresponding to the target nucleotide sequences are detected and distinguished by any of the previously-discussed techniques. The relative amounts of the target nucleotide sequences in the sample are then quantified by comparing the relative amounts of ligation product sequences generated. This provides a quantitative measure of the relative level of the target nucleotide sequences in the sample.

Another quantification method, in accordance with the present invention, involves analysis of a sample containing two or more of a plurality of target nucleotide sequences with a plurality of sequence differences, where one or more target nucleotide sequences is in excess (majority) over other minority target nucleotide sequences. Here, in addition to the allele-specific oligonucleotide probes for the minority target nucleotide sequences, modified wild-type allele-specific oligonucleotide probes are also utilized in the LDR phase at low levels and/or are modified to yield less ligation product corresponding to the majority target. The presence of both minority target specific ligation products and majority target specific ligation products is identified by detection of reporter labels. The amount of minority target nucleotide sequences in the sample is determined by comparing the amount of low yield ligation product sequences generated from the majority target nucleotide sequences with the amount of other ligation products.

The preferred thermostable ligase is that derived from *Thermus aquaticus*. This enzyme can be isolated from that organism. M. Takahashi, et al., "Thermophillic DNA Ligase," *J. Biol. Chem.* 259:10041–47 (1984), which is hereby incorporated by reference. Alternatively, it can be prepared recombinantly. Procedures for such isolation as well as the recombinant production of Thermus aquaticus ligase (as well as *Thermus themophilus* ligase) are disclosed in WO 90/17239 to Barany, et. al., and F. Barany, et al., "Cloning, Overexpression and Nucleotide Sequence of a Thermostable DNA-Ligase Encoding Gene," *Gene* 109:1–11 (1991), which are hereby incorporated by reference. These references contain complete sequence information for this ligase as well as the encoding DNA. Other suitable ligases include *E. coli* ligase, T4 ligase, and Pyrococcus ligase.

The ligation detection reaction mixture may include a carrier DNA, such as salmon sperm DNA.

The hybridization step in the ligation detection reaction, which is preferably a thermal hybridization treatment discriminates between nucleotide sequences based on a distinguishing nucleotide at the ligation junctions. The difference between the target nucleotide sequences can be, for example, a single nucleic acid base difference, a nucleic acid deletion, a nucleic acid insertion, or rearrangement. Such sequence differences involving more than one base can also be detected. Preferably, the oligonucleotide probe sets have substantially the same length so that they hybridize to target nucleotide sequences at substantially similar hybridization conditions. As a result, the process of the present invention is able to detect infectious diseases, genetic diseases, and cancer. It is also useful in environmental monitoring, forensics, and food science.

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli*, Salmonella, Shigella, Klebsiella, Pseudomonas, *Listeria monocytogenes, Mycobacterium tuberculosis, Mycobacterium aviumintracellulare*, Yersinia, Francisella, Pasteurella, Brucella, Clostridia, *Bordetella pertussis*, Bacteroides, *Staphylococcus aureus, Streptococcus pneumonia, B-Hemolytic strep., Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis*, Rickettsial pathogens, Nocardia, and Acitnomycetes.

Fungal infectious agents which can be detected by the present invention include *Cryptococcus neoformans, Blastomyces dermatitidis, Histoplasma capsulatum, Coccidioides immitis, Paracoccidioides brasiliensis, Candida albicans*, Aspergillusfumigautus, Phycomycetes (Rhizopus), *Sporothrix schenckii*, Chromomycosis, and Maduromycosis.

Viral infectious agents which can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus*, Leishmania, Trypanosoma spp., Schistosoma spp., *Entamoeba histolytica*, Cryptosporidum, Giardia spp., Trichimonas spp., *Balatidium coli, Wuchereria bancrofti*, Toxoplasma spp., *Enterobius vermicularis, Ascaris lumbricoides, Trichuris trichiura, Dracunculus*

*medinesis*, trematodes, *Diphyllobothrium latum*, Taenia spp., *Pneumocystis carinii*, and *Necator americanis*.

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Cancers which can be detected by the process of the present invention generally involve oncogenes, tumor suppressor genes, or genes involved in DNA amplification, replication, recombination, or repair. Examples of these include: BRCA1 gene, p53 gene, APC gene, Her2/Neu amplification, Bcr/Abl, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

Desirably, the oligonucleotide probes are suitable for ligation together at a ligation junction when hybridized adjacent to one another on a corresponding target nucleotide sequence due to perfect complementarity at the ligation junction. However, when the oligonucleotide probes in the set are hybridized to any other nucleotide sequence present in the sample, there is a mismatch at a base at the ligation junction which interferes with ligation. Most preferably, the mismatch is at the base at the 3' base at the ligation junction. Alternatively, the mismatch can be at the bases adjacent to bases at the ligation junction.

As noted supra, detection and quantification can be carried out using capillary or gel electrophoresis or on a solid support with an array capture oligonucleotides.

Figure 4:
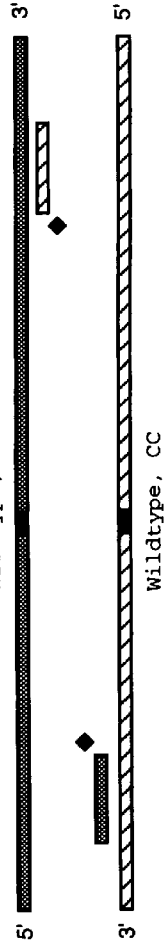
FIG. 4 is a schematic diagram depicting the PCR/LDR process of FIG. 1 using electrophoresis to separate ligation products.

FIG. 4 is a schematic diagram depicting the PCR/LDR process of FIG. 1 using electrophoresis to separate ligation products. More particularly, this diagram relates to detection of codon 12 of the K-ras gene which has a GGT sequence that codes for glycine ("Gly"). A small percentage of the cells contain the G to A mutation in GAT, which codes for aspartic acid ("Asp"). As illustrated, this process involves an initial PCR amplification in step 1, an LDR procedure in step 2, and a separation of fluorescent products followed by quantification in step 3. Alternatively, step 3 can involve ethidium bromide staining or running an additional LDR reaction on diluted product using normal oligonucleotide probes (See FIGS. 23 and 29 infra). The LDR probes for wild-type (i.e. normal) sequences are missing from the reaction. If the normal LDR probes (with the discriminating base being G) were included, they would ligate to the common probes and overwhelm any signal coming from the minority mutant target. Instead, as shown in FIG. 4, the existence of a 44 base ligation product sequence with fluorescent label F1 coupled to a single nucleotide (designated $N_1$) and the $A_n$ tail indicates the presence of the aspartic acid encoding mutant. This ligation product sequence has the same F1 label as that formed by the existence of the arginine and valine encoded mutations. However, these sequences are distinguishable by virtue of their different lengths due to different length tails and different numbers of nucleotides N coupling the label to the remainder of the ligation product sequence. More particularly, the presence of an F1 labelled, 48 base ligation product sequence suggests the presence of the arginine encoding codon, while the presence of an F1 labelled, 46 base ligation product sequence indicates the presence of the valine encoding codon. These ligation product sequences are distinguished by size with the longer products having a lower electrophoretic mobility. The F2 labelled ligation products are similarly distinguished by their length which varies as a result of the different length tails and the number of nucleotides N coupling the label to the remainder of the ligation product sequence. More particularly, the 49 base ligation product sequence (due to 2 nucleotides N coupling the label and the $A_{n+4}$ tail) indicates the presence of the cysteine encoding codon, the 47 base ligation product sequence (due to no nucleotides N coupling the label and the $A_{n+4}$ tail) indicates the presence of the serine encoding codon, and the 45 base ligation product sequence (due to 2 nucleotides N coupling the label and the $A_n$ tail) indicates the presence of the alanine encoding codon.

FIG. 5 is a schematic diagram depicting the PCR/LDR process of FIG. 2 using electrophoresis to separate ligation products. More particularly, this diagram relates to detection of codon 12 of the K-ras gene which has a GGT sequence that codes for glycine ("Gly"). A small percentage of the cells contain the G to A mutation in GAT, which codes for aspartic acid ("Asp"). As illustrated, this process involves an initial PCR amplification in step 1, an LDR procedure in step 2, and a separation of fluorescent products followed by quantification in step 3. After amplification, the PCR products are quantified. A marker template is added prior to the LDR phase where both allele-specific and marker-specific oligonucleotide probes are utilized. The LDR probes for wild-type (i.e. normal) sequences are missing from the reaction. If the normal LDR probes (with the discriminating base being G) were included, they would ligate to the common probes and overwhelm any signal coming from the minority mutant target. Instead, as shown in FIG. 5, the existence of a 44 base ligation product sequence with fluorescent label F1 coupled to a single nucleotide (designated $N_1$) and the $A_n$ tail indicates the presence of the aspartic acid encoding mutant. This ligation product sequence has the same F1 label as that formed by the existence of the arginine and valine encoded mutations. However, these sequences are distinguishable by virtue of their different lengths due to different length tails and different numbers of nucleotides N coupling the label to the remainder of the ligation product sequence. More particularly, the presence of an F1 labelled, 48 base ligation product sequence suggests the presence of the arginine encoding codon, while the presence of an F1 labelled, 46 base ligation product sequence indicates the presence of the valine encoding codon. These ligation product sequences are distinguished by size with the longer products having a lower electrophoretic mobility. The F2 labelled ligation products are similarly distinguished by their length which varies as a result of the different length tails and the number of nucleotides N coupling the label to the remainder of the ligation product sequence. More particularly, the 49 base ligation product sequence (due to 2 nucleotides N coupling the label and the $A_{n+4}$ tail) indicates the presence of the cysteine encoding codon, the 47 base ligation product sequence (due to no nucleotides N coupling the label and the $A_{n+4}$ tail) indicates the presence of the serine encoding codon, and the 45 base ligation product sequence (due to 2 nucleotides N coupling the label and the $A_n$ tail) indicates the presence of the alanine encoding codon. The ligation product formed by the marker-specific oligonucleotide probe is 43 bases and has the $F_2$ label (due to 0 nucleotides N coupling the label and the $A_n$ tail). As discussed above, the amount of minority target nucleotide sequences in the sample is determined by comparing the amount of ligation product sequence generated from known amounts of marker target nucleotide sequences with the amount of other ligation product sequences.

Figure 6:
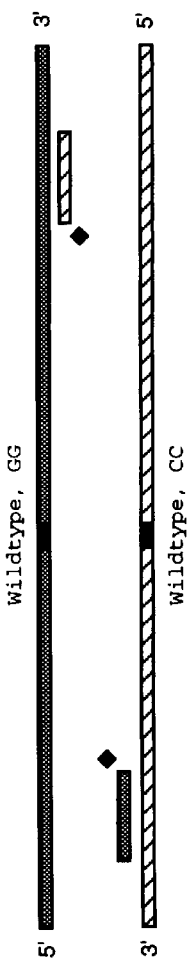
FIG. 6 is a schematic diagram depicting the PCR/LDR process of FIG. 3 using electrophoresis to separate ligation products.

FIG. 6 is a schematic diagram depicting the PCR/LDR process of FIG. 3 using electrophoresis to separate ligation products. More particularly, this diagram relates to detection of codon 12 of the K-ras gene which has a <u>GGT</u> sequence that codes for glycine ("Gly"). A small percentage of the cells contain the G to A mutation in <u>GAT</u>, which codes for aspartic acid ("Asp"). As illustrated, this process involves an initial PCR amplification in step 1, an LDR procedure in step 2, and a separation of fluorescent products followed by quantification in step 3. The LDR probes for wild-type (i.e. normal) sequences are used at low level and/or are modified to yield less ligation product sequence corresponding to wild type target nucleotide sequence. As shown in FIG. 6, the existence of a 44 base ligation product sequence with fluorescent label F1 coupled to a single nucleotide (designated $N_1$) and the An tail indicates the presence of the aspartic acid encoding mutant. This ligation product sequence has the same F1 label as that formed by the existence of the arginine and valine encoded mutations. However, these sequences are distinguishable by virtue of their different lengths due to different length tails and different numbers of nucleotides N coupling the label to the remainder of the ligation product sequence. More particularly, the presence of an F1 labelled, 48 base ligation product sequence suggests the presence of the arginine encoding codon, while the presence of an F1 labelled, 46 base ligation product sequence indicates the presence of the valine encoding codon. These ligation product sequences are distinguished by size with the longer products having a lower electrophoretic mobility. The F2 labelled ligation products are similarly distinguished by their length which varies as a result of the different length tails and the number of nucleotides N coupling the label to the remainder of the ligation product sequence. More particularly, the 49 base ligation product sequence (due to 2 nucleotides N coupling the label and the $A_{n+4}$ tail) indicates the presence of the cysteine encoding codon, the 47 base ligation product sequence (due to no nucleotides N coupling the label and the $A_{n+4}$ tail) indicates the presence of the serine encoding codon, and the 45 base ligation product sequence (due to 2 nucleotides N coupling the label and the $A_n$ tail) indicates the presence of the alanine encoding codon. The ligation product formed by the wild type allele-specific oligonucleotide probe is 43 bases and has the $F_2$ label (due to 0 nucleotides N coupling the label and the $A_n$ tail). In the labelled probe forming that ligation product, there is a base N located 3 base positions away from the ligation junction which can be either the conventional, proper nucleotide for the wild type target (if that probe is used at low level), or a mismatch, or a nucleotide base analogue. Use of a mismatched nucleotide, a nucleotide base analogue, and/or a modification in the sugar phosphate backbone reduces the amount of ligation product formed off wild-type target. Thus, the presence of wild type target can be detected without overwhelming the signal generated by the presence of minority mutant target. The amount of minority target nucleotide sequences in the sample is determined by comparing the amount of low yield ligation product sequences generated from the majority target nucleotide sequences with the amount of other ligation products.

FIGS. 4–6 show the use of the ligase detection reaction to detect mismatches at the 3' end of the distinguishing oligonucleotide probe. In other cases, however, the mismatch can be at the penultimate position to the 3' end or and the third position away from the 3' end.

The use of capillary and gel electrophoresis for such purposes is well known. See e.g., Grossman, et. al., "High-density Multiplex Detection of Nucleic Acid Sequences: Oligonucleotide Ligation Assay and Sequence-coded Separation," *Nucl. Acids Res.* 22(21): 4527–34 (1994), which is hereby incorporated by reference.

FIG. 7 is a schematic diagram depicting the PCR/LDR process of FIG. 1 for detection of cancer-associated mutations at adjacent alleles using an addressable array. FIG. 7 relates to the detection of codon 12 of the K-ras gene which has a wild-type <u>GGT</u> sequence that codes for glycine ("Gly") and minority mutant <u>GAT</u> sequence coding for aspartic acid ("Asp"). The process of FIG. 7 involves an initial PCR amplification in step 1, an LDR procedure in step 2, and capture on a solid support in step 3. As in FIG. 4, the LDR probes for the wild-type target sequence are missing from the reaction to avoid overwhelming signal produced by the mutant target sequence. According to this embodiment of the present invention, as shown in FIG. 7, the presence of the aspartic acid encoding <u>GGT</u> sequence produces a ligation product sequence with label F and addressable array-specific portion Z4. The existence of such a ligation product sequence is indicated by the presence of a nucleic acid, having label F, hybridized at an address on a solid support with a capture oligonucleotide complementary to addressable array-specific portion Z4. As shown in FIG. 7, the support has an array of addresses with capture oligonucleotides complementary to different addressable array-specific portions Z1 to Z6. Since common oligonucleotide probes with label F are used, by observing which site on the solid support they hybridize to, different ligation product sequences are distinguished.

Figure 8:
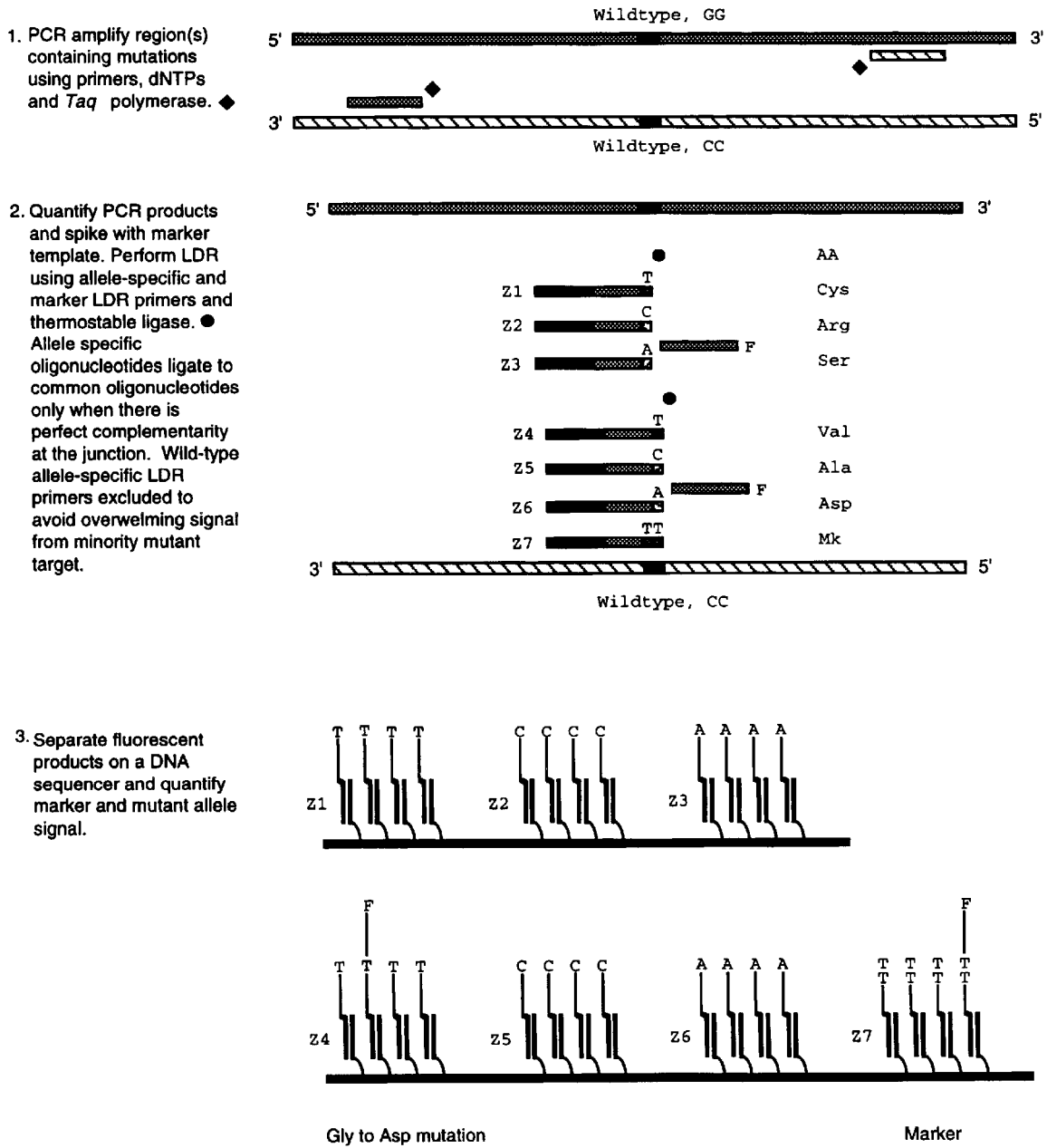
FIG. 8 is a schematic diagram depicting the PCR/LDR process of FIG. 2 using an addressable array.

FIG. 8 is a schematic diagram depicting the PCR/LDR process of FIG. 2 for detection of cancer-associated mutations at adjacent alleles using an addressable array. FIG. 8 relates to the detection of codon 12 of the K-ras gene which has a wild-type GGT sequence that codes for glycine ("Gly") and minority mutant GAT sequence coding for aspartic acid ("Asp"). The process of FIG. 8 involves an inital PCR amplification in step 1, an LDR procedure in step 2, and capture on a solid support in step 3. As in FIG. 5, the LDR probes for the wild-type target sequence are missing from the reaction to avoid overwhelming signal produced by the mutant target sequence. According to this embodiment of the present invention, as shown in FIG. 8, the presence of the aspartic acid encoding AT sequence produces a ligation product sequence with label F and addressable array-specific portion Z4. The existence of such a ligation product sequence is indicated by the presence of a nucleic acid, having label F, hybridized at an address on a solid support with a capture oligonucleotide complementary to addressable array-specific portion Z4. As shown in FIG. 8, the support has an array of addresses with capture oligonucleotides complementary to different addressable array-specific portions Z1 to Z7. Since common oligonucleotide probes with label F are used, by observing which site on the solid support they hybridize to, different ligation product sequences are distinguished. The presence of ligation product sequence produced from a marker-specific probe is indicated by the existence of a nucleic acid, having label F, hybridized at an address on a solid support with a capture oligonucleotide complementary to addressable array-specific portion Z7. The amount of target nucleotide sequences in the sample is determined by comparing the amount of ligation product sequence generated from known amounts of marker target nucleotide sequences with the amount of other ligation product sequences.

FIG. 9 is a schematic diagram depicting the PCR/LDR process of FIG. 3 for detection of cancer-associated mutations at adjacent alleles using an addressable array. FIG. 9 relates to the detection of codon 12 of the K-ras gene which has a wild-type GGT sequence that codes for glycine ("Gly") and minority mutant GAT sequence coding for aspartic acid ("Asp"). The process of FIG. 9 involves an inital PCR amplification in step 1, an LDR procedure in step 2, and capture on a solid support in step 3. The LDR probes for wild-type (i.e. normal) sequences are used at low level and/or are modified to yield less ligation product sequence corresponding to wild type target nucleotide sequence. According to this embodiment of the present invention, as shown in FIG. 9, the presence of the aspartic acid encoding GAT sequence produces a ligation product sequence with label F and addressable array-specific portion Z4. The existence of such a ligation product sequence is indicated by the presence of a nucleic acid, having label F, hybridized at an address on a solid support with a capture oligonucleotide complementary to addressable array-specific portion Z4. As shown in FIG. 9, the support has an array of addresses with capture oligonucleotides complementary to different addressable array-specific portions Z1 to Z7. Since common oligonucleotide probes with label F are used, different ligation product sequences are distinguished by which site on the solid support they hybridize to. The ligation product formed by the wild type allele-specific oligonucleotide probe is indicated by the existence of a nucleic acid, having label F, hybridized at an address on a solid support with a capture oligonucleotide complementary to addressable array-specific portion Z7. In the labelled probe forming that ligation product, there is a base N located 3 base positions away from the ligation junction that can be either a conventional nucleotide for the wild type target (if that probe is used at low level), or a mismatch nucleotide, or a nucleotide base analogue. Use of a mismatched nucleotide, a nucleotide base analogue, and/or a modification in the sugar phosphate backbone reduces the amount of ligation product formed off wild-type target. Thus, the presence of wild type target can be detected without overwhelming the signal generated by the presence of minority mutant target. The amount of minority target nucleotide sequences in the sample is determined by comparing the amount of low yield ligation product sequences generated from the majority target nucleotide sequences with the amount of other ligation products.

The use of a solid support with an array of capture oligonucleotides is fully disclosed in pending provisional U.S. patent application Ser. No. 60/011,359, which is hereby incorporated by reference. When using such arrays, the oligonucleotide probes used in the above-described LDR phase have an addressable array-specific portion. After the LDR phase is completed, the addressable array-specific portions for the products of such processes remain single stranded and are caused to hybridize to the capture oligonucleotides during a capture phase. See Newton, et al., "The Production of PCR Products With 5' Single-Stranded Tails Using Primers That Incorporate Novel Phosphoramidite Intermediates," *Nucl. Acids Res.* 21(5): 1155–62 (1993), which is hereby incorporated by reference.

During the capture phase of the process, the mixture is contacted with the solid support at a temperature of 45–90 C and for a time period of up to 60 minutes. Hybridizations may be accelerated by adding cations, volume exclusion or chaotropic agents. When an array consists of dozens to hundreds of addresses, it is important that the correct ligation product sequences have an opportunity to hybridize to the appropriate address. This may be achieved by the thermal motion of oligonucleotides at the high temperatures used, by mechanical movement of the fluid in contact with the array surface, or by moving the oligonucleotides across the array by electric fields. After hybridization, the array is washed sequentially with a low stringency wash buffer and then a high stringency wash buffer.

It is important to select capture oligonucleotides and addressable nucleotide sequences which will hybridize in a stable fashion. This requires that the oligonucleotide sets and the capture oligonucleotides be configured so that the oligonucleotide sets hybridize to the target nucleotide sequences at a temperature less than that which the capture oligonucleotides hybridize to the addressable array-specific portions. Unless the oligonucleotides are designed in this fashion, false positive signals may result due to capture of adjacent unreacted oligonucleotides from the same oligonucleotide set which are hybridized to the target.

The capture oligonucleotides can be in the form of ribonucleotides, deoxyribonucleotides, modified ribonucleotides, modified deoxyribonucleotides, peptide nucleotide analogues, modified peptide nucleotide analogues, modified phosphate-sugar backbone oligonucleotides, nucleotide analogues, and mixtures thereof.

Where an array is utilized, the detection phase of the process involves scanning and identifying if LDR products have been produced and correlating the presence of such products to a presence or absence of the target nucleotide sequence in the test sample. Scanning can be carried out by scanning electron microscopy, confocal microscopy, charge-coupled device, scanning tunneling electron microscopy, infrared microscopy, atomic force microscopy, electrical conductance, and fluorescent or phosphor imaging. Correlating is carried out with a computer.

The present invention is useful in distinguishing a minority target nucleotide sequence from the majority nucleotide sequence in a sample at a respective ratio of 1:500 for a G:T or T:G mismatch between the majority target nucleotide sequence and one of the oligonucleotide probes. Further, this method can distinguish a minority target nucleotide sequence from the majority nucleotide sequence in a sample at a respective ratio of 1:2000 for other than a G:T or T:G mismatch between the majority target nucleotide sequence and one of the oligonucleotide probes.

For low abundance multiple allele differences at multiple nearby or adjacent positions, the process of the present invention distinguishes minority target nucleotide sequences from the majority target sequence at a respective ratio of 1:100 for all mismatches between the majority target nucleotide sequence and one of the oligonucleotide probes. In such situations, the minority target nucleotide sequence to majority target nucleotide sequence respective ratio is 1:500 for other than G:T or T:G mismatches between the majority target nucleotide sequence and one of the oligonucleotide probes.

The second aspect of the present invention also relates to a method for identifying one or more of a plurality of sequences differing by one or more single-base changes, insertions, deletions, or translocations in a plurality of target nucleotide sequences. As noted above, a sample and one or more oligonucleotide probe sets are blended with a ligase to form a ligase detection reaction mixture. The ligase detection reaction mixture is subjected to one or more ligase detection reaction cycles, and the presence of ligation product sequences is detected. Here, however, a thermostable mutant ligase is utilized. This ligase is characterized by a fidelity ratio which is defined as the initial rate constant for ligating the first and second oligonucleotide probes hybridized to a target nucleotide sequence with a perfect match at the ligation junction between the target nucleotide sequence and the oligonucleotide probe having its 3' end at the ligation junction to the initial rate constant for ligating the first and second oligonucleotide probes hybridized to a target with a mismatch at the ligation junction between the target nucleotide sequence and the oligonucleotide probe having its 3' end dt the ligation junction. The fidelity ratio for the thermostable mutant ligase is greater than the fidelity ratio for wild-type ligase.

The use of a mutant ligase in accordance with the process of the present invention can be explained as follows. The specificity of an enzymatic reaction is determined by the catalytic constant, $k_{cat}$, and the apparent binding constant, $K_M$, and expressed as the specificity constant $k_{cat}/K_M$. Any modifications made on the enzyme itself, substrate, or reaction conditions, which affect $k_{cat}$ or $K_M$ or both, will change the specificity. The use of a mutant enzyme may influence the stability of the perfect matched and mismatched enzyme-DNA complexes to a different extent, so that discrete $K_M$ effects are exerted on these ligation reactions. In a competitive reaction, such as ligation of perfectly matched and mismatched substrates, the ratio of the specificity constant may be altered as a consequence of $K_M$, and possible $k_{cat}$ changes for each substrate. All mutant enzymes which satisfy the equation below (shown for K294R) will give increased discrimination of cancer-associated mutations in the presence of an excess of normal DNA.

$$\frac{[k_{cat}/K_M]_{K294R,match}}{[k_{cat}/K_M]_{K294R,mismatch}} > \frac{[k_{cat}/K_M]_{Wt,match}}{[k_{cat}/K_M]_{Wt,mismatch}}$$

Alternatively, the second aspect of the present invention can be expressed in terms of a fidelity ratio (i.e. the initial rate of ligating a substrate with a perfect match at the 3' end divided by the initial rate of ligating a substrate with a mismatch at the 3' end) as follows:

$$\frac{[k_1]_{K294R,match}}{[k_1]_{K294R,mismatch}} > \frac{[k_1]_{Wt,match}}{[k_1]_{Wt,mismatch}} = \text{Fidelity ratio}$$

In the above equation, $[k1]_{match}$ represents the initial rate constant for ligating the first and second oligonucleotide probes hybridized to a target nucleotide sequence with a perfect match at the ligation junction between the target nucleotide sequence and the oligonucleotide probe having its 3' end at the ligation junction. $[k_1]_{mismatch}$ represents the initial rate constant for ligating the first and second oligonucleotide probes hybridized to a target with a mismatch at the ligation junction between the target nucleotide sequence and the oligonucleotide probe having its 3' end at the ligation junction. For the mutant thermostable ligase, $[k_1]_{match}$ divided by $[k_1]_{mismatch}$ (=fidelity ratio) is greater than the fidelity ratio for wild-type ligase. All mutant enzymes which satisfy the equation above (shown for K294R) will give increased discrimination of cancer-associated mutations in the presence of an excess of normal DNA. This can also be stated more generally and in terms of a signal to noise ratio as follows:

$$\frac{[LDR\ product]_{minority\ target} + [LDR\ product]_{majority\ target}}{[LDR\ product]_{majority\ target}} =$$

Signal-to-noise ratio

In the above equation, $[LDR\ product]_{minority\ target}$ represents the amount of ligation product sequences produced when the first and second oligonucleotide probes hybridize to a minority target nucleotide sequence and the oligonucleotide probe having its 3' end at the ligation junction. $[LDR\ product]_{majority\ target}$ represents the amount of ligation product sequences produced when the same first and second oligonucleotide probes hybridize to the majority target nucleotide sequence with a mismatch at the ligation junction between the majority target nucleotide sequence and the oligonucleotide probe having its 3' end at the ligation junction. The ligase has a signal-to-noise ratio, for the amount of ligation product sequences produced from both the minority and majority target nucleotide sequences divided by the amount of ligation product sequences produced from the same amount of majority target nucleotide sequences alone.

Both mutant and wild-type ligases have associated signal-to-noise ratios for detection of minority mutations, and the second aspect of the present invention can be expressed as the mutant ligase signal-to-noise ratio is greater than the wild-type ligase signal-to-noise ratio.

$$\frac{\frac{[LDR\ product]_{minority\ target} + [LDR\ product]_{majority\ target}}{[LDR\ product]_{majority\ target}}\ \text{Mutant ligase}}{\frac{[LDR\ product]_{minority\ target} + [LDR\ product]_{majority\ target}}{[LDR\ product]_{majority\ target}}\ \text{Wild-type ligase}} > 1$$

The above equation may be restated more simply as:

$$\frac{\text{Signal-to-noise ratio for Mutant ligase}}{\text{Signal-to-noise ratio for Wild-type ligase}} > 1$$

For the mutant thermostable ligase, the signal-to-noise ratio is greater than the signal-to-noise ratio for wild-type ligase. All mutant enzymes which satisfy the equation above will give increased discrimination of cancer-associated mutations in the presence of an excess of normal DNA.

The third aspect of the present invention also relates to a method for identifying one or more of a plurality of sequences differing by one or more single-base changes, insertions, deletions, or translocations in a plurality of target nucleotide sequences. As noted above, a sample and one or more oligonucleotide probe sets are blended with a ligase to form a ligase detection reaction mixture. The ligase detection reaction mixture is subjected to one or more ligase detection reaction cycles, and the presence of ligation product sequences is then detected. Here, however, with regard to the oligonucleotide probe sets, the oligonucleotide probe which has its 3' end at the junction where ligation occurs has a modification. This modification differentially alters the ligation rate when the first and second oligonucleotide probes hybridize to a minority target nucleotide sequence in the sample with a perfect match at the ligation junction between the minority target nucleotide sequence and the oligonucleotide probe having its 3' end at the ligation junction compared to the ligation rate when the first and second oligonucleotide probes hybridize to the sample's majority target nucleotide sequence with a mismatch at the ligation junction between the majority target nucleotide sequence and the nucleotide probe having its 3' end at the ligation junction. Ligation with the modified oligonucleotide probe has a signal-to-noise ratio, of the ligation product sequence amounts for the minority and majority target nucleotide sequences to the amount of ligation product sequences produced from the same amount of majority target sequence alone, which is greater than the signal-to-noise ratio for ligation using an oligonucleotide probe lacking the modification.

The use of a modified oligonucleotide probe in accordance with the process of the present invention can be explained as follows:

Introduction of the $Q_2$ or $Q_{18}$ analogues at the 3rd position of the discriminating primer improves the signal to noise ratio about 2 to 3-fold, thereby increasing the power of the LDR system to discriminate cancer signal from background. This assay compares the ability of ligase to discriminate the most difficult case; a T:G mismatch from a T:A perfect match. $Q_2$ or $Q_{18}$ analogues located three nucleotides in from the 3'-end of a probe enhance local melting when present in conjunction with a mismatch at the 3'-position, while at the same time preserving helix integrity more than a mismatch when present in conjunction with a base pair match at the 3'-end. The use of a $Q_2$ or $Q_{18}$ analogue near the 3' end of a probe may influence the stability of the perfect matched and mismatched enzyme-DNA complexes to a different extent, so that discrete $K_M$ effects are exerted on these ligation reactions. In a competitive reaction, such as ligation of perfectly matched and mismatched substrates, the ratio of the specificity constant may be altered as a consequence of $K_M$, and possible $k_{cat}$ changes for each substrate. All modified probes which satisfy the equation below (shown for Q analogues) will give increased discrimination of cancer-associated mutations in the presence of an excess of normal DNA.

$$\frac{[k_{cat}/K_M]_{SLP3'QTT,match}}{[k_{cat}/K_M]_{SLP3'QTT,mismatch}} > \frac{[k_{cat}/K_M]_{SLP3'TTT,match}}{[k_{cat}/K_M]_{SLP3'TTT,mismatch}}$$

Alternatively, the third aspect of the present invention can be expressed in terms of a fidelity ratio (i.e. the initial rate of ligating a substrate with an analogue located three nucleotides in from the 3' end as well as a perfect match at the 3' end divided by the initial rate of ligating a substrate with an analogue located three nucleotides in from the 3' end as well as a mismatch at the 3' end) as follows:

$$\frac{[k_1]_{SLP3'QTT,match}}{[k_1]_{SLP3'QTT,mismatch}} > \frac{[k_1]_{SLP3'TTT,match}}{[k_1]_{SLP3'TTT,mismatch}} = \text{Fidelity ratio}$$

The above may be restated more generally to include other nucleotide analogue or sugar phosphate backbone modifications as follows:

$$\frac{[k_1]_{Modified\ oligo,match}}{[k_1]_{Modified\ oligo,mismatch}} > \frac{[k_1]_{Unmodified\ oligo,match}}{[k_1]_{Unmodified\ oligo,mismatch}} = \text{Fidelity ratio}$$

In the above equation, $[k_1]_{Modified\ oligo}$, match represents the initial rate constant for ligating the first and second oligonucleotide probes hybridized to a target nucleotide sequence wherein one oligonucleotide probe contains a modification as well as having a perfect match at the ligation junction between the target nucleotide sequence and the oligonucleotide probe having its 3' end at the ligation junction. $[k_1]_{Modified\ oligo,\ mismatch}$ represents the initial rate constant for ligating the first and second oligonucleotide probes hybridized to a target nucleotide sequence wherein one oligonucleotide probe contains a modification as well as having a mismatch at the ligation junction between the target nucleotide sequence and the oligonucleotide probe having its 3' end at the ligation junction. $[k_1]_{Unmodified\ oligo,\ match}$ represents the initial rate constant for ligating the first and second oligonucleotide probes hybridized to a target nucleotide sequence with a perfect match at the ligation junction between the target nucleotide sequence and the oligonucleotide probe having its 3' end at the ligation junction. $[k_1]_{Unmodified\ oligo,\ mismatch}$ represents the initial rate constant for ligating the first and second oligonucleotide probes hybridized to a target with a mismatch at the ligation junction between the target nucleotide sequence and the oligonucleotide probe having its 3' end at the ligation junction. For the modified oligonucleotide probe, $[k_1]_{Modified\ oligo,\ match}$ divided by $[k_1]_{Modified\ oligo,\ mismatch}$ (=fidelity ratio) is greater than the fidelity ratio for the corresponding unmodified oligonucleotide probe. All modified oligonucleotide probes which satisfy the equation above will give increased discrimination of cancer-associated mutations in the presence of an excess of normal DNA.

Another explanation for the above equation is the oligonucleotide probe which has its 3' end at the ligation junction has one or more modification which differentially alters the rate of ligation when the first and second oligonucleotide probes hybridize to a minority target nucleotide sequence with a perfect match at the ligation junction between the minority target nucleotide sequence and the oligonucleotide probe having its 3' end at the ligation junction, compared to the rate of ligation when the first and second oligonucleotide probes hybridize to the majority target nucleotide sequence with a mismatch at the ligation junction between the majority target nucleotide sequence and the oligonucleotide probe having its 3' end at the ligation junction.

This can also be stated more generally in terms of a signal-to-noise ratio defined as follows:

$$\frac{[LDR\ product]_{minority\ target} + [LDR\ product]_{majority\ target}}{[LDR\ product]_{majority\ target}} = \text{Signal-to-noise ratio}$$

In the above equation, $[LDR\ product]_{minority\ target}$ represents the amount of ligation product sequences produced when the first and second oligonucleotide probes hybridize to a minority target nucleotide sequence with a perfect match at the ligation junction between the minority target nucleotide sequence and the oligonucleotide probe having its 3' end at the ligation junction. $[LDR\ product]_{majority\ target}$ represents the amount of ligation product sequences produced when the same first and second oligonucleotide probes hybridize to the majority target nucleotide sequence with a mismatch at the ligation junction between the majority target nucleotide sequence and the oligonucleotide probe having its 3' end at the ligation junction. The ligase, using either modified or unmodified oligonucleotide probes, has a signal-to-noise ratio, for the amount of ligation product sequences produced from both the minority and majority target nucleotide sequences divided by the amount of ligation product sequences produced from the same amount of majority target nucleotide sequence alone.

When using thermostable ligase with both modified and unmodified oligonucleotide probes, there are signal-to-noise ratios associated with each probe for detection of minority mutations, and the third aspect of the present invention can be expressed as the signal-to-noise ratio obtained using modified oligonucleotide probes is greater than the signal-to-noise ratio obtained using unmodified oligonucleotide probes.

The above equation may be restated more simply as:

$$\frac{\text{Signal-to-noise ratio for modified oligonucleotide}}{\text{Signal-to-noise ratio for unmodified oligonucleotide}} > 1$$

Ligation using the modified oligonucleotide probe has a signal-to-noise ratio, of the amount of LDR product produced from both the minority and majority target nucleotide sequences, to the amount of LDR product produced from the same amount of majority target nucleotide sequence alone, which is greater than the signal-to-noise ratio for ligation using an oligonucleotide probe lacking the modification. All modified oligonucleotide probes which satisfy the equation above will give increased discrimination of cancer-associated mutations in the presence of an excess of normal DNA.

Suitable modifications include the use of nucleotide analogues, such as 1-(2'-Deoxy-β-D-ribofuranosyl) imidazole-4-carboxamide, 1-(2'-Deoxy-β-D-ribofuranosyl)-3-nitropyrrole, 4-(2'-Deoxy-β-D-ribofuranosyl)imidazole-2-carboxamide, 2'-Deoxy-5-fluorouridine, 2'-Deoxyinosine, 6-(2'-Deoxy-β-D-ribofuranosyl)-6H,8H-3,4-dihydropyrimido[4,5-c][1,2]oxazine-7-one, 2-Amino-7-(2'-deoxy-β-D-ribofuranosyl)-6-methoxyaminopurine, 1-(2'-Deoxy-β-D-ribofuranosyl)-5-nitroindole, 1-(2'-Deoxy-β-D-ribofuranosyl)pyrazole-4-carboxamide, 1-(2'-Deoxy-β-D-ribofuranosyl)-1,2,4-triazole-3-carboxamide, 3-Amino-1-(2'-deoxy-β-D-ribofuranosyl)-1,2,4-triazole, 5-(2'-Deoxy-β-D-ribofuranosyl)-2-pyrimidinone, 5-(2'-Deoxy-β-D-ribofuranosyl)-2-thiopyrimidine, 5-Amino-1-(2'-deoxy-β-D-ribofuranosyl)imidazole-4-carboxamide, 1-(2'-Deoxy-β-D-ribofuranosyl)-3-nitropyrazole, 1-(2'-Deoxy-β-D-ribofuranosyl)-4-iodopyrazole, 1-(2'-Deoxy-β-D-ribofuranosyl)-4-propynylpyrazole, 1-(2'-Deoxy-β-D-ribofuranosyl)pyrrole-3-carboxamide, 1-(2'-Deoxy-β-D-ribofuranosyl)pyrazone-4-carboxamide, 1-(2'-Deoxy-β-D-ribofuranosyl)-4-nitroimidazole, or 1-(2'-Deoxy-β-D-ribofuranosyl)-4-nitropyrazole. Alternatively, the modified oligonucleotide probe contains thiophosphate, dithiophosphate, 2'-methoxy, or 3'-amino-2',3'-dideoxy-modifications to the sugar phosphate backbone of the oligonucleotide probe. This modification is either at the position which undergoes ligation, the adjacent position, or the third position for that undergoing ligation.

EXAMPLES

Example 1

Construction of *Thermus thermophilus* DNA Ligase Mutants at Amino Acid Residue 294 Using Site-Specific Mutagenesis

*Thermus thermophilus* ("Tth") DNA ligase mutants were created using a two-step PCR method (Horton et al., "Engineering Hybrid Genes Without the Use of Restriction Enzymes: Gene Splicing By Overlap Extension," *Gene,*

$$\frac{\frac{[LDR\ product]_{minority\ target} + [LDR\ product]_{majority\ target}}{[LDR\ product]_{majority\ target}}\ \text{Modified Oligo}}{\frac{[LDR\ product]_{minority\ target} + [LDR\ product]_{majority\ target}}{[LDR\ product]_{majority\ target}}\ \text{Unmodified Oligo}} > 1$$

77:61–68 (1989), which is hereby incorporated by reference). Plasmid pDZ15 (linearized by HindIII) was used as a template in the first round of PCR reactions. In the upper panel of FIG. 10, plasmid pDZ 15 which contains the cloned Tth DNA ligase gene (Barany, F., et al., "Cloning, Overexpression, and Nucleotide Sequence of a Thermostable DNA Ligase Gene," Gene, 109:1–11 (1991), which is hereby incorporated by reference), is shown schematically as if opened at a PstI site with genes drawn approximately to scale. In pDZ 15, the Tth ligase gene and direction is represented by the strongly hatched arrow; the vector ApR (bla) gene represented by the stippled (gray) arrow; the truncated end of a nonfunctional Taq I endonuclease gene represented by the lightly hatched arrow, and the pBR origin of replication represented by the open bar. The phoA, and T7 promoters are indicated by right angle arrows and point in the direction of transcription. Restriction sites are: Av, AvrII; Bm, BamHI; Bg, BglII; (Bg/Bm recombined site is not cleavable by either BamHI or BglII;) Hd, HindIII; RI, EcoRI; Ps, PstI, Pv, PvuII. Polylinker regions from pTZ18R are indicated by the triangular "rake", with only the outside restriction sites listed. *Escherichia coli* host strains used in the constructions described below were obtained from the following sources: N3098 (ligts7; (Wilson, G. G., et al., "Molecular Cloning of the DNA Ligase Gene From the Bacteriophage T4.I. Characterization of the Recombinants," *J. Mol. Biol.,* 132:471–491 (1979), which is hereby incorporated by reference), from N. Murray; JH132 (mrr-, TnlO; (Heitman, J., et al., "Site-Specific Methylases Induce the SOS DNA Repair Response in *Escherichia coli,*" *J. Bacteriol,* 169:3243–3250 (1987), which is hereby incorporated by reference), from J. Heitman; MM294 (endA$^-$, hsdR$^-$, hsdM$^+$, thi-1, supE44; (Miller, J. H., "Experiments in Molecular Genetics," Cold Spring Harbor Laboratory, Cold Spring Harbor, N.Y., pp. 201–205 (1972), which is hereby incorporated by reference), from our collection. Strains AK53 (mrrB$^-$, MM294) and AK76 (mrrB$^-$, N3098) were constructed by transducing the mrrB-phenotype from JH132 as described (Miller, J. H., "Experiments in Molecular Genetics," Cold Spring Harbor Laboratory, Cold Spring Harbor, N.Y., pp. 201–205 (1972), which is hereby incorporated by reference). Presence of the mrrB$^-$ phenotype was confirmed by tolerance of these strains to the Taq MTase-encoding gene present on plasmid pFBT71 (Barany, F., "A Genetic System for Isolation and Characterization of TaqI Restriction Endonuclease Mutants," *Gene,* 56:13–27 (1987) and Barany, F., et al., "Cloning and Sequencing of the TthHB8I DNA Restriction and Modification Enzymes, and Comparison With the Isoschizomeric TaqI Enzymes," *Gene,* 112:3–12 (1992), which is hereby incorporated by reference).

Figure 10:
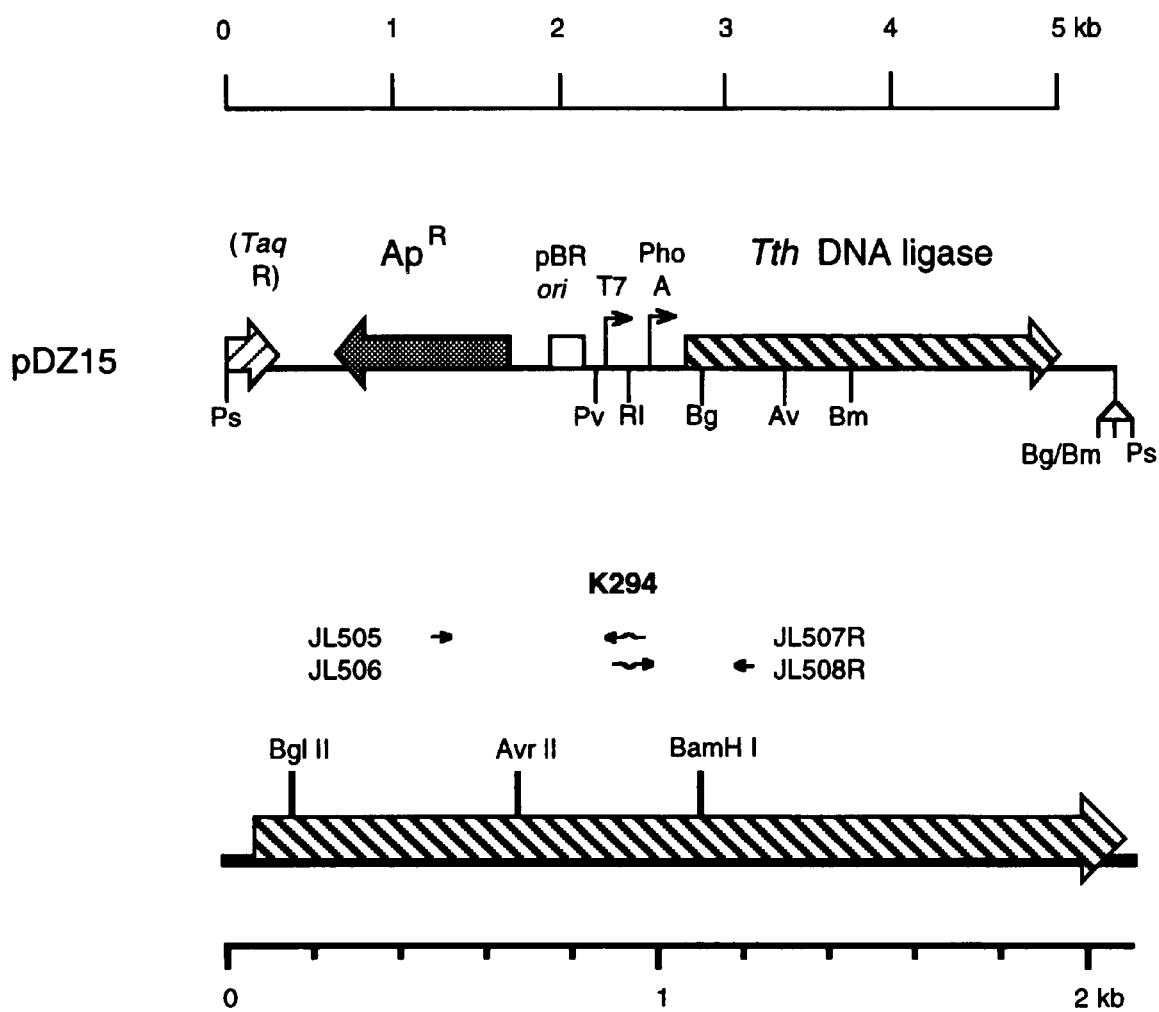
FIG. 10 relates to the construction of the Themus thermophilus DNA ligase mutants at amino acid residue 294 using site-specific mutagenesis.

In the lower panel of FIG. 10, the Tth DNA ligase gene and its direction of transcription is represented by a hatched arrow. The cleavage sites of some restriction endonucleases in the Tth DNA ligase gene are indicated by short solid bars. Approximate positions of oligonucleotide primers used for PCR reactions are depicted by arrows and primer names above the Tth ligase gene. The site of mutation, amino acid residue K294 is also indicated.

Site-directed mutagenesis at residue K294 was carried out as follows: (1) With HindIII-linearized pDZ15 as the template, two independent PCR reactions were performed. In one reaction tube, 400 ng of primers JL505 and JL507R were added to 200 ng of HindIII digested pDZ15 containing 50 μmoles of dATP, dCTP, dGTP, and dTTP each, and 2.5 units Amplitaq™ in 100 μl PCR buffer and cycled as described (Saiki, R. K., et al., "Primer-Directed Enzymatic Amplification of DNA With a Thermostable DNA Polymerase," *Science,* 239:487–491 (1988), which is hereby incorporated by reference); Perkin-Elmer Cetus Instruments, Emoryville Calif.) A second reaction tube contained 400 ng of primers JL506 and JL508R, 200 ng of HindIII digested pDZ15, and 2.5 units Amplitaq™ in the same reaction buffer, and incubated as above. (2) A third PCR reaction was then carried out in 100 μl PCR buffer containing 1 μl of the products from the two initial reactions, 400 ng primers JL505 and JL508 and 2.5 units Amplitaq™ and incubated as above. After removal of Amplitaq™ the larger product PCR fragment was digested with AvrII and BamHI, and electrophoresed in low melting agarose. The 436bp AvrII-BamHI fragment was excised from the gel, and purified as described previously (Barany, F., "Overproduction, Purification, and Crystallization of TaqI Restriction Endonuclease," *Gene,* 63:167–177 (1988), which is hereby incorporated by reference). In addition, plasmid pDZ 15 was also digested with AvrII and BamHI, and electrophoresed in low melting agarose. The bigger fragment, which equals pDZl 5 minus the 436bp AvrII-BamHI fragment, was excised and purified. This big fragment was incubated with the 436bp AvrII-BamHI fragment purified from the product of the third PCR reaction in the presence of T4 DNA ligase for 16 hours at 14° C. The ligation mixture was transformed into *E. coli* strain AK76 (ts lig) as described previously (Hanahan, D., "Studies on Transformation of *E. coli* With Plasmids," *J. Mol. Biol.,* 166:557–580 (1983), which is hereby incorporated by reference). Plasmid carrying cells were replica plated onto Fortified Broth plates supplemented with either high concentration of phosphates (10 mM K2HPO4, pH 7.6) or low concentration of phosphates (0.2 mM $K_2HPO_4$, pH 7.6) grown at 32° C. and 42° C. to test the complementation ability of mutant Tth DNA ligase to the ts lig host. Independent clones were picked from FB-high phos plates, and grown in liquid Fortified Broth supplemented with 10 mM $K_2HPO_4$, pH 7.6. Plasmid minipreps were made using the Magic Miniprep kit from Promega, and the AvrII-BamHI region was sequenced to confirm site-specific mutations at K294 using the Prism Dye DeoxyTerminator Cycle sequencing kit and DNA sequencer 373A from Applied Biosystems Division of the Perkin-Elmer Corporation.

Example 2

Construction of Tth DNA Ligase Mutants K294R and K294P

Figure 11:
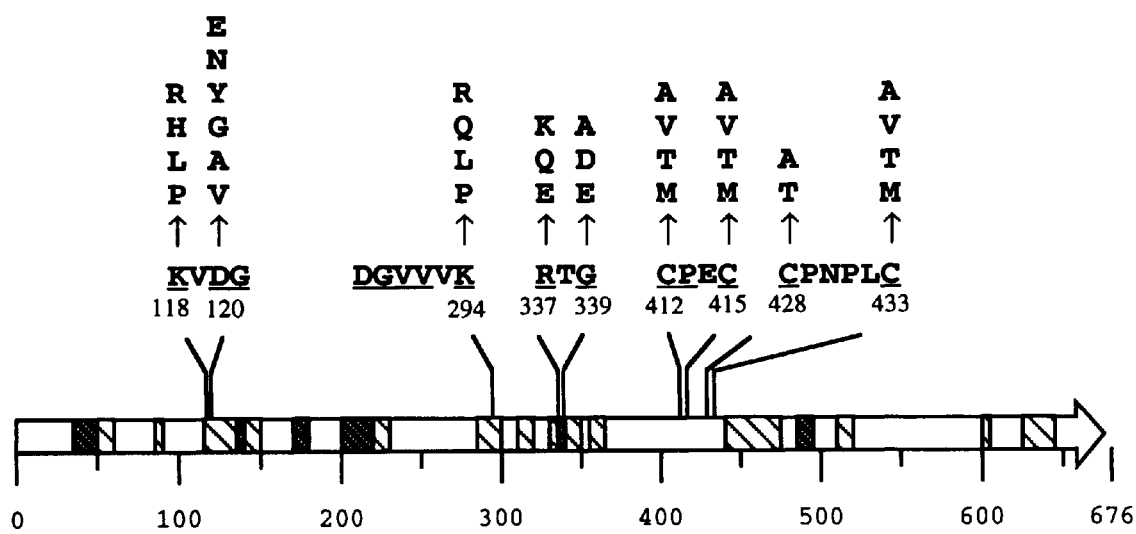
FIG. 11 shows the site-directed mutagenesis of possible active site regions of Tth ligase. The horizontal bar represents the full-length Tth DNA ligase protein with the arrow indicating the C-terminal end. Dark hatched bars represent regions with strong homology between Tth (i.e. *Thermus thermophilus*) DNA ligase and *E. coli* ligase, while the light hatched bars indicate regions with less homology. Amino acid substitutions produced by site-directed mutagenesis at K118, D120, K294, R337, G339, C412, C415, C428, and C433 are indicated. Amino acid residues which are identical among known NAD$^+$-dependent ligases are underlined.
Figure 15A:
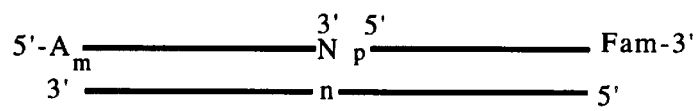
FIGS. 15A–E show the fidelity of nick closure by Tth DNA ligase at the 3'-side of the nick. The ligase substrate (nicked DNA duplex), shown in FIG. 15A, is formed by annealing the discriminating oligonucleotide LP3' (A, C, G, or T) with a phosphorylated common oligonucleotide (3'-fluorescently labeled, com3F) on the template strand. The discriminating base "N" on the 3'-side of the discriminating oligonucleotide, and the "n" in a template strand were varied to give all 16 possible combinations of base-paring. "$A_m$" represents the "A" tail at the 5'-end of a discriminating oligonucleotide. Reactions were carried out in 40 μl mixture containing 1 mM NAD$^+$, 12.5 nM (500 fmoles) of nicked DNA duplex substrates and 0.125 nM (5 fmoles) Tth DNA ligase at 65° C. Aliquots (5 μl) were removed at 0 hr, 2 hr, 4 hr, 6 hr, 8 hr, and 23 hr and separated on denaturing polyacrylamide gels. Data was analyzed using Genescan version 1.2 software. Results are plotted using Deltagraph Pro3 Software.
Figure 15B:
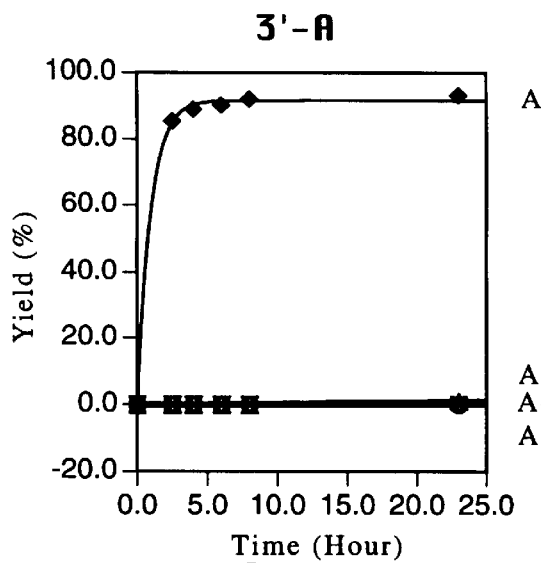
Figure 15C:
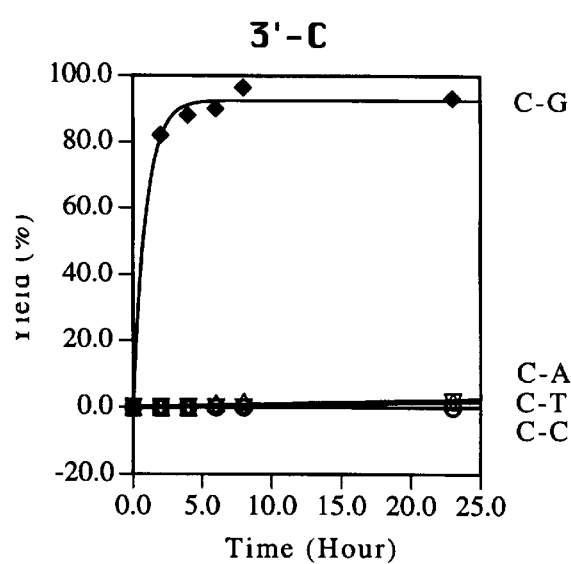
Figure 15D:
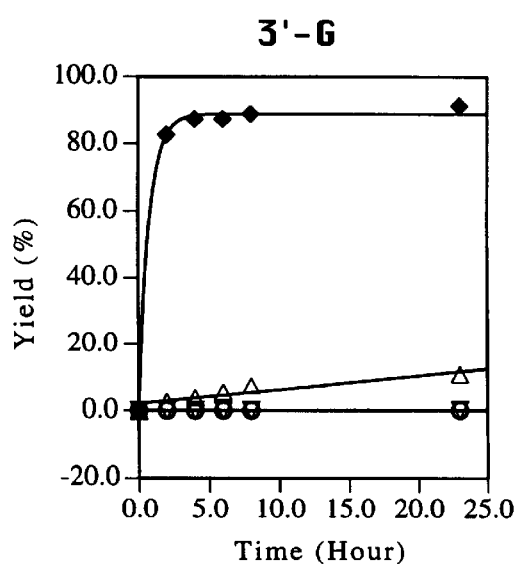
Figure 15E:
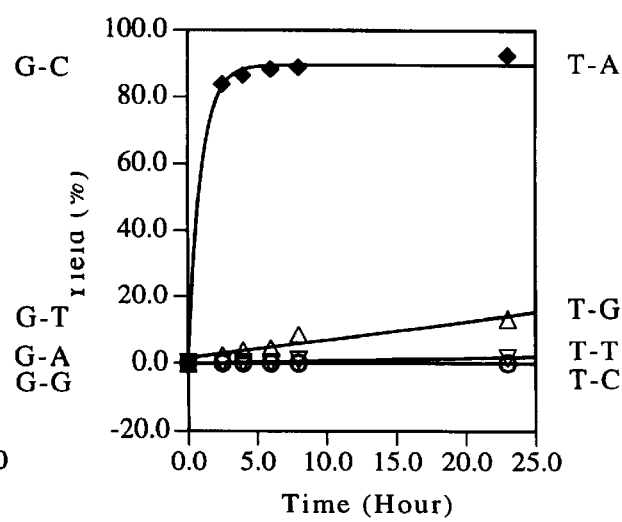
Figure 16A:
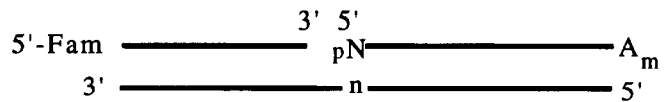
FIGS. 16 A–E show the fidelity of nick closure by a thermostable DNA ligase at the 5'-side of the nick. Reaction conditions were the same as in FIG. 15 except that different discriminating and common oligonucleotides were used. The discriminating base was on the 5'-side of the nick (phosphorylated oligonucleotides RP5'A, C, G, or T), while the common oligonucleotide was on the 3'-side of the nick, and was 5'-labeled with FAM (i.e. 6-carboxyfluorescein, fluorescent dye used in sequencing and mutation detection). See FIG. 16A. In panel 5'-A (FIG. 16B), the discriminating oligonucleotide was RP5'A. A-T (♦), A-C (Δ), A-A (▽), and A-G (○) represent DNA substrates containing TLg, CLg, ALg, and GLg as the template strand, respectively. In panel 5'-G (FIG. 16D), the discriminating oligonucleotide was RP5'G. G-C (♦), G-T (Δ), G-A (▽), and G-G (○) represent DNA substrate with CLg, TLg, ALg, and GLg as the template strand, respectively. In panel 5'-C (FIG. 16C), RP5° C. was the discriminating oligonucleotide. C-G (♦), C-A (Δ), C-T (▽), and C-C (○) indicate DNA substrates containing GLg, ALg, TLg, and CLg as the template strand, respectively. In panel 5'-T (FIG. 16E), RP5'T was the discriminating oligonucleotide. T-A (♦), T-G (Δ), T-T (▽), and T-C (○) represent DNA substrates containing ALg, GLg, TLg, or CLg as the template strand, respectively.
Figure 16B:
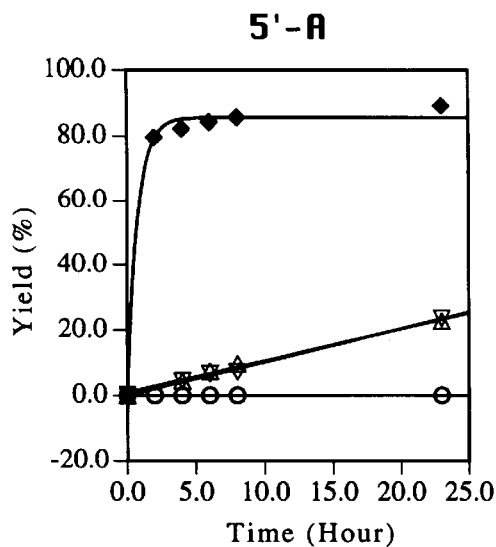
Figure 16C:
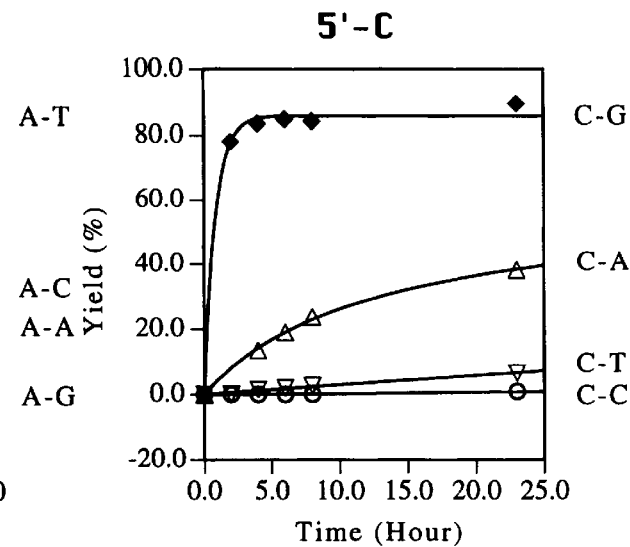
Figure 16D:
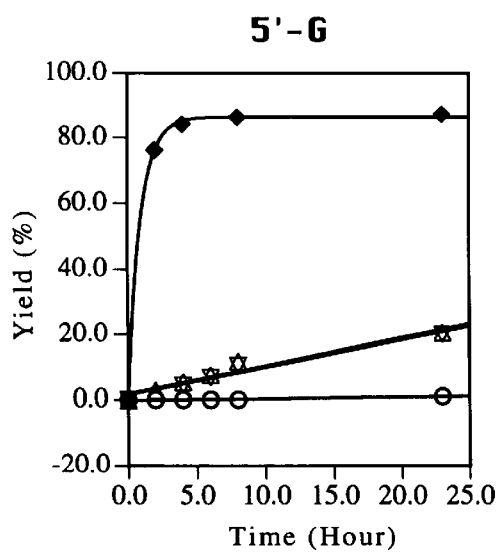
Figure 16E:
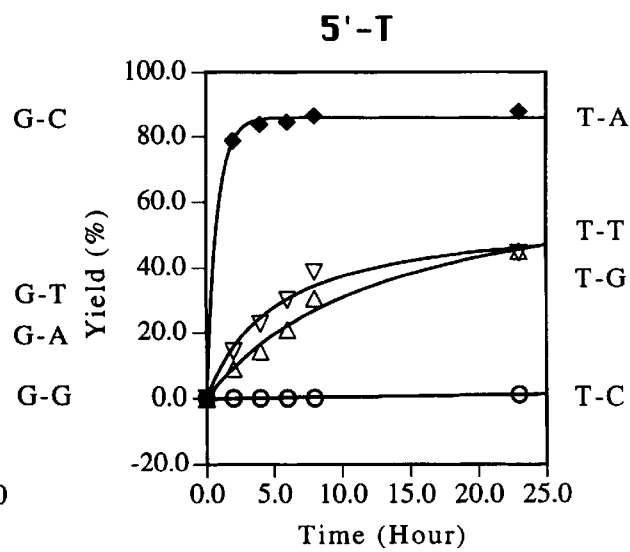

The mutant ligases of FIG. 11 were prepared using the oligonucleotides of FIG. 12A–B as described infra. Four oligonucleotide primers for PCR reactions were designed for creating multiple site-specific mutations at K294 site. Their sequences are as follows: Primer a (JL505) (SEQ ID NO: 78): 5'CAG AAC CTC CTC ACC ATC 3'; Primer b (JL507R) (SEQ ID NO: 78): 5CTC GTC CAG (G,C) (T, G, C, A) G CAC CAC CAC CCC GTC 3'; Primer c (JL506) (SEQ ID NO: 88): 5' TGG TGG TGC (A, C, G, T) (C, G) C TGG ACG AGC TTG CCC T 3'; and Primer d (JL508R) (SEQ ID NO: 96): 5'CTC TAT GTA GCT CTC GTT GTG 3'. Primers b and c are overlapping primers containing degenerate codons at mutation site. These primers were synthesized using reagents and a 394 automated DNA synthesizer from Applied Biosystems Division of Perkin-Elmer Corporation, Foster City, Calif. After synthesis, primers were deprotected in 30% ammonium hydroxide at 55° C. for 12 hours, dried in speedvac, resuspended in 100 μl of ddH20 (i.e. double distilled water), and purified by ethanol precipitation. The pellet was resuspended in 200 μl of ddH20, and their concentrations were determined by spectrophotometry at $OD_{260}$. Primers were then aliquoted and stored in a −20° C. freezer before use.

Site-specific mutagenesis in Tth DNA ligase gene (Tth lig) was carried out using a two-stage PCR-based overlap extension strategy as described previously (Ho et al., *Gene* 77:51–59 (1989), which is hereby incorporated by reference). Plasmid pDZ15, the expression plasmid (Barany, et al., *Gene* 109:1–11 (1991), and Horton, et al., "Engineering Hybrid Genes Without the Use of Restriction Enzymes: Gene Splicing by Overlap Extension," *Gene* 77:61–68 (1989), which are hereby incorporated by reference) of Tth DNA ligase was linearlized with a restriction endonuclease HindIII, and used as the template for the first round of PCR reactions. Two separate first round PCR reactions were carried out using primers a (JL505) and b (JL507R) or primers c (JL506) and d (JL508R), respectively. One microliter of the product from each first round PCR reaction was used as the template for the second round PCR reaction with primers a (JL505) and d (JL508R). The resulting product was digested with restriction endonucleases AvrII and BamHI, and separated on SeePlaque low-melting agarose gel. The DNA fragments assumed to contain the mutation site were cut from the low-melting agarose gel, purified by phenol extraction before ligated to the bigger fragment created from pDZ 15 by digestion with AvrII and BamHI. The ligation reaction was carried out at 14° C. for 16 hours. The resulting ligation mixture was used to transform AK76, a bacterial strain (lig ts7 strain, Barany, et al., *Gene* 109:1–11 (1991), which is hereby incorporated by reference) which contains a temperature-lethal mutation in ligase gene on bacterial chromosome. Positive transformants were selected by growing transformants on TY plates containing 50 µg/ml Ampicillin. Plasmid DNA minipreps were made from the transformants using the Magic Minipreps columns from Promega, and used for sequencing. Regions which was amplified in PCR reactions were sequenced to confirm the mutations using the Prism Dye DeoxyTerminator Cycle sequencing kit and DNA sequencer 373A from Applied Biosystems Division of Perkin-Elmer Corporation, Foster City, Calif.

Example 3

Expression of Mutant Tth DNA Ligases in *E. coli*

Plasmids containing mutant Tth DNA ligase gene under control of a phoA promoter were introduced into *E. coli* strain, AK53 via transformation. Mutant Tth DNA ligase proteins were overexpressed at 30° C. for 15 hours in 6 ml MOPS medium (Neidhardt, et al., *J. Bacteriol.*, 119:736–47 (1974), which is hereby incorporated by reference) containing 0.2 mM K2HPO4 and 75 µg/ml ampicillin (F. Barany, et al., *Gene* 109:1–11 (1991), which is hereby incorporated by reference). Cells were harvested by centrifugation, resuspended in 400 µl TE, (10 mM Tris, pH 8.5, 1 mM EDTA) sonicated for 3×10 seconds with a microprobe on a Sonifier 350 cell disruptor from VWR, and centrifuged for 10 min. at 4° C. The supernatant was adjusted to 20 mM Tris-HCl, pH 8.5, 50 mM KCl, 10 mM MgCl$_2$, and 0.5 mM EDTA, 1 mM DTT, and 2 mM 2-mercaptoethanol. After incubation at 64° C. for 25 min, the cloudy suspension was clarified by centrifugation at 4° C. for 15 min. Over 70% of the total protein in the resulting clear supernatant is Tth DNA ligase, as determined by staining of a 7.5% polyacrylamide gel containing 0.1% SDS with Coomassie Brilliant Blue. Approximately 200 jig of Tth DNA ligase was isolated from a 6 ml culture. Every mutant Tth DNA ligase was overexpressed in AK53, and remained soluble after heat treatment at 65° C.

Example 4

Complementation Assay

Plasmids containing mutated Tth DNA ligase genes were introduced into a temperature sensitive ligase defective *E. coli* strain, AK76 (fig ts7 strain) (F. Barany, et al., *Gene* 109:1–11 (1991), which is hereby incorporated by reference) via transformation. Individual transformants were replica plated onto high phosphate plates (0.6% NaCl, 2.5% Bacto-Tryptone, 0.75% yeast extract, 0.1% dextrose, and 10 mM K2HPO4, pH 7.6, and 50 µg/ml ampicillin), and low phosphate plates (0.2 mM K$_2$HPO$_4$) (Neidhardt, et al., *J. Bacteriol.*, 119:736–47 (1974), which is hereby incorporated by reference); and incubated overnight at permissive (32° C.) and non-permissive (42° C.) temperatures, respectively. The Tth DNA ligase gene is induced only at low phosphate concentration. An active enzyme encoded by the plasmid enables the temperature sensitive host to grow at 42° C. on low phosphate plates.

Example 5

Adenylation Assays

Adenylation was assayed by incubating approximately 8 fig (100 fmoles) wild-type and mutant Tth DNA ligase, prepared as described above, in 100 µl of reaction buffer containing 20 mM Tris-HCl, pH 7.6, 50 mM KCl, 10 mM MgCl$_2$, 0.5 mM EDTA, 1 mM NAD$^+$, 1 mM DTT, 2 mM 2-mercaptoethanol at 65° C. for 25 min. Under these conditions, virtually all the wild-type ligase was found in the adenylated form. The reaction was stopped by adding an equal volume of 2×sample buffer containing 120 mM Tris-HCl, pH 7.6, 2% SDS, 20% glycerol, 0.02% bromophenol blue, and 300 mM 2-mercaptoethanol. Samples were boiled for 5 min, and were analyzed by loading 50 µl on to a 7.5% polyacrylamide-0.1%-SDS gel. The adenylated enzyme can be distinguished by its higher apparent molecular weight (81 Kd), compared to the deadenylated form (78Kd).

To rule out the possibility that some mutants may not change mobility after adenylation, experiments were also performed with radioactive [$^{32}$P] NAD$^+$. In this case, the reaction was carried out in 25 µl reaction mixture under the same conditions described above except that 3.3 µCi [$^{32}$P] NAD$^+$ (800 Ci/mmol, NEN-Du Pont Company, Chadds Ford, Pa.) was used. After 15 min incubation at 65° C., 1.5 pmoles of non-radioactive NAD$^+$ was added to the reaction mixture, and incubated for 5 more min to drive the adenylation reaction to near completion. Reactions were stopped by adding 25 ll of 2×sample buffer. The resulting mixture was boiled at 100° C. for 5 min prior to analysis on a 7.5% polyacrylamide—0.1% SDS gel. The gel was autoradiographed at room temperature for 3 hours against a Kodak XAR-5 film. In order to verify protein samples in each lane, the gel was then stained with Coomassie Brilliant Blue.

Example 6

Deadenylation Assays

To assay for the deadenylation activity (transfer of the adenyl group from enzyme to DNA substrate), the same conditions were used as for the adenylation experiment, except that 1 mM NAD$^+$ was replaced by 5 µg of nicked salmon sperm DNA; prepared by incubating salmon sperm DNA (Sigma, St. Louis) with pancreatic DNase I (Barany, et al., *Gene* 109:1–11 (1991), which is hereby incorporated by reference). The deadenylated enzyme was recognized as a fast migrating band (78 Kd) when separated by electrophoresis on a 7.5% polyacrylamide-0.1%-SDS gel.

Example 7
5'-Labeling of Oligonucleotide Probe with [γ-$^{32}$P] ATP

Oligonucleotide probe JL514 was 5' labeled in a 10 Pl reaction containing 50 mM Tris-HCl, pH 7.6, 10 mM MgCl$_2$, 1 mM EDTA, 10 mM DTT, 45 pmole of [g-$^{32}$P] ATP (6000 Ci/mmol, NEN-Du Pont Company), 15 pmole of gel-purified oligonucleotides, and 10 units of T4 polynucleotide kinase (New England Biolabs, Beverly, Mass.) after incubation at 37° C. for 45 min. 1 μl of 10 mM ATP was added to the reaction mixture, and the incubation was continued for two more minutes. The reaction was quenched by adding 17 μl of 60 mM EDTA. The kinase was heat-inactivated by incubation at 64° C. for 20 min. Phosphorylated oligonucleotides were separated on a Sephadex G-25 column equilibrated in TE buffer. Fractions containing phosphorylated oligonucleotides were combined, and stored at −20° C. in aliquots before use. The specific radioactivity of phosphorylated oligonucleotide JL514 was 9×10$^6$ cpm/pmol.

Example 8
Assay for Nick-Closure Activity

The nicked DNA duplex substrate was formed by annealing two short oligonucleotide probes (JL538 and JL514) to a longer complementary oligonucleotide target (JL 539). Their nucleotide sequences are: JL538: 5' AAC CAC AGG CTG CTG CGG ATG CCG GTC GGA G 3' (SEQ ID NO: 75); JL514: 5' AGA GCC GCC ACC CTC AGA ACC GCC ACC CTC 3' (SEQ ID NO: 76); JL539: 5' GAG GGT GGC GGT TCT GAG GGT GGC GGC TCT CTC CGA CCG GCA TCC GCA GCA GCC TGT GGT T 3' (SEQ ID NO: 77). The reaction was carried out in 40 μl of buffer containing 20 mM Tris-HCl, pH 7.6, 10 mM MgCl$_2$, 100 mM KCl, 10 mM DTT, 1 mM NAD$^+$, and 60 fmol of nicked DNA duplex substrates. DNA probes and target were denatured by incubating the reaction mixture at 94° C. for 2 min, and re-annealed at 65° C. for 2 min. Ligation reactions were initiated by addition of Tth DNA ligase and carried out at 65° C. for 30 min. Reactions were terminated by adding 40 μl of stop solution (83% formamide, 8.3 mM EDTA, and 0.17% blue dextran). Samples were denatured at 93° C. for 2 min, chilled rapidly on ice prior to loading 20 μl on an 8 M urea-10% polyacrylamide gel. After electrophoresis, the gel was exposed to a phosphorimager screen for 20 min. Radioactively labeled ligation products were analyzed on a Molecular Dynamics Phosphorimager (Sunnyvale, Calif.) and quantified using Image-Quant software.

The amino acid sequence of the Tth DNA ligase gene contains two short sequences, K$^{118}$VDG and DGVVVK$^{294}$, which resemble the active site sequence (KYDGQR) of human DNA ligase I. Since human DNA ligase I requires ATP as a cofactor while the Tth DNA ligase uses NAD$^+$ instead, it is possible that their active sites for enzyme-adenylate formation may differ. Although, the sequence K$^{118}$VDG resembles the active site sequence (KY/LDGXR) of human DNA ligases I, III and IV more than the sequence DGVVVK$^{294}$ does, both sequences were tested for adenylation.

Site-specific mutants were constructed at three amino acid sites, Ki 18, D120, and K294 (FIG. 11). At least four different single amino acid substitutions were made at each site to explore a range of side chain changes (FIG. 11). Mutant Tth DNA ligases were overexpressed in AK53 cells, partially purified, and analyzed on a 7.5% polyacrylamide-0.1%-SDS gel (Barany, et al., "Cloning, Overexpression, and Nucleotide Sequence of a Thermostable DNA Ligase Gene," *Gene* 109:1–11 (1991), which is hereby incorporated by reference). *E. coli* cells transformed with the plasmid vector lacking the Tth DNA ligase gene showed no protein in the molecular weight range of Tth DNA ligase (76–81 Kd), although some heat-resistant impurities from the host bacteria are visible. Wild-type Tth DNA ligase and mutant ligases with amino acid substitution at K294 migrate as doublet bands during electrophoresis. The upper band, with an apparent molecular weight of 81 Kd is the adenylated form while the lower one at 78Kd is the deadenylated form. Id. Nine out of ten mutant ligases of K118 and D120 migrated as a single band. The exception was D120E, the majority of which was expressed as the adenylated form while a very small amount of the deadenylated form was seen.

Partially purified mutant Tth DNA ligases were assayed for adenylation in the presence of NAD$^+$, and deadenylation in the presence of nicked salmon sperm DNA. Both wild-type enzyme and all K294 mutants tested became adenylated in the presence of NAD$^+$ and deadenylated upon incubation with nicked salmon sperm DNA (See Table 1).

TABLE 1

Effects of amino acid substitutions at K118, D120, and K294 of Tth DNA ligase on enzyme activities[a]

| Plasmid | Mutant | Adenylation | Deadenylation | Complementation of ts7 lig (in vivo) | Nick-closure activity (%) (in vitro) |
|---|---|---|---|---|---|
| pDZ15 | Wildtype | + | + | + | 100 |
| pJLBE3 | K118R | − | NA | − | ND |
| pJLBE12 | K118H | − | NA | − | ND |
| pJLBE5 | K118L | − | NA | − | ND |
| pJLBE9 | K118P1 (CCC) | − | NA | − | ND |
| pJLBE1I | K118P2 (CCG) | − | NA | − | ND |
| pJLBg3 | D120E | + | ± | − | 6.2 |
| pJLBF9 | D120N | + | ± | − | 8.5 |
| pJLBF7 | D120Y | ± | − | − | 0.11 |
| pJLBc4 | D120G | ± | − | − | 0.07 |
| pJLBd6 | D120A | ± | − | − | 0.48 |
| pJLBf6 | D120V | − | NA | − | ND |
| pJLBH7 | K294R | + | + | + | 100 |
| pJLBH2 | K294Q | + | + | + | 77 |
| pJLBH6 | K294L1 (CTG) | + | + | + | 90 |
| pJLBH10 | K294L2 (CTC) | + | + | + | 87 |
| pJLBH8 | K294P | + | + | + | 26 |
| pJLBH9 | K294P* | + | + | − | ND |

[a]Abbreviations: (+), similar activity to wildtype enzyme; (−), no activity; (±), intermediate activity; Deadenylation refers to transfer of the adenyl group from enzyme to nicked DNA substrate; NA, "Deadenylation" could not be determined since these mutants do not adenylate; ND, not detectable; (*), Mutant encoded in plasmid pJLBH9 also contains the G339E second site mutation. For the nick-closure activity experiment, 100% activity represents the formation of 58 fmol product in 30 min. at 65° C. using 6 fmol of partially purified wild type Tth DNA ligase under conditions described herein. The amount of partially purified mutant enzymes used in this experiment were: 60 fmol for mutants at K118 and D120 sites, 6 fmol for mutants at K294 site, and 60 fmol for mutant K294P* (K294P/G229E). The relative nick-closure activity for mutant Tth DNA ligase shown in this Table was normalized based on the amount of enzyme used.

All mutants at K118 site were unchanged by treatments with either NAD$^+$ or nicked salmon sperm DNA, indicating a possible defect in the adenylation or deadenylation reaction. Likewise, mutant D120V was also defective in adenylation or deadenylation (Table 1). Mutants D120A, D120G, D120Y, and D120N underwent adenylation (see below), although the mobility shifts were difficult to distinguish for some of the mutants. Most of the mutant D120E protein remained in the adenylated form when isolated from *E. coli* cells, indicating a possible defect during the deadenylation step. When 5 μg of mutant D120E and wild-type enzyme were incubated with 2.5 jig of nicked salmon sperm DNA, wild-type enzyme became completely deadenylated, while most of DI 20E remained as the adenylated form (data not shown). However, mutant D120E was substantially deadenylated when the amount of nicked salmon sperm DNA was raised above 25 µg. It is unlikely that this change is due to the reversal of the adenylation step since no β-nicotinamide mononucleotide (NMN) was added in the reaction mixture. Thus, mutant D120E either has a reduced affinity to the DNA substrate, or has a reduced rate of transferring the AMP moiety to the 5' phosphate of the DNA substrate.

To rule out the possibility that some mutants may become adenylated without altering mobility on SDS gels, adenylation was also carried out using [$^{32}$p] NAD$^+$. None of the K118 mutants were adenylated when assayed with radioactive substrate, while the wild-type enzyme yielded a strong radioactive adenylated-enzyme band. This indicates that K118 is essential for enzyme-adenylate formation. All mutants at D120 site except D120V had incorporated a comparable amount of radioactive AMP relative to that by wild type enzyme. However, when the gel was stained with Coomassie Blue after autoradiography, mutant proteins D120Y and DI 20G showed only partial adenylation, indicating the higher sensitivity of the radioactive assay. Mutant D120A formed the enzyme-adenylate without changing its electrophoretic mobility, while mutants K118P1 and K118P2 changed mobility not as a result of adenylation, but due to a conformational change caused by the proline for lysine substitution. Thus, a conformational change (as evidenced by altered mobility on an SDS gel) is usually observed upon successful adenylation, but may also be achieved by some of the same mutations which abolish formation of the enzyme-adenylate complex.

The effects of amino acid substitution at K118, D120, and K294 on the overall activity of Tth DNA ligase were tested by a complementation assay and an in vitro ligation assay (Table 1). In this in vitro assay, varying concentrations of wild-type and mutant Tth DNA ligases were incubated with a nicked-DNA duplex substrate (composed of two probes hybridized to a synthetic target), and ligation product separated on a denaturing gel. Wild-type Tth DNA ligase complemented the E. co lig ts7 host while none of the mutants at Kl 18 and D120 did. All K118 mutants were also defective for in vitro ligation activity, but unexpectedly, several D120 mutants retained some in vitro activity (Table 1). Mutants D120E and D120N had 6.2% and 8.5% activity respectively, while D120Y, D120G, and D120A all had less than 0.5% activity. No in vitro activity was detected for D120V. All K294 mutants with the exception of one double mutant K294P/G339E, supported the E. coli lig ts7 host growth at 42° C., as well as retaining significant in vitro enzymatic activity. The aberrant clone did not complement the E. coli lig ts7 host, but showed normal activity for adenylation and deadenylation. Sequencing this clone revealed a second mutation of G339E in addition to K294P. The possible involvement of G339 in the formation of phosphodiester bonds was studied further and is discussed below.

The results on single amino acid substitutions of K118, D120, and K294 indicate that K118 is critical for enzyme-adenylate formation, D120 facilitates deadenylation, and K$^{118}$VDG is thus inferred to be the site of Tth DNA ligase-adenylate formation. This supports the prediction from sequence alignment that KXDG may also be the active site of NAD$^+$-dependent DNA ligases. Similar results using site-directed mutagenesis were reported for ATP-dependent human DNA ligase I (Kodama, K., et al., *Nucleic Acids Res.*, 19:6093–99 (1991), which is hereby incorporated by reference) and vaccinia DNA ligase (Cong, P., et al., *J. Biol. Chem.*, 268:7256–60 (1993) and Shuman, S., et al., *Virology*, 211:73–83 (1995), which are hereby incorporated by reference). Substitution of the active site Lys (K568) by His or Arg in human DNA ligase I, and of K231 by Asn or Arg in vaccinia DNA ligase caused a loss of the adenylation activity. Mutations at the conserved Asp (D570) to Asn, Glu, and Gln in human DNA ligase I reduced enzyme-adenylate formation and caused loss of in vivo complementation (Kodama, K., et al., *Nucleic Acids Res.*, 19:6093–99 (1991), which is hereby incorporated by reference). A KEDG motif was identified as the active site of T4 RNA ligase, based on mass spectrometry of an adenylated peptide (Thogersen, H. C., et al., *Eur. J. Biochem*, 147:325–29 (1985), which is hereby incorporated by reference), and site-directed mutagenesis studies (Heaphy, S., et al., *Biochemistry*, 26:1688–96 (1987), which is hereby incorporated by reference). In this enzyme, substitution of the conserved Asp (D101) by Asn, Ser, or Glu was well tolerated for enzyme-adenylate formation, while deadenylation and phosphodiester bond formation steps were prevented completely by each mutation. It was suggested that this Asp residue interacts with the substrate 5'-phosphate terminus rather than the substrate 3'-OH terminus or the adenylate group. All of our D120 substitutions also caused loss of complementation activity (assayed in vivo at 42° C.), yet D120E and D120N still retained some in vitro ligation activity (assayed at 65° C., see Table 1). Therefore, while D120 clearly facilitates deadenylation in Tth DNA ligase, it is not strictly essential for ligation. This finding corroborates a similar conclusion by Shuman and Schwer based on studies of capping enzymes and ATP dependent ligases (Shuman, S., et al., *Molec. Microbiol.*, 17:405–10 (1995), which is hereby incorporated by reference).

A KTDG motif was deduced to be the active site of the mRNA capping enzymes of the Vaccinia virus (Cong, P., et al., *J. Biol. Chem.*, 268:7256–60 (1993), which is hereby incorporated by reference), S. cerevisiae (Fresco, L. D., et al., *Proc. Natl. Acad. Sci. USA*, 91:6624–28 (1994) and Schwer, B., et al., *Proc. Natl. Acad. Sci. USA*, 91:4328–32 (1994), which are hereby incorporated by reference), and S. pombe (Shuman, S., et al., *Proc. Natl. Acad. Sci. USA*, 91:12046–50 (1994), which is hereby incorporated by reference), for enzyme-guanylate formation. In Yeast tRNA ligase, the amino acid sequence KANG was identified by sequencing the adenylated peptide (Xu, Q., et al., *Biochemistry*, 29:6132–38 (1990), which is hereby incorporated by reference). A comparison of 5 capping enzymes and 14 ATP dependent DNA and RNA ligases suggests a superfamily of five evolutionarily conserved motifs which plays a role in nucleotidyl binding and transfer to an RNA or DNA substrate (Shuman, S., et al., *Molec. Microbiol.*, 17:405–10 (1995); Shuman, S., et al., *Proc. Natl. Acad. Sci. USA*, 91:12046–50 (1994); and Cong, P., et al., *Molec. Cell. Biol.*, 15:6222–31 (1995), which are hereby incorporated by reference). These earlier studies, plus the present work on an NAD$^+$ requiring ligase, allow us to consider KXDING as a general active site motif for creating a charged enzyme-nucleotide complex, which provides the energy to form a covalent phosphodiester bond in nucleic acid substrates.

The observation that the double mutant (K294P/G339E) lost ligase activity suggests that G339 may be important for the third step of the ligation reaction; i.e. formation of the phosphodiester bond. To confirm that this effect is caused by one mutation at G339 site, and not by an additive effect of two mutations, single amino acid substitutions were made at G339 by site-directed mutagenesis. Site-specific mutations were also made at R337, a conserved positively charged amino acid near G339, and at C412, C415, C428, and C433 (FIG. 11). There are only four Cys residues in Tth DNA ligase, all conserved among the five NAD$^+$-dependent bacterial ligases that are sequenced. These four Cys residues may form a zinc-binding site and be involved in the interaction between bacterial DNA ligase and DNA substrates (Thorbjarnardottir, S. H., et al., Gene, 161:1–6 (1995), which is hereby incorporated by reference).

All Tth DNA ligase mutants constructed at these six sites were able to form the enzyme-adenylate complex in the presence of NAD$^+$, and were deadenylated in the presence of nicked salmon sperm DNA (Table 2). The effects on the overall ligase activity varied with each mutation, but was generally consistent, when comparing in vivo and in vitro activities (Table 2).

TABLE 2

Effects of single amino acid substitutions at R337, G339, C412, C415, C428, C433 of Tth DNA ligase on enzyme activity[a]

| Plasmid | Mutant | Adenylation | Deadenylation | Complementation of ts7 lig (in vivo) | Nick-closure activity (%) (in vitro) |
|---|---|---|---|---|---|
| pDZ15 | Wildtype | + | + | + | 100 |
| pJLBK8 | R337K | + | + | + | 3.1 |
| pJLBK4 | R337Q | + | + | − | 0.70 |
| pJLBK5 | R337E | + | + | − | 0.04 |
| pJLBJ6 | G339A | + | + | − | 0.71 |
| pJLBJ5 | G339D | + | + | − | 0.34 |
| pJLBA6 | G339E | + | + | − | 0.22 |
| pJLBB4 | C412A | + | + | + | 41 |
| pJLBB9 | C412V | + | + | − | 0.16 |
| pJLBB11 | C412T | + | + | − | 0.11 |
| pJLBB12 | C412M | + | + | − | 0.17 |
| pJLBC18 | C415A | + | + | + | 79 |
| pJLBC3 | C415V | + | + | + | 100 |
| pJLBC9 | C415T | + | + | + | 3.0 |
| pJLBC19 | C415M | + | + | + | 0.47 |
| pJLBD10 | C428A | + | + | + | 57 |
| pJLBD6 | C428T | + | + | − | 0.43 |
| pJLBI11 | C433A | + | + | − | 0.15 |
| pJLBI6 | C433V | + | + | − | 0.02 |
| pJLBI4 | C433T | + | + | − | 0.07 |
| pJLBI1 | C433M | + | + | − | 0.06 |

[a]Abbreviations: (+), similar activity to wildtype enzyme; (−), no activity; ND, not detectable. For the nick-closure activity experiment, 100% activity represents the formation of 58 fmol product in 30 min. at 65° C. using 6 fmol of partially purified wild type Tth DNA ligase or the formation of 16.2 fmol product in 30 min at 65° C. using 0.6 fmol. The amount of the other enzymes used was either 0.6 fmol, 6 fmol, or 60 fmol. The relative nick-closure activity for mutant Tth DNA ligases shown in this Table was normalized based on the amount of enzyme used.

Mutants R337Q and R337E lost activity and were unable to complemen E. coli lig ts7 host, while mutant R337K retained partial in vitro activity and complementation activity. Substitution of G339 by Ala, Asp, or Glu all rendered the enzyme inactive, both in vivo and in vitro. At C412, substitution by Ala had no effect in both in vivo and in vitro experiments, while substitution by Val, Thr, and Met caused the loss of the overall enzyme activity. Similar results were also observed at C428. Three of four mutations at C415 site (C415A, C415V, and C41 ST), all retained complementation and enzymatic activity. It is not clear why C415M retained complementation activity (assayed at 42° C.) with such poor enzymatic activity (assayed at 65° C.), although the mutation may have rendered the enzyme thermolabile. In contrast, all mutations at C433 site (C433A, C433V, C433T, or C433M) caused loss of both complementation and enzymatic activity.

While the adenylation active site in many DNA ligases has been well defined, the possible active site for formation of the phosphodiester bond remains poorly understood. Residues G339 and C433 may be involved in this third step of the ligation reaction, because conservative mutations at both sites abolished the overall enzyme activity without affecting the first two steps, adenylation and deadenylation. Residue G339 may allow a local structure critical for enzymatic activity, or interact with the DNA substrate via the peptide backbone, in a manner which would be incompatible with an Ala, Glu, or Asp substitution. Glycine residues play essential roles in mRNA capping enzymes, although these mutations interfered primarily with enzyme-guanylate formation (Shuman, S., et al., Proc. Natl. Acad. Sci. USA, 91:12046–50 (1994) and Cong, P., et al., Molec. Cell. Biol., 15:6222–31 (1995), which are hereby incorporated by reference). Residues R337, C412, and C428 may play an indirect, but not essential, role in the third step of ligation reaction since only nonconservative mutations caused loss of activity for this step. For all mutants at these five residues, there were no dramatic global conformational changes induced by these mutations as indicated by their ability to form enzyme-adenylate complex in the presence of NAD$^+$, and to deadenylate in the presence of nicked DNA substrate. The active site for the third step of ligation may well be separated from that of the first two steps. These active sites function independent of one another and damage at one site may not affect the activity of the other.

In summary, site-directed mutagenesis studies were carried out to identify active sites for Tth DNA ligase. The adenylation active site and facilitated deadenylation site of Tth DNA ligase was identified as the Lys and Asp residues of motif K$^{118}$VDG. These results are consistent with other mutagenesis studies on the active sites of DNA ligases (Kodama, K., et al., Nucleic Acids Res., 19:6093–99 (1991); Cong, P., et al., J. Biol. Chem., 268:7256–60 (1993); and Shuman, S., et al., Virology, 211:73–83 (1995), which are hereby incorporated by reference), T4 RNA ligase (Heaphy, S., et al., Biochemistry, 26:1688–96 (1987), which is hereby incorporated by reference) and mRNA capping enzymes (Cong, P., et al., J. Biol. Chem., 268:7256–60 (1993); Fresco, L. D., et al., Proc. Natl. Acad. Sci. USA, 91:6624–28 (1994); Schwer, B., et al., Proc. Natl. Acad. Sci. USA, 91:4328–32 (1994); Shuman, S., et al., Proc. Natl. Acad. Sci. USA, 91:12046–50 (1994); and Cong, P., et al., Molec. Cell. Biol., 6222–31 (1995), which are hereby incorporated by reference). Together, they support the idea that KXD/NG is the active site motif for the formation of enzyme-nucleotide complex. Mutations at residues G339 and C433 did not inhibit adenylation and deadenylation steps but abolished the overall activity, indicating that these two amino acid residues may be involved in the third step of ligation, the formation of the phosphodiester bond.

Example 9

Synthesis of Oligonucleotide Probes

Oligonucleotide probes were synthesized using reagents and a model 394 automated DNA synthesizer from Applied Biosystems Division of Perkin-Elmer Corporation, (Foster City, Calif.). Fluorescent label was attached to the 5' end of oligonucleotides using 6-FAM (6-carboxy fluorescein) amidites, or attached to a 3'-amino group (C3-CPG column from Glen Research (Sterling, Va.)) using NHS-FAM (N-hydroxysuccinimide ester of FAM) from Applied Biosystems Division of Perkin-Elmer Corporation. A universal nucleotide analogue, 1-(2'-deoxy-β-D-ribofuranosyl)-3-nitropyrrole, herein designated as Q, was synthesized, transformed to the phosphoramidite, and oligonucleotides syn-

Example 10
5'-Phosphorylation of Oligonucleotide Probes

One nmole of gel-purified oligonucleotide was phosphorylated in a 25 μl reaction containing 50 mM Tris-HCl, pH 7.6, 10 mM MgCl$_2$, 1 mM EDTA, 10 mM DTT, 1 mM ATP, and 10 units of T4 polynucleotide kinase (New England Biolabs, Beverly, Mass.) at 37° C. for 45 minutes. The reaction was quenched by adding 0.5 μl of 0.5 M EDTA, and the kinase was heat-inactivated by incubation at 64° C. for 20 minutes. The phosphorylated oligonucleotides were stored at −20° C. in 5 μl aliquots before use.

Example 11
Purification of Wild-Type and Mutant Tth DNA Ligase

Wild-type Tth DNA ligase was purified from an *E. coli* strain containing the Tth ligase gene under phoA promoter control as described (Barany, F., et al., *Gene,* 109:1–11 (1991)), which is hereby incorporated by reference) with some modifications. Briefly, cells were grown overnight at 30° C. in low phosphate (inducing) medium, harvested, resuspended in lysis buffer (20 mM Tris-HCl pH 8.5, 1 mM EDTA, 10 mM 2-mercaptoethanol, 0.15 mM PMSF) and sonicated (Barany, F., et al., *Gene,* 109:1–11 (1991), which is hereby incorporated by reference). After removal of cellular debris, the supernatant was adjusted to 20 mM Tris-HCl pH 8.5, 50 mM KCl, 10 mM MgCl$_2$, 0.5 mM EDTA, 1 mM DTT, and 2 mM 2-mercaptoethanol, incubated at 65° C. for 30 min., and cleared by centrifugation at 4° C. The supernatant was diluted with an equal volume of 10 mM Tris-HCl, pH 7.6, 0.5 mM EDTA, filtered, and loaded onto a 10 ml Red-Sepharose column (Pharmacia) equilibrated with 20 mM Tris-HCl, pH 8.5, 50 mM KCl, 1 mM EDTA, 20% glycerol. The protein was eluted with a 30 ml linear salt gradient of 50 mM to 1 M KCl (Takahaski, M., et al., *Agric. Biol. Chem.,* 50:1333–1334 (1986), which is hereby incorporated by reference), using an FPLC apparatus from Pharmacia. Tth DNA ligase eluted between 0.4–0.8 M KCl, and fractions containing pure Tth DNA ligase (seen as a doublet of adenylated and deadenylated forms on Coomassie-stained 7.5% polyacrylamide-0.1% SDS polyacrylamide gels), were pooled. The enzyme was precipitated with an equal volume of saturated ammonium sulfate, the pellet dissolved in 1.5 ml dH20, and dialyzed at 4° C. against 500 ml storage buffer containing 10 mM Tris-HCl, pH 8.5, 1 mM EDTA, 1 mM DTT, 0.2 mg/ml BSA, and 50% glycerol. Protein concentration was determined by the Bradford method (Bradford, M. M., *Anal. Biochem.,* 72:248–254 (1976), which is hereby incorporated by reference). About 4 mg of Tth DNA ligase was obtained from 450 ml culture. Mutant Tth DNA ligase was partially purified as described previously.

Example 12
Fidelity Assays of Nick Closure by Tth DNA Ligase

Each reaction was performed in 40 μl of buffer containing 20 mM Tris-HCl, pH 7.6; 10 mM MgCl$_2$; 100 mM KCl; 10 mM DTT; 1 mM NAD$^+$; and 12.5 nM (500 fmoles) of nicked DNA duplex substrates. DNA probes were denatured (94° C. for 2 min), re-annealed (65° C. for 2 min), and ligations initiated by the addition of 0.125 nM (5 fmoles) Tth DNA ligase and carried out at 65° C. Five ll aliquots were removed at 0 hr, 2 hr, 4 hr, 6 hr, 8 hr, and 23 hr, and mixed with 18 pi of a stop solution (83% formamide, 8.3 mM EDTA, and 0.17% Blue Dextran). To 5 μl of this mixture, 0.5 μl of ROX-1000, a fluorescently labeled in-lane size standard (Applied Biosystems Division of Perkin-Elmer) was added. Samples were denatured at 93° C. for 2 min, rapidly chilled on ice prior to loading on an 8 M urea-10% polyacrylamide gel, and electrophoresed at 1400 V (constant voltage) on a model 373A automated DNA Sequencer (Applied Biosystems Division of Perkin-Elmer Corporation). Electrophoresis conditions were modified as suggested by the manufacturer. The gel was polymerized in 1.2×TBE (54 mM Tris-Borate and 1.2 mM EDTA, pH 8.0) and was pre-run before loading samples in a running buffer of 0.6×TBE (27 mM Tris-Borate and 0.6 mM EDTA, pH 8.0) for 30 min with an electrode polarity opposite to the normal run with samples. After pre-run and sample-loading, the gel was run in 0.6×TBE in the normal top to bottom direction for 2.5 hrs. Fluorescently labeled ligation products were analyzed and quantified using Genescan 672 version 1.2 software (Applied Biosystems Division of Perkin-Elmer Corporation), and the results were plotted using DeltaGraph Pro3 software (DeltaPoint, Inc. Monterey, Calif.).

Example 13
Measurement of Initial Rates of Perfect Match and Mismatch Ligations by Tth DNA Ligase Conditions for these experiments were the same as that for the fidelity assay except that different amounts of Tth DNA ligase and different probes were used, as indicated in Brief Description of the Drawings. Reactions were carried out in 160 VI of reaction buffer containing 12.5 nM (2 pmoles) of nicked DNA duplex substrates at 65° C. DNA probes and target were denatured by incubating the reaction mixture at 94° C. for 2 min, and re-annealed at 65° C. for 2 min. Ligations were initiated by the addition of the Tth DNA ligase. Aliquots (10 1) were removed at 0, 2, 4, 6, 8, and 10 hr for reactions containing mismatched substrates; and at 0, 10, 20, 30, 40, 50, 60, and 70 sec for reactions containing matched substrates. For assays using matched substrates, 2.5 μl samples were mixed with 2.5 μl loading buffer, 0.5 μl of ROX-1000 before gel electrophoresis. Since the linear detection range of fluorescent samples on the 373A DNA Sequencer is from 0.1 fmol to 10 fmol, products from mismatch ligation with a yield less than 1% were concentrated by ethanol precipitation for accurate quantification. From 10 μl aliquot, 9.5 μl was brought up to 200 μl with TE buffer (10 mM Tris-HCl, pH 8.0, 1 mM EDTA) and ethanol precipitated with 4 μl of Yeast tRNA as carriers. The pellet was resuspended in 5 μl loading buffer and 0.5 μl ROX-1000 before gel electrophoresis. The amount of unreacted fluorescent probe was determined by diluting 0.5 pi of the 10 μl aliquot with 4.5 μl loading buffer plus 0.5 μl ROX-1000. Samples were separated on denaturing polyacrylamide gels, and results analyzed as described above. The initial rates were calculated as the slope of the straight line in the graph with the x-axis as the time, and the y-axis as the yield of products.

Figure 17C:
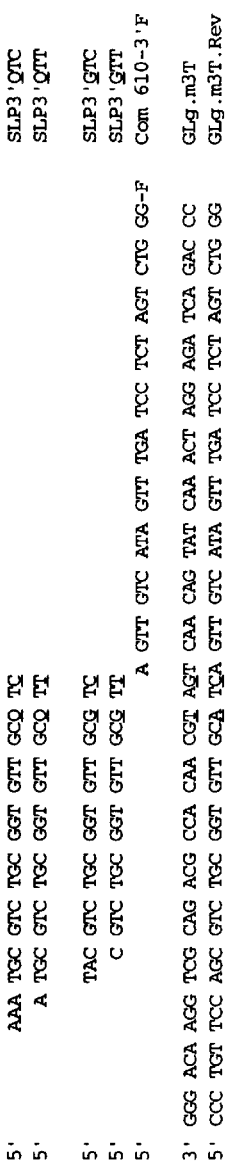

Example 14
Preparation of Oligonucleotide Probes Containing Base Analogues and Mismatch in Third Position on the 3' Side of the Nick Oligonucleotide probes were designed to test the possibility of improving the fidelity of LDR reactions using the Tth DNA ligase by introducing a base analogue or a mismatch at the third position on the 3'-side of the nick. These ten descriminating probes were made in 5 pairs. The two probes in each pair differ by one base at the 3' end ("C" or "T"). The probe with the "C" at the 3' end has two more bases at its 5' end than the "T" probe, allowing one to distinguish the ligation products on a sequencing gel. The base analogue "Q" and other bases at the third position from the 3' end are underlined. A nicked DNA duplex substrate is formed by annealing one of left side probes, (for example, SLP3'TTT), and the common fluorescently labeled probe Com 610-3'F to a template probe (for example, GLg.m3A). This substrate contains a T-G mismatch on the 3' side of the nick. Accurate quantification of mismatch and perfect match ligation products can be achieved by scanning the fluorescently labeled products using Genescan program. A ratio of initial rates of perfect match ligation over mismatch ligation indicates the fidelity of the LDR reaction. An extra mismatch or a base analogue was introduced in the third position on the 3' side of the nick in order to improve the fidelity. In FIG. 17A, probes SLP3'$Q_2$TC, SLP3'$Q_2$TT, SLP3'TTC, and SLP3'TTT were used on targets GLg.m3A to test the contribution of $Q_2$:A to increased fidelity compared with a T:A match at the 3rd position from the 3'-side. The SLP3'TTC and SLP3'TTT probes were used on mixtures of targets GLg.m3A and ALg.m3A to test for detecting a rare target (cancer mutation) in the excess of a common target (normal DNA). In FIG. 13B, probes SLP3'ATC and SLP3'ATT were used on targets GLg to test the contribution of A:C to increased fidelity compared with a G:C match at the 3rd position from the 3'-side. In FIG. 17C, probes SLP3'$Q_2$TC, SLP3'$Q_2$TT, SLP3'$Q_{18}$TC, SLP3'$Q_{18}$TT, SLP3'GTC, and SLP3'GTT were used on target GLg.m3T to test the contribution of $Q_2$:T, $Q_{18}$:T or G:T to increased fidelity compared with a T:A match at the 3rd position from the 3'-side.

Example 15
Fluorescent Assay

As shown in FIGS. 13A–C, one of the four long oligonucleotides GLg, ALg, TLg or CLg (shown in the FIG. 13C) was used as the template strand, which vary at the underlined base. FIGS. 13A–B represent the formation of nicked DNA duplex using one of the template strands, ALg, as an example. Shown in FIG. 13A, 4 different nicked DNA substrates are formed by annealing the common fluorescently labeled oligo, com5F, and one of the discriminating oligos (RP5'A, RP5° C., RP5'G, RP5'T) to the template strand, ALg. In FIG. 13B, 4 different nicked DNA substrates are formed by annealing the fluorescently labeled oligo, com3F, and one of the discriminating oligos (LP3'A, LP3° C., LP3'G, LP3'T) to the template strand, ALg. A matrix of nicked DNA duplexes is thus formed with all possible combinations of match and mismatch base pairing on the 3' and the 5' side of the nick, when ALg is replaced by one of the following template strands, GLg, TLg, and CLg. Products formed by ligation to the common fluorescently labeled probes can be discriminated by size on denaturing polyacrylamide gel due to the incorporation of different length of "A" tails.

Sequences of these probes (shown in FIG. 14) were derived from that of human eukaryotic protein synthesis initiation factor eIF-4E (Rychlik, W., et al., "Amino Acid Sequence of the mRNA Cap-Binding Protein From Human Tissue," *Proc. Natl. Acad. Sci. USA*, 84:945–949 (1987), which is hereby incorporated by reference). A random DNA sequence from a eukaryotic source was chosen to avoid any false signal arising from possible bacterial DNA contamination in Tth DNA ligase preparation. The melting temperature of probes were predicted using the nearest neighbor thermodynamic method (Breslauer, K. J., et al., "Predicting DNA Duplex Stability From the Base Sequence," *Proc. Natl. Acad. Sci. USA*, 83:3746–3750 (1986), which is hereby incorporated by reference). OLIGO 4.0 program from National Biosciences Inc., Plymouth, Minn. was used to rule out possible hairpin structure, repetitive sequences, and false priming. The templates and detecting oligonucleotides for this assay have been designed such that their melting temperature is sufficiently higher than the temperature used in the assay (65° C.) to minimize the effect of the melting temperature of probes on ligation efficiency.

All oligonucleotide probes were synthesized using reagents and a 394 automated DNA synthesizer from Applied Biosystem Division of Perkin-Elmer Corporation, Foster City, Calif. Synthesis of oligonucleotides with a fluorescent dye, 6-FAM (6-carboxy Fluorescin), attached at the 5' end was done using 6-FAM Amidites from Applied Biosystem Division of Perkin-Elmer Corporation. The oligonucleotide with a 3' FAM was made by using a 3'-Aminomodifier C3-CPG column from Glen Research (Sterling, Va.) for the initial DNA synthesis, and the FAM group was then attached through the 3'-amino group using NHS-FAM (N-hydroxyl Succinimide ester of FAM) from the Applied Biosystem Division of Perkin-Elmer Corporation. All oligonucleotides used in this study were purified by polyacrylamide gel electrophoresis and recovery of DNA from gel slices using C-18 Sep-Pak Cartridges from Waters Division of Millipore.

Oligonucleotide probes, RP5'A, RP5° C., RP5'G, RP5'T, and Com3'F were 5'-phosphorylated in a solution containing 50 mM Tris-HCl, pH 7.6, 10 mM MgCl$_2$, 1 mM EDTA, 10 mM DTT, 1 mM ATP, 1 nmole of gel-purified oligonucleotides and 10 units of T4 polynucleotide kinase (New England Biolabs, Beverly, Mass.) at 37° C. for 45 minutes. The reaction was stopped by adding 0.5 μl of 0.5 M EDTA, and the kinase was heat-inactivated by incubation at 64° C. for 20 minutes. The phosphorylated oligonucleotides were stored at −20° C. in aliquots before use.

The fluorescent fidelity assay of Tth DNA ligase was carried out in 40 μl of buffer containing 20 mM Tris-HCl, pH 7.6; 10 mM MgCl$_2$; 100 mM KCl; 10 mM DTT; 1 mM NAD$^+$; and 500 fmol (12.5 nM) of nicked duplex substrates. DNA probes were denatured by incubating the reaction mixture at 94° C. for 2 min, and re-annealed at 65° C. for 2 min. Ligations were started by the addition of 5 fmol of the thermostable ligase and carried out at 65° C. 5 μl aliquots were removed at 0 hr, 2 hr, 4 hr, 6 hr, 8 hr, and 23 hr, and mixed with 18 μl of a stop solution (83% Formamide, 8.3 mM EDTA, and 0.17% Blue Dextran). 5 μl of this mixture was denatured at 93° C. for 2 min, chilled rapidly on ice prior to loading on an 8 M urea-10% polyacrylamide gel, and electrophoresed on a 373A automated DNA Sequencer from Applied Biosystem Division of Perkin-Elmer Corporation, Foster City, Calif. Fluorescently labeled ligation products were analyzed and quantitated using Genescan 672 software (Applied Biosystem Division of Perkin-Elmer Corporation, Foster City, Calif.). Genescan 672 software provided analyzed data in the form of a gel image and a table containing the peak height and peak area of each peak in each lane. Typically, two bands were seen in each lane representing each reaction. The lower one was the free fluorescent common oligonucleotide, the upper one was the upper strand of the ligation product. The product yield in percentage was calculated as product over total initial substrates times 100. The amount of product was calculated as the peak area of the appropriate ligation product. The amount of initial substrates were calculated by adding the peak area of the product peak to that of the free fluorescent oligonucleotide peak. Results were plotted using Delta-Graph Pro3 software (DeltaPoint, Inc. Monterey, Calif.) with time as the X-axis and yield as the Y-axis.

Strategy for testing wild-type Tth DNA ligase fidelity

A fluorescent assay using nicked substrates was developed for testing Tth DNA ligase fidelity. The nicked duplex substrate was generated by annealing two adjacent oligonucleotide probes (one of them containing a fluorescent dye FAM) to a longer complementary template (bottom) strand (see FIG. 13 for sequences). For clarity, the fluorescently labeled probe is defined as the common oligonucleotide while the probe containing the test base at its terminus is called the discriminating oligonucleotide. A set of 14 oligonucleotides (FIG. 13) were used to generate all possible combinations of different single-base pair matches and mismatches at the 3'- and 5'-sides of the nick. Both common and discriminating oligonucleotides were designed such that their melting temperature was at least 10C higher than the assay temperature (65° C.). This presumably minimized the effect of differences in oligonucleotide hybridization on ligation efficiency. The ligation time was extended to 23 hours allowing for accurate quantification of mismatch ligation products. Ligation of the two adjacent oligonucleotides formed a longer fluorescent product, which was separated on a denaturing polyacrylamide gel and analyzed.

Fidelity of nick closure by wild-type TtIh DNA ligase

A time course for nick closure by Tth DNA ligase using substrates where the discriminating base is on the 3'-side of the nick is recorded in Table 3 and is shown in FIG. 15.

TABLE 3

Ligation yield generated by Tth DNA ligase with different DNA substrates containing different baseparing on the 3' side of the nick.

| Base-pairing | 0 hour | 2 hour | 4 hour | 6 hour | 8 hour | 23 hour |
|---|---|---|---|---|---|---|
| A-A | 0% | 0% | 0% | 0% | 0% | 0% |
| A-T | 0% | 85.3% | 88.9% | 90.2% | 92% | 93.2% |
| A-G | 0% | 0% | 0% | 0% | 0% | 0% |
| A-C | 0% | 0% | 0% | 0% | 0% | 1.1% |
| C-A | 0% | 0% | 0% | 1.3% | 1.8% | 2% |
| C-T | 0% | 0% | 0% | 0% | 0% | 0% |
| C-G | 0% | 82% | 88% | 90% | 96.5% | 93.3% |
| C-C | 0% | 0% | 0% | 0% | 0% | 0% |
| G-A | 0% | 0% | 0% | 0% | 0% | 0% |
| G-T | 0% | 2.5% | 3.8% | 5.46% | 7.5% | 11% |
| G-G | 0% | 0% | 0% | 0% | 0% | 0% |
| G-C | 0% | 82.6% | 87.4% | 87.4% | 88.9% | 91.3% |
| T-A | 0% | 83.8% | 86.5% | 88.4% | 89% | 92.6% |
| T-T | 0% | 0% | 0% | 0% | 0% | 0% |
| T-G | 0% | 2.2% | 3.8% | 4.45% | 8.8% | 13.4% |
| T-C | 0% | 0% | 0% | 0% | 0% | 0% |

Each panel in FIG. 15 shows the yield of product formed with the same discriminating oligonucleotide and common oligonucleotide annealed to four template strands which differ by a single base. All perfectly matched substrates yielded over 80% product within 2 hrs. (FIG. 15). Of all 12 mismatches tested on the 3'-side of the nick, T-G and G-T mismatches were less efficiently discriminated, with yields of about 2% after 2 hrs. accumulating to about 15% after 23 hrs. incubation, (FIG. 15). These results on discriminating different 3' side mismatches with Tth DNA ligase are similar to those reported for T4 DNA ligase (Landegren, U., et al., Science, 241:1077–1080 (1988), which is hereby incorporated by reference), although Tth DNA ligase does not require high salt, spermidine, or very low enzyme concentrations to suppress mismatch ligations (Wu, D. Y., et al., Gene, 76:245–254 (1989) and Landegren, U., et al., Science, 241:1077–1080(1988), which are hereby incorporated by reference).

When the mismatches were located at the 5'-side of the nick, the enzyme still exhibited stringent discrimination against A-G, C-C, G-G, and T-C mismatches. The results of this experiment are recorded in Table 4 and are plotted in FIG. 16.

TABLE 4

Ligation yield generated by Tth DNA ligase with different DNA substrates containing different baseparing on the 5' side of the nick.

| Base-pairing | 0 hour | 2 hour | 4 hour | 6 hour | 8 hour | 23 hour |
|---|---|---|---|---|---|---|
| A-A | 0% | 3.2% | 4.45% | 6.7% | 7.45% | 23.6% |
| A-T | 0% | 79.6% | 82.2% | 84.2% | 85.6% | 89.1% |
| A-G | 0% | 0% | 0% | 0% | 0% | 0% |
| A-C | 0% | 2.8% | 4.4% | 7.4% | 8.7% | 22.8% |
| C-A | 0% | 7.3% | 13.5% | 19% | 23.7% | 38.2% |
| C-T | 0% | 0% | 1.47% | 2% | 2.7% | 6.5% |
| C-G | 0% | 78% | 83.5% | 84.8% | 84.2% | 89.5% |
| C-C | 0% | 0% | 0% | 0% | 0% | 0.86% |
| G-A | 0% | 1.8% | 4.4% | 6.8% | 10.5% | 20% |
| G-T | 0% | 2.1% | 5.34% | 7.5% | 11.7% | 20.5% |
| G-G | 0% | 0% | 0% | 0% | 0% | 1.03% |
| G-C | 0% | 76.2% | 80.9% | 84.1% | 86.3% | 87.2% |
| T-A | 0% | 78.7% | 83.8% | 84.5% | 86.4% | 87.8% |
| T-T | 0% | 14.3% | 22.7% | 30% | 38.6% | 44.5% |
| T-G | 0% | 8.9% | 14.3% | 20.8% | 30.4% | 44.9% |
| T-C | 0% | 0% | 0% | 0% | 0% | 1.1% |

Ligation yields of mismatches A-C, A-A, C-A, G-A and T-T, were barely detectable after extended incubation (23 hrs.) when placed at the 3'-side of the nick, but became quite significant when placed at the 5'-side of the nick. Different ligation rates observed between isosteric mismatched substrates, G-A and A-G, or C-T and T-C, suggest that these rates are influenced by other factors, possibly stacking interactions with neighboring bases. Overall, these results indicate that Tth DNA ligase discriminates all mismatches at the 3'-side of the nick more efficiently than mismatches at the 5'-side of the nick.

If ligation fidelity were mainly dependent on the cumulative stability of base pairing near the junction, the internal stability would have been predicted to be higher for the DNA sequence at the 5'-side of the nick than at the 3'-side of the nick. The internal stability is calculated as the sum of the free energy of five continuous bases, and was found to be lower on the 5'-side of the nick (calculated using the Oligo 4.0 program from National Biosciences Inc., Plymouth, Minn.). Therefore, the observed higher fidelity to mismatches on the 3'-side of the nick by Tth DNA ligase was not caused by a specific sequence within the discriminating oligonucleotides, but by specific requirements of the nick structure recognized by this enzyme.

Improved discrimination of mismatches located at the 3'-side of the nick compared to those at the 5'-side of the nick was reported for A-A and T-T mismatches using bacteriophage T4 DNA ligase (Wu, D. Y., et al., Gene, 76:245–254 (1989), which is hereby incorporated by reference). This difference was attributed to either (i) a single-base mismatch which destablized annealing of the octamer probe used on the 3'-side more than the tetradecamer probe used on the 5' side, or (ii) an intrinsic feature of T4 DNA ligase (Wu, D. Y., et al., Gene, 76:245–254 (1989), which is hereby incorporated by reference). These results support the second hypothesis, because the oligonucleotides used in this assay were similar in length and melting temperature. A detailed analysis of the Vaccinia virus ligase showed that all mismatches on the 5'-side were ligated more efficiently than mismatches on the 3'-side (Shuman, S., Biochem., 34:16138–16147 (1995), which is hereby incorporated by reference). Similar results have also been shown for DNA ligase from Saccharomyces cerevisiae although the mismatches tested on the 5'-side of the nick were not the same as those at the 3'-side of the nick (Tomkinson, A. E., et al., *Biochemistry*, 31:11762–11771 (1992), which is hereby incorporated by reference). Also, the AP sites at the 3'-side of nicks were less efficiently ligated by T4 DNA ligase compared to the AP sites at the 5'-side of nicks (Goffin, C., et al., *Nucleic Acids Res.*, 15(21): 8755–8771 (1987), which is hereby incorporated by reference). Therefore, the more stringent requirement for the canonical structure at the 3'-side of the nick compared to the 5'-side of the nick may be general to all DNA ligases.

The lower fidelity against T-G or G-T mismatches on the 3'-side by Tth and T4 DNA ligases mirrors the fidelity of DNA polymerases. The most common mispairs formed by insertion errors of DNA polymerase involve G pairing with T, although there were substantial variations observed depending on the DNA polymerase, the method of assay, and the specific site investigated (Echols, H., et al., *Annu. Rev. Biochem.*, 60:477–511 (1991), which is hereby incorporated by reference). It was also shown that G-T, A-C, and G-A mispairings were the most frequent ones allowed by the *E. coli* pol III both in vivo (Schaaper, R. M., *Proc. Natl. Acad. Sci. USA*, 85:8126–8130 (1988), which is hereby incorporated by reference) and in vitro (Sloane, D. L., et al., *Nucleic Acids Res.*, 16:6465–6475 (1988), which is hereby incorporated by reference). Furthermore, Taq DNA polymerase extension of a 3' mismatched primer is more efficient for T-G and G-T mismatches than other mismatches at low dNTP concentrations (Kwok, S., et al., *Nucleic Acids Res.*, 18:999–1005 (1990), which is hereby incorporated by reference). NMR and X-ray crystallography analysis of the structure of aberrant base pairs in duplex DNA oligonucleotide have indicated that G-T, A-C, and G-A pairs existed as "wobble" structures which differs slightly in dimensions from a normal Watson-Crick base pair (Hunter, W. N., et al., *Nature*, 320:552–555 (1986) and Patel, D. J., et al., *Fed. Proc. Fed. Am. Soc. Exp. Biol.*, 43:2663–2670 (1984), which are hereby incorporated by reference). It was suggested that a well-stacked wobble pair may result in a more stable structure than a poorly stacked base pair approximating Watson-Crick geometry more closely. Both bacterial and mammalian DNA ligases have a very high fidelity against all purine-purine mismatches, including G-A or A-G mismatches on the 3'-side (Landegren, U., et al., *Science*, 241:1077–1080 (1988); Husain, I., et al., *J. Biol. Chem.*, 270:9683–9690 (1995); and Shuman, S., *Biochem.*, 34:16138–16147 (1995), which are hereby incorporated by reference), suggesting that base pair stability is not the predominant factor influencing ligase fidelity. Furthermore, the related Vaccinia virus ligase and mammalian DNA ligase III both demonstrate even lower fidelity for C-T mismatches than G-T mismatches (Husain, I., et al., *J. Biol. Chem.*, 270:9683–9690 (1995); and Shuman, S., *Biochem.*, 34:16138–16147 (1995), which are hereby incorporated by reference), while the Tth and T4 DNA ligases have a lower fidelity for G-T mismatches (Landegren, U., et al., *Science*, 241:1077–1080 (1988), which is hereby incorporated by reference, with regard to T4 ligase), with the Tth DNA ligase having virtually no mis-ligations for C-T mismatches on the 3'-side. Thus, the fidelity of ligases is influenced not only by the compromise between increased stability and decreased helix distortion of a mismatched base pair, but also by specific structural determinants of the individual ligase protein.

Improving the fidelity of Tth DNA ligase

The fidelity of T4 DNA ligase has been expressed as a specificity ratio; defined as the ratio of ligation product formed in the presence of matched versus mismatch template in the presence of 100 nM of template at 30C with one unit of enzyme (Wu, D. Y., et al., *Gene*, 76:245–254 (1989), which is hereby incorporated by reference). At high salt concentrations (200 mM), the specificity ratio increased from 6 to 60 for T-T mismatches and from 1.5 to 40 for A-A mismatches. These more stringent conditions also increased the Km 4 fold and decreased the $V_{max}$ approximately 30 fold (Wu, D. Y., et al., *Gene*, 76:245–254 (1989), which is hereby incorporated by reference). The fidelity of S. cerevisiae DNA ligase I was defined as the ligation efficiency of substrates containing perfect matches vs. mismatches in the presence of 3 to 900 ng of enzyme at 20° C. for 30 min (Tomkinson, A. E., et al., *Biochemistry*, 31:11762–11771 (1992), which is hereby incorporated by reference). The efficiency of this DNA ligase was found to decrease 50 fold when a T-G mismatch was present on the 3'-side of the nick. The ligation efficiency decreased by greater than 100-fold when a C-T mismatch was present on the 3'-side of the nick and a T-C mismatch on the 5' side of the nick in the same substrate. It is difficult to compare the fidelity of different DNA ligases using either of the two terms described above, because they will vary when different incubation times and substrates are used.

In order to standardize comparisons with different substrates and enzymes, the fidelity of Tth DNA ligase is defined as a ratio of the initial rate of perfect match ligation over the initial rate of mismatch ligation. Among substrates containing a mismatch on the 3'-side of the nick, T-G or G-T mismatches are the most difficult to discriminate, and were therefore used as a standard assay for determining the fidelity ratio of Tth DNA ligase. Initial rates of C-G perfect-match ligation over T-G mismatch ligation at 65° C. gave a fidelity ratio of $4.5 \times 10^2$ by Tth DNA ligase (Row 1, FIG. 18). Use of shorter discriminating probes ($T_m$ approximately 65° C.) did not dramatically change perfect-match ligations, but did decrease mismatch ligation. Thus, destabilizing the mismatched probe improved the fidelity ratio about 3-fold to $1.5 \times 10^3$ (Row 2, FIG. 18). This Tth DNA ligase fidelity ratio is at least 24 fold higher than reported for T4 ligase (Wu, D. Y., et al., *Gene*, 76:245–254 (1989), which is hereby incorporated by reference), on a T-T mismatch which is far easier to discriminate than a G-T mismatch used herein, see FIG. 15).

This exquisite specificity of Tth DNA ligase has been exploited in ligase chain reaction (i.e. LCR) to detect a mutant allele (A-T match) in the presence of a 200-fold molar excess of wild-type sequence (G-T mismatch) (Balles, J., et al., *Mol. Gen. Genet.*, 245:734–40 (1994), which is hereby incorporated by reference). Several medical DNA detection problems will require an even greater specificity. Two approaches to improve further the fidelity ratio of Tth DNA ligase by destabilizing the enzyme-substrate interactions have been devised as described below.

Improving the fidelity of Tth DNA ligase by modifying the DNA substrate

An elegant method for improving allele-specific PCR is based on using primers with a deliberate mismatch adjacent to the discriminating 3' base (Cha, R. S., et al., *PCR Methods and Applications*, 2:14–20 (1992) and Rust, S., et al., *Nucleic Acids Res.*, 21(16): 3623–3629 (1993), which are hereby incorporated by reference). This destabilizing mismatch did not dramatically reduce Taq polymerase extension of the correct target allele, but owing to a double mismatch of the other allele, the extension efficiency of the incorrect allele was reduced by a factor of I 00 to 1000-fold (Cha, R. S., et al., *PCR Methods and Applications*, 2:14–20 (1992), which is hereby incorporated by reference).

This approach was adapted for use in ligation reactions by deliberately introducing an A-C mismatch at the third position on the 3'-side of the nick. (Shown as bold letters in both perfect match and mismatch DNA substrates, FIG. 18, Row 3). The original perfect match substrate now has a single mismatch, and the original mismatch substrate now has two mismatches (one right on the 3'-side of the nick; the other, three bases in on the 3'-side of the same probe). This A-C mismatch in the third position reduced the ligation efficiency of a 3' matched (C-G) substrate almost 10 fold with 5 fmol Tth DNA ligase (data not shown). In order to obtain an initial rate comparable to that with normal perfect match ligations, the amount of enzyme was increased to 50 fmol. The ligase fidelity ratio increased by about 4-fold (to $5.8 \times 10^3$) when the extra mismatch was introduced (FIG. 18, Row 3). The internal mismatch has a greater destabilizing effect on the structure near the nick for the probe containing the 3' mismatch at the nick, than the probe containing the perfect match at the nick. Therefore, the overall fidelity of the ligase was improved. Similar results (4-fold increase) were also obtained when a T-G or G-T mismatch was introduced at the same third position on the 3'-side of the nick (data not shown). If the extra mismatch (C-A) was introduced into the second position on the 3' side of the nick, the ligation of perfect match at the 3'-side of the nick by Tth DNA ligase was strongly inhibited (175-fold lower than with no mismatch at the second position). In contrast, Taq DNA polymerase was not affected by the extra mismatch at the second position from the 3'-end of the primer (Cha, R. S., et al., *PCR Methods and Applications*, 2:14–20 (1992), which is hereby incorporated by reference). A key difference between PCR and LCR is that an adjacent mismatch only affects extension from the target during the initial PCR cycle, whereas, in LCR, ligation on the target and products is affected during every cycle of the LCR reaction.

As an alternative to a mismatched base pair, a universal nucleotide analogue might maintain DNA helix integrity with a perfect match substrate while still destabilizing a nearby mismatch, and thus further improve ligation fidelity. Oligonucleotides containing the nucleotide analogue 3-nitropyrrole deoxyribonucleotide (Q) at multiple sites in place of the natural nucleotides have been shown to function effectively as sequencing and PCR primers (Bergstrom, D. E., et al., *JACS*, 117:1201–1209 (1995) and Nichols, R., et al., *Nature*, 369:492–493 (1994), which are hereby incorporated by reference). 3-Nitropyrrole presumably allows preservation of helix integrity, because it is sufficiently small to fit opposite any of the four natural bases and has high stacking potential due to a highly polarized n-electronic configuration. $T_m$ studies on Q containing oligonucleotides indicate that Q base pairs with relatively little discrimination ($\Delta T_m = 3°$ C.) but the stability of Q-A (most stable), Q-T, Q-C, and Q-G (least stable) base pairs is significantly less than that of an A-T or C-G base pair. Consequently, Q, if located three nucleotides in from the 3'-end of a probe could significantly enhance local melting if it were present in conjunction with a mismatch at the 3'-position, while at the same time preserving helix integrity more than a mismatch when present in conjunction with a base pair match at the 3'-end. When sequences SLP3'QTC and SLP3'QTT were tested as ligation substrates for Tth DNA ligase, an even better fidelity ratio (9-fold increase) was obtained (FIG. 18, Row 4). Note that the base on the template strand was changed from C to A. As determined by the initial rates of perfect match ligation, the Q base analogue appears to pair to A and T equally well, less well to C, and very poorly with G. The ratio of initial rates obtained when Q was paired with different bases is T:A:C:G=23:16:5:1. As observed with C/A mismatches above, when the Q analogue is located at the second position, the ligation rate is also strongly inhibited (55 fold lower than with no analogue at the second position).

On the basis of modeling studies (QUANTA/CHARMM), Q can fit opposite both T and A with minimal perturbation of the helix structure (Bergstrom, D. E., et al., *JACS*, 117:1201–1209 (1995), which is hereby incorporated by reference). In one case, Q would assume the anti conformation (Q-T), and in the other a syn conformation (Q-A). Nevertheless, studies in progress suggest that hydrogen bonding plays only a minor role in 3-nitropyrrole-natural base interactions.

Improving the fidelity of TtlI DNA ligase by site-directed mutagenesis of the ligase protein The fidelity of DNA polymerases may be decreased by site-directed mutagenesis of motifs associated with primer-template binding (HIV polymerase) (Beard, W. A., et al., *J. Biol. Chem.*, 269:28091–28097 (1994), which is hereby incorporated by reference) or the exoIII motif of Phi29 DNA polymerase (Soengas, M. D., et al., *The EMBO J.*, 11(11): 4227–4237 (1992), which is hereby incorporated by reference), T4 DNA polymerase (Reha-Krantz, L. J., et al., *J. Virol.*, 67(1): 60–66 (1993) and Reha-Krantz, L. J., et al., *J. Biol. Chem.*, 269:5635–5643 (1994), which are hereby incorporated by reference), or human DNA polymerase alpha (Dong, Q., et al., *J. Biol. Chem.*, 268:24163–24174 (1993), which is hereby incorporated by reference). Occasionally, this same exoIII motif or motif "A" yields increased fidelity mutants also known as "antimutator" strains, which reflects the complex interplay between the polymerizing and 3'-5' exonuclease activities of these enzymes in modulating overall fidelity (Reha-Krantz, L. J., et al., *J. Virol.*, 67(l): 60–66 (1993); Reha-Krantz, L. J., et al., *J. Biol. Chem.*, 269:5635–5643 (1994); Dong, Q., et al., *J. Biol. Chem.*, 268:24175–24182 (1993); and Copeland, W. C., et al., *J. Biol. Chem.*, 268:11041–11049 (1993), which are hereby incorporated by reference).

Mutant Tth DNA ligases, which retained near wild-type nick-closing activity, were assayed for changes in fidelity. Two mutant ligases, K294R and K294P were shown to have increased their fidelity ratios (FIG. 18, Rows 5–8). With regular substrates, the fidelity increased about 4-fold by K294R and 11-fold with K294P. When Q base analogues were used together with mutant Tth DNA ligases, the fidelity of the ligation reactions were increased by almost 20-fold (K294R and K294P), although higher concentrations of mutant ligase were required. In subsequent experiments (see Table 5 below), K294Q and K294L were also shown to have increased fidelity ratios.

In summary, a quantitative fluorescence assay has been developed for analyzing the fidelity of Tth DNA ligase. This enzyme exhibits significantly greater discrimination against all single-base mismatches at the 3'-side of the nick by comparison to those at the 5'-side of the nick. Among all twelve possible single-base pair mismatches at the 3'-side of the nick, only T-G and G-T mismatches generated a quantifiable level of ligation products after extended incubation. The fidelity of Tth DNA ligase can be improved further by designing discriminating oligonucleotides with melting temperature values near the ligation temperature of 65° C., by introducing a deliberate mismatch base or a nucleotide analogue into the left third position on the 3'-side of the nick, and/or by using mutant Tth DNA ligase.

Numerous medical problems will require exquisite single-base discrimination, for example, finding rare cancer cells among many normal cells, distinguishing pathogenic microorganisms among normal flora, identifying oncogenic HPV strains in mixed infections, and detecting the emergence of drug resistant organisms. While these model studies were limited to either pure mismatched or matched target substrates, nucleotide analogues and mutant Tth DNA ligases have recently been used to improve discrimination of a minor correct target in a mixture of incorrect target. This more closely mimics DNA detection in biological samples.

Example 16
Oligonucleotide Synthesis and Purification

All oligonucleotides were synthesized on an ABI 394 DNA Synthesizer (Applied Biosystems Inc., Foster City, Calif.). For oligonucleotides labeled with FAM (i.e. Corn 610 3'F), a fluorescein CPG (Glen Research) column was used to introduce a fluorescein molecule to the 3'-terminus of the oligonucleotide. Cleavage of the oligonucleotide from the support with 30% (Wt./Vol) NH40H required 2 hr. at room temperature. The oligonucleotide was subsequently deprotected at 55° C. for 4 hr. All other oligonucleotides used in LDR were purified by polyacrylamide gel electrophoresis on 10% acrylamide/7M urea gels. Oligonucleotides were visualized after electrophoresis by UV shadowing against a lightning screen and excised from the gel (Applied Biosystems Inc., 1992). They were then eluted overnight at 64° C. in TNE buffer (100 mM Tris/HCl pH 8.0 containing 500 mM NaCl and 5 mM EDTA) and recovered from the eluate using Sep Pak cartridges (Millipore Corp, Milford, Mass.) following the manufactures instructions.

Oligonucleotides were resuspended in 100 µl TE. Typical concentration of a stock solution is about 1 mM. For LDR, gel purified stock solutions were about 100 µM=100 pmoles/El.

Example 17
Chemical Phosphorylation of oligo Corn 610-3'F

The downstream, common oligonucleotide was phosphorylated at the 5' end using a chemical phosphorylation reagent (Glen Research). The use of this reagent is an alternative to the enzymatic techniques for oligonucleotide phosphorylation, with the advantage of allowing phosphorylation efficiency to be determined. Chemical phosphorylation reagent has proved to be a fast and convenient method for phosphorylation at the 5'-terminus of oligonucleotides. The compound is stored desiccated at 4° C. For synthesis on the ABI394 machine, a 0.1M solution is prepared by adding 1 ml of anhydrous acetonitrile per 100 µmoles of the compound. The liquid is allowed to sit for approximately 5 minutes, swirling occasionally to ensure complete dissolution. Synthesis of the oligonucleotide was performed with modifications to the synthesis cycle according to the manufacturer's instructions. For example, the DMT group was removed on the synthesizer by the standard deblocking method to determine the coupling efficiency.

Quantitative detection of target containing a single-base mutation (T:G mismatch), in the presence of an excess of normal template, using wild-type and mutant Tth DNA ligases An assay has been developed which can quantify the amount of a low abundance sequence (cancer mutation) in an excess of normal DNA. Using wild-type and mutant Tth DNA ligases in an LDR assay, the fraction of "cancer" DNA in a mixture of normal and cancer DNA could be quantified. The probes used to determine the limits of detection are shown in FIG. 19, with sequences in FIG. 20. Two oligonucleotides were hybridized to the target such that the 3' end of the upstream probe (SLP3'TTT) is immediately adjacent to the 5' end of the downstream probe (Com 610-3'F). Tth DNA ligase can then join the two adjacent oligonucleotides, provided that the nucleotides at the junction are correctly base-paired with the target strand. The probes used in this reaction create a T:G mismatch on the "Normal" template and an T:A match on the "Cancer" template at the ligation junction. LDR experiments were done in triplicate using 12.5 nM (250 fmole) of the T:G mismatched template ("Normal"; GLg.m3A and Glg.m3Arev), containing from 0 to 2.5 nM (50 fmole) of perfect matched template ("Cancer"; ALg.m3A and Alg.m3Arev) in the presence of 25 fmol of purified wild-type and mutant enzyme K294R (See FIG. 21). Products are separated on an ABI 373A DNA sequencing apparatus and fluorescent signal quantified. If yield is defined as Product/(Product+Probe), the yields are artificially high due to quenching of the overloaded probe signal. Therefore, a diluted product control was run to generate a calibration number (1 fmole=600 peak area units). The amount of product in a given sample in fmol was calculated by dividing the total peak area of product by 600. This method will underestimate product formation if less than the full 5 µl ligation mix is loaded per lane. Both enzymes generated about the same amount of product, but the mutant K294R enzyme gave less background mismatch ligation. Therefore, the signal-to-noise ratio was almost double for the mutant enzyme compared to the wild-type ligase (See FIG. 22). With the K294R mutant enzyme, the signal-to-noise ratio was 3.3 for distinguishing one "Cancer" template in 500 "Normal" template, and increased to 5.4 for distinguishing one in 250 "Normal" templates (See numbers in FIG. 22, as well as a similar experiment described in Table 5). This assay compares the ability of ligase to discriminate the most difficult case; a T:G mismatch from an T:A perfect match.

The results shown in FIGS. 21 and 22 demonstrate the ability of Tth DNA ligase to distinguish the presence of a perfect match substrate ("Cancer" mutation) in the presence of an excess of mismatch substrate ("Normal"). To quantify precisely the amount of "cancer" template, it is necessary to determine the amount of "normal" template present, which may be done in two ways. The simplest method is to include a small ratio of fluorescently labeled probe in the original PCR mix, and quantify the amount of product generated using capillary electrophoresis or an automated DNA sequencer. The second approach uses the quantitative nature of ligation reactions to determine the original product concentration. FIG. 23 shows the amount of LDR product generated from 0.005 nM (0.1 finol), to 0.5 nM (10 fmol) "Normal" template (GLg.m3A and Glg.m3Arev) using probes that are perfectly matched at the junction (SLP3'TTC and Com 610-3'F). With the K294R mutant enzyme, the signal-to-noise ratio was 4.5 for detecting 0.005 nM (0.1 fmol) "Normal" template and improved to 7.4 for detecting 0.0125 nM (0.25 fmol) "Normal" template (data not shown). By comparing the amount of LDR product from an unknown sample with the calibration curve, the total DNA in a sample can be quantified. This can be achieved by directly testing undiluted samples of amounts from 100 attomoles (0.005 nM) to 10 femtomoles (0.5 nM), or testing dilutions when working with higher quantities/concentrations of DNA. These results demonstrate that the amount of specific DNA present in an unknown sample can be determined, as well as the percentage (amount) containing a single-base ("Cancer") mutation.

Detection of target containing a single-base mutation in the presence of an excess of normal template using wild-type and mutant Tth DNA ligases.

To explore further the use of wild-type and mutant Tth DNA ligases in cancer detection, the ligation detection reaction was optimized in a competition assay which more closely mimics the biological problem of distinguishing a cancer cell in an excess of normal cells. This type of assay requires not only that the ligase seal the correct sequence, but that it must do so when most of the enzyme is bound to the incorrect substrate. Therefore, higher concentrations of enzyme are required than in the previous assay, and these higher concentrations may lead to increased background (mismatched) ligations. Two oligonucleotides (SLP 3'TTT and Com 610 3'F) are permitted to hybridize to the denatured target such that the 3' end of one oligonucleotide is adjacent to the 5' end of a fluorescent labeled oligonucleotide (see FIG. 19). The ligase can then join the two adjacent oligonucleotides, provided that the nucleotides at the junction are correctly base-paired with the target strand. Initial experiments on LDR were done in triplicate using the mismatched template ("Normal"), and perfect match template ("Cancer") independently, or in combination with each other in the presence of 25 fmol of purified wild type and mutant enzymes K294R and K294L (Table 5).

TABLE 5

Amount of Product Formed (fmol) with Different Templates

| Tth DNA Ligase Conc (1.25 nM) | 250 fmol N Template | 10 fmol C Template | 10 fmol C Template in 250 fmol of N Template (1:25) | 2.5 fmol of C Template in 250 fmol of N Template (1:100) |
|---|---|---|---|---|
| Wild-Type | 1.45 | 32.5 | 11.2 | 4.9 |
| Mutant K294R | 0.56 | 33.2 | 12.9 | 3.3 |
| Mutant K294L | ND | 29.6 | 9.7 | 3.4 |
| Signal/Noise Ratio Wild-Type | — | — | 7.7 | 3.4 |
| Mutant K294R | — | — | 23.1 | 5.9 |

(The K294P mutation causes loss of thermostability and, therefore, was not used in further studies). The amount of LDR product generated (0.56 fmol) by the mutant K294R on the mismatched template, was reduced by more than 2-fold as compared to the wild-type enzyme (1.45 fmol). LDR was also performed with the perfect match and mismatch templates together in a ratio of 1:25 and 1:100, respectively. For both wild-type and mutant enzymes, the product generated in the presence of the mismatch template was less than the product generated by the perfect match template alone. The use of K294R results in a 1.75 to 3 fold higher signal-to-noise ratio. Since no background was detected with the K294L mutant, a signal-to-noise ratio could not be calculated. Thus, these results support the finding that the mutant K294R exhibits a higher fidelity in discriminating a mismatch over the wild-type enzyme. This increased fidelity is probably due to a change in the specificity constant of this mutant thermostable enzyme. The specificity of an enzymatic reaction is determined by the catalytic constant, $k_{cat}$, and the apparent binding constant, $K_M$, and expressed as the specificity constant $k_{cat}/K_M$. Any modifications made on the enzyme itself, substrate, or reaction conditions, which affect $k_{cat}$ or $K_M$ or both, will change the specificity. The use of a mutant enzyme may influence the stability of the perfect matched and mismatched enzyme-DNA complexes to a different extent, so that discrete $K_M$ effects are exerted on these ligation reactions. In a competitive reaction, such as ligation of perfectly matched and mismatched substrates, the ratio of the specificity constant may be altered as a consequence of $K_M$, and possible $k_{cat}$ changes for each substrate. All mutant enzymes which satisfy the equation below (shown for K294R) will give increased discrimination of cancer-associated mutations in the presence of an excess of normal DNA.

$$\frac{[k_{cat}/K_M]_{K294R,match}}{[k_{cat}/K_M]_{K294R,mismatch}} > \frac{[k_{cat}/K_M]_{Wt,match}}{[k_{cat}/K_M]_{Wt,mismatch}}$$

Alternatively, the second aspect of the present invention can be expressed in terms of a fidelity ratio (i.e. the initial rate of ligating a substrate with a perfect match at the 3' end divided by the initial rate of ligating a substrate with a mismatch at the 3' end) as follows:

$$\frac{[k_1]_{K294R,match}}{[k_1]_{K294R,mismatch}} > \frac{[k_1]_{Wt,match}}{[k_1]_{Wt,mismatch}} = \text{Fidelity ratio}$$

In the above equation, $[k_1]_{match}$ represents the initial rate constant for ligating the first and second oligonucleotide probes hybridized to a target nucleotide sequence with a perfect match at the ligation junction between the target nucleotide sequence and the oligonucleotide probe having its 3' end at the ligation junction. $[k_1]_{mismatch}$ represents the initial rate constant for ligating the first and second oligonucleotide probes hybridized to a target with a mismatch at the ligation junction between the target nucleotide sequence and the oligonucleotide probe having its 3' end at the ligation junction. For the mutant thermostable ligase, $[k_1]_{match}$ divided by $[k_1]_{mismatch}$ (=fidelity ratio) is greater than the fidelity ratio for wild-type ligase. All mutant enzymes which satisfy the equation above (shown for K294R) will give increased discrimination of cancer-associated mutations in the presence of an excess of normal DNA.

Detection of target containing a single-base mutation in the presence of an excess of normal template using nucleotide analogue containing probes.

In an effort further to increase ligase fidelity, probes were synthesized containing the $Q_2$ or $Q_{18}$ (I-(2'-deoxy-β-D-ribofuranosyl)pyrrole-3-carboxamide) nucleotide analogues in the 3rd position from the 3' end of the discriminating probe (see FIG. 24). In these experiments, the template base opposite the probe analogue was either A or T, to allow assaying of the more favored $Q_2$:A, $Q_2$:T, and $Q_{18}$:T pairings. Using these analogue probes, products generated from the mismatch ligation were reduced approximately by 2 to 3-fold as compared to the regular primers (Table 6).

FIG. 24 shows nucleotide analogue containing probes used for assaying ligase fidelity. Four different conditions were used to assess the fidelity of the wild-type and mutant Tth DNA ligase in a typical LDR assay as shown in Table 6. Each reaction was carried out in a 20 µl mixture containing 20 mM Tris-HCl, pH 7.6; 10 mM MgCl$_2$; 100 mM KCl; 10 mM DTT; 1 mM NAD$^+$; 25 nM (500 fmol) of the two short detecting probes and 12.5 nM (250 fmol) of the normal template when used alone, or 125 nM (2.5 fmol), and 0.5 nM (10 fmol), of the cancer template when used together with the normal template in a ratio of 1:100, and 1:25, respectively. The probes used in this reaction create a T:G mismatch on the "Normal" template and an T:A match on the "Cancer" template at the ligation junction. In addition, probe SLP3'QTT creates a $Q_2$:A or $Q_{18}$:T pairing at the 3rd position from the 3' end. The reaction mixture was heated in a GeneAmp 9600 thermocycler (Perkin Elmer) for 1.5 sec. at 94° C. before adding 25 fmol of the wild-type Tth DNA ligase. After incubation with the enzymes for another 30 sec, LDR reactions were run for 15 sec at 94° C., and 4 min. at 65° C. per cycle for 20 cycles. Reactions were completely stopped by chilling the tubes in an ethanol-dry ice bath, and adding 0.5 μl of 0.5 mM EDTA. 2.5 μl of reaction was mixed with 2.5 μl of loading buffer (83% Formamide, 8.3 mM EDTA, and 0.17% Blue Dextran) and 0.5 μl Gene Scan Rox-1000 molecular weight marker, denatured at 94° C. for 2 min, chilled rapidly on ice prior to loading on an 8 M urea-i 0% polyacrylamide gel, and electrophoresed on an ABI 373 DNA sequencer. Fluorescent labeled ligation products were analyzed and quantified using the ABI Gene Scan 672 software.

FIGS. 25A–D show different forms of oligonucleotide probes with nucleotide analogues for the LDR phase of the PCR/LDR process of the present invention. In FIG. 25A, one oligonucleotide probe hybridized to a target nucleotide sequence where the probe has the discriminating base at its 3' end (i.e. at the ligation junction) and a nucleotide analogue at the third position from the ligation junction. Such an oligonucleotide probe is a bit unstable but will still undergo ligation, because its 3' end is complementary to the target nucleotide sequence to which it is hybridized. FIG. 25B is similar to FIG. 25A except that no ligation occurs, because its 3' end is not complementary to the target nucleotide sequence to which it is hybridized. In FIG. 25C, the oligonucleotide probe hybridized to the target nucleotide sequence has a discriminating base at its 3' end (i.e. at the ligation junction) as well as at the 2 adjacent positions. In the positions 4, 5, and 6 bases from the ligation junction, there are nucleotide analogues. As a result, in FIG. 25C, although the presence of the 3 oligonucleotide analogues makes the oligonucleotide probe unstable, ligation will still occur, because there is complete complementarity at the 3 positions closest to the ligation junction. On the other hand, where there is a mismatch at one or more of the 3 positions closest to the ligation junction, as shown in FIG. 25D, no ligation will occur. Comparing the oligonucleotide probes used in the procedure of FIGS. 25A–B to those of FIG. 25C–D, it is apparent that the former has a potential zone of instability at the 3 positions closest to ligation junction, while the latter has a potential zone of instability at the 6 positions closest to ligation junction. The use of a 6 position zone of instability instead of a 3 position zone of instability has the potential to improve LDR fidelity, because such a larger zone of instability reduces the likelihood that a ligation product will form despite the existence of a mismatch at the ligation junction.

TABLE 6

Amount of Product Formed (fmol) With Different Templates

| Nucleotide Analogue | Wild type Tth. ligase (nM) | 250 fmol N Template | 10 fmol C Template | 10 fmol of C Template in 250 fmol of N Template | 2.5 fmol of C Template in 250 of N Template | Signal/ Noise (1:25) | Signal/ Noise (1:100) |
|---|---|---|---|---|---|---|---|
| $Q_2$:A | 1.25 | 0.56 | 40.6 | 11.4 | 3.4 | 20.4 | 6.0 |
|  | 2.5 | 0.72 | 51.6 | 15.0 | 4.7 | 20.8 | 6.6 |
|  | 5.0 | 1.40 | 57.9 | 20.9 | 6.5 | 14.9 | 4.6 |
|  | 10.0 | 2.51 | 62.9 | 31.0 | 10.2 | 12.4 | 4.I |
| $Q_2$:T | 1.25 | N.D. | 12.9 | 5.2 | 1.5 | — | — |
|  | 2.5 | N.D. | 23.5 | 8.6 | 2.8 | — | — |

TABLE 6-continued

Amount of Product Formed (fmol) With Different Templates

| Nucleotide Analogue | Wild type Tth. ligase (nM) | 250 fmol N Template | 10 fmol C Template | 10 fmol of C Template in 250 fmol of N Template | 2.5 fmol of C Template in 250 of N Template | Signal/ Noise (1:25) | Signal/ Noise (1:100) |
|---|---|---|---|---|---|---|---|
|  | 5.0 | 0.61 | 35.9 | 12.4 | 4.6 | 20.4 | 7.5 |
|  | 10.0 | 0.78 | 38.1 | 21.2 | 6.9 | 27.1 | 8.9 |
| $Q_{18}$:T | 1.25 | 0.86 | 43.2 | 13.4 | 3.7 | 15.6 | 4.4 |
|  | 2.5 | 0.74 | 28.4 | 10.1 | 3.9 | 13.7 | 5.3 |
|  | 5.0 | 0.82 | 30.1 | 14.5 | 5.3 | 17.7 | 6.4 |
|  | 10.0 | 1.05 | 35.3 | 15.8 | 4.6 | 15.1 | 4.3 |
| Regular Probes 3'TTT + 61 03'F | 1.25 | 1.45 | 32.5 | 11.2 | 4.9 | 7.7 | 3.4 |

However, the amount of signal generated from the perfect match ligations remained relatively constant. Higher enzyme concentration (for example, 10 nM (200 fmol)) leads to the saturation of the perfect match template with the nucleotide analogues, so that more enzyme is free to bind to the mismatch template. As a consequence, higher mismatch signals were observed with increased enzyme concentrations. In the presence of perfect match and mismatch templates (1:25 and 1:100), the absolute signals generated from the perfect match was less than that generated by the perfect match alone, for both unmodified probe and probes containing the $Q_2$ or $Q_{18}$ nucleotide analogues. A higher signal to noise ratio was achieved with the analogue probes, due to lower mismatch ligations. The signal to noise ratios with the $Q_2$ analogue appeared consistently higher than the regular probes at the enzyme concentration up to 5 nM (100 fmol). Furthermore, a higher signal to noise ratio was maintained at enzyme concentrations up to 10 nM (200 fmol) with the $Q_{18}$ analogue, indicating that $Q_{18}$ may be better than $Q_2$ in tolerating variations of enzyme concentration.

Introduction of the $Q_2$ or $Q_{18}$ analogues at the 3rd position of the discriminating probe improves the signal to noise ratio about 2 to 3-fold, thereby increasing the power of the LDR system to discriminate cancer signal from background. This assay compares the ability of ligase to discriminate the most difficult case; a T:G mismatch from an T:A perfect match. The $Q_2$ or $Q_{18}$ analogues located three nucleotides in from the 3'-end of a probe enhance local melting when present in conjunction with a mismatch at the 3'-position, while at the same time preserving helix integrity more than a mismatch when present in conjunction with a base pair match at the 3'-end. The use of a $Q_2$ or $Q_{18}$ analogue near the 3' end of a probe may influence the stability of the perfect matched and mismatched enzyme-DNA complexes to a different extent, so that discrete $K_M$ effects are exerted on these ligation reactions. In a competitive reaction, such as ligation of perfectly matched and mismatched substrates, the ratio of the specificity constant may be altered as a consequence of $K_M$, and possible $k_{cat}$ changes for each substrate. All modified probes which satisfy the equation below (shown for Q analogues) will give increased discrimination of cancer-associated mutations in the presence of an excess of normal DNA.

$$\frac{[k_{cat}/K_M]_{SLP3'QTT,match}}{[k_{cat}/K_M]_{SLP3'QTT,mismatch}} > \frac{[k_{cat}/K_M]_{SLP3'TTT,match}}{[k_{cat}/K_M]_{SLP3'TTT,mismatch}}$$

Alternatively, the third aspect of the present invention can be expressed in terms of a fidelity ratio (i.e. the initial rate of ligating a substrate with an analogue located three nucleotides in from the 3' end as well as a perfect match at the 3' end divided by the initial rate of ligating a substrate with an analogue located three nucleotides in from the 3' end as well as a mismatch at the 3' end) as follows:

$$\frac{[k_1]_{SLP3'QTT,match}}{[k_1]_{SLP3'QTT,mismatch}} > \frac{[k_1]_{SLP3'TTT,match}}{[k_1]_{SLP3'TTT,mismatch}} = \text{Fidelity ratio}$$

Detection of target containing a C:A mismatch in the presence of an excess of normal template using wild type and mutant Tth DNA ligases.

The assay, which can quantify the amount of a low abundance sequence (cancer mutation) in an excess of normal DNA, was extended to determine the limits of detecting a C:G match in the presence of an excess C:A mismatches. Using wild-type and mutant Tth DNA ligases in an LDR assay, the fraction of "cancer" DNA in a mixture of normal and cancer DNA was quantified. The probes used to determine the limits of detection are shown in FIG. 26, with sequences in Table 7.

templates (See numbers in FIG. 28, as well as a similar experiment described in Table 8).

TABLE 8

Amount of Product Formed (fmol) with different Templates using the C/A mismatch

| Tth Ligase Conc (fmol) | 250 fmol N Template | 10 fmol C Template | 10 fmol C Template in 250 fmol of N Template (1:25) | 2.5 fmol of C Template in 250 fmol of N Template (1:100) |
|---|---|---|---|---|
| Mutant Enzyme K294 R (50 fmol) | 0.82 | 33.26 | 14.53 | 6.62 |
| Wild Type Enzyme (50 fmol) | 1.48 | 35.69 | 16.70 | 7.60 |
| Mutant Enzyme K294 R (25 fmol) | 0.95 | 36.52 | 17.91 | 5.66 |
| Wild Type Enzyme (25 fmol) | 1.04 | 24.94 | 13.50 | 7.47 |
| Signal/Noise Ratio | | | | |
| K294 R (50 fmol) | — | — | 17.72 | 8.07 |
| Wild Type Enzyme (50 fmol) | — | — | 11.28 | 5.13 |
| Mutant Enzume K294 R (25 fmol) | — | — | 18.85 | 5.95 |
| Wild Type Enzyme (25 fmol) | — | — | 12.98 | 7.19 |

TABLE 7

| Probe Name | Size (bp) | Sequence (5'--->3') |
|---|---|---|
| Com610-3'F (SEQ. ID No. 31) | 30 | Fam-GGGTCTGATCTCCTAGTTTGATACTGTTGA |
| SLP3'TTT (SEQ. ID. No. 30) | 21 | ATGCGTCTGCGGTGTTGCTTT |
| SLP3'TTC (SEQ. ID. No. 29) | 23 | AAATGCGTCTGCGGTGTTGCTTC |
| Template Name | | |
| Glg.m3A (SEQ. ID. No. 32) | 59 | CCCAGACTAGAGGATCAAACTATGACAACTGAA GCAACACCGCAGACGCTGGAACAGGG |
| Glg.m3A.Rev (SEQ. ID. No. 33) | 59 | CCCTGTTCCAGCGTCTGCGGTGTTGCTTCAGTTGT CATAGTTTGATCCTCTAGTCTGGG |
| Alg.m3A (SEQ. ID. No. 34) | 59 | CCCAGACTAGAGGATCAAACTATGACAACTAAA GCAACACCGCAGACGCTGGAACAGGG |
| Alg.m3A.Rev (SEQ. ID. No. 35) | 59 | CCCTGTTCCAGCGTCTGCGGTGTTGCTTTAGTTGT CATAGTTTGATCCTCTAGTCTGGG |

Two oligonucleotides were hybridized to the target such that the 3' end of the upstream probe (SLP3'TTC) is immediately adjacent to the 5' end of the downstream probe (Corn 610-3'F). The probes used in this reaction create a C:A mismatch on the "Normal" template and an C:G match on the "Cancer" template at the ligation junction. LDR experiments were done in triplicate using 12.5 nM (250 fmole) of the C:A mismatched template ("Normal"; ALg.m3A and Alg.m3Arev), containing from 0 to 2.5 nM (50 fmole) of perfect matched template ("Cancer"; GLg.m3A and Glg.m3A.rev) in the presence of 25 fmol of purified wild-type and mutant enzyme K294R (See FIG. 27). Both enzymes generated about the same amount of product, and the mutant K294R enzyme gave somewhat less background mismatch ligation. Thus, the signal-to-noise ratio was only slightly improved for the mutant enzyme compared to the wild-type ligase (See FIG. 28). With the K294R mutant enzyme, the signal-to-noise ratio was 2.2 for distinguishing one "Cancer" template in 500 "Normal" template, and increased to 3.1 for distinguishing one in 250 "Normal"

Can conditions where the mutant K294R enzyme is superior to wild-type enzyme in distinguishing a C:A mismatch be found? Initial experiments on LDR were done in triplicate using the mismatched ("Normal") template and perfect match ("Cancer") template independently, or in combination with each other in the presence of 25 and 50 fmol of purified wild-type and mutant enzyme K294R (Table 8). The results obtained with the C:A mismatch were comparable to the results obtained with the T:G mismatch using 25 fmol of enzyme. However, when using the higher enzyme amount (50 fmoles), the amount of LDR product generated by the wild-type enzyme on the mismatch template was at least 1.8 fold greater than generated by the mutant enzyme. LDR was also performed with the perfect match and mismatch templates together in a ratio of 1:25 and 1:100, respectively. For both wild type and mutant enzymes product generated in the presence of the mismatch template was less than the product generated by the perfect match template alone. The mutant K294R, generated slightly less product than the wild type enzyme under identical conditions, however, combined with a lower background signal from the normal template, the use of K294R results in about a 1.5 to 2-fold higher signal-to-noise ratio. Hence these results are in conjunction with our previous results and support the earlier finding that the mutant K294R exhibits a higher fidelity in discriminating a mismatch over the -wild type enzyme. We also note that 50 fmoles of enzyme gave the best signal-to-noise ratio when using Q analogue containing probes (Table 8).

Example 18
Quantitative Detection of Target Containing a Single-Base Mutation, in the Presence of an Excess of Normal Template, Using Wild-Type and Mutant Tth Ligases An assay has been developed to quantify the amount of cancer mutation in a given sample. Using wild-type and mutant Tth ligases in an LDR assay, the fraction of "cancer" DNA in a mixture of normal and cancer DNA was quantified. The probes used to determine the limits of detection are shown in FIG. 30. Two oligonucleotides were hybridized to the target such that the 3' end of the upstream probe is immediately adjacent to the 5' end of downstream probe. Tth DNA ligase can then join the two adjacent oligonucleotides, provided that the nucleotides at the junction are correctly base-paired with the target strand. LDR experiments were done in triplicate using 12.5 nM (250 fmole) of the mismatched template ("Normal"), containing from 0 to 2.5 nM (50 fmole) of perfect matched template ("Cancer") in the presence of 25 fmol of purified wild-type and mutant enzyme K294R (See FIG. 21). Both enzymes generated about the same amount of product, but the mutant K294R enzyme gave less background mismatch ligation. Therefore, the signal-to-noise ratio was somewhat better (about 1.5-fold) for the mutant enzyme compared to the wild-type ligase (FIG. 22). With the K294R mutant enzyme, the signal-to-noise ratio was 3.3 for distinguishing one "Cancer" template in 500 "Normal" templates and increased to 5.4 for distinguishing one in 250 "Normal" templates. This assay compares the ability of ligase to discriminate the most difficult case; a G:T mismatch from an A:T perfect match. Since the Tth DNA ligase shows five-fold greater fidelity in distinguishing a C:A mismatch (the second most difficult case) compared to a G:T mismatch, the mutant enzyme would be predicted to distinguish all other mismatches at 1 in 2,500 or better.

The experiment using synthetic substrates which generate a C:A mismatch has been carried out (See Table 7), and the limits of detection and signal to noise values were determined (see FIGS. 27 and 29). Control ligations to quantify the amount of normal DNA gave qualitatively similar results as before (see FIG. 28). There was no significant difference between wild-type and mutant enzyme with these substrates. With the K294R mutant enzyme, the signal-to-noise ratio was 2.2 for distinguishing one "Cancer" template in 500 "Normal" templates, and increased to 3.1 for distinguishing one in 250 "Normal" templates. Although the synthetic substrate results suggest there is no fundamental difference in distinguishing a G:T mismatch from a C:A mismatch, experiments with natural PCR products containing the K-ras gene suggest that significantly better discrimination may be achieved with C:A mismatches than with G:T mismatches.

Example 19
Design and Synthesis of LDR Probes to Detect all Possible Mutations in Codons 12, 13, and 61 of the K-ras Oncogene.

The K-ras gene presents two significant challenges for mutation detection techniques. Extensive sequence homology between the H-, N- and K-ras genes requires a primary exon-specific PCR reaction to amplify selectively the correct gene. A subsequent allele-specific PCR has been used to detect individual K-ras mutations, but a multiplex PCR to detect all mutations is complicated by the proximity of codon 12 and codon 13 mutations.

The scheme for simultaneously assaying mutations in codons 12, 13, and 61 of the K-ras gene is shown in FIG. 30. Two independent PCR primer pairs which correctly PCR amplify the K-ras gene in the regions surrounding codons 12 and 13, and codon 61 have been synthesized. All possible LDR probes for these codons were designed and synthesized (FIGS. 31A–B). The discriminating oligonucleotides have calculated $T_m$ values of about 66° C. and contain the discriminating bases at their 3' ends. These oligonucleotides generate products distinguished by alternating FAM- or TET-fluorescent peaks when separated on an automated ABI 373A DNA sequencer. The common oligonucleotides have calculated $T_m$ values of about 69° C. and contain poly-A tails with spacer C3 blocking groups at their 3' ends. The blocking groups prevent residual polymerase extension of LDR primers, and the poly-A tails allow the LDR products to be separated on sequencing gels. Common probes were chemically phosphorylated at their 5' ends.

The LDR probes were designed such that the most common mutations would generally provide the smaller ligation products. Thus, for the seven most common K-ras mutations in colon cancer, the products would be 44 bp for G12D (G$\underline{A}$T), 45 bp for G12A (G$\underline{C}$T), 46 bp for G12V (G$\underline{T}$T), 47 bp for G12S ($\underline{A}$GT), 48 bp for G12R ($\underline{C}$GT), 49 bp for G12C ($\underline{T}$GT), and 51 bp for G13D (GA$\underline{C}$). Probes specific for wild-type DNA have also been designed to quantify the amount of PCR product prior to detection of mutant DNA. PCR product is estimated by ethidium bromide staining in a 3% agarose gel.

Example 20
Testing PCR/LDR to Identify K-ras Codons 12, 13, and 61 Mutations in a Multiplex Format This experiment verifies that all LDR probes can be multiplexed for detecting the mutations at codons 12, 13, and 61 of K-ras. DNA was prepared from cell lines with known mutations in codons 12 and 13 (SW620, G12V; SWI 116, G12A; LS180, G12D; DLD1, G13D). PCR/LDR using individual probes complementary to the particular mutation yielded the correct ligation products. Furthermore, equal mixing of two DNA targets containing separate mutations (G12D and G12V) in an excess of normal DNA gave both LDR products in roughly equimolar amounts.

The sensitivity of PCR/LDR was determined by reconstructing samples containing various dilutions of mutant DNA derived from cell lines in wild-type DNA. Samples were PCR amplified independently, and then mixed, allowing the testing of a variety of conditions. Exploratory experiments allowed optimization of the total amount of normal and mutant DNA (2,000 fmoles total in 201 µl reaction), fluorescently labeled discriminating probes (500 fmoles each), common probes (from 500 to 1,500 fmoles each), and finally Tth DNA ligase (100 fmoles of either wild-type or K294R mutant enzyme). A standard PCR/LDR reaction included 30 PCR cycles and 20 LDR cycles.

In an initial experiment, from 0.025 nM (0.5 fmol) to 5 nM (100 fmol) of PCR amplified DNA containing the G12D mutation was diluted into 100 nM (2000 fmol) of wild-type PCR amplified DNA. The amount of LDR product formed with either wild-type or K294R mutant enzyme was approximately the same, with similar signal-to-noise values (See FIGS. 33 and 34). With the K294R mutant enzyme, the signal-to-noise ratio was 1.7 for distinguishing one G12D template in 2,000 wild-type templates, and increased to 3.2 for distinguishing one in 1,000 wild-type templates.

When probe sets are combined to test all six possible single-base mutations at K-ras codon 12 in a multiplexed LDR reaction, the greatest background noise was obtained from probes designed to detect G12D, i.e. representing a C:A mismatch. Therefore, for determining signal-to-noise values in a multiplexed assay, the G12V mutant was used so that both "signal" (from the G12V) and "noise" (C:A misligations from the G12D probes on wild-type template) could be quantified in the same reaction. For the six probe set, similar amounts of product were formed with both enzymes, with the K294 mutant demonstrating slightly better signal-to-noise values (See FIGS. 35–38). However, with 20 fmol, 40 fmol, 80 fmol, 100 fmol, and 200 fmol of cancer template in 2000 fmol of wild-type DNA, the signal to noise ratio obtained w/K294R were significantly higher than obtained with wild type ligase. With the K294R mutant enzyme, the signal-to-noise ratio was 3.2 for distinguishing one G12V template in 1,000 wild-type templates and increased to 5.5 for distinguishing one in 500 wild-type templates. Thus, surprisingly, despite the potential for interference during hybridization, the signal-to-noise values obtained with the six mutation multiplex reaction are comparable to those obtained with a single probe set at the lowest dilutions. At higher cancer DNA concentrations, the interference between overlapping probes becomes more apparent as less signal is generated when using the full complement of all 26 probes compared to using either 8 probes or a single set of probes.

The full complement of all 26 probes was used to test all 19 possible single-base mutations at K-ras codons 12, 13 and 61 in a multiplexed LDR reaction. The background noise for probes designed to detect $Q_{61}R$, i.e. representing a G:T mismatch was about 10-fold higher than that observed for probes designed to detect G12D, i.e. representing a C:A mismatch. Probes may be designed to avoid G:T mismatches by using the opposite strand sequences. For the 26 probe set, similar amounts of product were formed with both enzymes, although they were clearly less than with the 6 probe set (See FIGS. 39–40). With the K294R mutant enzyme, the signal-to-noise ratio (comparing to the G12D C:A misligation) was 3.2 for distinguishing one G12V template in 500 wild-type templates, and increased to 7.2 for distinguishing one in 250 wild-type templates. Thus, use of 16 overlapping probes which hybridize to codons 12 and 13 does reduce both overall signal, as well as signal to noise, yet can still distinguish one mutation in 500. While others have reported using T4 ligase to detect 3 mutations in codon 12 with a 1% sensitivity (requiring blocking oligonucleotides and high salt to suppress mis-ligations on wild-type template), thermostable enzyme gives far greater sensitivity for simultaneously detecting all 12 mutations in codons 12 and 13. Powell et. al., *N.E. J. Med.* 329:1982–87 (1993), Jen, et. al., *Cancer Res.* 54:5523–26 (1994), and Redston, et. al., *Gastroent.* 108:383–92 (1995), which are hereby incorporated by reference.

Use has been made of PCR-amplified templates from microdissected tissue, for which the K-ras mutations have already been determined using direct sequencing. In blinded experiments, 148 coded samples, mostly containing K-ras mutations were provided to determine which mutation is present using PCR/LDR. Presence of a single mutation was clearly indicated by appearance of a single band migrating at a given length (See FIGS. 41–42). By comparing observed length with expected LDR product length, the mutation was determined (Table 9, and FIG. 40).

TABLE 9

| LDR Product | K-ras Mutation |
|---|---|
| 44-Fam | Asp-12 |
| 45-Tet | Ala-12 |
| 46-Fam | Val-12 |
| 47-Tet | Ser-12 |
| 48-Fam | Arg-12 |
| 49-Tet | Cys-12 |
| 51-Fam | Asp-13 |
| 52-Tet | Ala-13 |
| 53-Fam | Val-13 |
| 54-Tet | Ser-13 |
| 55-Fam | Arg-13 |
| 56-Tet | Cys-13 |
| 59-Tet | His-61 |
| 60-Fam | His-61 |
| 61-Tet | Arg-61 |
| 62-Fam | Leu-61 |
| 63-Tet | Pro-61 |
| 64-Fam | Lys-61 |
| 65-Tet | Glu-61 |

Of the 148 unknown samples and 10 known samples tested, there was agreement on all known samples and 138 unknown samples. FIG. 43 is a table comparing the 10 discordant samples. The results obtained by multiplex PCR/LDR were confirmed by PCR/LDR using only the LDR probe set specific to the mutation. Nine of the ten discordant samples were accurately typed by PCR/LDR which only missed a single, very rare double mutation found by sequencing. In other experiments, detection of mutations was compared in micro-dissected tumors versus whole paraffin sections containing both normal and tumor tissue. Multiplex PCR/LDR detected all known mutations even without the requirement for micro-dissection.

Thus, the utility of multiplexed PCR/LDR on samples derived from cell lines, microdissected tumors, and paraffin embedded tissues has been shown. The technique is both highly accurate (99.3%) and sensitive (i.e. able to detect 1 mutation in 500 normal sequences).

Example 21

Use of Low Level Normal Probes to Provide Low Level LDR Products Which Quantify Total Normal DNA in Sample LDR reactions were run for 15 sec at 94° C., and 4 min. at 65° C. per cycle for 20 cycles. The reactions were completely stopped by chilling the tubes in an ethanol-dry ice bath and adding 0.5 μl of 0.5 mM EDTA. Aliquots of 2.5 μl of the reaction products were mixed with 2.5 μl of loading buffer (83% Formamide, 8.3 mM EDTA, and 0.17% Blue Dextran) and 0.5 μl GeneScan TAMRA 350 molecular weight marker, denatured at 94° C. for 2 min, chilled rapidly on ice prior to loading on an 8 M urea-10% polyacrylamide gel, and electrophoresed on an ABI 373 DNA sequencer at 1400 volts. Fluorescent ligation products were analyzed and parameters of an exponential equation fit to the data using the Deltagraph Pro 3.5. software.

FIGS. 44–45 show the quantitative detection of different amounts of K-ras Normal template when varying amounts of wild-type probes were used by either wild-type or K294R Tth DNA ligase. The amount of LDR product formed when 25 nM (500 fmol), 50 nM (1000 fmol), and 100 nM (2000 fmol) of the "Normal" template was reacted with 0.5 nM (10 fmol), 2.5 nM (50 fmol), and 5 nM (100 fmol) of the wild type discriminating probe (Tet-K-ras c12.2 WtG) and common probe (K-ras c12 Com-2) in the presence of 25 nM (500 fmol) of nineteen discriminating probes (Tet-K-ras c12.2A, Tet-K-ras c12. 1 S, Tet-K-ras c12. 1 C, Tet-K-ras c13.4A, Tet-K-ras c13.3S, Tet-K-ras c13.3C, Tet-K-ras c61.7HT, Tet-K-ras c61.6R, Tet-K-ras c61.5K, Tet-K-ras c61.6P, Fam-K-ras c12.1R, Fam-K-ras ci2.2D, Fam-K-ras c 12.2V, Fam-K-ras c13.4D, Fam-K-ras c13.4V, Fam-K-ras c13.3R, Fam-K-ras c61.7HC, Fam-K-ras c61.6L, Fam-K-ras c61.5K); 50 nm (1000 fmol) of two common probes (K-ras c6, Com-7 and K-ras c12 Com-5); and 75 nm (1500 fmol) of five common probes (K-ras c12 Com-2, K-ras c12 Com-1, K-ras c13 Com-4, K-ras c13 Com-3, and K-ras c61 Com-6) and 5 rn (100 fmol) of the wild type or K294R mutant enzymes. The X-axis indicated the different amounts of the Normal Template, while the Y-axis indicated the amount of LDR product generated. (■, Δ, □) represents 0.5 nM (10 fmol), 2.5 nM (50 fmol), and 5 nM (100 fmol), respectively, of the wild type probes used with the wild-type enzyme whereas (●, ◆, ○) represents 0.5 (10 fmol), 2.5 nM (50 fmol), and 5 nM (100 fmol) of the wild type probes used with the K294R mutant enzyme.

Although the invention has been described in detail for the purpose of illustration, it is understood that such details are solely for that purpose and that variations can be made therein by those skilled in the art without departing from the spirit of the scope of the invention which is defined by the following claims.

What is claimed:

1. A method for detecting one or more minority target nucleotide sequences in a sample containing the one or more minority tar et nucleotide sequences and one or more majority target nucleotide sequences, respectively in a ratio of less than 1:10 and more than 1:1,000, wherein the minority target nucleotide sequences differ from the majority target nucleotide sequences by one or more single-base changes, insertions, deletions, or translocations, said method comprising:

providing one or more oligonucleotide probe sets, each set characterized by (a) a first oligonucleotide probe having a target-specific portion complementary to the minority target nucleotide sequence and (b) a second oligonucleotide probe having a target-specific portion complementary to the minority target nucleotide sequence, wherein the oligonucleotide probes in a particular set are suitable for ligation together when hybridized adjacent to one another on a corresponding minority target nucleotide sequence, but have a mismatch which interferes with such ligation when hybridized to any other nucleotide sequence present in the sample, and wherein the one or more oligonucleotide probe sets do not include an oligonucleotide probe sot which hybridizes to complements of the target nucleotide sequence;

providing a ligase;

blending the sample, the one or more oligonucleotide probe sets, and the ligase to form a ligase detection reaction mixture;

subjecting the ligase detection reaction mixture to more than one ligase detection reaction cycle comprising a denaturation treatment wherein any hybridized oligonucleotides are separated from the target nucleotide sequences, and a hybridization treatment, wherein the oligonucleotide probe sets hybridize at adjacent positions in a base-specific manner to their respective target nucleotide sequences, if present in the sample, and ligate to one another to achieve linear amplification and to form a ligation product sequence containing the target-specific portions connected together with the ligation product sequence for each set being distinguishable from other nucleic acids in the ligase detection reaction mixture, wherein the oligonucleotide probe sets may hybridize to nucleotide sequences in the sample other than their respective target nucleotide sequences but do not ligate together due to a presence of one or more mismatches and individually separate during the denaturation treatment; and detecting the presence of ligation product sequences produced as a result of the minority target nucleotide sequence being present in the same, wherein the method achieves a signal to noise ratio, measured in terms of the ratio of the ligation product sequence amount produced with the minority target nucleotide sequence in the presence of majority target nucleotide sequence to ligation product sequence amount produced with the majority target nucleotide sequence alone of more than 3.4:1 and less than 106:1.

2. A method according to claim 1, wherein the ligation product sequences of the oligonucleotide probes in a particular set have a unique length so that they can be distinguished from other nucleic acids in the ligase detection reaction mixture, said method further comprising:

separating the ligation product sequences by size or electrophoretic mobility and distinguishing, after said detecting, the ligation product sequences which differ in size.

3. A method according to claim 1, wherein the second oligonucleotide probe of each set has an addressable array-specific portion, said method further comprising:

providing a solid support with different capture oligonucleotides immobilized at different particular sites, wherein the capture oligonucleotides have nucleotide sequences complementary to the addressable array-specific portions and contacting the ligase detection reaction mixture, after said subjecting it to one or more ligase detection reaction cycles, with the solid support under conditions effective to hybridize the ligation product sequences to the capture oligonucleotides in a base-specific manner, thereby capturing the addressable array-specific portions to the solid support at the site with the complementary capture oligonucleotide, wherein said detecting indicates the presence of ligation product sequences captured using the addressable array-specific portions and immobilized to the solid support at particular sites, thereby indicating the presence of one or more target nucleotide sequences in the sample.

4. A method according to claim 1, wherein the relative amounts of the majority and minority nucleotide sequences present in the sample in unknown amounts are quantified, said method further comprising:

amplifying by polymerase chain reaction, prior to said blending, the majority and minority target nucleotide sequences in the sample with an oligonucleotide primer common to both the majority and minority target nucleotide sequences;

detecting the majority ligation product sequence produced as a result of the majority target nucleotide sequence being present in the sample;

quantifying the detected majority ligation product sequence; and quantifying the detected minority ligation product sequence.

5. A method according to claim 1, wherein the relative amounts of the majority and minority nucleotide sequences present in the sample in unknown amounts are quantified, said method further comprising:

amplifying by polymerase chain reaction, prior to said blending, the majority and minority target nucleotide sequences in the sample with an oligonucleotide primer common to both the majority and minority target nucleotide sequences;

providing a known amount of one or more marker target nucleotide sequences;

providing one or more sequence-specific probe sets, including probe sets specifically designed for the marker target nucleotide sequences;

blending the marker target nucleotide sequences, and the probe sets specifically designed for the marker target nucleotide sequences with ligase detection reaction mixture;

quantifying the amount of the majority and minority ligation product sequences; and comparing the amount of the majority and minority ligation product sequences generated from the unknown sample with the amount of ligation product sequences generated from known amounts of marker target nucleotide sequences to provide a quantitative measure of the relative level of one or more target nucleotide sequences in the sample.

6. A method according to claim 5, wherein the second oligonucleotide probe has an addressable array-specific portion, said method further comprising:

providing a solid support with different capture oligonucleotides immobilized at different particular sites, wherein the capture oligonucleotides have nucleotide sequences complementary to the addressable array-specific portions;

contacting the ligase detection reaction mixture, after said subjecting it to one or more ligase detection reaction cycles, with the solid support under conditions effective to hybridize the ligation product sequences to the capture oligonucleotides in a base-specific manner, thereby capturing the addressable array-specific portions to the solid support at the site with the complementary capture oligonucleotide;

quantifying the amount of ligation product sequences captured using the addressable array-specific portions and immobilized to the solid support at particular sites; and comparing the amount of captured ligation product sequences generated from the unknown sample with the amount of captured ligation product sequences generated from known amounts of marker target nucleotide sequences to provide a quantitative measure of the relative level of the majority and minority target nucleotide sequences in the sample.

7. A method according to claim 5, wherein the one or more marker target nucleotide sequences differ from the target nucleotide sequences at one or more single nucleotide positions.

8. A method according to claim 5, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, there is a common first oligonucleotide probe, having a detectable reporter label, and a second oligonucleotide probe which hybridizes to a given allele or marker nucleotide sequence in a base-specific manner, each second oligonucleotide probe having a different length and, wherein the ligation product sequences of oligonucleotide probes in a particular set generate a unique length product, said method further comprising:

separating the ligation product sequences by size or electrophoretic mobility and distinguishing the ligation product sequences which differ in size.

9. A method according to claim 5, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, there is a common first oligonucleotide probe and a second oligonucleotide probe which hybridizes to a given allele or marker nucleotide sequence in a base-specific manner, each second oligonucleotide probe having a different detectable reporter label and wherein the ligation product sequences of oligonucleotide probes in a particular set generate a unique length product, said method further comprising:

separating the ligation product sequences by size or electrophoretic mobility and distinguishing the ligation product sequences which differ in size.

10. A method according to claim 6, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, there is a common first oligonucleotide probe having a detectable reporter label and a second oligonucleotide probe which hybridizes to a given allele or a marker nucleotide sequence in a base-specific manner, each second oligonucleotide probe each having different addressable array-specific portions.

11. A method according to claim 6, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe set of each group, there is a common first oligonucleotide probe, having an addressable array-specific portion, and a second oligonucleotide probe which hybridizes to a given allele or a marker nucleotide sequence in a base-specific manner, each second oligonucleotide probe having a different detectable reporter label.

12. A method according to claim 1, wherein multiple allele differences at two or more nearby or adjacent nucleotide positions in a single target nucleotide sequence or multiple allele differences at two or more nearby or adjacent nucleotide positions in multiple target nucleotide sequences are distinguished with oligonucleotide probe sets having portions which may overlap.

13. A method according to claim 1, wherein a low abundance of multiple allele differences at multiple nearby or adjacent positions in a single target nucleotide sequence in the presence of an excess of normal sequence, or a low abundance of multiple allele differences at multiple nearby positions in multiple target nucleotide sequences in the presence of an excess of normal sequence in a sample are distinguished, the oligonucleotide probe set forming a plurality of oligonucleotide probe groups, each group comprised of one or more oligonucleotide probe sets designed for distinguishing multiple allele differences at a single nucleotide position, wherein one or more sets within a group share common first oligonucleotide probes, and the second oligonucleotide probes hybridize to a given allele excluding the normal allele in a base-specific manner, wherein, in said detecting, the labels of ligation product sequences are detected, thereby indicating a presence, in the sample, of one or more low abundance alleles at one or more nucleotide positions in one or more target nucleotide sequences.

14. A method according to claim 1, wherein a low abundance of multiple allele differences at multiple nearby or adjacent positions in a single target nucleotide sequence, in the presence of an excess of normal sequence, or a low abundance of multiple allele differences at multiple nearby positions in multiple target nucleotide sequences, in the presence of an excess of normal sequence, in the sample in unknown amounts are quantified, said method further comprising:

providing a known amount of one or more marker target nucleotide sequences;

providing one or more marker-specific oligonucleotide probe sets, each set characterized by (a) a first oligonucleotide probe having a target-specific portion complementary to a marker target nucleotide sequence and (b) a second oligonucleotide probe, having a target-specific portion complementary to a marker target nucleotide sequence and a detectable reporter label, wherein the oligonucleotide probes in a particular marker-specific oligonucleotide set are suitable for ligation together when hybridized adjacent to one another on a corresponding marker target nucleotide sequence, but, when hybridized to any other nucleotide sequence present in the sample or added marker sequences, have a mismatch which interferes with such ligation, wherein said plurality of oligonucleotide probe sets and said plurality of marker-specific oligonucleotide probe sets may form oligonucleotide probe groups for distinguishing multiple allele differences at a single nucleotide position, including marker nucleotide sequences, wherein one or more sets within a group, containing marker-specific oligonucleotide probes, share a common first oligonucleotide probe and a second oligonucleotide probe which hybridizes to a given allele excluding the normal allele in a base-specific manner, wherein said blending to form the ligase detection reaction mixture comprises blending the marker target nucleotide sequences and the probe sets specifically designed for the marker target nucleotide sequences with the ligase detection reaction mixture;

quantifying the amount of ligation product sequences; and comparing the amount of ligation product sequences generated from the low abundance unknown sample with the amount of ligation product sequences generated from known amounts of marker target nucleotide sequences, to provide a quantitative measure of the level of one or more low abundance target nucleotide sequences in the sample.

15. A method according to claim 1, wherein a low abundance of multiple allele differences at multiple nearby or adjacent positions in a single target nucleotide sequence in the presence of an excess of normal sequence, or a low abundance of multiple allele differences at multiple nearby positions in multiple target nucleotide sequences, in the presence of an excess of normal sequence in a sample, are distinguished, the oligonucleotide probe sets forming a plurality of oligonucleotide probe groups, each group comprised of one or more oligonucleotide probe sets designed for distinguishing multiple allele differences at a single nucleotide position, wherein one or more sets within a group share common first oligonucleotide probes, and the second oligonucleotide probes hybridize to a given allele excluding the normal allele in a base-specific manner, wherein one or more sets within a group share common first oligonucleotide probes, and the second oligonucleotide probes hybridize to a given allele including the normal allele in a base-specific manner, wherein the normal allele-specific probes are present in the ligation detection reaction mixture at a lower concentration than the mutant allele-specific probes, whereby the quantity of ligation product generated from the majority normal target is similar to the quantity of ligation product sequence expected from a known dilution of the minority target, quantifying the amount of ligation product sequences;

comparing the amount of ligation product sequences generated from the low abundance unknown sample with the amount of ligation product sequences generated from the high abundance normal target nucleotide sequences; and determining the amount of the high abundance normal target nucleotide sequences based on the low level of normal ligation product sequence formation, to provide a quantitative measure of the ratio of one or more low abundance target nucleotide sequences compared to the the high abundance normal target nucleotide sequences in the sample.

16. A method according to claim 1, wherein a low abundance of multiple allele differences at multiple nearby or adjacent positions in a single target nucleotide sequence in the presence of an excess of normal sequence, or a low abundance of multiple allele differences at multiple nearby positions in multiple target nucleotide sequences, in the presence of an excess of normal sequence in a sample, are distinguished, the oligonucleotide probe sets forming a plurality of oligonucleotide probe groups, each group comprised of one or more oligonucleotide probe sets designed for distinguishing multiple allele differences at a single nucleotide position, wherein one or more sets within a group share common first oligonucleotide probes, and the second oligonucleotide probes hybridize to a given allele excluding the normal allele in a base-specific manner, wherein one or more sets within a group share common first oligonucleotide probes, and the second oligonucleotide probes hybridize to a given allele including the normal allele in a base-specific manner, wherein the normal allele-specific probes are present in the ligation detection reaction mixture at a lower concentration and/or contain one or more internal mismatches or modifications, whereby the quantity of ligation product sequence generated from the majority normal target is similar to the quantity of ligation product sequence expected from a known dilution of the minority target, quantifying the amount of ligation product sequences;

comparing the amount of ligation product sequences generated from the low abundance unknown sample with the amount of ligation product sequences generated from the high abundance normal target nucleotide sequences; and determining the amount of the high abundance normal target nucleotide sequences based on the low level of normal ligation product sequence formation, to provide a quantitative measure of the ratio of one or more low abundance target nucleotide sequences compared to the the high abundance normal target nucleotide sequences in the sample.

17. A method according to claim 16, wherein the normal allele-specific probes contain the normal base at the 3' end.

18. A method according to claim 17, wherein the normal allele-specific probes contain the one or more internal mismatches or modifications within 4 bases from the 3' end.

19. A method as in claim 16, wherein the modification is a nucleotide analogue selected from the group consisting of 1-(2'-Deoxy-β-D-ribofuranosyl)imidazole-4-carboxamide, 1-(2'-Deoxy-β-D-ribofuranosyl)-3-nitropyrrole, 4-(2'-Deoxy-β-D-ribofuranosyl)imidazole-2-carboxamide, 2'-Deoxy-5-fluorouridine, 2'-Deoxyinosine, 6-(2'-Deoxy-β-D-ribofuranosyl)-6H,8H-3,4-dihydropyrimido[4,5-c][1,2] oxazine-7-one, 2-Amino-7-(2'-deoxy-β-D-ribofuranosyl)-6-methoxyaminopurine, 1-(2'-Deoxy-β-D-ribofuranosyl)-5-nitroindole, 1-(2'-Deoxy-β-D-ribofuranosyl)pyrazole-4-carboxamide, 1-(2'-Deoxy-β-D-ribofuranosyl)-1,2,4-triazole-3-carboxamide, 3-Amino-1-(2 '-deoxy-,-D-ribofuranosyl)-1,2,4-triazole, 5-(2'-Deoxy-β-D-ribofuranosyl)-2-pyrimidinone, 5-(2'-Deoxy-β-D-ribofuranosyl)-2-thiopyrimidine, 5-Amino-1-(2'-deoxy-,-D-ribofuranosyl)imidazole-4-carboxamide, 1-(2'-Deoxy-β-D-ribofuranosyl)-3-nitropyrazole, 1-(2'-Deoxy-β-D-ribofuranosyl)-4-iodopyrazole, 1-(2'-Deoxy-β-D-ribofuranosyl)-4-propynylpyrazole, 1-(2'-Deoxy-β-D-ribofuranosyl)pyrrole-3-carboxamide, 1-(2'-Deoxy-β-D-ribofuranosyl)pyrazone-4-carboxamide, 1-(2'-Deoxy--3-D-ribofuranosyl)-4-nitroimidazole, and 1-(2'-Deoxy-β-D-ribofuranosyl)-4-nitropyrazole.

20. A method as in claim 16, wherein the modified oligonucleotide probe contains thiophosphate, dithiophosphate, 2'-methoxy, or 3'-amino-2',3'-dideoxy-modifications to its sugar phosphate backbone at any one or a combination of 4 bases positions from the ligation junction.

21. A method according to claim 1, wherein the minority target nucleotide sequence is distinguished from the majority target nucleotide sequence in the sample at a respective ratio of 1:500 for a G:T or T:G mismatch between the majority target nucleotide sequence and one of the oligonucleotide probes.

22. A method according to claim 1, wherein the minority target nucleotide sequence is distinguished from the majority target nucleotide sequence in the sample at a respective ratio of 1:2000 for other than a G:T or T:G mismatch between the majority target nucleotide sequence and one of the oligonucleotide probes.

23. A method according to claim 1, wherein the minority target nucleotide sequence is distinguished from the majority target nucleotide sequence, for low abundance multiple allele differences at multiple nearby or adjacent positions, at a respective ratio of 1:100 for all mismatches between the majority target nucleotide sequence and one of the oligonucleotide probes.

24. A method according to claim 1, wherein the minority target nucleotide sequence is distinguished from the majority target nucleotide sequence, for low abundance multiple allele differences at multiple nearby or adjacent positions, at a respective ratio of 1:500 for other than a G:T or T:G mismatch between the majority target nucleotide sequence and one of the oligonucleotide probes.

25. A method for detecting one or ore minority target nucleotide sequences in a sample containing the one or more minority tar et nucleotide sequences and one or more majority target nucleotide sequences, respectively, in a ratio of less than 1:10 and more than 1:1,000, wherein the minority target nucleotide sequences differ from the majority target nucleotide sequences by one or more single-base changes, insertions, deletions, or translocations, said method comprising:

providing one or more oligonucleotide probe sets, each set characterized by (a) a first oligonucleotide probe having a target-specific portion and (b) a second oligonucleotide probe having a target-specific portion, wherein the oligonucleotide probes in a particular set are suitable for ligation together at a ligation junction when hybridized adjacent to one another on a corresponding target minority nucleotide sequence, but have a mismatch which interferes with such ligation when hybridized to any other nucleotide sequence present in the sample, wherein the first and second oligonucleotide probes hybridize to a minority target nucleotide sequence with a perfect match at the ligation junction between the minority target nucleotide sequence and the first oligonucleotide probe having its 3' end at the ligation junction and the first and second oligonucleotide probes hybridize to the majority target nucleotide sequence with a mismatch at the ligation junction between the majority target nucleotide sequence and the first oligonucleotide probe having its 3' end at the ligation junction, and wherein the one or more oligonucleotide probe sets do not include an oligonucleotide probe set which hybridizes to complements of the target nucleotide sequence;

providing a thermostable mutant ligase, wherein the thermostable mutant ligase has a signal-to-noise ratio, for the amount of ligation product sequences produced from both the minority and majority target nucleotide sequences, to the amount of ligation product sequences produced from the same amount of majority target nucleotide sequence alone, which is greater than the signal-to-noise ratio for wild-type ligase;

blending the sample, the one or more oligonucleotide probe sets, and the ligase to form a ligase detection reaction mixture;

subjecting the ligase detection reaction mixture to more than one ligase detection reaction cycle comprising a denaturation treatment wherein any hybridized oligonucleotides are separated from the target nucleotide sequences, and a hybridization treatment, wherein the oligonucleotide probe sets hybridize It adjacent positions in a base-specific manner to their respective target nucleotide sequences, if present in the sample, and ligate to one another to achieve linear amplification and to form a ligation product sequence containing the target-specific portions connected together with the ligation product sequence for each set being distinguishable from other nucleic acids in the ligase detection reaction mixture, wherein the oligonucleotide probe sets may hybridize to nucleotide sequences in the sample other than their respective target nucleotide sequences but do not ligate together due to a presence of one or more mismatches and individually separate during the denaturation treatment; and detecting the presence of ligation product sequence.

26. A method according to claim 25, wherein the ligase has a fidelity ratio, of an initial rate constant for ligating the first and second oligonucleotide probes hybridized to a target nucleotide sequence with a perfect match at the ligation junction between the target nucleotide sequence and the oligonucleotide probe having its 3' end at the ligation junction to the initial rate constant for ligating the first and second oligonucleotide probes hybridized to a target with a mismatch at the ligation junction between the target nucleotide sequence and the oligonucleotide probe having its 3' end at the ligation junction, which is greater than the fidelity ratio for wild-type ligase.

27. A method according to claim 25, wherein the ligation product sequences of the oligonucleotide probes in a particular set have a unique length so that they can be distinguished from other nucleic acids in the ligase detection reaction mixture, said method further comprising:

separating the ligation product sequences by size or electrophoretic mobility and distinguishing, after said detecting, the ligation product sequences which differ in size.

28. A method according to claim 25, wherein the second oligonucleotide probe of each set has an addressable array-specific portion, said method further comprising:

providing a solid support with different capture oligonucleotides immobilized at different particular sites, wherein the capture oligonucleotides have nucleotide sequences complementary to the addressable array-specific portions and contacting the ligase detection reaction mixture, after said subjecting it to one or more ligase detection reaction cycles, with the solid support under conditions effective to hybridize the ligation product sequences to the capture oligonucleotides in a base-specific manner, thereby capturing the addressable array-specific portions to the solid support at the site with the complementary capture oligonucleotide, wherein said detecting indicates the presence of ligation product sequences captured using the addressable array-specific portions and immobilized to the solid support at particular sites, thereby indicating the presence of one or more target nucleotide sequences in the sample.

29. A method according to claim 25, wherein the relative amounts of the majority and minority nucleotide sequences present in the sample in unknown amounts are quantified, said method further comprising:

amplifying by polymerase chain reaction, prior to said blending, the majority and minority target nucleotide sequences in the sample with an oligonucleotide primer common to both the majority and minority target nucleotide sequences;

detecting the majority ligation product sequence produced as a result of the majority target nucleotide sequence being present in the sample;

quantifying the detected majority ligation product sequence; and quantifying the detected minority ligation product sequence.

30. A method according to claim 25, wherein the relative amounts of the majority and minority nucleotide sequences present in the sample in unknown amounts are quantified, said method further comprising:

amplifying by polymerase chain reaction, prior to said blending, the majority and minority target nucleotide sequences in the sample with an oligonucleotide primer common to both the majority and minority target nucleotide sequences;

providing a known amount of one or more marker target nucleotide sequences;

providing one or more sequence-specific probe sets, including probe sets specifically designed for the marker target nucleotide sequences;

blending the marker target nucleotide sequences, and the probe sets specifically designed for the marker target nucleotide sequences with ligase detection reaction mixture;

quantifying the amount of the majority and minority ligation product sequences; and comparing the amount of the majority and minority ligation product sequences generated from the unknown sample with the amount of ligation product sequences generated from known amounts of marker target nucleotide sequences to provide a quantitative measure of the relative level of one or more target nucleotide sequences in the sample.

31. A method according to claim 30, wherein the second oligonucleotide probe has an addressable array-specific portion, said method further comprising:

providing a solid support with different capture oligonucleotides immobilized at different particular sites, wherein the capture oligonucleotides have nucleotide sequences complementary to the addressable array-specific portions;

contacting the ligase detection reaction mixture, after said subjecting it to one or more ligase detection reaction cycles, with the solid support under conditions effective to hybridize the ligation product sequences to the capture oligonucleotides in a base-specific manner, thereby capturing the addressable array-specific portions to the solid support at the site with the complementary capture oligonucleotide;

quantifying the amount of ligation product sequences captured using the addressable array-specific portions and immobilized to the solid support at particular sites; and comparing the amount of captured ligation product sequences generated from the unknown sample with the amount of captured ligation product sequences generated from known amounts of marker target nucleotide sequences to provide a quantitative measure of the relative level of the majority and minority target nucleotide sequences in the sample.

32. A method according to claim 30, wherein the one or more marker target nucleotide sequences differ from the target nucleotide sequences at one or more single nucleotide positions.

33. A method according to claim 30, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, there is a common first oligonucleotide probe, having detectable reporter label, and a second oligonucleotide probe which hybridizes to a given allele or marker nucleotide sequence in a base-specific manner, each second oligonucleotide probe having a different length and, wherein the ligation product sequences of oligonucleotide probes in a particular set generate a unique length product, said method further comprising:

separating the ligation product sequences by size or electrophoretic mobility and distinguishing the ligation product sequences which differ in size.

34. A method according to claim 30, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, there is a common first oligonucleotide probe and a second oligonucleotide probe which hybridizes to a given allele or marker nucleotide sequence in a base-specific manner, each second oligonucleotide probe having a different detectable reporter label and wherein the ligation product sequences of oligonucleotide probes in a particular set generate a unique length product, said method further comprising:

separating the ligation product sequences by size or electrophoretic mobility and distinguishing the ligation product sequences which differ in size.

35. A method according to claim 31, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, there is a common first oligonucleotide probe having a detectable reporter label and a second oligonucleotide probe which hybridizes to a given allele or a marker nucleotide sequence in a base-specific manner, each second oligonucleotide probe having different addressable array-specific portions.

36. A method according to claim 31, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe set of each group, there is a common first oligonucleotide probe, having an addressable array-specific portion, and a second oligonucleotide probe which hybridizes to a given allele or a marker nucleotide sequence in a base-specific manner, each second oligonucleotide probe having a different detectable reporter label.

37. A method according to claim 25, wherein multiple allele differences at two or more nearby or adjacent nucleotide positions in a single target nucleotide sequence or multiple allele differences at two or more nearby or adjacent nucleotide positions in multiple target nucleotide sequences are distinguished with oligonucleotide probe sets having portions which may overlap.

38. A method according to claim 25, wherein a low abundance of multiple allele differences at multiple nearby or adjacent positions in a single target nucleotide sequence in the presence of an excess of normal sequence, or a low abundance of multiple allele differences at multiple nearby positions in multiple target nucleotide sequences in the presence of an excess of normal sequence in a sample are distinguished, the oligonucleotide probe set forming a plurality of oligonucleotide probe groups, each group comprised of one or more oligonucleotide probe sets designed for distinguishing multiple allele differences at a single nucleotide position, wherein one or more sets within a group share common first oligonucleotide probes, and the second oligonucleotide probes hybridize to a given allele excluding the normal allele in a base-specific manner, wherein, in said detecting, the labels of ligation product sequences are detected, thereby indicating a presence, in the sample, of one or more low abundance alleles at one or more nucleotide positions in one or more target nucleotide sequences.

39. A method according to claim 25, wherein a low abundance of multiple allele differences at multiple nearby or adjacent positions in a single target nucleotide sequence, in the presence of an excess of normal sequence, or a low abundance of multiple allele differences at multiple nearby positions in multiple target nucleotide sequences, in the presence of an excess of normal sequence, in the sample in unknown amounts are quantified, said method further comprising:

providing a known amount of one or more marker target nucleotide sequences;

providing one or more marker-specific oligonucleotide probe sets, each set characterized by (a) a first oligonucleotide probe having a target-specific portion complementary to a marker target nucleotide sequence and (b) a second oligonucleotide probe, having a target-specific portion complementary to a marker target nucleotide sequence and a detectable reporter label, wherein the oligonucleotide probes in a particular marker-specific oligonucleotide set are suitable for ligation together when hybridized adjacent to one another on a corresponding marker target nucleotide sequence, but, when hybridized to any other nucleotide sequence present in the sample or added marker sequences, have a mismatch which interferes with such ligation, wherein said plurality of oligonucleotide probe sets and said plurality of marker-specific oligonucleotide probe sets may form oligonucleotide probe groups for distinguishing multiple allele differences at a single nucleotide position, including marker nucleotide sequences, wherein one or more sets within a group, containing marker-specific oligonucleotide probes, share a common first olig nucleotide probe and a second oligonucleotide probe which hybridizes to a given allele excluding the normal allele in a base-specific manner, wherein said blending to form the ligase detection reaction mixture comprises blending the marker target nucleotide sequences and the probe sets specifically designed for the marker target nucleotide sequences with the ligase detection reaction mixture;

quantifying the amount of ligation product sequences; and comparing the amount of ligation product sequences generated from the low abundance unknown sample with the amount of ligation product sequences generated from known amounts of marker target nucleotide sequences, to provide a quantitative measure of the level of one or more low abundance target nucleotide sequences in the sample.

40. A method according to claim 25, wherein low abundance of multiple allele differences at multiple nearby or adjacent positions in a single target nucleotide sequence in the presence of an excess of normal sequence, or a low abundance of multiple allele differences at multiple nearby positions in multiple target nucleotide sequences, in the presence of an excess of normal sequence in a sample, are distinguished, the oligonucleotide probe sets forming a plurality of oligonucleotide probe groups, each group comprised of one or more oligonucleotide probe sets designed for distinguishing multiple allele differences at a single nucleotide position, wherein one or more sets within a group, share common first oligonucleotide probes, and the second oligonucleotide probes, hybridize to a given allele excluding the normal allele in a base-specific manner, wherein one or more sets within a group share common first oligonucleotide probes, and the second oligonucleotide probes hybridize to a given allele including the normal allele in a base-specific manner, wherein the normal allele-specific probes are present in the ligation detection reaction mixture at a lower concentration than he mutant allele-specific probes, whereby the quantity of ligation product sequence generated from the majority normal target is similar to the quantity of ligation product sequence expected from a known dilution of the minority target, quantifying the amount of ligation product sequences;

comparing the amount of ligation product sequences generated from the low abundance unknown sample with the amount of ligation product sequences generated from the high abundance normal target nucleotide sequences; and determining the amount of the high abundance normal target nucleotide sequences based on the low level of normal ligation product sequence formation, to provide a quantitative measure of the ratio of one or more low abundance target nucleotide sequences compared to the the high abundance normal target nucleotide sequences in the sample.

41. A method according to claim 25, wherein, low abundance of multiple allele differences at multiple nearby or adjacent positions in a single target nucleotide sequence in the presence of an excess of normal sequence, or a low abundance of multiple allele differences at multiple nearby positions in multiple target nucleotide sequences, in the presence of an excess of normal sequence in a sample, are distinguished, the oligonucleotide probe set forming plurality of oligonucleotide probe groups, each group comprised of one or ore oligonucleotide probe sets designed for distinguishing multiple allele differences at a single nucleotide position, wherein one or more sets within a group share common first oligonucleotide probes, and the second oligonucleotide probes hybridize to a given allele excluding the normal allele in a base-specific manner, wherein one or more sets within a group share common first oligonucleotide probes, and the second oligonucleotide probes hybridize to a given allele including the normal allele in a base-specific manner, wherein the normal allele-specific probes are present in the ligation detection reaction mixture at a lower concentration and/or contain one or more internal mismatches or modifications, whereby the quantity of ligation product sequence generated from the majority normal target is similar to the quantity of ligation product sequence expected from a known dilution of the minority target, quantifying the amount of ligation product sequences;

comparing the amount of ligation product sequences generated from the low abundance unknown sample with the amount of ligation product sequences generated from the high abundance normal target nucleotide sequences;

determining the amount of the high abundance normal target nucleotide sequences based on the low level of normal ligation product sequence formation, to provide a quantitative measure of the ratio of one or more low abundance target nucleotide sequences compared to the the high abundance normal target nucleotide sequences in the sample.

42. A method according to claim 41, wherein the normal allele-specific probes contain the normal base at the 3' end.

43. A method according to claim 42, wherein the normal allele-specific probes contain the one or more internal mismatches or modifications within 4 bases from the 3' end.

44. A method as in claim 41, wherein the modification is a nucleotide analogue selected from the group consisting of 1-(2'-Deoxy-β-D-ribofuranosyl)imidazole-4-carboxamide, 1-(2'-Deoxy-β-D-ribofuranosyl)-3-nitropyrrole, 4-(2'-Deoxy-β-D-ribofuranosyl)imidazole-2-carboxamide, 2'-Deoxy-5-fluorouridine, 2'-Deoxyinosine, 6-(2'-Deoxy-β-D-ribofuranosyl)-6H,8H-3,4-dihydropyrimido[4,5-c] [1,2] oxazine-7-one, 2-Amino-7-(2 '-deoxy-β-D-ribofuranosyl)-6-methoxyaminopurine, 1-(2'-Deoxy-β-D-ribofuranosyl)-5-nitroindole, 1-(2'-Deoxy-β-D-ribofuranosyl)pyrazole-4-carboxamide, 1-(2'-Deoxy-β-D-ribofuranosyl)-1,2,4-triazole-3-carboxamide, 3-Amino-1-(2 '-deoxy-β-D-ribofuranosyl)-1,2,4-triazole, 5-(2'-Deoxy-β-D-ribofuranosyl)-2-pyrimidinone, 5-(2'-Deoxy-β-D-ribofuranosyl)-2-thiopyrimidine, 5-Amino-1-(2'-deoxy-β-D-ribofuranosyl)imidazole-4-carboxamide, 1-(2'-Deoxy-β-D-ribofuranosyl)-3-nitropyrazole, 1-(2'-Deoxy-β-D-ribofuranosyl)-4-iodopyrazole, 1-(2'-Deoxy-β-D-ribofuranosyl)-4-propynylpyrazole, 1-(2'-Deoxy-β-D-ribofuranosyl)pyrrole-3-carboxamide, 1-(2'-Deoxy-β-D-ribofuranosyl)pyrazone-4-carboxamide, 1-(2'-Deoxy-β-D-ribofuranosyl)-4-nitroimidazole, and 1-(2'-Deoxy-β-D-ribofuranosyl)-4-nitropyrazole.

45. A method as in claim 41, wherein the modified oligonucleotide probe contains thiophosphate, dithiophosphate, 2'-methoxy, or 3'-amino-2',3'-dideoxy-modifications to its sugar phosphate backbone at any one or combination of positions within 4 bases from the ligation junction.

46. A method according to claim 25, wherein the minority target nucleotide sequence is distinguished from the majority target nucleotide sequence in the sample at a respective ratio of 1:500 for a G:T or T:G mismatch between the majority target nucleotide sequence and one of the oligonucleotide probes.

47. A method according to claim 25, wherein the minority target nucleotide sequence is distinguished from the majority target nucleotide sequence in the sample at a respective ratio of 1:2000 for other than a G:T or T:G mismatch between the majority target nucleotide sequence and one of the oligonucleotide probes.

48. A method according to claim 25, wherein the minority target nucleotide sequence is distinguished from the majority target nucleotide sequence, for low abundance multiple allele differences at multiple nearby or a adjacent positions, at a respective ratio of 1:100 for all mismatches between the majority target nucleotide sequence and one of the oligonucleotide probes.

49. A method according to claim 25, wherein the minority target nucleotide sequence is distinguished from the majority target nucleotide sequence, for low abundance multiple allele differences at multiple nearby or adjacent positions, at a respective ratio of 1:500 for other than a G:T or T:G mismatch between the majority target nucleotide sequence and one of the oligonucleotide probes.

50. A method for detecting one or ore minority target nucleotide sequences in a sample containing the one or more minority tar et nucleotide sequences and one or more majority target nucleotide sequences, respectively in a ratio of less than 1:10 and more than 1:1,000, wherein the minority target nucleotide sequences differ from the majority target nucleotide sequences by one or more sing base changes, insertions, deletions, or translocations, said method comprising:

providing one or more oligonucleotide probe sets, each set characterized by (a) a first oligonucleotide probe having a target-specific portion and (b) a second oligonucleotide probe having a target-specific portion, wherein the oligonucleotide probes in a particular set are suitable for ligation together at a ligation junction when hybridized adjacent to one another on a corresponding target minority nucleotide sequence, but have a mismatch which interferes with such ligation when hybridized to any other nucleotide sequence present in the sample, wherein the first oligonucleotide probe which has its 3' end at the ligation junction, has one or more modifications which differentially alters the ligation rate when the first and second oligonucleotide probes hybridize to the minority target nucleotide sequence in the sample with a perfect match at the ligation junction between the minority target nucleotide sequence and the first oligonucleotide probe having its 3' end at the ligation junction compared to the ligation rate when the first and second oligonucleotide probes hybridize to the sample's majority target nucleotide sequence with a mismatch at the ligation junction between the majority target nucleotide sequence and the first oligonucleotide probe having its 3' end at the ligation junction, herein the ligation detection process using the modified first oligonucleotide probe has a sig al-to-noise ratio, defined as the ratio of the sum of the ligation products produced from the minority and majority target nucleotide sequences in the sample to the amount of ligation product produced from the same amount of majority target nucleotide sequence as in the sample but without the minority target nucleotide sequence, which is greater than the signal-to-noise ratio for a ligation detection reaction using a first oligonucleotide probe licking the modification, and wherein the one or more oligonucleotide probe sets do not include an oligonucleotide probe set which hybridizes to complements of the target nucleotide sequence;

providing a ligase;

blending the sample, the one or more oligonucleotide probe sets, and the ligase to form a ligase detection reaction mixture;

subjecting the ligase detection reaction mixture to more than one ligase detection reaction cycles comprising a denaturation treatment, wherein any hybridized oligonucleotides are separated from the target nucleotide sequences, and a hybridization treatment, wherein the oligonucleotide probe sets hybridize at adjacent positions in a base-specific manner to their respective target nucleotide sequences, if present in the sample, and ligate to one another without modification of the oligonucleotide probes to achieve linear amplification and to form a ligation product sequence containing the target-specific portions connected together with the ligation product sequence for each set being distinguishable from other nucleic acids in the ligase detection mixture, wherein the oligonucleotide probe sets may hybridize to nucleotide sequences in the simple other than their respective target nucleotide sequences but do not ligate together due to a presence of one or more mismatches and individually separate during the denaturation treatment; and detecting the presence of ligation product sequence.

51. A method according to claim 50, wherein the one or more modification is a nucleotide analogue within 9 bases from the ligation junction.

52. A method according to claim 51, where in the modification is within 9 bases away from the 3' end of the first oligonucleotide probe.

53. A method according to claim 51, wherein the modification is a nucleotide analogue at a position 3 nucleotide bases away form the 3' nd of the first oligonucleotide probe.

54. A method according to claim 53, wherein the modification is selected from the group consisting of 1-(2'-Deoxy-β-D-ribofuranosyl)imidazole-4-carboxamide, 1-(2'-Deoxy-β-D-ribofuranosyl)-3-nitropyrrole, 4-(, '-Deoxy-β-D-ribofuranosyl)imidazole-2-carboxamide, 2'-Deoxy-5-fluorouridine, 2'-Deoxyinosine, 6-(2 '-Deoxy-β-D-ribofuranosyl)-6H,8H-3,4-dihydropyrimido[4,5 c] [1,2] oxazine-7-one, 2-Amino-7-(2 '-deoxy-β-D-ribofuranosyl)-6-methoxyaminopurine, 1-(2 '-Deoxy-β-D-ribofuranosyl)-5-nitroindole, 1-(2'-Deoxy-β-D-ribofuranosyl)pyrazole-4-carboxamide, 1-(2'-Deoxy-β-D-ribofuranosyl)-1,2,4-triazole-3-carboxamide, 3-Amino-1-(2'-deoxy-β-D-ribofuranosyl)-1,2,4-triazole, 5-(2'-Deoxy-β-D-ribofuranosyl)-2-pyrimidinone, 5-(2'-Deoxy-β-D-ribofuranosyl)-2-thiopyrimidine, 5-Amino-1-(2 '-deoxy-β-D-ribofuranosyl)imidazole-4-carboxamide, 1-(2 '-Deoxy-β-D-ribofuranosyl)-3-nitropyrazole, 1-(2'-Deoxy-β-D-ribofuranosyl)-4 iodopyrazole, 1-(2'-Deoxy-β-D-ribofuranosyl)-4-propynylpyrazole, 1-(2'-Deoxy-β-D-ribofuranosyl)pyrrole-3-carboxamide, 1-(2'-Deoxy-β-D-ribofuranosyl)pyrazone-4-carboxamide, 1-(2'-Deoxy-β-D-ribofuranosyl)-4-nitroimidazole, and 1-(2'-Deoxy-β-D-ribofuranosyl)-4-nitropyrazole.

55. A method according to claim 50, wherein the modification is in the first oligonucleotide probe's sugar phosphate backbone at any on or combination of positions within 9 bases from the ligation junction.

56. A method according to claim 55, wherein the modified first oligonucleotide probe contains thiophosphate, dithiophosphate, 2'-methoxy, and 3'-amino-2',3 '-dideoxy-modifications.

57. A method according to claim 50, wherein the ligation product sequences of the oligonucleotide probes in a particular set have a unique length so that they can be distinguished from other nucleic acids in the ligase detection reaction mixture, said method further comprising:

separating the ligation product sequences be size or electrophoretic mobility and distinguishing, after said detecting, the ligation product sequences which differ in size.

58. A method according to claim 50, wherein the second oligonucleotide probe of each set has an addressable array-specific portion, said method further comprising:

providing a solid support with different capture oligonucleotides immobilized at different particular sites, wherein the capture oligonucleotides have nucleotide sequences complementary to the addressable array-specific portions and contacting the ligase detection reaction mixture, after said subjecting it to one or more ligase detection reaction cycles, with the solid support under conditions effective to hybridize the ligation product sequences to the capture oligonucleotides in a base-specific manner, thereby capturing the addressable array-specific portions to the solid support at the site with the complementary capture oligonucleotide, wherein said detecting indicates the presence of ligation product sequences captured using the addressable array-specific portions and immobilized to the solid support at particular sites, thereby indicating the presence of one or more target nucleotide sequences in the sample.

59. A method according to claim 50, wherein the relative amounts of the majority and minority nucleotide sequences present in the sample in unknown amounts are quantified, said method further comprising:

amplifying by polymerase chain reaction, prior to said blending, the majority and minority target nucleotide sequences in the sample with an oligonucleotide primer common to both the majority and minority target nucleotide sequences;

detecting the majority ligation product sequence produced as a result of the majority target nucleotide sequence being present in the sample;

quantifying the detected majority ligation product sequence; and quantifying the detected minority ligation product sequence.

60. A method according to claim 50, wherein the relative amounts of the majority and minority nucleotide sequences present in the sample in unknown amounts are quantified, said method further comprising:

amplifying by polymerase chain reaction, prior to said blending, the majority and minority target nucleotide sequences in the sample with an oligonucleotide primer common to both the majority and minority target nucleotide sequences;

providing a known amount of one or more marker target nucleotide sequences;

providing one or more sequence-specific probe sets, including probe sets specifically designed for the marker target nucleotide sequences;

blending the marker target nucleotide sequences, and the probe sets specifically designed for the marker target nucleotide sequences with ligase detection reaction mixture;

quantifying the amount of the majority and minority ligation product sequences; and comparing the amount of the majority and minority ligation product sequences generated from the unknown sample with the amount of ligation product sequences generated from known amounts of marker target nucleotide sequences to provide a quantitative measure of the relative level of one or more target nucleotide sequences in the sample.

61. A method according to claim 60, wherein the second oligonucleotide probe has an addressable array-specific portion, said method further comprising:

providing a solid support with different capture oligonucleotides immobilized at different particular sites, wherein the capture oligonucleotides have nucleotide sequences complementary to the addressable array-specific portions;

contacting the ligase detection reaction mixture, after said subjecting it to one or more ligase detection reaction cycles, with the solid support under conditions effective to hybridize the ligation product sequences to the capture oligonucleotides in a base-specific manner, thereby capturing the addressable array-specific portions to the solid support at the site with the complementary capture oligonucleotide;

quantifying the amount of ligation product sequences captured using the addressable array-specific portions and immobilized to the solid support at particular sites; and comparing the amount of captured ligation product sequences generated from the unknown sample with the amount of captured ligation product sequences generated from known amounts of marker target nucleotide sequences to provide a quantitative measure of the relative level of the majority and minority target nucleotide sequences in the sample.

62. A method according to claim 60, wherein the one or more marker target nucleotide sequences differ from the target nucleotide sequences at one or more single nucleotide positions.

63. A method according to claim 60, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, there is a common first oligonucleotide probe, having a a detectable reporter label, and a second oligonucleotide probe which hybridizes to a given allele or marker nucleotide sequence in a base-specific manner, each second oligonucleotide probe having a different length and, wherein the ligation product sequences of oligonucleotide probes in a particular set generate a unique length product, said method further comprising:

separating the ligation product sequences by size or electrophoretic mobility and distinguishing the ligation product sequences which differ in size.

64. A method according to claim 60, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, there is a common first oligonucleotide probe and a second oligonucleotide probe which hybridizes to a given allele or marker nucleotide sequence in a base-specific manner, each second oligonucleotide probe having a different detectable reporter label and wherein the ligation product sequences of oligonucleotide probes in a particular set generate a unique length product, said method further comprising:

separating the ligation product sequences by size or electrophoretic mobility and distinguishing the ligation product sequences which differ in size.

65. A method according to claim 61, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe sets of each group, there is a common first oligonucleotide probe having a detectable reporter label and a second oligonucleotide probe which hybridizes to a given allele or a marker nucleotide sequence in a base-specific manner, each second oligonucleotide probe having different addressable array-specific portions.

66. A method according to claim 61, wherein the oligonucleotide probe sets form a plurality of oligonucleotide probe groups, each group comprised of one or more oligonucleotide probe sets designed for distinguishing multiple allele differences at a single nucleotide position, wherein, in the oligonucleotide probe set of each group, there is a common first oligonucleotide probe, having an addressable array-specific portion, and a second oligonucleotide probe which hybridizes to a given allele or a marker nucleotide sequence in a base-specific manner, each second oligonucleotide probe having a different detectable reporter label.

67. A method according to claim 50, wherein multiple allele differences at two or more nearby or adjacent nucleotide positions in a single target nucleotide sequence or multiple allele differences at two or more nearby or adjacent nucleotide positions in multiple target nucleotide sequences are distinguished with oligonucleotide probe sets having portions which may overlap.

68. A method according to claim 50, wherein a Low abundance of multiple allele differences at multiple nearby or adjacent positions in a single target nucleotide sequence in the presence of an excess of normal sequence, or a low abundance of multiple allele differences at multiple nearby positions in multiple target nucleotide sequences in the presence of an excess of normal sequence in a sample are distinguished, the oligonucleotide probe set forming a plurality of oligonucleotide probe groups, each group comprised of one or more oligonucleotide probe sets designed for distinguishing multiple allele differences at a single nucleotide position, wherein one or more sets within a group share common first oligonucleotide probes, and the second oligonucleotide probes hybridize to a given allele excluding the normal allele in a base-specific manner, wherein, in said detecting, the labels of ligation product sequences are detected, thereby indicating a presence, in the sample, of one or more low abundance alleles at one or more nucleotide positions in one or more target nucleotide sequences.

69. A method according to claim 50, wherein a low abundance of multiple allele differences at multiple nearby or adjacent positions in a single target nucleotide sequence, in the presence of an excess of normal sequence, or a low abundance of multiple allele differences at multiple nearby positions in multiple target nucleotide sequences, in the presence of an excess of normal sequence, in the sample in unknown amounts are quantified, said method further comprising:

providing a known amount of one or more marker target nucleotide sequences;

providing one or more marker-specific oligonucleotide probe sets, each set characterized by (a) a first oligonucleotide probe having a target-specific portion complementary to a marker target nucleotide sequence and (b) a second oligonucleotide probe, having a target-specific portion complementary to a marker target nucleotide sequence and a detectable reporter label, wherein the oligonucleotide probes in a particular marker-specific oligonucleotide set are suitable for ligation together when hybridized adjacent to one another on a corresponding marker target nucleotide sequence, but, when hybridized to any other nucleotide sequence present in the sample or added marker sequences, have a mismatch which interferes with such ligation, wherein said plurality of oligonucleotide probe sets and said plurality of marker-specific oligonucleotide probe sets may form oligonucleotide probe groups for distinguishing multiple allele differences at a single nucleotide position, including marker nucleotide sequences, wherein one or more sets within a group, containing marker-specific oligonucleotide probes, share a common first oligonucleotide probe and a second oligonucleotide probe which hybridizes to a given allele excluding the normal allele in a base-specific manner, wherein said blending to form the ligase detection reaction mixture comprises blending the marker target nucleotide sequences and the probe sets specifically designed for the marker target nucleotide sequences with the ligase detection reaction mixture;

quantifying the amount of ligation product sequences; and comparing the amount of ligation product sequences generated from the low abundance unknown sample with the amount of ligation product sequences generated from known amounts of marker target nucleotide sequences, to provide a quantitative measure of the level of one or more low abundance target nucleotide sequences in the sample.

70. A method according to claim 50, wherein a low abundance of multiple allele differences at multiple nearby or adjacent positions in a single target nucleotide sequence in the presence of an excess of normal sequence, or a low abundance of multiple allele differences at multiple nearby positions in multiple target nucleotide sequences, in the presence of an excess of normal sequence in a sample, are distinguished, the oligonucleotide probe sets forming a plurality of oligonucleotide probe groups, each group comprised of one or more oligonucleotide probe sets designed for distinguishing multiple allele differences at a single nucleotide position, wherein one or more sets within a group shire common first oligonucleotide probes, and the second oligonucleotide probes hybridize to a given allele excluding the normal allele in a base-specific manner, wherein one or more sets within a group share common first oligonucleotide probes, and the second oligonucleotide probes hybridize to a given allele including the normal allele in a base-specific manner, wherein the normal allele-specific probes are present in the ligation detection reaction mixture at a lower concentration than the mutant allele-specific probes, whereby the quantity of ligation product sequence generated from the majority normal target is similar to the quantity of ligation product sequence expected from a known dilution of the minority target;

quantifying the amount of ligation product sequences;

comparing the amount of ligation product sequences generated from the low abundance unknown sample with the amount of ligation product sequences generated from the high abundance normal target nucleotide sequences; and determining the amount of the high abundance normal target nucleotide sequences based on the low level of normal ligation product sequence formation, to provide a quantitative measure of the ratio of one or more low abundance target nucleotide sequences compared to the the high abundance normal target nucleotide sequences in the sample.

71. A method according to claim 50, wherein a low abundance of multiple allele differences at multiple nearby or adjacent positions in a single target nucleotide sequence in the presence of an excess of normal sequence, or a low abundance of multiple allele differences at multiple nearby positions in multiple target nucleotide sequences, in the presence of an excess of noel sequence in a sample, are distinguished, the oligonucleotide probe sets forming a plurality of oligonucleotide probe groups, each group comprised of one or mere oligonucleotide probe sets designed for distinguishing multiple allele differences at a single nucleotide position, wherein one or more sets within a group share common first oligonucleotide probes, and the second oligonucleotide probes hybridize to a given allele excluding the normal allele in a base-specific manner, wherein one or more sets within a group share common first oligonucleotide probes, and the second oligonucleotide probes hybridize to a given allele including the normal allele in a base-specific manner, wherein the normal allele-specific probes are present in the ligation detection reaction mixture at a lower concentration and/or contain one or more internal mismatches or modifications, whereby the ligation product sequence generated from the majority normal target is similar to the quantity of ligation product sequence expected from a known dilution of the minority target;

quantifying the amount of ligation product sequences;

comparing the amount of ligation product sequences generated from the low abundance unknown sample with the amount of ligation product sequences generated from the high abundance normal target nucleotide sequences; and determining the amount of the high abundance normal target nucleotide sequences based on the low level of normal ligation product sequence formation, to provide a quantitative measure of the ratio of one or more low abundance target nucleotide sequences compared to the the high abundance normal target nucleotide sequences in the sample.

72. A method according to claim 71, wherein the normal allele-specific probes contain the normal base at the 3' end.

73. A method according to claim 72, wherein the normal allele-specific probes contain the one or more internal mismatches or modifications within 4 bases from the 3' end.

74. A method as in claim 71, wherein the modification is a nucleotide analogue selected from the group consisting of 1-(2'-Deoxy-β-D-ribofuranosyl)imidazole-4-carboxamide, 1-(2'-Deoxy-β-D-ribofuranosyl)-3-nitropyrrole, 4-(2'-Deoxy-D-ribofuranosyl)imidazole-2-carboxamide, 2'-Deoxy-5-fluorouridine, 2'-Deoxyinosine, 6-(2'-Deoxy-β-D-ribofuranosyl)-6H,8H-3,4-dihydropyrimido[4,5-c] [1,2] oxazine-7-one, 2-Amino-7-(2'-deoxy-β-D-ribofuranosyl)-6-methoxyaminopurine, 1-(2'-Deoxy-β-D-ribofuranosyl)-5-nitroindole, 1-(2'-Deoxy-β-D-ribofuranosyl)pyrazole-4-carboxamide, 1-(2'-Deoxy-β-D-ribofuranosyl)-1,2,4-triazole-3-carboxamide, 3-Amino-1-(2 '-deoxy-β-D-ribofuranosyl)-1,2,4-triazole, 5-(2'-deoxy-β-D-ribofuranosyl)-2-pyrimidinone, 5-(2'-Deoxy-β-D-ribofuranosyl)-2-thiopyrimidine, 5-Amino-1-(2'-deoxy-β-D-ribofuranosyl)imidazole-4-carboxamide, 1-(2'-Deoxy-β-D-ribofuranosyl)-3-nitropyrazole, 1-(2'-Deoxy-β-D-ribofuranosyl)-4-iodopyrazole, 1',2'-Deoxy-β-D-ribofuranosyl)-4-propynylpyrazole, 1-(2'-Deoxy-β-D-ribofuranosyl)pyrrole-3-carboxamide, 1-(2'-Deoxy-β-D-ribofuranosyl)pyrazone-4-carboxamide, 1-(2'-Deoxy-β-D-ribofuranosyl)-4-nitroimidazole, and 1-(2'-Deoxy-β-D-ribofuranosyl)-4-nitropyrazole.

75. A method as in claim 71, wherein the modified oligonucleotide probe contains thiophosphate, dithiophosphate, 2'-methoxy, or 3'-amino-2',3'-dideoxy-modifications to its sugar phosphate backbone.

76. A method according to claim 50, wherein the minority target nucleotide sequence is distinguished from the majority target nucleotide sequence in the sample at a respective ratio of 1:500 for a G:T or T:G mismatch between the majority target nucleotide sequence and one of the oligonucleotide probes.

77. A method according to claim 50, wherein the minority target nucleotide sequence is distinguished from the majority target nucleotide sequence in the sample at a respective ratio of 1:2000 for other than a G:T or T:G mismatch between the majority target nucleotide sequence and one of the oligonucleotide probes.

78. A method according to claim 50, wherein the minority target nucleotide sequence is distinguished from the majority target nucleotide sequence, for low abundance multiple allele differences at multiple nearby or adjacent positions, at a respective ratio of 1:100 for all mismatches between the majority target nucleotide sequence and one of the oligonucleotide probes.

79. A method according to claim 50, wherein the minority target nucleotide sequence is distinguished from the majority target nucleotide sequence, for low abundance multiple allele differences at multiple nearby or adjacent positions, at a respective ratio of 1:500 for other than a G:T or T:G mismatch between the majority target nucleotide sequence and one of the oligonucleotide probes.

80. A method according to claim 1, wherein the ligase detection mixture does not contain discriminating oligonucleotide probes which hybridize to the majority target nucleotide sequence without mismatch.

81. A method according to claim 1, wherein the ligase detection mixture contains discriminating oligonucleotide probes which hybridize to the majority target nucleotide sequence without mismatch to the majority target nucleotide sequence in an amount both lower than that of the oligonucleotide probes specific to the minority target nucleotide sequence and effective to yield an amount of ligation product sequence corresponding to the majority target nucleotide sequence which does not preclude said detecting the presence of ligation product sequence produced as a result of the minority target nucleotide sequence being present in the sample.

82. A method according to claim 1, wherein the ligase detection mixture contains modified oligonucleotide probes which hybridize to the majority target nucleotide sequence in a form effective to yield an amount of ligation product sequence corresponding to the majority target nucleotide sequence which does not preclude said detecting the presence of ligation product sequence produced as a result of the minority target nucleotide sequence being present in the sample.

83. A method according to claim 25, wherein the ligase detection mixture does not contain discriminating oligonucleotide probes which hybridize to the majority target nucleotide sequence without mismatch.

84. A method according to claim 25, wherein the ligase detection mixture contains discriminating oligonucleotide probes which hybridize to the majority target nucleotide sequence without mismatch to the majority target nucleotide sequence in an amount both lower than that of the oligonucleotide probes specific to the minority target nucleotide sequence and effective to yield an amount of ligation product sequence corresponding to the majority target nucleotide sequence which does not preclude said detecting the presence of ligation product sequence produced as a result of the minority target nucleotide sequence being present in the sample.

85. A method according to claim 25, wherein the ligase detection mixture contains modified oligonucleotide probes which hybridize to the majority target nucleotide sequence in a form effective to yield an amount of ligation product sequence corresponding to the majority target nucleotide sequence which does not preclude said detecting the presence of ligation product sequence produced as a result of the minority target nucleotide sequence being present in the sample.

86. A method according to claim 50, wherein the ligase detection mixture does not contain discriminating oligonucleotide probes which hybridize to the majority target nucleotide sequence without mismatch.

87. A method according to claim 50, wherein the ligase detection mixture contains discriminating oligonucleotide probes which hybridize to the majority target nucleotide sequence without mismatch to the majority target nucleotide sequence in an amount both lower than that of the oligonucleotide probes specific to the minority target nucleotide sequence and effective to yield an amount of ligation product sequence corresponding to the majority target nucleotide sequence which does not preclude said detecting the presence of ligation product sequence produced as a result of the minority target nucleotide sequence being present in the sample.

88. A method according to claim 50, wherein the ligase detection mixture contains modified oligonucleotide probes which hybridize to the majority target nucleotide sequence in a form effective to yield an amount of ligation product sequence corresponding to the majority target nucleotide sequence which does not preclude said detecting the presence of ligation product sequence produced as a result of the minority target nucleotide sequence being present in the sample.

* * * * *

UNITED STATES PATENT AND TRADEMARK OFFICE
CERTIFICATE OF CORRECTION

| | |
|---|---|
| PATENT NO. | : 6,312,892 B1 |
| APPLICATION NO. | : 08/891292 |
| DATED | : November 6, 2001 |
| INVENTOR(S) | : Barany et al. |

It is certified that error appears in the above-identified patent and that said Letters Patent is hereby corrected as shown below:

Col. 1 at lines 7-9, delete "This invention was developed with government funding under National Institutes of Health Grant No. GM41337-06. The U.S. Government may retain certain rights." and insert --This invention was made with government support under grant GM41337-06 awarded by National Institutes of Health. The government has certain rights in the invention-- in its place.

Signed and Sealed this

Twenty-third Day of December, 2008

JON W. DUDAS
*Director of the United States Patent and Trademark Office*

SEQUENCE LISTING

<160> NUMBER OF SEQ ID NOS: 96

<210> SEQ ID NO: 1
<211> LENGTH: 18
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 1
gaccctggaa gaggcgag                                                        18

<210> SEQ ID NO: 2
<211> LENGTH: 27
<212> TYPE: DNA
<213> ORGANISM: Artificial Sequence
<220> FEATURE:
<223> OTHER INFORMATION: Description of Artificial Sequence:  Primer for
      PCR or LDR
<221> NAME/KEY: unsure
<222> LOCATION: (9)
<223> OTHER INFORMATION: N at position 9 is either A, C, G, or T

<400> SEQUENCE: 2
cgtccacsng gtgctccacg gtgtagg                                              27

<210> SEQ ID NO: 3
<211> LENGTH: 28
<212> TYPE: DNA
<213> ORGANISM: Artificial Sequence
<220> FEATURE:
<223> OTHER INFORMATION: Description of Artificial Sequence:  Primer for
      PCR or LDR
<221> NAME/KEY: unsure
<222> LOCATION: (10)
<223> OTHER INFORMATION: N at position 10 is either A, C, G, or T

<400> SEQUENCE: 3
tggagcaccn sgtggacggg ctttccgt                                             28

<210> SEQ ID NO: 4
<211> LENGTH: 17
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 4
gcaaactggg tcgccac                                                         17

```
<210> SEQ ID NO: 5
<211> LENGTH: 29
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 5
gaaagcccgt dcaccttgtg ctccacggt                                29

<210> SEQ ID NO: 6
<211> LENGTH: 26
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 6
acaaggtgha cgggctttcc gtgaac                                   26

<210> SEQ ID NO: 7
<211> LENGTH: 29
<212> TYPE: DNA
<213> ORGANISM: Artificial Sequence
<220> FEATURE:
<223> OTHER INFORMATION: Description of Artificial Sequence: Primer for
      PCR or LDR
<221> NAME/KEY: unsure
<222> LOCATION: (10)
<223> OTHER INFORMATION: N at position 10 is either A, C, G, or T

<400> SEQUENCE: 7
gaaagccctn ccaccttgtg ctccacggt                                29

<210> SEQ ID NO: 8
<211> LENGTH: 28
<212> TYPE: DNA
<213> ORGANISM: Artificial Sequence
<220> FEATURE:
<223> OTHER INFORMATION: Description of Artificial Sequence: Primer for
      PCR or LDR
<221> NAME/KEY: unsure
<222> LOCATION: (10)
<223> OTHER INFORMATION: N at position 10 is either A, C, G, or T

<400> SEQUENCE: 8
acaaggtggn agggctttcc gtgaacct                                 28

<210> SEQ ID NO: 9
<211> LENGTH: 28
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 9
ccctgttcca gcgtctgcgg tgttgcgt                                 28

<210> SEQ ID NO: 10
<211> LENGTH: 37
<212> TYPE: DNA
<213> ORGANISM: Artificial Sequence
<220> FEATURE:
<223> OTHER INFORMATION: Description of Artificial Sequence: Primer for
      PCR or LDR
```

<400> SEQUENCE: 10
aagttgtcat agtttgatcc tctagtctgg gaaaaaa                        37

<210> SEQ ID NO: 11
<211> LENGTH: 35
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 11
cagttgtcat agtttgatcc tctagtctgg gaaaa                          35

<210> SEQ ID NO: 12
<211> LENGTH: 33
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 12
gagttgtcat agtttgatcc tctagtctgg gaa                            33

<210> SEQ ID NO: 13
<211> LENGTH: 31
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 13
tagttgtcat agtttgatcc tctagtctgg g                              31

<210> SEQ ID NO: 14
<211> LENGTH: 59
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 14
gggacaaggt cgcagacgcc acaacgcaat caacagtatc aaactaggag atcagaccc     59

<210> SEQ ID NO: 15
<211> LENGTH: 30
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 15
agttgtcata gtttgatcct ctagtctggg                                30

<210> SEQ ID NO: 16
<211> LENGTH: 35
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 16 aaaaaacct gttccagcgt ctgcggtgtt gcgta                                    35

<210> SEQ ID NO: 17
<211> LENGTH: 33
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 17
aaaaccctgt tccagcgtct gcggtgttgc gtc                                     33

<210> SEQ ID NO: 18
<211> LENGTH: 31
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 18
aaccctgttc cagcgtctgc ggtgttgcgt g                                       31

<210> SEQ ID NO: 19
<211> LENGTH: 29
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 19
ccctgttcca gcgtctgcgg tgttgcgtt                                          29

<210> SEQ ID NO: 20
<211> LENGTH: 59
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 20
gggacaaggt cgcagacgcc acaacgcagt caacagtatc aaactaggag atcagaccc         59

<210> SEQ ID NO: 21
<211> LENGTH: 59
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 21
gggacaaggt cgcagacgcc acaacgcatt caacagtatc aaactaggag atcagaccc         59

<210> SEQ ID NO: 22
<211> LENGTH: 59
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 22
gggacaaggt cgcagacgcc acaacgcact caacagtatc aaactaggag atcagaccc      59

<210> SEQ ID NO: 23
<211> LENGTH: 20
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 23
tacgtctgcg gtgttgcgtc      20

<210> SEQ ID NO: 24
<211> LENGTH: 18
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 24
cgtctgcggt gttgcgtt      18

<210> SEQ ID NO: 25
<211> LENGTH: 21
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 25
atgcgtctgc ggtgttgcat c      21

<210> SEQ ID NO: 26
<211> LENGTH: 19
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 26
gcgtctgcgg tgttgcatt      19

<210> SEQ ID NO: 27
<211> LENGTH: 23
<212> TYPE: DNA
<213> ORGANISM: Artificial Sequence
<220> FEATURE:
<223> OTHER INFORMATION: Description of Artificial Sequence: Primer for
      PCR or LDR
<221> NAME/KEY: unsure
<222> LOCATION: (21)
<223> OTHER INFORMATION: N at position 21 is either A, C, G, or T

<400> SEQUENCE: 27
aaatgcgtct gcggtgttgc ntc      23

<210> SEQ ID NO: 28
<211> LENGTH: 21
<212> TYPE: DNA
<213> ORGANISM: Artificial Sequence
<220> FEATURE:
<223> OTHER INFORMATION: Description of Artificial Sequence: Primer for
      PCR or LDR
<221> NAME/KEY: unsure

```
<222> LOCATION: (19)
<223> OTHER INFORMATION: N at position 19 is either A, C, G, or T

<400> SEQUENCE: 28
atgcgtctgc ggtgttgcnt t                                              21

<210> SEQ ID NO: 29
<211> LENGTH: 23
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 29
aaatgcgtct gcggtgttgc ttc                                            23

<210> SEQ ID NO: 30
<211> LENGTH: 21
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 30
atgcgtctgc ggtgttgctt t                                              21

<210> SEQ ID NO: 31
<211> LENGTH: 30
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 31
agttgtcata gtttgatcct ctagtctggg                                     30

<210> SEQ ID NO: 32
<211> LENGTH: 59
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 32
gggacaaggt cgcagacgcc acaacgaagt caacagtatc aaactaggag atcagaccc     59

<210> SEQ ID NO: 33
<211> LENGTH: 59
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 33
ccctgttcca gcgtctgcgg tgttgcttca gttgtcatag tttgatcctc tagtctggg     59

<210> SEQ ID NO: 34
<211> LENGTH: 59
<212> TYPE: DNA
<213> ORGANISM: Artificial Sequence
<220> FEATURE:
<223> OTHER INFORMATION: Description of Artificial Sequence:  Primer for
```

PCR or LDR

<400> SEQUENCE: 34
gggacaaggt cgcagacgcc acaacgaaat caacagtatc aaactaggag atcagaccc     59

<210> SEQ ID NO: 35
<211> LENGTH: 59
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 35
ccctgttcca gcgtctgcgg tgttgcttta gttgtcatag tttgatcctc tagtctggg     59

<210> SEQ ID NO: 36
<211> LENGTH: 59
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 36
gggacaaggt cgcagacgcc acaacgcagt caacagtatc aaactaggag atcagaccc     59

<210> SEQ ID NO: 37
<211> LENGTH: 59
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 37
ccctgttcca gcgtctgcgg tgttgcgtca gttgtcatag tttgatcctc tagtctggg     59

<210> SEQ ID NO: 38
<211> LENGTH: 20
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 38
tacgtctgcg gtgttgcgtc                                                20

<210> SEQ ID NO: 39
<211> LENGTH: 18
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 39
cgtctgcggt gttgcgtt                                                  18

<210> SEQ ID NO: 40
<211> LENGTH: 59
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 40
gggacaaggt cgcagacgcc acaacgtagt caacagtatc aaactaggag atcagaccc    59

<210> SEQ ID NO: 41
<211> LENGTH: 59
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 41
ccctgttcca gcgtctgcgg tgttgcatca gttgtcatag tttgatcctc tagtctggg    59

<210> SEQ ID NO: 42
<211> LENGTH: 21
<212> TYPE: DNA
<213> ORGANISM: Artificial Sequence
<220> FEATURE:
<223> OTHER INFORMATION: Description of Artificial Sequence: Primer for
      PCR or LDR
<221> NAME/KEY: unsure
<222> LOCATION: (19)
<223> OTHER INFORMATION: N at position 19 is either A, C, G, or T

<400> SEQUENCE: 42
atgcgtctgc ggtgttgcnt t                                             21

<210> SEQ ID NO: 43
<211> LENGTH: 21
<212> TYPE: DNA
<213> ORGANISM: Artificial Sequence
<220> FEATURE:
<223> OTHER INFORMATION: Description of Artificial Sequence: Primer for
      PCR or LDR
<221> NAME/KEY: unsure
<222> LOCATION: (19)
<223> OTHER INFORMATION: N at position 19 is either A, C, G, or T

<400> SEQUENCE: 43
atgcgtctgc ggtgttgcnt t                                             21

<210> SEQ ID NO: 44
<211> LENGTH: 21
<212> TYPE: DNA
<213> ORGANISM: Artificial Sequence
<220> FEATURE:
<223> OTHER INFORMATION: Description of Artificial Sequence: Primer for
      PCR or LDR
<221> NAME/KEY: unsure
<222> LOCATION: (19)
<223> OTHER INFORMATION: N at position 19 is either A, C, G, or T

<400> SEQUENCE: 44
atgcgtctgc ggtgttgcnt t                                             21

<210> SEQ ID NO: 45
<211> LENGTH: 20
<212> TYPE: DNA
<213> ORGANISM: Artificial Sequence
<220> FEATURE:
<223> OTHER INFORMATION: Description of Artificial Sequence: Primer for
      PCR or LDR
<221> NAME/KEY: unsure
<222> LOCATION: (19)
<223> OTHER INFORMATION: N at position 19 is either A, C, G, or T

<400> SEQUENCE: 45
atgcgtctgc ggtgttgcnc                                           20

<210> SEQ ID NO: 46
<211> LENGTH: 21
<212> TYPE: DNA
<213> ORGANISM: Artificial Sequence
<220> FEATURE:
<223> OTHER INFORMATION: Description of Artificial Sequence:  Primer for
      PCR or LDR
<221> NAME/KEY: unsure
<222> LOCATION: (16)
<223> OTHER INFORMATION: N at any position in this sequence is A, C, G,
      or T

<400> SEQUENCE: 46
atgcgtctgc ggtgtnnngt t                                         21

<210> SEQ ID NO: 47
<211> LENGTH: 21
<212> TYPE: DNA
<213> ORGANISM: Artificial Sequence
<220> FEATURE:
<223> OTHER INFORMATION: Description of Artificial Sequence:  Primer for
      PCR or LDR
<221> NAME/KEY: unsure
<222> LOCATION: (16)
<223> OTHER INFORMATION: N at any position in this sequence is A, C, G,
      or T

<400> SEQUENCE: 47
atgcgtctgc ggtgtnnngt c                                         21

<210> SEQ ID NO: 48
<211> LENGTH: 20
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 48
acgcagacgc cacaacgcaa                                           20

<210> SEQ ID NO: 49
<211> LENGTH: 24
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 49
aaaacttgtg gtagttggag ctga                                      24

<210> SEQ ID NO: 50
<211> LENGTH: 25
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 50
caaaacttgt ggtagttgga gctgc                                     25

<210> SEQ ID NO: 51
<211> LENGTH: 27

```
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 51
acaaaaactt gtggtagttg gagctgt                                         27

<210> SEQ ID NO: 52
<211> LENGTH: 20
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 52
tggcgtaggc aagagtgcct                                                 20

<210> SEQ ID NO: 53
<211> LENGTH: 26
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 53
atataaactt gtggtagttg gagcta                                          26

<210> SEQ ID NO: 54
<211> LENGTH: 27
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 54
aatataaact tgtggtagtt ggagctc                                         27

<210> SEQ ID NO: 55
<211> LENGTH: 28
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 55
caatataaac ttgtggtagt tggagctt                                        28

<210> SEQ ID NO: 56
<211> LENGTH: 22
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 56
gtggcgtagg caagagtgcc aa                                              22

<210> SEQ ID NO: 57
<211> LENGTH: 21
<212> TYPE: DNA
```

```
<213> ORGANISM: Artificial Sequence
<220> FEATURE:
<223> OTHER INFORMATION: Description of Artificial Sequence:  Primer for
      PCR or LDR

<400> SEQUENCE: 57
tgtggtagtt ggagctggtg a                                            21

<210> SEQ ID NO: 58
<211> LENGTH: 22
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 58
atgtggtagt tggagctggt gc                                           22

<210> SEQ ID NO: 59
<211> LENGTH: 23
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 59
aatgtggtag ttggagctgg tgt                                          23

<210> SEQ ID NO: 60
<211> LENGTH: 30
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 60
cgtaggcaag agtgccttga caaaaaaaaa                                   30

<210> SEQ ID NO: 61
<211> LENGTH: 22
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 61
cttgtggtag ttggagctgg ta                                           22

<210> SEQ ID NO: 62
<211> LENGTH: 22
<212> TYPE: DNA
<213> ORGANISM: Artificial Sequence
<220> FEATURE:
<223> OTHER INFORMATION: Description of Artificial Sequence:  Primer for
      PCR or LDR

<400> SEQUENCE: 62
acttgtggta gttggagctg gt                                           22

<210> SEQ ID NO: 63
<211> LENGTH: 24
<212> TYPE: DNA
<213> ORGANISM: Artificial Sequence
```

```
<220> FEATURE:
<223> OTHER INFORMATION: Description of Artificial Sequence: Primer for
      PCR or LDR

<400> SEQUENCE: 63
aacttgtggt agttggagct ggtt                                              24

<210> SEQ ID NO: 64
<211> LENGTH: 32
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 64
gcgtaggcaa gagtgccttg aaaaaaaaaa aa                                     32

<210> SEQ ID NO: 65
<211> LENGTH: 25
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 65
agatattctc gacacagcag gtcat                                             25

<210> SEQ ID NO: 66
<211> LENGTH: 26
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 66
aagatattct cgacacagca ggtcac                                            26

<210> SEQ ID NO: 67
<211> LENGTH: 34
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 67
gaggagtaca gtgcaatgag ggacaaaaaa aaaa                                   34

<210> SEQ ID NO: 68
<211> LENGTH: 23
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 68
gatattctcg acacagcagg tcg                                               23

<210> SEQ ID NO: 69
<211> LENGTH: 24
<212> TYPE: DNA
<213> ORGANISM: Artificial Sequence
<220> FEATURE:
```

```
<223> OTHER INFORMATION: Description of Artificial Sequence: Primer for
      PCR or LDR

<400> SEQUENCE: 69
agatattctc gacacagcag gtct                                              24

<210> SEQ ID NO: 70
<211> LENGTH: 25
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 70
aagatattct cgacacagca ggtcc                                             25

<210> SEQ ID NO: 71
<211> LENGTH: 38
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 71
agaggagtac agtgcaatga gggaaaaaaa aaaaaaaa                               38

<210> SEQ ID NO: 72
<211> LENGTH: 23
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 72
ggatattctc gacacagcag gta                                               23

<210> SEQ ID NO: 73
<211> LENGTH: 24
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 73
aggatattct cgacacagca ggtg                                              24

<210> SEQ ID NO: 74
<211> LENGTH: 41
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 74
aagaggagta cagtgcaatg agggcaaaaa aaaaaaaaaa a                           41

<210> SEQ ID NO: 75
<211> LENGTH: 31
<212> TYPE: DNA
<213> ORGANISM: Artificial Sequence
<220> FEATURE:
<223> OTHER INFORMATION: Description of Artificial Sequence: Primer for
```

```
        PCR or LDR

<400> SEQUENCE: 75
aaccacaggc tgctgcggat gccggtcgga g                              31

<210> SEQ ID NO: 76
<211> LENGTH: 30
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 76
agagccgcca ccctcagaac cgccaccctc                                30

<210> SEQ ID NO: 77
<211> LENGTH: 61
<212> TYPE: DNA
<213> ORGANISM: Artificial Sequence
<220> FEATURE:
<223> OTHER INFORMATION: Description of Artificial Sequence: Primer for
      PCR or LDR

<400> SEQUENCE: 77
gagggtggcg gttctgaggg tggcggctct ctccgaccgg catccgcagc agcctgtggt    60
t                                                                   61

<210> SEQ ID NO: 78
<211> LENGTH: 18
<212> TYPE: DNA
<213> ORGANISM: Artificial Sequence
<220> FEATURE:
<223> OTHER INFORMATION: Description of Artificial Sequence: primer for
      PCR or LDR

<400> SEQUENCE: 78
cagaacctcc tcaccatc                                             18

<210> SEQ ID NO: 79
<211> LENGTH: 27
<212> TYPE: DNA
<213> ORGANISM: Artificial Sequence
<220> FEATURE:
<223> OTHER INFORMATION: Description of Artificial Sequence: primer for
      PCR or LDR
<221> NAME/KEY: unsure
<222> LOCATION: (10)
<223> OTHER INFORMATION: N at position 10 is either G or C
<221> NAME/KEY: unsure
<222> LOCATION: (11)
<223> OTHER INFORMATION: N at position 11 is either A, C, G, Or T

<400> SEQUENCE: 79
ctcgtccagn ngcaccacca ccccgtc                                   27

<210> SEQ ID NO: 80
<211> LENGTH: 28
<212> TYPE: DNA
<213> ORGANISM: Artificial Sequence
<220> FEATURE:
<223> OTHER INFORMATION: Description of Artificial Sequence: primer for
      PCR or LDR
<221> NAME/KEY: unsure
<222> LOCATION: (11)
<223> OTHER INFORMATION: N at position 11 is either C, G, or T

<400> SEQUENCE: 80
```

```
cgcccggttt ncccacctg gaagacca                                        28

<210> SEQ ID NO: 81
<211> LENGTH: 26
<212> TYPE: DNA
<213> ORGANISM: Artificial Sequence
<220> FEATURE:
<223> OTHER INFORMATION: Description of Artificial Sequence:  primer for
      PCR or LDR
<221> NAME/KEY: unsure
<222> LOCATION: (10)
<223> OTHER INFORMATION: N at position 10 is either G or T

<400> SEQUENCE: 81
gtcacccggn cggtgcgccc cacctg                                         26

<210> SEQ ID NO: 82
<211> LENGTH: 27
<212> TYPE: DNA
<213> ORGANISM: Artificial Sequence
<220> FEATURE:
<223> OTHER INFORMATION: Description of Artificial Sequence:  primer for
      PCR or LDR

<400> SEQUENCE: 82
ctcgtccagc ttcaccacca ccccgtc                                        27

<210> SEQ ID NO: 83
<211> LENGTH: 24
<212> TYPE: DNA
<213> ORGANISM: Artificial Sequence
<220> FEATURE:
<223> OTHER INFORMATION: Description of Artificial Sequence:  primer for
      PCR or LDR
<221> NAME/KEY: unsure
<222> LOCATION: (7)
<223> OTHER INFORMATION: N at position 7 is either A or G
<221> NAME/KEY: unsure
<222> LOCATION: (8)
<223> OTHER INFORMATION: N at position 8 is either C or T

<400> SEQUENCE: 83
tcgggcnngg tctcgggcca gcga                                           24

<210> SEQ ID NO: 84
<211> LENGTH: 24
<212> TYPE: DNA
<213> ORGANISM: Artificial Sequence
<220> FEATURE:
<223> OTHER INFORMATION: Description of Artificial Sequence:  primer for
      PCR or LDR
<221> NAME/KEY: unsure
<222> LOCATION: (8)
<223> OTHER INFORMATION: N at position 8 is either A or G
<221> NAME/KEY: unsure
<222> LOCATION: (9)
<223> OTHER INFORMATION: N at position 9 is either C or T

<400> SEQUENCE: 84
gtggcccnnc tcggggcagg tctc                                           24

<210> SEQ ID NO: 85
<211> LENGTH: 26
<212> TYPE: DNA
<213> ORGANISM: Artificial Sequence
<220> FEATURE:
<223> OTHER INFORMATION: Description of Artificial Sequence:  primer for
      PCR or LDR
<221> NAME/KEY: unsure
```

```
<222> LOCATION: (8)
<223> OTHER INFORMATION: N at position 8 is either A or G
<221> NAME/KEY: unsure
<222> LOCATION: (9)
<223> OTHER INFORMATION: N at position 9 is either C or T

<400> SEQUENCE: 85
gttgggcnng cggtggacct tcccct                                          26

<210> SEQ ID NO: 86
<211> LENGTH: 25
<212> TYPE: DNA
<213> ORGANISM: Artificial Sequence
<220> FEATURE:
<223> OTHER INFORMATION: Description of Artificial Sequence:  primer for
      PCR or LDR
<221> NAME/KEY: unsure
<222> LOCATION: (8)
<223> OTHER INFORMATION: N at position 8 is either A or G
<221> NAME/KEY: unsure
<222> LOCATION: (9)
<223> OTHER INFORMATION: N at position 9 is either C or T

<400> SEQUENCE: 86
ggcgggcnnc aaggggttgg ggcag                                           25

<210> SEQ ID NO: 87
<211> LENGTH: 26
<212> TYPE: DNA
<213> ORGANISM: Artificial Sequence
<220> FEATURE:
<223> OTHER INFORMATION: Description of Artificial Sequence:  primer for
      PCR or LDR
<221> NAME/KEY: unsure
<222> LOCATION: (9)
<223> OTHER INFORMATION: N at position 9 is either A, C, or T

<400> SEQUENCE: 87
acaaggtgna cgggctttcc gtgaac                                          26

<210> SEQ ID NO: 88
<211> LENGTH: 28
<212> TYPE: DNA
<213> ORGANISM: Artificial Sequence
<220> FEATURE:
<223> OTHER INFORMATION: Description of Artificial Sequence:  primer for
      PCR or LDR
<221> NAME/KEY: unsure
<222> LOCATION: (10)
<223> OTHER INFORMATION: N at position 10 is either A, C, G, or T
<221> NAME/KEY: unsure
<222> LOCATION: (11)
<223> OTHER INFORMATION: N at position 11 is either C or G

<400> SEQUENCE: 88
tggtggtgcn nctggacgag cttgccct                                        28

<210> SEQ ID NO: 89
<211> LENGTH: 25
<212> TYPE: DNA
<213> ORGANISM: Artificial Sequence
<220> FEATURE:
<223> OTHER INFORMATION: Description of Artificial Sequence:  primer for
      PCR or LDR
<221> NAME/KEY: unsure
<222> LOCATION: (8)
<223> OTHER INFORMATION: N at position 8 is either A, C, or G

<400> SEQUENCE: 89 ggtgggnaa accgggcgtg tgacc                                            25
```

<210> SEQ ID NO: 90
<211> LENGTH: 24
<212> TYPE: DNA
<213> ORGANISM: Artificial Sequence
<220> FEATURE:
<223> OTHER INFORMATION: Description of Artificial Sequence: primer for
      PCR or LDR
<221> NAME/KEY: unsure
<222> LOCATION: (8)
<223> OTHER INFORMATION: N at position 8 is either A or C

<400> SEQUENCE: 90
cgcaccgncc gggtgacccc tgtg                                              24

<210> SEQ ID NO: 91
<211> LENGTH: 28
<212> TYPE: DNA
<213> ORGANISM: Artificial Sequence
<220> FEATURE:
<223> OTHER INFORMATION: Description of Artificial Sequence: primer for
      PCR or LDR

<400> SEQUENCE: 91
tggtggtgaa gctggacgag cttgccct                                          28

<210> SEQ ID NO: 92
<211> LENGTH: 26
<212> TYPE: DNA
<213> ORGANISM: Artificial Sequence
<220> FEATURE:
<223> OTHER INFORMATION: Description of Artificial Sequence: primer for
      PCR or LDR
<221> NAME/KEY: unsure
<222> LOCATION: (10)
<223> OTHER INFORMATION: N at position 10 is either A or G
<221> NAME/KEY: unsure
<222> LOCATION: (11)
<223> OTHER INFORMATION: N at position 11 is either C or T

<400> SEQUENCE: 92
cccgagaccn ngcccgagtg cggcca                                            26

<210> SEQ ID NO: 93
<211> LENGTH: 28
<212> TYPE: DNA
<213> ORGANISM: Artificial Sequence
<220> FEATURE:
<223> OTHER INFORMATION: Description of Artificial Sequence: primer for
      PCR or LDR
<221> NAME/KEY: unsure
<222> LOCATION: (10)
<223> OTHER INFORMATION: N at position 10 is either A or G
<221> NAME/KEY: unsure
<222> LOCATION: (11)
<223> OTHER INFORMATION: N at position 11 is either C or T

<400> SEQUENCE: 93
tgccccgagn ngggccaccg cctcctca                                          28

<210> SEQ ID NO: 94
<211> LENGTH: 28
<212> TYPE: DNA
<213> ORGANISM: Artificial Sequence
<220> FEATURE:
<223> OTHER INFORMATION: Description of Artificial Sequence: primer for
      PCR or LDR
<221> NAME/KEY: unsure
<222> LOCATION: (10)
<223> OTHER INFORMATION: N at position 10 is either A or G

```
<221> NAME/KEY: unsure
<222> LOCATION: (11)
<223> OTHER INFORMATION: N at position 11 is either C or T

<400> SEQUENCE: 94
gtccaccgcn ngcccaaccc cttgtgcc                                          28

<210> SEQ ID NO: 95
<211> LENGTH: 28
<212> TYPE: DNA
<213> ORGANISM: Artificial Sequence
<220> FEATURE:
<223> OTHER INFORMATION: Description of Artificial Sequence: primer for
      PCR or LDR
<221> NAME/KEY: unsure
<222> LOCATION: (10)
<223> OTHER INFORMATION: N at position 10 is either A or G
<221> NAME/KEY: unsure
<222> LOCATION: (11)
<223> OTHER INFORMATION: N at position 11 is either C or T

<400> SEQUENCE: 95
aaccccttgn ngcccgccaa gcgctttg                                          28

<210> SEQ ID NO: 96
<211> LENGTH: 21
<212> TYPE: DNA
<213> ORGANISM: Artificial Sequence
<220> FEATURE:
<223> OTHER INFORMATION: Description of Artificial Sequence: primer for
      PCR or LDR

<400> SEQUENCE: 96
ctctatgtag ctctcgttgt g                                                 21
```